United States Patent
Sommadossi et al.

(10) Patent No.: US 10,711,029 B2
(45) Date of Patent: Jul. 14, 2020

(54) BETA-D-2'-DEOXY-2'-ALPHA-FLUORO-2'-BETA-C-SUBSTITUTED-4'FLUORO-N6-SUBSTITUTED-6-AMINO-2-SUBSTITUTED PURINE NUCLEOTIDES FOR THE TREATMENT OF HEPATITIS C VIRUS INFECTION

(71) Applicant: Atea Pharmaceuticals, Inc., Boston, MA (US)

(72) Inventors: Jean-Pierre Sommadossi, Boston, MA (US); Adel Moussa, Burlington, MA (US)

(73) Assignee: ATEA Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/317,665

(22) PCT Filed: Jul. 14, 2017

(86) PCT No.: PCT/US2017/042159
§ 371 (c)(1),
(2) Date: Jan. 14, 2019

(87) PCT Pub. No.: WO2018/013937
PCT Pub. Date: Jan. 18, 2018

(65) Prior Publication Data
US 2019/0153017 A1    May 23, 2019

Related U.S. Application Data

(60) Provisional application No. 62/362,277, filed on Jul. 14, 2016.

(51) Int. Cl.
*C07H 19/20*    (2006.01)
*A61P 31/14*    (2006.01)

(52) U.S. Cl.
CPC .............. *C07H 19/20* (2013.01); *A61P 31/14* (2018.01)

(58) Field of Classification Search
None
See application file for complete search history.

(56) References Cited

FOREIGN PATENT DOCUMENTS

| WO | 2010091386 A2 | 8/2010 |
| WO | 2014100505 A1 | 6/2014 |
| WO | WO -2014100505 A1 * | 6/2014 |
| WO | 2016100441 A1 | 6/2016 |

OTHER PUBLICATIONS

Wolff, Manfred E., "Burger's Medicinal Chemistry, 5ed, Part I", John Wiley & Sons,.*
Banker, G.S. et al, "Modern Pharmaceutics, 3ed.", Marcel Dekker, New York, 1996, p. 596 (Year: 1996).*
Written Opinion and International Search Report cited in PCT/US2017/042159 dated Oct. 23, 2017, 14 pages.

* cited by examiner

*Primary Examiner* — Traviss C Mcintosh, III
(74) *Attorney, Agent, or Firm* — Rothwell, Figg, Ernst & Manbeck, P.C.

(57) ABSTRACT

Compounds of Formula I, Formula II, Formula III, Formula IV, Formula V, Formula VI, Formula VII, Formula VIII, Formula IX and Formula X that are highly active against the HCV virus when administered in an effective amount to a host in need thereof. The host can be a human or any animal that carries the viral infection. Methods of treating a subject suffering from a condition related to viral infections are also provided.

32 Claims, No Drawings

BETA-D-2'-DEOXY-2'-ALPHA-FLUORO-2'-BETA-C-SUBSTITUTED-4'FLUORO-N6-SUBSTITUTED-6-AMINO-2-SUBSTITUTED PURINE NUCLEOTIDES FOR THE TREATMENT OF HEPATITIS C VIRUS INFECTION

CROSS-REFERENCE TO RELATED APPLICATION

This application claims the benefit under 35 U.S.C. § 119(e) of the filing date of provisional patent application Ser. No. 62/362,277 filed Jul. 14, 2016, the disclosures of which is incorporated herein by reference in its entirety.

FIELD OF THE INVENTION

The present disclosure relates generally to nucleotide compounds, their uses, and compositions thereof to treat patients suffering from conditions caused by viral infections, including the Hepatitis C virus ("HCV").

BACKGROUND OF THE INVENTION

Hepatitis C (HCV) is an RNA single stranded virus and member of the Hepacivirus genus. It is estimated that 75% of all cases of liver disease are caused by HCV. HCV infection can lead to cirrhosis and liver cancer, and if left to progress, liver failure which may require a liver transplant. Approximately 170-200 million people worldwide are infected, with an estimated 3-4 million infections in the United States.

RNA polymerase is a key component in the targeting of RNA single stranded viruses. The HCV non-structural protein NS5B RNA-dependent RNA polymerase is a key enzyme responsible for initiating and catalyzing viral RNA synthesis. As a result, HCV NS5B is an attractive target for the current drug discovery and development of anti-HCV agents. There are two major subclasses of NS5B inhibitors: nucleoside analogs, which are anabolized to their active triphosphates—which act as alternative substrates for the polymerase—and non-nucleoside inhibitors (NNIs), which bind to allosteric regions on the protein. Nucleoside or nucleotide inhibitors mimic natural polymerase substrate and act as chain terminators. They inhibit the initiation of RNA transcription and elongation of a nascent RNA chain.

In addition to targeting RNA polymerase, other RNA viral proteins may also be targeted in combination therapies. For example, HCV proteins that are additional targets for therapeutic approaches are NS3/4A (a serine protease) and NS5A (a non-structural protein that is an essential component of HCV replicase and exerts a range of effects on cellular pathways).

In December 2013, the first nucleoside NS5B polymerase inhibitor sofosbuvir (Sovaldi®, Gilead Sciences) was approved. Sovaldi® is a uridine phosphoramidate prodrug that is taken up by hepatocytes and undergoes intracellular activation to afford the active metabolite; 2'-deoxy-2'-α-fluoro-β-C-methyluridine-5'-triphosphate see structures below:

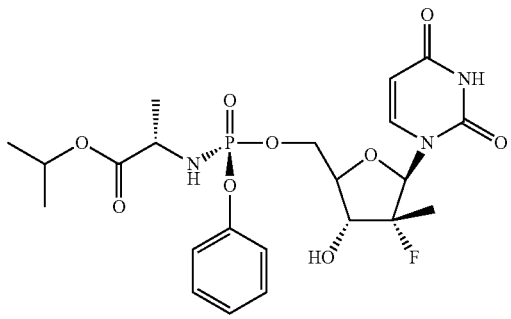

Sovaldi®

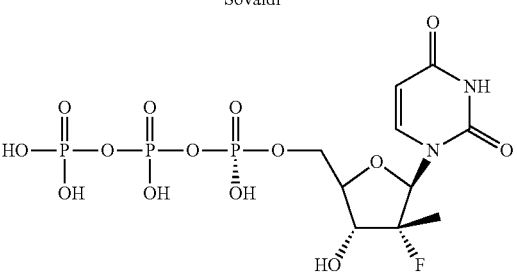

2'-Deoxy-2'-α-fluoro-β-C-methyluridine-5'-triphosphate

Sovaldi® is the first drug that has demonstrated safety and efficacy to treat certain types of HCV infection without the need for co-administration of interferon. Sovaldi® is the third drug with breakthrough therapy designation to receive FDA approval.

In 2014, the U.S. FDA approved Harvoni® (ledispasvir, a NS5A inhibitor, and sofosbuvir) to treat chronic hepatitis C virus genotype 1 infection. Harvoni® is the first combination pill approved to treat chronic HCV genotype 1 infection. It is also the first approved regimen that does not require administration with interferon or ribavirin. In addition, the FDA approved simeprevir (Olysio™) in combination with sofosbuvir (Sovaldi®) as a once-daily, all oral, interferon and ribavirin-free treatment for adults with genotype 1 HCV infection.

The U.S. FDA also approved AbbVie's VIEKIRA Pak™ in 2014, a multipill pack containing dasabuvir (a non-nucleoside NS5B polymerase inhibitor), ombitasvir (a NS5A inhibitor), paritaprevir (a NS3/4A inhibitor), and ritonavir. The VIEKIRA Pak™ can be used with or without the ribavirin to treat genotype 1 HCV infected patients including patients with compensated cirrhosis. VIEKIRA Pak™ does not require interferon co-therapy.

In July 2015, the U.S. FDA approved Technivie™ and Daklinza™ for the treatment of HCV genotype 4 and HCV genotype 3 respectively. Technivie™ (Ombitasvir/paritaprevir/ritonavir) was approved for use in combination with ribavirin for the treatment of HCV genotype 4 in patients without scarring and cirrhosis and is the first option for HCV-4 infected patients who do not require co-administration with interferon. Daklinza™ was approved for use with Sovaldi® to treat HCV genotype 3 infections. Daklinza™ is the first drug that has demonstrated safety and efficacy in treating HCV genotype 3 without the need for co-administration of interferon or ribavirin.

In October 2015, the U.S. FDA warned that HCV treatments Viekira Pak and Technivie can cause serious liver injury primarily in patients with underlying advanced liver disease, and required that additional information about safety be added to the label.

Other current approved therapies for HCV include interferon alpha-2b or pegylated interferon alpha-2b (Pegintron®), which can be administered with ribavirin (Rebetol®), NS3/4A telaprevir (Incivek®, Vertex and Johnson & Johnson), boceprevir (Victrelis™, Merck), simeprevir (Olysio™, Johnson & Johnson), paritaprevir (AbbVie), Ombitasvir (AbbVie), (NNI) Dasabuvir (ABT-333) and Merck's Zepatier™ (a single-tablet combination of the two drugs grazoprevir and elbasvir).

Additional NS5B polymerase inhibitors are currently under development. Merck is developing the uridine nucleotide prodrug MK-3682 (formerly Idenix IDX21437). The drug is currently in Phase II combination trials. United States patents and WO applications which describe nucleoside polymerase inhibitors for the treatment of Flaviviridae, including HCV, include those filed by Idenix Pharmaceuticals (U.S. Pat. Nos. 6,812,219; 6,914,054; 7,105,493; 7,138,376; 7,148,206; 7,157,441; 7,163,929; 7,169,766; 7,192,936; 7,365,057; 7,384,924; 7,456,155; 7,547,704; 7,582,618; 7,608,597; 7,608,600; 7,625,875; 7,635,689; 7,662,798; 7,824,851; 7,902,202; 7,932,240; 7,951,789; 8,193,372; 8,299,038; 8,343,937; 8,362,068; 8,507,460; 8,637,475; 8,674,085; 8,680,071; 8,691,788; 8,742,101; 8,951,985; 9,109,001; 9,243,025; US2016/0002281; US2013/0064794; WO/2015/095305; WO/2015/081133; WO/2015/061683; WO/2013/177219; WO/2013/039920; WO/2014/137930; WO/2014/052638; WO/2012/154321); Merck (U.S. Pat. Nos. 6,777,395; 7,105,499; 7,125,855; 7,202,224; 7,323,449; 7,339,054; 7,534,767; 7,632,821; 7,879,815; 8,071,568; 8,148,349; 8,470,834; 8,481,712; 8,541,434; 8,697,694; 8,715,638, 9,061,041; 9,156,872 and WO/2013/009737); Emory University (U.S. Pat. Nos. 6,348,587; 6,911,424; 7,307,065; 7,495,006; 7,662,938; 7,772,208; 8,114,994; 8,168,583; 8,609,627; US 2014/0212382; and WO2014/1244430); Gilead Sciences/Pharmasset Inc. (7,842,672; 7,973,013; 8,008,264; 8,012,941; 8,012,942; 8,318,682; 8,324,179; 8,415,308; 8,455,451; 8,563,530; 8,841,275; 8,853,171; 8,871,785; 8,877,733; 8,889,159; 8,906,880; 8,912,321; 8,957,045; 8,957,046; 9,045,520; 9,085,573; 9,090,642; and 9,139,604) and (U.S. Pat. Nos. 6,908,924; 6,949,522; 7,094,770; 7,211,570; 7,429,572; 7,601,820; 7,638,502; 7,718,790; 7,772,208; RE42,015; 7,919,247; 7,964,580; 8,093,380; 8,114,997; 8,173,621; 8,334,270; 8,415,322; 8,481,713; 8,492,539; 8,551,973; 8,580,765; 8,618,076; 8,629,263; 8,633,309; 8,642,756; 8,716,262; 8,716,263; 8,735,345; 8,735,372; 8,735,569; 8,759,510 and 8,765,710); Hoffman La-Roche (U.S. Pat. No. 6,660,721), Roche (U.S. Pat. Nos. 6,784,166; 7,608,599, 7,608,601 and 8,071,567); Alios BioPharma Inc. (U.S. Pat. Nos. 8,895,723; 8,877,731; 8,871,737, 8,846,896, 8,772,474; 8,980,865; 9,012,427; US 2015/0105341; US 2015/0011497; US 2010/0249068; US2012/0070411; WO 2015/054465; WO 2014/209979; WO 2014/100505; WO 2014/100498; WO 2013/142159; WO 2013/142157; WO 2013/096680; WO 2013/088155; WO 2010/108135), Enanta Pharmaceuticals (U.S. Pat. Nos. 8,575,119; 8,846,638; 9,085,599; WO 2013/044030; WO 2012/125900), Biota (U.S. Pat. Nos. 7,268,119; 7,285,658; 7,713,941; 8,119,607; 8,415,309; 8,501,699 and 8,802,840), Biocryst Pharmaceuticals (U.S. Pat. Nos. 7,388,002; 7,429,571; 7,514,410; 7,560,434; 7,994,139; 8,133,870; 8,163,703; 8,242,085 and 8,440,813), Alla Chem, LLC (U.S. Pat. No. 8,889,701 and WO 2015/053662), Inhibitex (U.S. Pat. No. 8,759,318 and WO/2012/092484), Janssen Products (U.S. Pat. Nos. 8,399,429; 8,431,588, 8,481,510, 8,552,021, 8,933,052; 9,006,29 and 9,012,428) the University of Georgia Foundation (U.S. Pat. Nos. 6,348,587; 7,307,065; 7,662,938; 8,168,583; 8,673,926, 8,816,074; 8,921,384 and 8,946,244), RFS Pharma, LLC (U.S. Pat. Nos. 8,895,531; 8,859,595; 8,815,829; 8,609,627; 7,560,550; US 2014/0066395; US 2014/0235566; US 2010/0279969; WO/2010/091386 and WO 2012/158811) University College Cardiff Consultants Limited (WO/2014/076490, WO 2010/081082; WO/2008/062206), Achillion Pharmaceuticals, Inc. (WO/2014/169278 and WO 2014/169280), Cocrystal Pharma, Inc. (U.S. Pat. No. 9,173,893), Katholieke Universiteit Leuven (WO 2015/158913), Catabasis (WO 2013/090420) and the Regents of the University of Minnesota (WO 2006/004637).

In 1976, Moffatt et al. reported on the synthesis of the nucleoside antibiotic nucleocidin; see structure below:

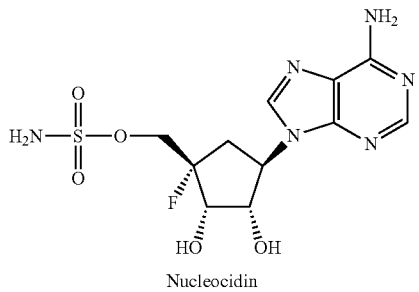 [SMILES: Nc1ncnc2c1ncn2[C@@H]1C[C@](F)(COS(N)(=O)=O)[C@@H](O)[C@H]1O]

Nucleocidin

The structure of nucleocidin was unique in that it was the first natural product to contain either a fluoro carbohydrate or an unsubstituted sulfamoyl group. In addition, it appeared to be the first example of a furanose sugar bearing a functional substituent at the 4'-position, see, "4'-Substituted Nucleosides. 2. Synthesis of the Nucleoside Antibiotic Nucleocidin", Moffatt, J. G. et al., J. Am. Chem. Soc., 98(11)3346-3357, 1976. Moffatt et al. also reported on the synthesis of 4'-fluorouridine derivatives, see, "4'-Substituted Nucleosides. 3. Synthesis of Some 4'-Fluorouridine Derivatives", Owens, G. R., et al., J. Org. Chem., 41(18)3010-3017, 1976.

In 2010, Verdine et al. disclosed concise syntheses of 4'-fluoro nucleosides. In one synthetic route Verdine et al. treated 1-O-acetyl-2,3,5-tri-O-benzoyl-β-D-ribose with N-bromosuccinimide under a sun lamp (275W) to afford a mixture of brominated products which were subjected to fluorination with silver tetrafluoroborate to afford 4-fluoro-β-D-ribofuranose in 30% yield, together with an almost equal amount of 4-fluoro-α-L-lyxofuranose. Using 4-fluoro-β-D-ribofuranose, Verdine synthesized 4'-fluoroadeno sine, 4'-fluoroinosine and 4'-fluorocytidine. In addition, Verdine disclosed the direct bromination: fluorination of the nucleoside 2',3',5'-tribenzoate 5-fluorouridine to afford uridine, 5-fluoro-4'-C-fluoro, 2',3',5'-tribenzoate. See, "A Concise Synthesis of 4'-Fluoro Nucleosides", Lee, S. et al., Org. Lett., 9(24)5007-5009, 2007.

In 2010, Alexandrova, L. A. et al. disclosed that 4'fluorouridine 5'-O-triphosphate was an effective inhibitor of HCV RNA-dependent RNA polymerase, see, "Synthesis and Biological Properties of Pyrimidine 4'-Fluoronucleosides and 4'-Fluorouridine 5'-Triphosphate", Ivanov, M. A. et al., Russian J. Bioorg. Chem., 36(4)488-496, 2010.

U.S. Pat. No. 7,429,572 filed by Pharmasset, Inc. titled "Modified Fluorinated Nucleoside Analogues" describes a large number of broad genuses of nucleoside compounds, including the broad formula:

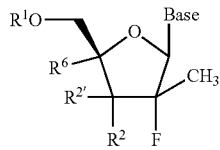

wherein Base refers to a naturally occurring or modified purine or pyrimidine base; $R^1$ can be a pharmaceutically acceptable leaving group which when administered in vivo is capable of providing a compound wherein $R^1$ is H or phosphate; $R^2$ can be H, $C_{1-4}$ alkyl, $C_{1-4}$ alkenyl, $C_{1-4}$ alkynyl, vinyl, $N_3$, CN, Cl, Br, F, I, $NO_2$, $C(O)O(C_{1-4}$ alkyl), $C(O)O(C_{1-4}$ alkynyl), $C(O)O(C_{1-4}$ alkenyl), $O(C_{1-4}$ acyl), $O(C_{1-4}$ alkyl), $O(C_{1-4}$ alkenyl), $S(C_{1-4}$ acyl), $S(C_{1-4}$ alkyl), $S(C_{1-4}$ alkynyl), $S(C_{1-4}$ alkenyl), $SO(C_{1-4}$ acyl), $SO(C_{1-4}$ alkyl), $SO(C_{1-4}$ alkynyl), $SO(C_{1-4}$ alkenyl), $SO_2(C_{1-4}$ acyl), $SO_2(C_{1-4}$ alkyl), $SO_2(C_{1-4}$ alkynyl), $SO_2(C_{1-4}$ alkenyl), $O_3S$ $(C_{1-4}$ acyl), etc.; and $R^6$ can be an optionally substituted alkyl (including lower alkyl), cyano (CN), $CH_3$, $OCH_3$, $OCH_2CH_3$, hydroxy methyl ($CH_2OH$), fluoromethyl ($CH_2F$), azido ($N_3$), CHCN, $CH_2N_3$, $CH_2NH_2$, $CH_2NHCH_3$, $CH_2N(CH_3)_2$, alkyne (optionally substituted), or fluoro. In regard to when $R^6$ is fluoro, there are no species disclosed falling within this very broad genus.

WO 2005/009148 filed by Idenix Ltd. titled "Purine Nucleoside Analogues for Treating Flaviviridae Including Hepatitis C" describes a compound of Formula I, see structure below, having broadly defined variables. For example, X is $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, CH-halogen, or C-(halogen)$_2$. The variable $R^{1'}$ is independently H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —$NO_2$, —$NH_2$, —NH(lower alkyl), —N(lower alkyl)$_2$, —NH(acyl), —N(acyl)$_2$, —C(O)NH$_2$, —C(O)NH(alkyl), —C(O)N(alkyl)$_2$, S(O)N-alkyl, S(O)N-alkenyl, S(O)N-alkynyl, or SCH-halogen, wherein alkyl, alkenyl, and/or alkynyl may optionally be substituted.

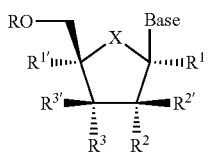

(I)

The Idenix application discloses no 4'-fluoro nucleosides of any genus. Additional Idenix patent applications and patents disclosing 4'-nucleosides include WO 2005/020884; U.S. Pat. Nos. 7,138,376 and 9,211,300.

WO 2008/121634 filed by Pharmasset, Inc. titled "Nucleoside Phosphoramidate Prodrugs" describes a large number of broad genuses of nucleoside compounds including the broad formula I-5:

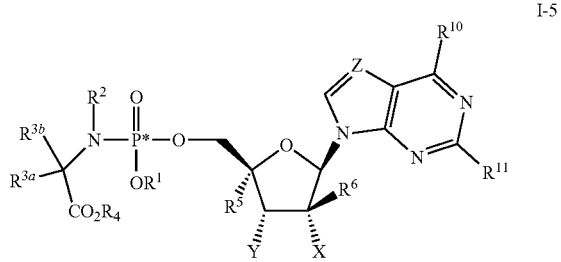

wherein: $R^5$ is H, a lower alkyl, CN, vinyl, O-(lower alkyl), hydroxyl lower alkyl, i.e., —(CH$_2$)pOH, where p is 1-6, including hydroxyl methyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including F, Cl, Br, or I, with the provisos that when X is OH, base is cytosine and $R^6$ is H, $R^5$ cannot be N$_3$ and when X is OH, $R^6$ is CH$_3$ or CH$_2$F and B is a purine base, $R^5$ cannot be H; $R^6$ is H, CH$_3$, CH$_2$F, CHF$_2$, CF$_3$, F or CN; X is H, OH, F, OMe, halogen, NH$_2$ or N$_3$. In regard to when $R^5$ is F, $R^6$ is CH$_3$ and X is F, there are no species disclosed falling within this very broad genus and there is no direction on how to prepare or how to select where to place additional substituent groups. Additional patent applications and patents to Pharmasset include WO 2009/152095; U.S. Pat. Nos. 7,964,580; 8,173,621; 8,334,270; 8,580,765; 8,735,372; 8,759,510; 8,906,880; 8,957,046; and 9,085,573.

WO 2010/091386 filed by RFS Pharma, LLC titled "Purine Nucleoside Monophosphate Prodrugs for Treatment of Cancer and Viral Infections" discloses a compound of Formula I

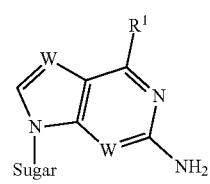

where the sugar is ribose or modified ribose of the general formula (II):

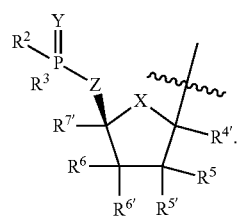

The application does not disclose any species wherein $R^{7'}$ is fluoro, $R^5$ is $C_1$-$C_6$ alkyl and $R^{5'}$ is fluoro.

WO 2012/012465 filed by Gilead Sciences, Inc. titled "Methods for the Preparation of Diastereomerically Pure Phosphoramidate Prodrugs" describes a large number of broad genuses of nucleoside compounds, including the broad formulas Ia and Ib:

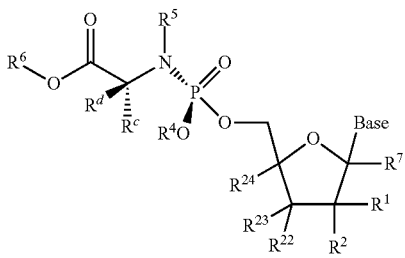 (Ia)

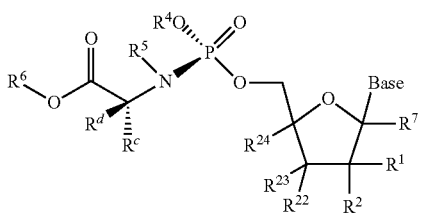 (Ib)

wherein each $R^1$, $R^2$, $R^7$, $R^{22}$, $R^{23}$ or $R^{24}$ is independently H, $OR^{11}$, $NR^{11}R^{12}$, $C(O)NR^{11}R^{12}$, —$OC(O)NR^{11}R^{12}$, $C(O)OR^{11}$, $OC(O)OR^{11}$, $S(O)_nR^a$, $S(O)_2NR^{11}R^{12}$, $N_3$, CN, halogen, $(C_1$-$C_8)$ alkyl, $(C_3$-$C_8)$carbocyclyl, $(C_4$-$C_8)$carbocyclylalkyl, $(C_2$-$C_8)$alkenyl, $(C_2$-$C_8)$alkynyl or aryl$(C_1$-$C_8)$alkyl. In regard to when $R^{24}$ is F, $R^1$ is $CH_3$ and $R^2$ is F; there are no species disclosed falling within this very broad genuses and there is no direction on how to prepare or how to select where to place substituent groups.

WO 2013/019874 filed by MBC Pharma, Inc. titled "Vitamin B6 Derivatives of Nucleotides, Acyclonucleotides and Acyclonucleoside Phosphonates" disclose a broad definition of a 5'-nucleoside, see below:

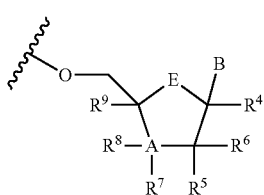

(5'-nucleoside)

wherein E is O, C, N, or S; $R^4$, $R^5$, $R^6$, $R^7$, $R^8$ and $R^9$ are independently, H, OH, F, $NH_2$, $N_3$, alkyl, alkenyl, or alkynyl. The application discloses no 4'-fluorofuranose compounds and the nucleoside compounds are derivitized with vitamin B6 at the 5'-position.

WO 2013/092481 filed by F. Hoffmann-La Roche AG titled "2',4'-Difluoro-2'-Methyl Substituted Nucleoside Derivatives as Inhibitors of HCV RNA Replication" discloses pyrimidine compounds of Formula I having anti-HCV activity, see structure below:

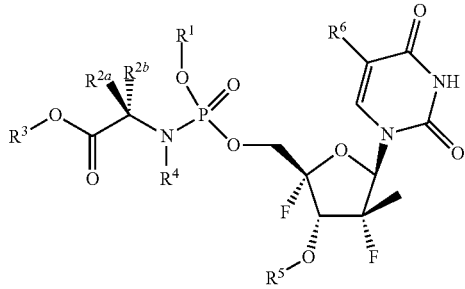 (I)

WO 2014/100505 filed by Alios Biopharma, Inc. titled Substituted Nucleosides, Nucleotides and Analogs Thereof" discloses the subgenus formula:

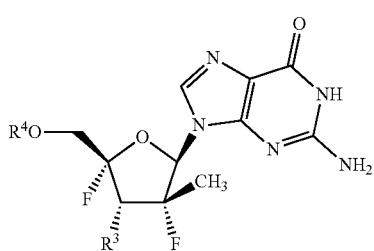

wherein $R^3$ can be hydroxy and $R^4$ can be a hydrogen or

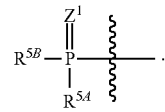

The only species disclosed is the guanine compound illustrated below:

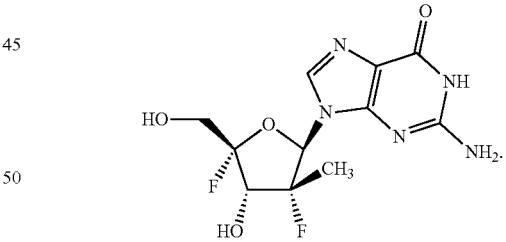

As the treatment options for people infected with HCV are limited, there remains a strong medical need to develop anti-HCV therapies that are safe, effective and well-tolerated. The need is accentuated by the expectation that drug resistance can arise, as seen in anti-HIV and anti-HCV therapies, and new combination drug therapies may be needed to treat the HCV virus. More potent direct-acting antivirals could significantly shorten treatment duration and improve compliance and SVR rates for patients infected with HCV.

It is therefore an object of the present invention to provide compounds, pharmaceutical compositions, and methods and uses to treat and/or prevent infections of HCV.

SUMMARY OF THE INVENTION

Compounds are provided of Formula I, Formula II, Formula III, Formula IV, Formula V, Formula VI, Formula VII, Formula VIII, Formula IX and Formula X that are highly active against the HCV virus when administered in an effective amount to a host in need thereof. The host can be a human or any animal that carries the viral infection.

In one embodiment, a therapeutically effective amount of one or more compounds of Formula I, Formula II, Formula III, Formula IV, Formula V, Formula VI, Formula VII, Formula VIII, Formula IX and Formula X or a pharmaceutically acceptable salt thereof, can be used to treat a HCV infection. In one embodiment, a therapeutically effective amount of one or more compounds of Formula I, Formula II, Formula III, Formula IV, Formula V, Formula VI, Formula VII, Formula VIII, Formula IX and Formula X or a pharmaceutically acceptable salt thereof, can be used to inhibit the HCV polymerase complex.

Thus, in one embodiment, the invention includes:

Formula I

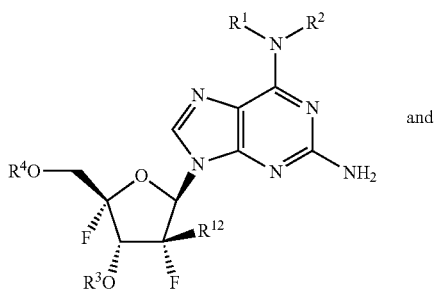

and

Formula II

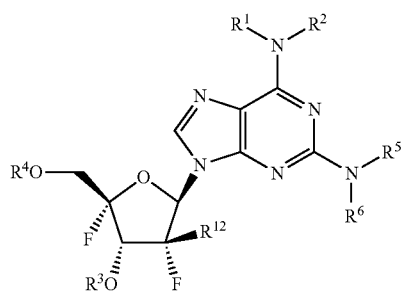

wherein:

$R^1$ is $C_1$-$C_5$alkyl (including methyl, ethyl, n-propyl, iso-propyl, n-butyl, iso-butyl, sec-butyl, tert-butyl and pentyl) or —($C_0$-$C_2$alkyl)($C_3$-$C_6$cycloalkyl);

$R^2$ is hydrogen, $C_1$-$C_5$alkyl (including methyl, ethyl, n-propyl, iso-propyl, n-butyl, iso-butyl, sec-butyl, tert-butyl and pentyl), $CHF_2$, $CH_2F$, $CF_3$, —($C_0$-$C_2$alkyl)($C_3$-$C_6$cycloalkyl), —C(O)$R^{3C}$, —($C_0$-$C_2$alkyl)(aryl), —($C_0$-$C_2$alkyl)(heterocycle), —($C_0$-$C_2$alkyl)(heteroaryl); or $R^1$ and $R^2$ together with the nitrogen to which they are bonded can form a heterocycle;

$R^3$ is hydrogen,

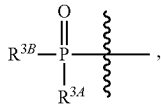

diphosphate, triphosphate, an optionally substituted carbonyl linked amino acid, or —C(O)$R^{3C}$;

$R^{3A}$ can be selected from O⁻, OH, an —O-optionally substituted aryl, an —O-optionally substituted heteroaryl, or an optionally substituted heterocyclyl;

$R^{3B}$ can be selected from O⁻, OH, an optionally substituted N-linked amino acid or an optionally substituted N-linked amino acid ester;

$R^3$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), —O—($C_0$-$C_2$)(heteroaryl), —S-alkyl, —S-alkenyl, —S-alkynyl, —S—($C_0$-$C_2$)(cycloalkyl), —S($C_0$-$C_2$)(heterocyclo), —S—($C_0$-$C_2$)(aryl), or —S—($C_0$-$C_2$)(heteroaryl) each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug;

$R^5$ is hydrogen, $C_1$-$C_5$alkyl (including methyl, ethyl, n-propyl, iso-propyl, n-butyl, iso-butyl, sec-butyl, tert-butyl and pentyl), or —($C_0$-$C_2$alkyl)($C_3$-$C_6$cycloalkyl);

$R^6$ is $C_1$-$C_5$alkyl (including methyl, ethyl, n-propyl, iso-propyl, n-butyl, iso-butyl, sec-butyl, tert-butyl and pentyl), —($C_0$-$C_2$alkyl)($C_3$-$C_6$cycloalkyl), —($C_{0-6}$alkyl)(aryl), —($C_{0-6}$alkyl)(heteroaryl), —($C_{0-6}$alkyl)(heterocycle) or —C(O)$R^{3C}$;

$R^{12}$ is $CH_3$, $CH_2F$, $CHF_2$, $CF_3$, or ethynyl.

In one embodiment, —C(O)$R^{3C}$ can be —C(S)$R^{3C}$.

In particular, it has been discovered that a 5'-stabilized phosphate prodrug or derivative of β-D-2'-deoxy-2'-α-fluoro-2'-β-methyl-4'-fluoro-$N^6$-methyl-2,6-diaminopurine nucleotide, as well as β-D-2'-deoxy-2'-α-fluoro-2'-β-methyl-4'-fluoro-$N^6$-dimethyl-2,6-diaminopurine nucleotide, and other β-D-2'-deoxy-2'-α-fluoro-2'-β-C-methyl-4'-fluoro-$N^6$-substituted-2,6-diaminopurine nucleotides, as well as β-D-2'-deoxy-2'-α-fluoro-2'-β-C-substituted-4'-fluoro-$N^6$-substituted-6-amino-2-substituted purine nucleotides as described below, are highly active against HCV.

Interestingly, the metabolism of the β-D-2'-deoxy-2'-α-fluoro-2'-β-methyl-4'-fluoro-$N^6$-methyl-2,6-diaminopurine nucleoside as a phosphoramidate involves the production of a 5'-monophosphate and the subsequent anabolism of the $N^6$-methyl-2,6-diaminopurine base to generate the β-D-2'-deoxy-2'-α-fluoro-2'-β-methyl-4'-fluoro-guanine nucleoside as the 5'-monophosphate. The monophosphate is then further anabolized to the active species; the 5'-triphosphate.

2'-Deoxy-2'-α-fluoro-2'-β-C-substituted-4-fluoro-$N^6$-substituted-2,6-diaminopurine nucleotides can be further substituted at the $N^2$-position by alkylation or acylation which may enhance the lipophilicity, pharmacokinetics or targeting of the nucleotide to the liver.

Despite the volume of antiviral nucleoside literature and patent filings, the 5'-stabilized phosphate derivatives of 2'-deoxy-2'-α-fluoro-2'-β-methyl-4'-fluoro-$N^6$-methyl-2,6-diaminopurine nucleoside, 2'-deoxy-2'-α-fluoro-2'-β-methyl-4'-fluoro-$N^6$-dimethyl-2,6-diaminopurine nucleoside, and other 2'-deoxy-2'-α-fluoro-2'-β-C-substituted-4'-fluoro-$N^6$-substituted-2,6-diaminopurine nucleoside derivatives have not been specifically disclosed.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$ stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. The amino acid of the phosphoramidate or thiophosphoramidate can also be a dehydroamino acid. All of the combinations of these stereoconfigurations are included in the invention described herein.

Accordingly, the present invention includes a compound of Formula I-X, or a pharmaceutically acceptable composition, salt, or prodrug thereof, as described herein:

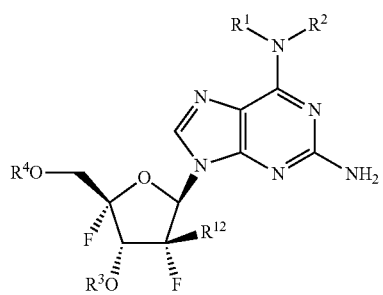

Formula I

In one specific embodiment, the parent nucleoside, i.e., the nucleoside wherein $R^4$ is hydrogen and the 5'-position thus has a hydroxyl group, is not substantially deaminated by adenosine deaminase under conditions that mimic the in vivo environment (e.g., ambient temperature and aqueous physiological pH), for a period of 7 minutes, 10 minutes, 30 minutes, 60 minutes or 120 minutes. Unless otherwise stated, the time period is 30 minutes. In this embodiment, the term "not substantially deaminated" means that the parent compound is not converted to the corresponding guanine derivative, or 6-oxo derivative, in an amount sufficient to provide a therapeutic effect in vivo. It has been reported that the $N^6$-dimethyl-2,6-diaminopurine is not substantially deaminated by adenosine deaminase over a long period (120 minutes), and for that reason it had been considered an inappropriate compound to derivatize as a drug (see for example, WO 2010/091386, page 86). However, it has been discovered that this property is advantageous for treating HCV infections in a host, as the compounds of the present invention are anabolized to a 5-monophosphate and then subsequently anabolized at the 6-position to generate active guanine triphosphate compounds.

Compounds, methods, and compositions are provided for the treatment of a host infected with a HCV virus via administration of an effective amount of the compound of Formula I-VIII or its pharmaceutically acceptable salt.

The compounds and compositions can also be used to treat related conditions such as anti-HCV antibody positive and antigen positive conditions, viral-based chronic liver inflammation, liver cancer resulting from advanced hepatitis C, cirrhosis, chronic or acute hepatitis C, fulminant hepatitis C, chronic persistent hepatitis C and anti-HCV-based fatigue. The compound or formulations that include the compounds can also be used prophylactically to prevent or restrict the progression of clinical illness in individuals who are anti-HCV antibody or antigen positive or who have been exposed to hepatitis C virus.

In another embodiment, compounds of Formula Ia are disclosed:

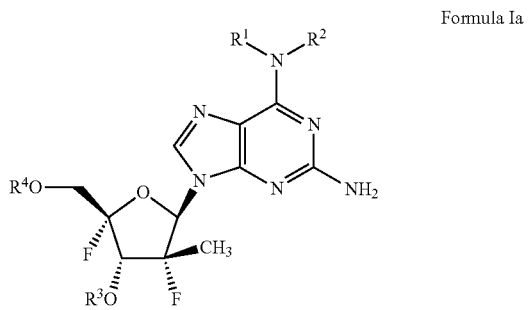

Formula Ia wherein:

$R^1$, $R^2$, $R^3$ and $R^4$ are as defined above.

In one embodiment of Formula Ia, $R^3$ is hydrogen.

In one embodiment of Formula Ia, $R^1$ is methyl and $R^2$ is hydrogen.

In one embodiment of Formula Ia, both $R^1$ and $R^2$ are methyl.

In one embodiment of Formula Ia, $R^1$ is methyl and $R^2$ is cyclopropyl.

In another embodiment, compounds of Formula Ib are disclosed:

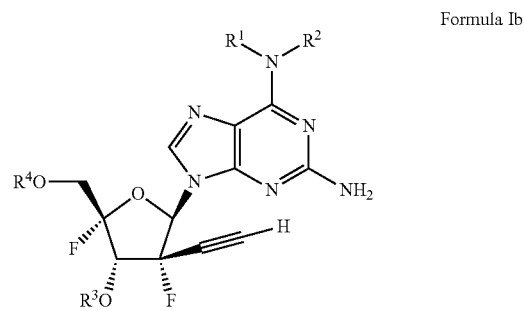

Formula Ib wherein:

$R^1$, $R^2$, $R^3$ and $R^4$ are as defined above.

In one embodiment of Formula Ib, $R^3$ is hydrogen.

In one embodiment of Formula Ib, $R^1$ is methyl and $R^2$ is hydrogen.

In one embodiment of Formula Ib, both $R^1$ and $R^2$ are methyl.

In one embodiment of Formula Ib, $R^1$ is methyl and $R^2$ is cyclopropyl.

In one embodiment, compounds of Formula II are disclosed:

Formula II

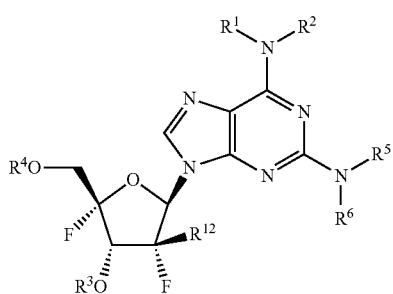

wherein:

$R^5$ is hydrogen, $C_1$-$C_5$alkyl (including methyl, ethyl, n-propyl, iso-propyl, n-butyl, iso-butyl, sec-butyl, tert-butyl and pentyl), or —($C_0$-$C_2$alkyl)($C_3$-$C_6$cycloalkyl);

$R^6$ is $C_1$-$C_5$alkyl (including methyl, ethyl, n-propyl, iso-propyl, n-butyl, iso-butyl, sec-butyl, tert-butyl and pentyl), —($C_0$-$C_2$alkyl)($C_3$-$C_6$cycloalkyl), —($C_{0-6}$alkyl)(aryl), —($C_{0-6}$alkyl)(heteroaryl), —($C_{0-6}$alkyl)(heterocycle) or —C(O)$R^{3C}$;

$R^1$, $R^2$, $R^3$, $R^4$ and $R^{12}$ are as defined above.

In another embodiment, compounds of Formula IIa are disclosed:

Formula IIa

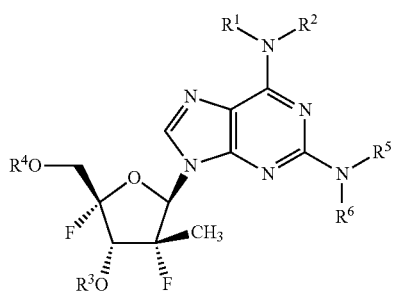

wherein:

$R^1$, $R^2$, $R^3$, $R^4$, $R^5$ and $R^6$ are as defined above.

In another embodiment, compounds of Formula IIb are disclosed:

Formula IIb

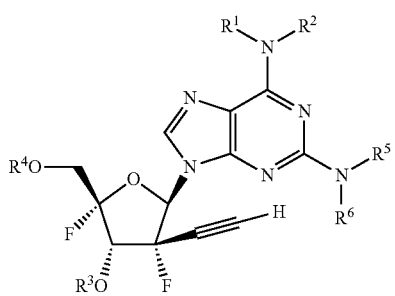

wherein:

$R^1$, $R^2$, $R^3$, $R^4$, $R^5$ and $R^6$ are as defined above.

In one embodiment, compounds of Formula III are disclosed:

Formula III

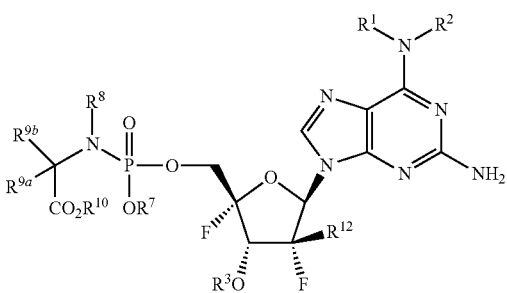

wherein the variables $R^1$, $R^2$, $R^3$, $R^7$, $R^8$, $R^{9a}$, $R^{9b}$, $R^{10}$ and $R^{12}$ are described herein.

In one embodiment, compounds of Formula IV are disclosed:

Formula IV

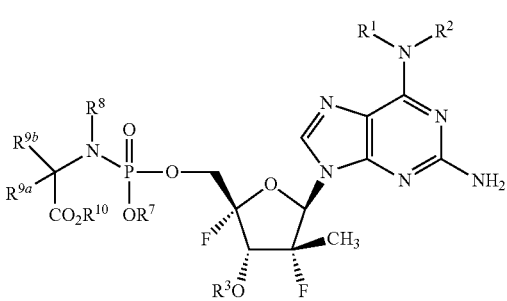

wherein the variables $R^1$, $R^2$, $R^3$, $R^7$, $R^8$, $R^{9a}$, $R^{9b}$ and $R^{10}$ are described herein.

In one embodiment, compounds of Formula V are disclosed:

Formula V

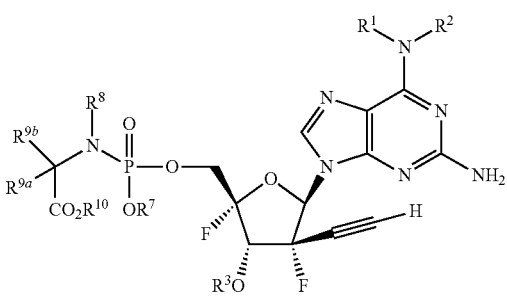

wherein the variables $R^1$, $R^2$, $R^3$, $R^7$, $R^8$, $R^{9a}$, $R^{9b}$ and $R^{10}$ are described herein.

In one embodiment, the compound is according to Formula VI:

Formula VI

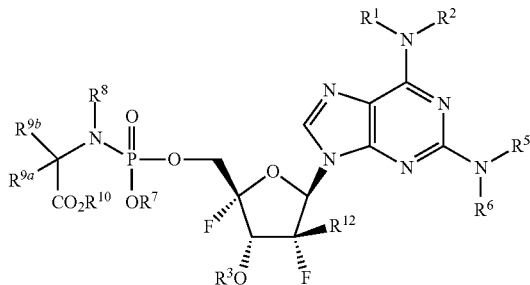

wherein:

$R^1$, $R^2$, $R^3$, $R^5$, $R^6$, $R^7$, $R^8$, $R^{9a}$, $R^{9b}$, $R^{10}$, and $R^{12}$ are as defined above.

In one embodiment, compounds of Formula VII are disclosed:

Formula VII

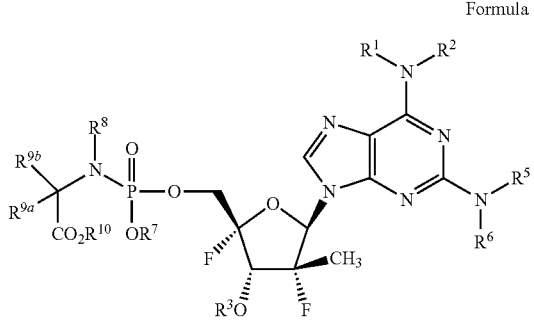

wherein the variables $R^1$, $R^2$, $R^3$, $R^5$, $R^6$, $R^7$, $R^8$, $R^{9a}$, $R^{9b}$ and $R^{10}$ are described herein.

In one embodiment, compounds of Formula VIII are disclosed:

Formula VIII

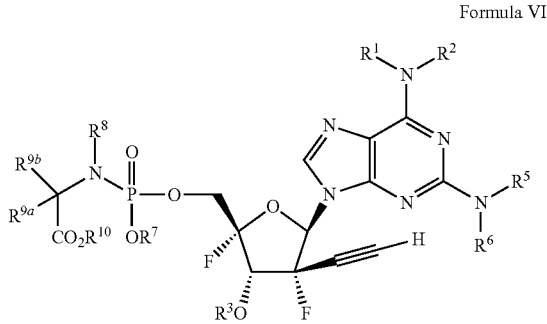

wherein the variables $R^1$, $R^2$, $R^3$, $R^5$, $R^6$, $R^7$, $R^8$, $R^{9a}$, $R^{9b}$ and $R^{10}$ are described herein.

In one embodiment, compounds of Formula IX are disclosed:

Formula IX

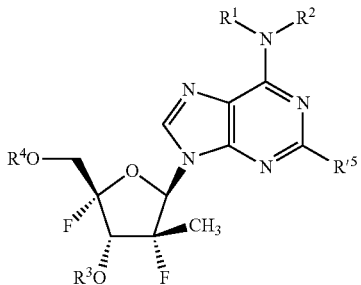

wherein the variables $R^1$, $R^2$, $R^3$, $R^4$ are described herein and $R'^5$ is Cl, Br, F, $N_3$, —NHOCH3, —ONHC(═O)OCH3, CN, $CONH_2$, $SO_2NH_2$ and $CF_3$, or a pharmaceutically acceptable salt thereof.

In one embodiment, compounds of Formula X are disclosed:

Formula X

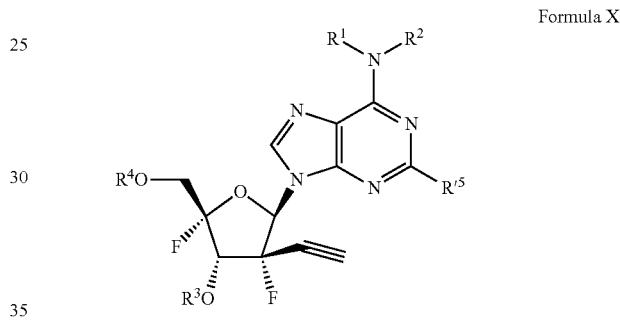

wherein the variables $R^1$, $R^2$, $R^3$, $R^4$ are described herein and $R'^5$ is Cl, Br, F, $N_3$, —NHOCH3, —ONHC(═O)OCH3, CN, $CONH_2$, $SO_2NH_2$ and $CF_3$, or a pharmaceutically acceptable salt thereof.

The phosphorus in any of the Formulas above may be chiral and thus can be provided as an R or S enantiomer or mixture thereof, including a racemic mixture.

In one embodiment, compounds, methods, and compositions are provided for the treatment of a host infected with or exposed to hepatitis C virus described herein. The compounds of the invention can be administered in an effective amount alone or in combination with another anti-HCV drug, to treat the infected host. In certain embodiments, it is useful to administer a combination of drugs that modulates the same or a different pathway or inhibits a different target in the virus. As the disclosed β-D-2'-deoxy-2'-α-fluoro-2'-β-C-substituted-4'-fluoro-$N^6$-substituted-2,6-diaminopurine nucleotides and other described analogs are NS5B polymerase inhibitors, it may be useful to administer the compound to a host in combination with with a protease inhibitor, such as an NS3/4A protease inhibitor (for example, telaprevir (Incivek®) boceprevir (Victrelis™) simeprevir (Olysio™), or paritaprevir, or an NS5A inhibitor (for example, Ombitasvir). The compounds of the invention can also be administered in combination with a structurally different NS5B polymerase inhibitor such as another compound described herein or below, including Gilead's Sovaldi®. The compounds of the invention can also be administered in combination with interferon alfa-2a, which may be pegylated or otherwise modified, and/or ribavirin.

The β-D-2'-deoxy-2'-α-fluoro-2-β-C-substituted-4'-fluoro-N⁶-substituted-2,6-diaminopurine nucleotides and β-D-2'-deoxy-2'-α-fluoro-2'-β-C-substituted-4'-fluoro-N², N⁶-disubstituted-2,6-diaminopurine nucleotides and β-D-2'-deoxy-2' α-fluoro-2'-β-C-substituted-4'-fluoro-2-substituted N⁶-substituted-aminopurine nucleotides of the invention are typically administered orally, for example in pill or tablet form, but may be administered via another route which the attending physician considers appropriate, including via intravenous, transdermal, subcutaneous, topical, parenteral, or other suitable route.

DETAILED DESCRIPTION OF THE INVENTION

The present disclosure includes a compound, method, and composition for the treatment of HCV infections in or exposure to humans and other host animals that includes the administration of an effective amount of a compound of Formula I-X as described herein or a pharmaceutically acceptable salt or prodrug thereof, optionally in a pharmaceutically acceptable carrier. The compounds of this invention either possess antiviral activity, or are metabolized to a compound that exhibits such activity.

The compounds and compositions can also be used to treat conditions related to or occurring as a result of a HCV viral exposure. For example, the active compound can be used to treat HCV antibody positive and HCV antigen positive conditions viral-based chronic liver inflammation, liver cancer resulting from advanced hepatitis C, cirrhosis, acute hepatitis C, fulminant hepatitis C, chronic persistent hepatitis C, and anti-HCV-based fatigue. In one embodiment, the compounds or formulations that include the compounds can also be used prophylactically to prevent or retard the progression of clinical illness in individuals who are HCV antibody or HCV antigen positive or who have been exposed to hepatitis C virus.

In particular, it has been discovered that a 5'-stabilized phosphate prodrug or derivative of β-D-2'-deoxy-2'-α-fluoro-2'-β-methyl-4'-fluoro-N⁶-methyl-2,6-diaminopurine nucleotide, as well as β-D-2'-deoxy-2'-α-fluoro-2'-β-methyl-4'-fluoro-N⁶-dimethyl-2,6-diaminopurine nucleotide, and other β-D-2'-deoxy-2'-α-fluoro-2'-β-methyl-4'-fluoro-N⁶-substituted-2,6-diaminopurine nucleotides, β-D-2'-deoxy-2'-α-fluoro-2'-β-methyl-4'-fluoro-N²,N⁶-disubstituted-2,6-diaminopurine nucleotides and β-D-2'-deoxy-2'-α-fluoro-2'-β-methyl-4'-fluoro-2-substituted-N⁶-substituted-aminopurine nucleotides, as described below, are highly active against HCV.

Despite the volume of antiviral nucleoside literature and patent filings, the 5'-stabilized phosphate derivative of β-D-2'-deoxy-2'-α-fluoro-2'-β-methyl-4'-fluoro-N⁶-methyl-2,6-diaminopurine nucleotide, as well as β-D-2'-deoxy-2'-α-fluoro-2'-β-methyl-4'-fluoro-N⁶-dimethyl-2,6-diaminopurine nucleotide, and other β-D-2'-deoxy-2'-α-fluoro-2'-β-methyl-4'-fluoro-N⁶-substituted-2,6-diaminopurine nucleotides and β-D-2'-deoxy-2'-β-methyl-4'-fluoro-2-substituted-N⁶-substituted-aminopurine nucleotides have not been specifically disclosed.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the R⁴ stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. All of the combinations of these stereo configurations are included in the invention described herein.

The present invention includes the following features:
(a) a compound of Formula I-X as described herein, and pharmaceutically acceptable salts and prodrugs thereof;
(b) Formulas I-X as described herein, and pharmaceutically acceptable salts and prodrugs thereof for use in the treatment or prophylaxis of a hepatitis C virus infection;
(c) use of Formulas I-X, and pharmaceutically acceptable salts and prodrugs thereof in the manufacture of a medicament for treatment of a hepatitis C virus infection;
(d) a method for manufacturing a medicament intended for the therapeutic use for treating a hepatitis C virus infection, characterized in that a compound of Formulas I-X as described herein is used in the manufacture;
(e) a pharmaceutical formulation comprising an effective host-treating amount of the compound of Formulas I-X or a pharmaceutically acceptable salt or prodrug thereof together with a pharmaceutically acceptable carrier or diluent;
(f) Formulas I-X as described herein substantially in the absence of stereoisomers of the described compound, or substantially isolated from other chemical entities; and,
(g) processes for the preparation of therapeutic products that contain an effective amount of a compound of Formulas I-X, as described herein.

I. β-D-2'-Deoxy-2'-α-Fluoro-2'-β-C-substituted-4'-Fluoro-N⁶-Substituted-2,6-Diaminopurine Nucleotides, β-D-2'-Deoxy-2'-α-Fluoro-2'-β-C-substituted-4'-Fluoro-N²,N⁶-Disubstituted-2,6-Diaminopurine Nucleotides and β-D-2'-deoxy-2'-α-fluoro-2'-β-methyl-4'-fluoro-2-substituted-N⁶-substituted-aminopurine nucleotides of the Invention The active compounds of the invention are those depicted, for example, in Formula I, which can be provided in a pharmaceutically acceptable composition, salt or prodrug thereof:

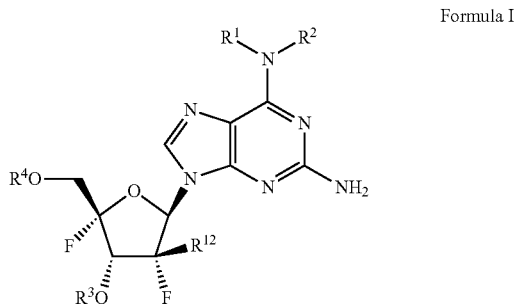

Formula I wherein:
R¹ is C₁-C₅alkyl (including methyl, ethyl, n-propyl, iso-propyl, n-butyl, iso-butyl, sec-butyl, tert-butyl and pentyl) or —(C₀-C₂alkyl)(C₃-C₆cycloalkyl);
R² is hydrogen, C₁-C₅alkyl (including methyl, ethyl, n-propyl, iso-propyl, n-butyl, iso-butyl, sec-butyl, tert-butyl and pentyl), CHF₂, CH₂F, CF₃, —(C₀-C₂alkyl)(C₃-

$C_6$cycloalkyl), —C(O)$R^{3C}$, —($C_0$-$C_2$alkyl)(aryl), —($C_0$-$C_2$alkyl)(heterocycle), —($C_0$-$C_2$alkyl)(heteroaryl); or $R^1$ and $R^2$ together with the nitrogen to which they are bonded can form a heterocycle;

$R^3$ is hydrogen,

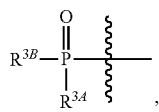

diphosphate, triphosphate, an optionally substituted carbonyl linked amino acid, or —C(O)$R^{3C}$;

$R^{3A}$ can be selected from O⁻, OH, an —O-optionally substituted aryl, an —O-optionally substituted heteroaryl, or an optionally substituted heterocyclyl;

$R^{3B}$ can be selected from O⁻, OH, an optionally substituted N-linked amino acid or an optionally substituted N-linked amino acid ester;

$R^3$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), —O—($C_0$-$C_2$)(hetero aryl), —S-alkyl, —S-alkenyl, —S-alkynyl, —S—($C_0$-$C_2$)(cycloalkyl), —S—($C_0$-$C_2$)(heterocyclo), —S—($C_0$-$C_2$)(aryl), or —S—($C_0$-$C_2$)(heteroaryl) each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug;

$R^{12}$ is $CH_3$, $CH_2F$, $CHF_2$, $CF_3$, or ethynyl.

A stabilized phosphate prodrug is any moiety that can deliver a mono, di, or triphosphate.

In another embodiment, compounds of Formula Ia are disclosed:

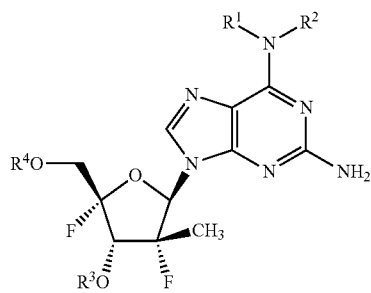

Formula Ia wherein:
$R^1$, $R^2$, $R^3$ and $R^4$ are as defined above.

In another embodiment, compounds of Formula Ib are disclosed:

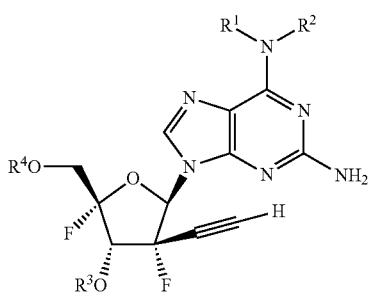

Formula Ib wherein:
$R^1$, $R^2$, $R^3$ and $R^4$ are as defined above.

In one embodiment, compounds of Formula II are disclosed:

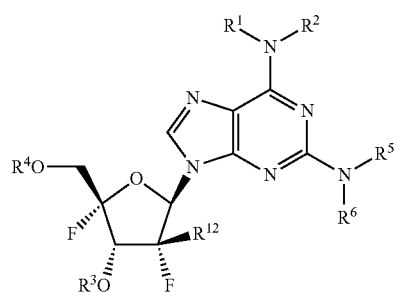

Formula II wherein:
$R^5$ is hydrogen, $C_1$-$C_5$alkyl (including methyl, ethyl, n-propyl, iso-propyl, n-butyl, iso-butyl, sec-butyl, tert-butyl and pentyl), or —($C_0$-$C_2$alkyl)($C_3$-$C_6$cycloalkyl);

$R^6$ is $C_1$-$C_5$alkyl (including methyl, ethyl, n-propyl, iso-propyl, n-butyl, iso-butyl, sec-butyl, tert-butyl and pentyl), —($C_0$-$C_2$alkyl)($C_3$-$C_6$cycloalkyl), —($C_{0-6}$alkyl)(aryl), —($C_{0-6}$alkyl)(heteroaryl), —($C_{0-6}$alkyl)(heterocycle) or —C(O)$R^{3C}$;

$R^1$, $R^2$, $R^3$, $R^4$ and $R^{12}$ are as defined above.

In another embodiment, compounds of Formula IIa are disclosed:

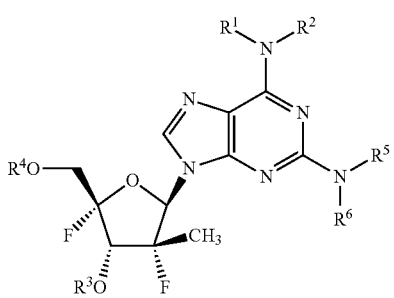

Formula IIa wherein:
$R^1$, $R^2$, $R^3$, $R^4$, $R^5$ and $R^6$ are as defined above.

In another embodiment, compounds of Formula IIb are disclosed:

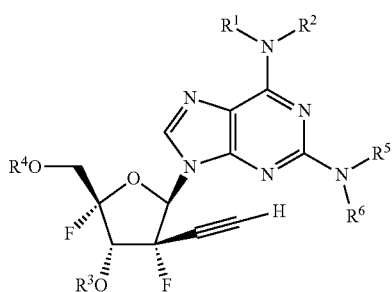

Formula IIb wherein:
$R^1$, $R^2$, $R^3$, $R^4$, $R^5$ and $R^6$ are as defined above.

In a typical embodiment, the compound is a β-D isomer with reference to the corresponding nucleoside (i.e., in the naturally occurring configuration). In an alternative configuration, the compound is provided as a β-L isomer. The compound is typically at least 90% free of the opposite enantiomer, and can be at least 98%, 99% or even 100% free of the opposite enantiomer. Unless described otherwise, the compound is at least 90% free of the opposite enantiomer.

In another embodiment, the compound is according to Formula III:

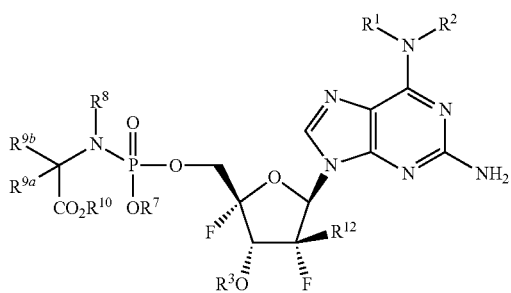

Formula III wherein:
$R^7$ is hydrogen, $C_{1-6}$alkyl; $C_{3-7}$cycloalkyl; heteroaryl, heterocyclic, or aryl, which includes, but is not limited to, phenyl or naphthyl, where phenyl or naphthyl are optionally substituted with $C_{1-6}$alkyl, $C_{2-6}$alkenyl, $C_{2-6}$ alkynyl, $C_{1-6}$alkoxy, F, Cl, Br, I, nitro, cyano, $C_{1-6}$halo alkyl, —N($R^{7'}$)$_2$, $C_{1-6}$acylamino, NHSO$_2$C$_{1-6}$alkyl, —SO$_2$N($R^{7'}$)$_2$, COR$^{7''}$, and —SO$_2$C$_{1-6}$alkyl; ($R^{7'}$ is independently hydrogen or $C_{1-6}$alkyl; $R^{7''}$ is —OR$^{11}$ or —N($R^7$)$_2$);

$R^8$ is hydrogen, $C_{1-6}$alkyl, or $R^{9a}$ or $R^{9b}$ and $R^8$ together are (CH$_2$)$_n$ so as to form a cyclic ring that includes the adjoining N and C atoms; where n is 2 to 4;

$R^{9a}$ and $R^{9b}$ are (i) independently selected from hydrogen, $C_{1-6}$alkyl, cycloalkyl, —(CH$_2$)$_c$(NR$^{9'}$)$_2$, $C_{1-6}$hydroxyalkyl, —CH$_2$SH, —(CH$_2$)$_2$S(O)(Me), —(CH$_2$)$_3$NHC(=NH)NH$_2$, (1H-indol-3-yl)methyl, (1H-imidazol-4-yl)methyl, —(CH$_2$)$_c$COR$^{9'''}$, aryl and aryl(C$_{1-3}$alkyl)-, the aryl groups can be optionally substituted with a group selected from hydroxyl, $C_{1-6}$alkyl, $C_{1-6}$alkoxy, halogen, nitro and cyano; (ii) $R^{9a}$ and $R^{9b}$ both are $C_{1-6}$alkyl; (iii) $R^{9a}$ and $R^{9b}$ together are (CH$_2$)$_r$ so as to form a spiro ring; (iv) $R^{9a}$ is hydrogen and $R^{9b}$ and $R^8$ together are (CH$_2$)$_n$ so as to form a cyclic ring that includes the adjoining N and C atoms (v) $R^{9b}$ is hydrogen and $R^{9a}$ and $R^8$ together are (CH$_2$)$_n$ so as to form a cyclic ring that includes the adjoining N and C atoms, where c is 1 to 6, n is 2 to 4, r is 2 to 5 and where $R^{9'}$ is independently hydrogen or $C_{1-6}$ alkyl and $R^{9'''}$ is —OR$^{11}$ or —N($R^{11'}$)$_2$; (vi) $R^{9a}$ is hydrogen and $R^{9b}$ is hydrogen, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (vii) $R^{9a}$ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{9b}$ is hydrogen;

$R^{10}$ is hydrogen, $C_{1-6}$alkyl optionally substituted with an alkoxy, di(lower alkyl)-amino, or halogen; $C_{1-6}$haloalkyl, (C$_0$-C$_2$)(C$_{3-7}$cycloalkyl), (C$_0$-C$_2$)(heterocycloalkyl), aminoacyl, (C$_0$-C$_2$)(aryl), such as (C$_0$-C$_2$)(phenyl), (C$_0$-C$_2$)(heteroaryl), such as (C$_0$-C$_2$)(pyridinyl), substituted (C$_0$-C$_2$) (aryl), or substituted (C$_0$-C$_2$)(heteroaryl);

$R^{11}$ is an optionally substituted $C_{1-6}$alkyl, an optionally substituted cycloalkyl; an optionally substituted $C_{2-6}$alkynyl, an optionally substituted $C_{2-6}$alkenyl, or optionally substituted acyl, which includes but is not limited to C(O) (C$_{1-6}$ alkyl); and $R^1$, $R^2$, $R^3$ and $R^{12}$ are as defined above.

In one embodiment, compounds of Formula IV are disclosed:

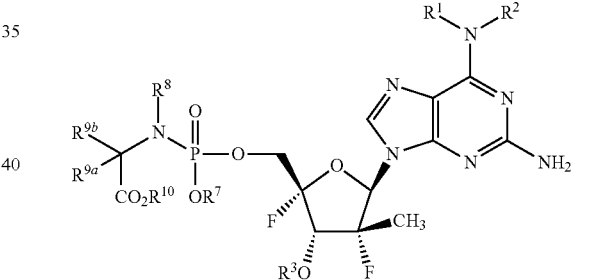

Formula IV wherein the variables $R^1$, $R^2$, $R^3$, $R^7$, $R^8$, $R^{9a}$, $R^{9b}$ and $R^{10}$ are described herein.

In one embodiment, compounds of Formula V are disclosed:

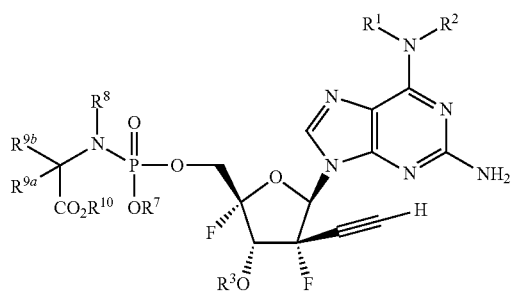

Formula V wherein the variables $R^1$, $R^2$, $R^3$, $R^7$, $R^8$, $R^{9a}$, $R^{9b}$ and $R^{10}$ are described herein.

In one embodiment, the compound is according to Formula VI:

Formula VI

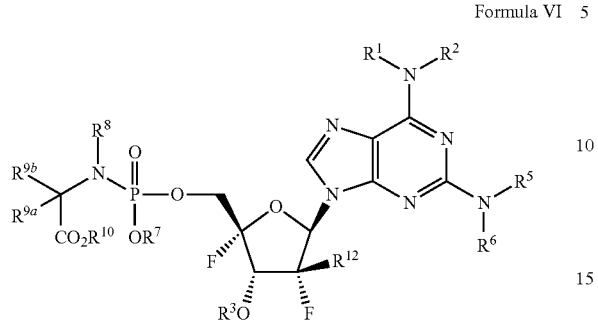

wherein:

$R^1$, $R^2$, $R^3$, $R^5$, $R^6$, $R^7$, $R^8$, $R^{9a}$, $R^{9b}$, $R^{10}$ and $R^{12}$ are as defined above.

In one embodiment, compounds of Formula VII are disclosed:

Formula VII

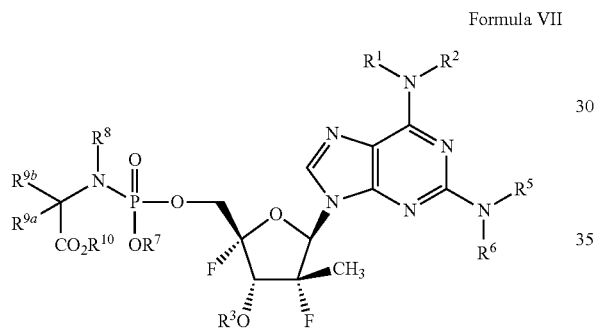

wherein the variables $R^1$, $R^2$, $R^3$, $R^5$, $R^6$, $R^7$, $R^8$, $R^{9a}$, $R^{9b}$ and $R^{10}$ are described herein.

In one embodiment, compounds of Formula VIII are disclosed:

Formula VIII

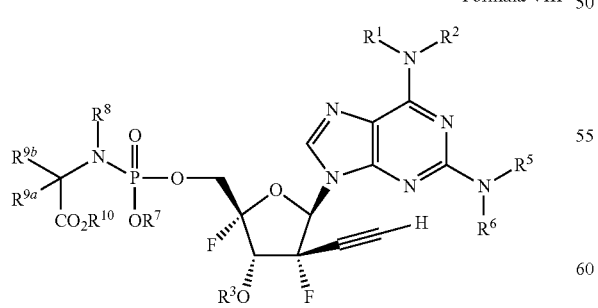

wherein the variables $R^1$, $R^2$, $R^3$, $R^5$, $R^6$, $R^7$, $R^8$, $R^{9a}$, $R^{9b}$ and $R^{10}$ are described herein.

In one embodiment, compounds of Formula IX are disclosed:

Formula IX

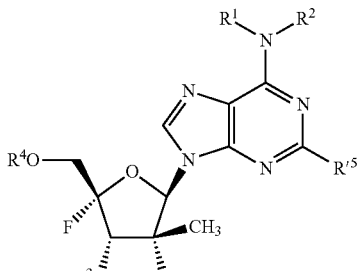

wherein the variables $R^1$, $R^2$, $R^3$, $R^4$ are described herein and $R'^5$ is Cl, Br, F, $N_3$, —NHOCH3, —ONHC(=O)OCH3, CN, $CONH_2$, $SO_2NH_2$ and $CF_3$, or a pharmaceutically acceptable salt thereof.

In one embodiment, compounds of Formula X are disclosed:

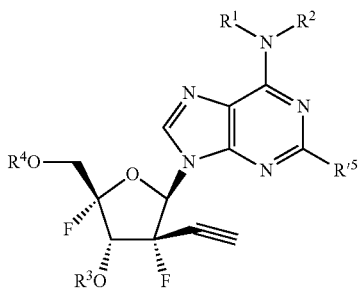

wherein the variables $R^1$, $R^2$, $R^3$, $R^4$ are described herein and $R'^5$ is Cl, Br, F, $N_3$, —NHOCH3, —ONHC(=O)OCH3, CN, $CONH_2$, $SO_2NH_2$ and $CF_3$, or a pharmaceutically acceptable salt thereof.

In an alternative embodiment, compounds, methods, and compositions are provided for the treatment of a host infected with or exposed to hepatitis C virus.

Metabolism of β-D-2'-deoxy-2'-α-fluoro-2'-β-C-substituted-4'-fluoro-N⁶-substituted-2,6-diaminopurine Nucleotides The metabolism of the β-D-2'-deoxy-2'-α-fluoro-2'-β-methyl-4'-fluoro-N⁶-methyl-2,6-diaminopurine nucleoside phosphoramidate involves the production of a 5'-monophosphate and the subsequent anabolism of the N⁶-methyl-2,6-diaminopurine base to generate the β-D-2'-deoxy-2'-α-fluoro-2'-β-methyl-4'-fluoro-guanine nucleoside as the 5'-monophosphate. The monophosphate is then further anabolized to the active species; the 5'-triphosphate. The metabolic pathway for the β-D-2'-deoxy-2'-α-fluoro-2'-β-methyl-4'-fluoro-N⁶-methyl-2,6-diaminopurine nucleoside phosphoramidate is illustrated in Scheme 1 below.

Scheme 1

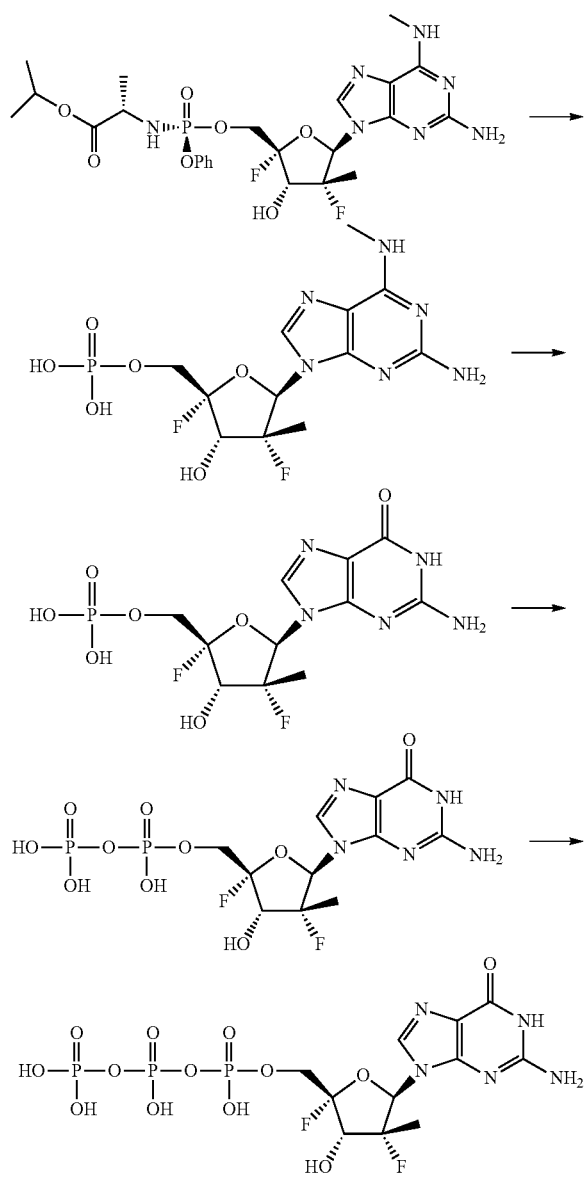

Stabilized Phosphate Prodrugs

Stabilized phosphate prodrugs are moieties that can deliver a mono, di, or triphosphate in vivo. For example, McGuigan has disclosed phosphoramidates in U.S. Pat. Nos. 8,933,053; 8,759,318; 8,658,616; 8,263,575; 8,119,779; 7,951,787 and 7,115,590. Alios has disclosed thiophosphoramidates in U.S. Pat. Nos. 8,895,723 and 8,871,737. Alios has also disclosed cyclic nucleotides in U.S. Pat. No. 8,772,474. Idenix has disclosed cyclic phosphoramidates and phosphoramidate/SATE derivatives in WO 2013/177219. Idenix has also disclosed substituted carbonyloxymethyl-phosphoramidate compounds in WO 2013/039920. Hostetler has disclosed lipid phosphate prodrugs, see, for example, U.S. Pat. No. 7,517,858. Hostetler has also disclosed lipid conjugates of phosphonate prodrugs, see, for example, U.S. Pat. Nos. 8,889,658; 8,846,643; 8,710,030; 8,309,565; 8,008,308; and 7,790,703. Emory University has disclosed nucleotide sphingoid and lipid derivatives in WO 2014/124430. RFS Pharma has disclosed purine nucleoside monophosphate prodrugs in WO 2010/091386. HepDirect™ technology is disclosed in the article "Design, Synthesis, and Characterization of a Series of Cytochrome P(450) 3A-Activated Prodrugs (HepDirect Prodrugs) Useful for Targeting Phosph(on)ate-Based Drugs to the Liver," (J. Am. Chem. Soc. 126, 5154-5163 (2004). Additional phosphate prodrugs include, but are not limited to phosphate esters, 3',5'-cyclic phosphates including CycloSAL, SATE derivatives (S-acyl-2thioesters) and DTE (dithiodiethyl) prodrugs. For literature reviews that disclose non-limiting examples see: A. Ray and K. Hostetler, "Application of kinase bypass strategies to nucleoside antivirals," Antiviral Research (2011) 277-291; M. Sofia, "Nucleotide prodrugs for HCV therapy," Antiviral Chemistry and Chemotherapy 2011; 22-23-49; and S. Peyrottes et al., "SATE Pronucleotide Approaches: An Overview," Mini Reviews in Medicinal Chemistry 2004, 4, 395. In one embodiment, a 5'-prodrug described in any of these patent filings or literature can be used in the $R^4$ position of the presented compounds.

EMBODIMENTS

In particular embodiments:
(i) in Formula Ia, $R^1$ is methyl, $R^2$ is hydrogen, $R^3$ is hydrogen, $R^4$ is a stabilized phosphate prodrug;
(ii) in Formula Ia, $R^1$ is methyl, $R^2$ is hydrogen, $R^3$ is hydrogen, and $R^4$ is a stabilized thiophosphate prodrug;
(iii) in Formula Ia, $R^1$ is methyl, $R^2$ is hydrogen, $R^3$ is hydrogen, and $R^4$ is a phosphoramidate;
(iv) in Formula Ia, $R^1$ is methyl, $R^2$ is hydrogen, $R^3$ is hydrogen, and $R^4$ is a thiophosphoramidate:
(v) in Formula Ia, $R^1$ is methyl, $R^2$ is hydrogen, $R^3$ is hydrogen, and $R^4$ is a monophosphate;
(vi) in Formula Ia, $R^1$ is methyl, $R^2$ is hydrogen, $R^3$ is hydrogen, and $R^4$ is a diphosphate;
(vii) in Formula Ia, $R^1$ is methyl, $R^2$ is hydrogen, $R^3$ is hydrogen, and $R^4$ is a triphosphate;
(viii) in Formula Ia, $R^1$ is methyl, $R^2$ is methyl, $R^3$ is hydrogen, $R^4$ is a stabilized phosphate prodrug;
(ix) in Formula Ia, $R^1$ is methyl, $R^2$ is methyl, $R^3$ is hydrogen, and $R^4$ is a stabilized thiophosphate prodrug;
(x) in Formula Ia, $R^1$ is methyl, $R^2$ is methyl, $R^3$ is hydrogen, and $R^4$ is a phosphoramidate;
(xi) in Formula Ia, $R^1$ is methyl, $R^2$ is methyl, $R^3$ is hydrogen, and $R^4$ is a thiophosphoramidate:
(xii) in Formula Ia, $R^1$ is methyl, $R^2$ is methyl, $R^3$ is hydrogen, and $R^4$ is a monophosphate;
(xiii) in Formula Ia, $R^1$ is methyl, $R^2$ is methyl, $R^3$ is hydrogen, and $R^4$ is a diphosphate;
(xiv) in Formula Ia, $R^1$ is methyl, $R^2$ is methyl, $R^3$ is hydrogen, and $R^4$ is a triphosphate;
(xv) in Formula Ia, $R^1$ is methyl, $R^2$ is cyclopropyl, $R^3$ is hydrogen, $R^4$ is a stabilized phosphate prodrug;
(xvi) in Formula Ia, $R^1$ is methyl, $R^2$ is cyclopropyl, $R^3$ is hydrogen, and $R^4$ is a stabilized thiophosphate prodrug;
(xvii) in Formula Ia, $R^1$ is methyl, $R^2$ is cyclopropyl, $R^3$ is hydrogen, and $R^4$ is a phosphoramidate;
(xviii) in Formula Ia, $R^1$ is methyl, $R^2$ is cyclopropyl, $R^3$ is hydrogen, and $R^4$ is a thiophosphoramidate:
(xix) in Formula Ia, $R^1$ is methyl, $R^2$ is cyclopropyl, $R^3$ is hydrogen, and $R^4$ is a monophosphate;
(xx) in Formula Ia, $R^1$ is methyl, $R^2$ is cyclopropyl, $R^3$ is methyl, and $R^4$ is a diphosphate;
(xxi) in Formula Ia, $R^1$ is methyl, $R^2$ is cyclopropyl, $R^3$ is hydrogen, and $R^4$ is a triphosphate;
(xxii) in Formula Ia, $R^1$ is ethyl, $R^2$ is hydrogen, $R^3$ is hydrogen, $R^4$ is a stabilized phosphate prodrug;

(xxiii) in Formula Ia, $R^1$ is ethyl, $R^2$ is hydrogen, $R^3$ is hydrogen, and $R^4$ is a stabilized thiophosphate prodrug;
(xxiv) in Formula Ia, $R^1$ is ethyl, $R^2$ is hydrogen, $R^3$ is hydrogen, and $R^4$ is a phosphoramidate;
(xxv) in Formula Ia, $R^1$ is ethyl, $R^2$ is hydrogen, $R^3$ is hydrogen, and $R^4$ is a thiophosphoramidate:
(xxvi) in Formula Ia, $R^1$ is ethyl, $R^2$ is hydrogen, $R^3$ is hydrogen, and $R^4$ is a monophosphate;
(xxvii) in Formula Ia, $R^1$ is ethyl, $R^2$ is hydrogen, $R^3$ is hydrogen, and $R^4$ is a diphosphate;
(xxviii) in Formula Ia, $R^1$ is ethyl, $R^2$ is hydrogen, $R^3$ is hydrogen, and $R^4$ is a triphosphate;
(xxix) in Formula Ia, $R^1$ is propyl, $R^2$ is hydrogen, $R^3$ is hydrogen, $R^4$ is a stabilized phosphate prodrug;
(xxx) in Formula Ia, $R^1$ is propyl, $R^2$ is hydrogen, $R^3$ is hydrogen, and $R^4$ is a stabilized thiophosphate prodrug;
(xxxi) in Formula Ia, $R^1$ is propyl, $R^2$ is hydrogen, $R^3$ is hydrogen, and $R^4$ is a phosphoramidate;
(xxxii) in Formula Ia, $R^1$ is propyl, $R^2$ is hydrogen, $R^3$ is hydrogen, and $R^4$ is a thiophosphoramidate:
(xxxiii) in Formula Ia, $R^1$ is propyl, $R^2$ is hydrogen, $R^3$ is hydrogen, and $R^4$ is a monophosphate;
(xxxiv) in Formula Ia, $R^1$ is propyl, $R^2$ is hydrogen, $R^3$ is hydrogen, and $R^4$ is a diphosphate;
(xxxv) in Formula Ia, $R^1$ is propyl, $R^2$ is hydrogen, $R^3$ is hydrogen, and $R^4$ is a triphosphate;
(xxxvi) in Formula Ia, $R^1$ is isopropyl, $R^2$ is hydrogen, $R^3$ is hydrogen, $R^4$ is a stabilized phosphate prodrug;
(xxxvii) in Formula Ia, $R^1$ is isopropyl, $R^2$ is hydrogen, $R^3$ is hydrogen, and $R^4$ is a stabilized thiophosphate prodrug;
(xxxviii) in Formula Ia, $R^1$ is isopropyl, $R^2$ is hydrogen, $R^3$ is hydrogen, and $R^4$ is a phosphoramidate;
(xxxix) in Formula Ia, $R^1$ is isopropyl, $R^2$ is hydrogen, $R^3$ is hydrogen, and $R^4$ is a thiophosphoramidate:
(xl) in Formula Ia, $R^1$ is isopropyl, $R^2$ is hydrogen, $R^3$ is hydrogen, and $R^4$ is a monophosphate;
(xli) in Formula Ia, $R^1$ is isopropyl, $R^2$ is hydrogen, $R^3$ is hydrogen, and $R^4$ is a diphosphate;
(xlii) in Formula Ia, $R^1$ is isopropyl, $R^2$ is hydrogen, $R^3$ is hydrogen, and $R^4$ is a triphosphate;
(xliii) in Formula Ia, $R^1$ is ethyl, $R^2$ is ethyl, $R^3$ is hydrogen, $R^4$ is a stabilized phosphate prodrug;
(xliv) in Formula Ia, $R^1$ is ethyl, $R^2$ is ethyl, $R^3$ is hydrogen, and $R^4$ is a stabilized thiophosphate prodrug;
(xlv) in Formula Ia, $R^1$ is ethyl, $R^2$ is ethyl, $R^3$ is hydrogen, and $R^4$ is a phosphoramidate;
(xlvi) in Formula Ia, $R^1$ is ethyl, $R^2$ is ethyl, $R^3$ is hydrogen, and $R^4$ is a thiophosphoramidate:
(xlvii) in Formula Ia, $R^1$ is ethyl, $R^2$ is ethyl, $R^3$ is hydrogen, and $R^4$ is a monophosphate;
(xlviii) in Formula Ia, $R^1$ is ethyl, $R^2$ is ethyl, $R^3$ is hydrogen, and $R^4$ is a diphosphate;
(xlix) in Formula Ia, $R^1$ is ethyl, $R^2$ is ethyl, $R^3$ is hydrogen, and $R^4$ is a triphosphate;
(l) in Formula Ia, $R^1$ is methyl, $R^2$ is propyl, $R^3$ is hydrogen, $R^4$ is a stabilized phosphate prodrug;
(li) in Formula Ia, $R^1$ is methyl, $R^2$ is propyl, $R^3$ is hydrogen, and $R^4$ is a stabilized thiophosphate prodrug;
(lii) in Formula Ia, $R^1$ is methyl, $R^2$ is propyl, $R^3$ is hydrogen, and $R^4$ is a phosphoramidate;
(liii) in Formula Ia, $R^1$ is methyl, $R^2$ is propyl, $R^3$ is hydrogen, and $R^4$ is a thiophosphoramidate:
(liv) in Formula Ia, $R^1$ is methyl, $R^2$ is propyl, $R^3$ is hydrogen, and $R^4$ is a monophosphate;
(lv) in Formula Ia, $R^1$ is methyl, $R^2$ is propyl, $R^3$ is hydrogen, and $R^4$ is a diphosphate;
(lvi) in Formula Ia, $R^1$ is methyl, $R^2$ is propyl, $R^3$ is hydrogen, and $R^4$ is a triphosphate;
(lvii) in Formula Ia, $R^1$ and $R^2$ together with the nitrogen to which they are bonded to form a 5-membered heterocyclic ring, $R^3$ is hydrogen, $R^4$ is a stabilized phosphate prodrug;
(lviii) in Formula Ia, $R^1$ and $R^2$ together with the nitrogen to which they are bonded to form a 5-membered heterocyclic ring, $R^3$ is hydrogen, and $R^4$ is a stabilized thiophosphate prodrug;
(lix) in Formula Ia, $R^1$ and $R^2$ together with the nitrogen to which they are bonded to form a 5-membered heterocyclic ring, $R^3$ is hydrogen, and $R^4$ is a phosphoramidate;
(lx) in Formula Ia, $R^1$ and $R^2$ together with the nitrogen to which they are bonded to form a 5-membered heterocyclic ring, $R^3$ is hydrogen, and $R^4$ is a thiophosphoramidate:
(lxi) in Formula Ia, $R^1$ and $R^2$ together with the nitrogen to which they are bonded to form a 5-membered heterocyclic ring, $R^3$ is hydrogen, and $R^4$ is a monophosphate;
(lxii) in Formula Ia, $R^1$ and $R^2$ together with the nitrogen to which they are bonded to form a 5-membered heterocyclic ring, $R^3$ is hydrogen, and $R^4$ is a diphosphate;
(lxiii) in Formula Ia, $R^1$ and $R^2$ together with the nitrogen to which they are bonded to form a 5-membered heterocyclic ring, $R^3$ is hydrogen, and $R^4$ is a triphosphate;
(lxiv) in Formula Ia, $R^1$ is cyclopentyl, $R^2$ is hydrogen, $R^3$ is hydrogen, $R^4$ is a stabilized phosphate prodrug;
(lxv) in Formula Ia, $R^1$ is cyclopentyl, $R^2$ is hydrogen, $R^3$ is hydrogen, and $R^4$ is a stabilized thiophosphate prodrug;
(lxvi) in Formula Ia, $R^1$ is cyclopentyl, $R^2$ is hydrogen, $R^3$ is hydrogen, and $R^4$ is a phosphoramidate;
(lxvii) in Formula Ia, $R^1$ is cyclopentyl, $R^2$ is hydrogen, $R^3$ is hydrogen, and $R^4$ is a thiophosphoramidate:
(lxviii) in Formula Ia, $R^1$ is cyclopentyl, $R^2$ is hydrogen, $R^3$ is hydrogen, and $R^4$ is a monophosphate;
(lxix) in Formula Ia, $R^1$ is cyclopentyl, $R^2$ is hydrogen, $R^3$ is hydrogen, and $R^4$ is a diphosphate;
(lxx) in Formula Ia, $R^1$ is cyclopentyl, $R^2$ is hydrogen, $R^3$ is hydrogen, and $R^4$ is a triphosphate;
(lxxi) in Formula Ia, $R^1$ is cyclopropyl, $R^2$ is cyclopropyl, $R^3$ is hydrogen, $R^4$ is a stabilized phosphate prodrug;
(lxxii) in Formula Ia, $R^1$ is cyclopropyl, $R^2$ is cyclopropyl, $R^3$ is hydrogen, and $R^4$ is a stabilized thiophosphate prodrug;
(lxxiii) in Formula Ia, $R^1$ is cyclopropyl, $R^2$ is cyclopropyl, $R^3$ is hydrogen, and $R^4$ is a phosphoramidate;
(lxxiv) in Formula Ia, $R^1$ is cyclopropyl, $R^2$ is cyclopropyl, $R^3$ is hydrogen, and $R^4$ is a thiophosphoramidate:
(lxxv) in Formula Ia, $R^1$ is cyclopropyl, $R^2$ is cyclopropyl, $R^3$ is hydrogen, and $R^4$ is a monophosphate;
(lxxvi) in Formula Ia, $R^1$ is cyclopropyl, $R^2$ is cyclopropyl, $R^3$ is hydrogen, and $R^4$ is a diphosphate;
(lxxvii) in Formula Ia, $R^1$ is cyclopropyl, $R^2$ is cyclopropyl, $R^3$ is hydrogen, and $R^4$ is a triphosphate;
(lxxviii) in Formula Ia, $R^1$ is methyl, $R^2$ is ethyl, $R^3$ is hydrogen, $R^4$ is a stabilized phosphate prodrug;
(lxxix) in Formula Ia, $R^1$ is methyl, $R^2$ is ethyl, $R^3$ is hydrogen, and $R^4$ is a stabilized thiophosphate prodrug;
(lxxx) in Formula Ia, $R^1$ is methyl, $R^2$ is ethyl, $R^3$ is hydrogen, and $R^4$ is a phosphoramidate;

(lxxxi) in Formula Ia, $R^1$ is methyl, $R^2$ is ethyl, $R^3$ is hydrogen, and $R^4$ is a thiophosphoramidate:
(lxxxii) in Formula Ia, $R^1$ is methyl, $R^2$ is ethyl, $R^3$ is hydrogen, and $R^4$ is a monophosphate;
(lxxxiii) in Formula Ia, $R^1$ is methyl, $R^2$ is ethyl, $R^3$ is hydrogen, and $R^4$ is a diphosphate;
(lxxxiv) in Formula Ia, $R^1$ is methyl, $R^2$ is ethyl, $R^3$ is hydrogen, and $R^4$ is a triphosphate;
(lxxxv) in Formula Ia, $R^1$ is cyclobutyl, $R^2$ is hydrogen, $R^3$ is hydrogen, $R^4$ is a stabilized phosphate prodrug;
(lxxxvi) in Formula Ia, $R^1$ is cyclobutyl, $R^2$ is hydrogen, $R^3$ is hydrogen, and $R^4$ is a stabilized thiophosphate prodrug;
(lxxxvii) in Formula Ia, $R^1$ is cyclobutyl, $R^2$ is hydrogen, $R^3$ is hydrogen, and $R^4$ is a phosphoramidate;
(lxxxviii) in Formula Ia, $R^1$ is cyclobutyl, $R^2$ is hydrogen, $R^3$ is hydrogen, and $R^4$ is a thiophosphoramidate:
(lxxxix) in Formula Ia, $R^1$ is cyclobutyl, $R^2$ is hydrogen, $R^3$ is hydrogen, and $R^4$ is a monophosphate;
(xc) in Formula Ia, $R^1$ is cyclobutyl, $R^2$ is hydrogen, $R^3$ is hydrogen, and $R^4$ is a diphosphate;
(xci) in Formula Ia, $R^1$ is cyclobutyl, $R^2$ is hydrogen, $R^3$ is hydrogen, and $R^4$ is a triphosphate;
(xcii) in Formula Ib, $R^1$ is methyl, $R^2$ is methyl, $R^3$ is hydrogen, $R^4$ is a stabilized phosphate prodrug;
(xciii) in Formula Ib, $R^1$ is methyl, $R^2$ is methyl, $R^3$ is hydrogen, and $R^4$ is a stabilized thiophosphate prodrug;
(xciv) in Formula Ib, $R^1$ is methyl, $R^2$ is methyl, $R^3$ is hydrogen, and $R^4$ is a phosphoramidate;
(xcv) in Formula Ib, $R^1$ is methyl, $R^2$ is methyl, $R^3$ is hydrogen, and $R^4$ is a thiophosphoramidate:
(xcvi) in Formula Ib, $R^1$ is methyl, $R^2$ is methyl, $R^3$ is hydrogen, and $R^4$ is a monophosphate;
(xcvii) in Formula Ib, $R^1$ is methyl, $R^2$ is methyl, $R^3$ is hydrogen, and $R^4$ is a diphosphate;
(xcviii) in Formula Ib, $R^1$ is methyl, $R^2$ is methyl, $R^3$ is hydrogen, and $R^4$ is a triphosphate;
(xcix) in Formula Ib, $R^1$ is methyl, $R^2$ is hydrogen, $R^3$ is hydrogen, $R^4$ is a stabilized phosphate prodrug;
(c) in Formula Ib, $R^1$ is methyl, $R^2$ is hydrogen, $R^3$ is hydrogen, and $R^4$ is a stabilized thiophosphate prodrug;
(ci) in Formula Ib, $R^1$ is methyl, $R^2$ is hydrogen, $R^3$ is hydrogen, and $R^4$ is a phosphoramidate;
(cii) in Formula Ib, $R^1$ is methyl, $R^2$ is hydrogen, $R^3$ is hydrogen, and $R^4$ is a thiophosphoramidate:
(ciii) in Formula Ib, $R^1$ is methyl, $R^2$ is hydrogen, $R^3$ is hydrogen, and $R^4$ is a monophosphate;
(civ) in Formula Ib, $R^1$ is methyl, $R^2$ is hydrogen, $R^3$ is hydrogen, and $R^4$ is a diphosphate;
(cv) in Formula Ib, $R^1$ is methyl, $R^2$ is hydrogen, $R^3$ is hydrogen, and $R^4$ is a triphosphate;
(cvi) in Formula Ib, $R^1$ is cyclopentyl, $R^2$ is hydrogen, $R^3$ is hydrogen, $R^4$ is a stabilized phosphate prodrug;
(cvii) in Formula Ib, $R^1$ is cyclopentyl, $R^2$ is hydrogen, $R^3$ is hydrogen, and $R^4$ is a stabilized thiophosphate prodrug;
(cviii) in Formula Ib, $R^1$ is cyclopentyl, $R^2$ is hydrogen, $R^3$ is hydrogen, and $R^4$ is a phosphoramidate;
(cix) in Formula Ib, $R^1$ is cyclopentyl, $R^2$ is hydrogen, $R^3$ is hydrogen, and $R^4$ is a thiophosphoramidate:
(cx) in Formula Ib, $R^1$ is cyclopentyl, $R^2$ is hydrogen, $R^3$ is hydrogen, and $R^4$ is a monophosphate;
(cxi) in Formula Ib, $R^1$ is cyclopentyl, $R^2$ is hydrogen, $R^3$ is hydrogen, and $R^4$ is a diphosphate;
(cxii) in Formula Ib, $R^1$ is cyclopentyl, $R^2$ is hydrogen, $R^3$ is hydrogen, and $R^4$ is a triphosphate;
(cxiii) in Formula Ib, $R^1$ and $R^2$ together with the nitrogen to which they are bonded to form a 5-membered heterocyclic ring, $R^3$ is hydrogen, $R^4$ is a stabilized phosphate prodrug;
(cxiv) in Formula Ib, $R^1$ and $R^2$ together with the nitrogen to which they are bonded to form a 5-membered heterocyclic ring, $R^3$ is hydrogen, and $R^4$ is a stabilized thiophosphate prodrug;
(cxv) in Formula Ib, $R^1$ and $R^2$ together with the nitrogen to which they are bonded to form a 5-membered heterocyclic ring, $R^3$ is hydrogen, and $R^4$ is a phosphoramidate;
(cxvi) in Formula Ib, $R^1$ and $R^2$ together with the nitrogen to which they are bonded to form a 5-membered heterocyclic ring, $R^3$ is hydrogen, and $R^4$ is a thiophosphoramidate:
(cxvii) in Formula Ib, $R^1$ and $R^2$ together with the nitrogen to which they are bonded to form a 5-membered heterocyclic ring, $R^3$ is hydrogen, and $R^4$ is a monophosphate;
(cxviii) in Formula Ib, $R^1$ and $R^2$ together with the nitrogen to which they are bonded to form a 5-membered heterocyclic ring, $R^3$ is hydrogen, and $R^4$ is a diphosphate;
(cxix) in Formula Ib, $R^1$ and $R^2$ together with the nitrogen to which they are bonded to form a 5-membered heterocyclic ring, $R^3$ is hydrogen, and $R^4$ is a triphosphate;
(cxx) in Formula Ib, $R^1$ is methyl, $R^2$ is cyclopropyl, $R^3$ is hydrogen, $R^4$ is a stabilized phosphate prodrug;
(cxxi) in Formula Ib, $R^1$ is methyl, $R^2$ is cyclopropyl, $R^3$ is hydrogen, and $R^4$ is a stabilized thiophosphate prodrug;
(cxxii) in Formula Ib, $R^1$ is methyl, $R^2$ is cyclopropyl, $R^3$ is hydrogen, and $R^4$ is a phosphoramidate;
(cxxiii) in Formula Ib, $R^1$ is methyl, $R^2$ is cyclopropyl, $R^3$ is hydrogen, and $R^4$ is a thiophosphoramidate:
(cxxiv) in Formula Ib, $R^1$ is methyl, $R^2$ is cyclopropyl, $R^3$ is hydrogen, and $R^4$ is a monophosphate;
(cxxv) in Formula Ib, $R^1$ is methyl, $R^2$ is cyclopropyl, $R^3$ is methyl, and $R^4$ is a diphosphate;
(cxxvi) in Formula Ia, $R^1$ is methyl, $R^2$ is cyclopropyl, $R^3$ is hydrogen, and $R^4$ is a triphosphate;
(cxxvii) in Formula Ib, $R^1$ is cyclopropyl, $R^2$ is cyclopropyl, $R^3$ is hydrogen, $R^4$ is a stabilized phosphate prodrug;
(cxxviii) in Formula Ib, $R^1$ is cyclopropyl, $R^2$ is cyclopropyl, $R^3$ is hydrogen, and $R^4$ is a stabilized thiophosphate prodrug;
(cxxix) in Formula Ib, $R^1$ is cyclopropyl, $R^2$ is cyclopropyl, $R^3$ is hydrogen, and $R^4$ is a phosphoramidate;
(cxxx) in Formula Ib, $R^1$ is cyclopropyl, $R^2$ is cyclopropyl, $R^3$ is hydrogen, and $R^4$ is a thiophosphoramidate:
(cxxxi) in Formula Ib, $R^1$ is cyclopropyl, $R^2$ is cyclopropyl, $R^3$ is hydrogen, and $R^4$ is a monophosphate;
(cxxxii) in Formula Ib, $R^1$ is cyclopropyl, $R^2$ is cyclopropyl, $R^3$ is hydrogen, and $R^4$ is a diphosphate;
(cxxxiii) in Formula Ib, $R^1$ is cyclopropyl, $R^2$ is cyclopropyl, $R^3$ is hydrogen, and $R^4$ is a triphosphate;

In alternative embodiments of compounds (i) through (cxxxiii), an L-nucleoside is used in Formula I-X.

In an alternate embodiment, the Formula I $R^{12}$ variable is $CH_2F$.

In an alternate embodiment, the Formula I $R^{12}$ variable is $CHF_2$.

In an alternate embodiment, the Formula I $R^{12}$ variable is $CF_3$.

In an alternate embodiment, the Formula II $R^{12}$ variable is $CH_2F$.
In an alternate embodiment, the Formula II $R^{12}$ variable is $CHF_2$.
In an alternate embodiment, the Formula II $R^{12}$ variable is $CF_3$.
In one embodiment, a compound of Formula Ia is provided. Non-limiting examples of compounds of Formula Ia include:
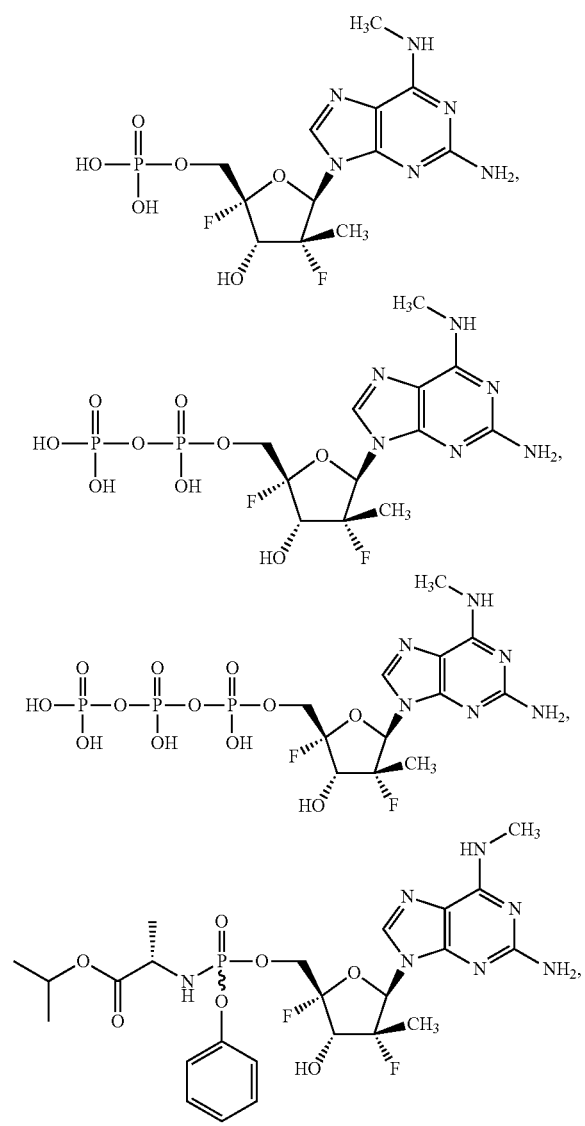
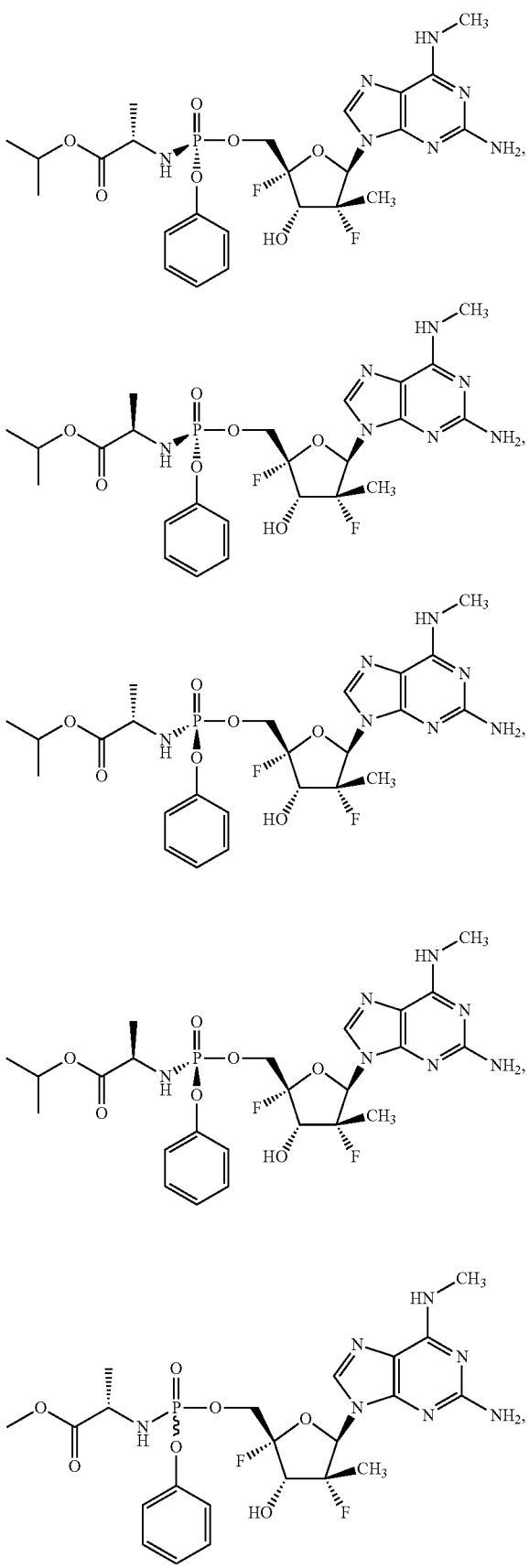

-continued
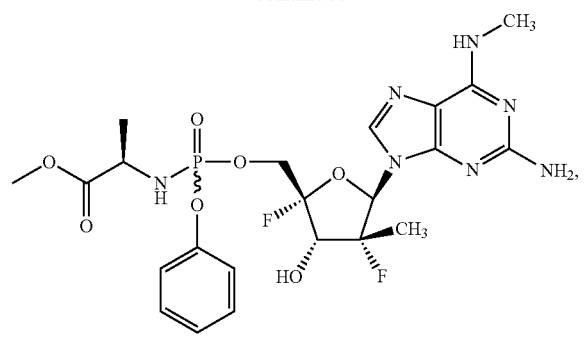
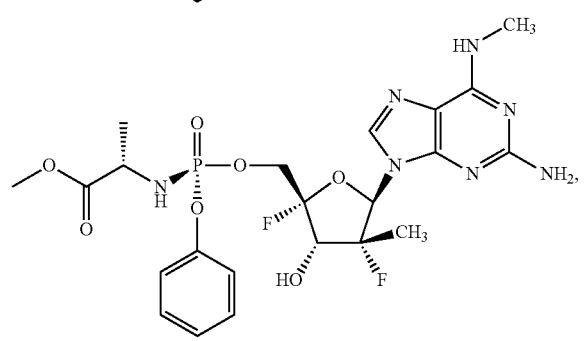
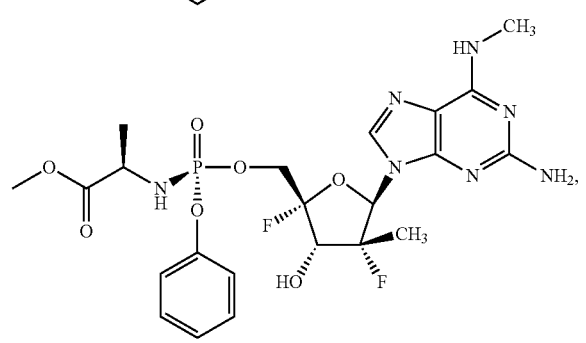
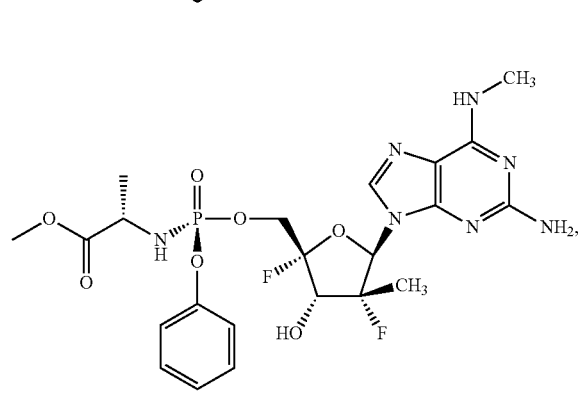
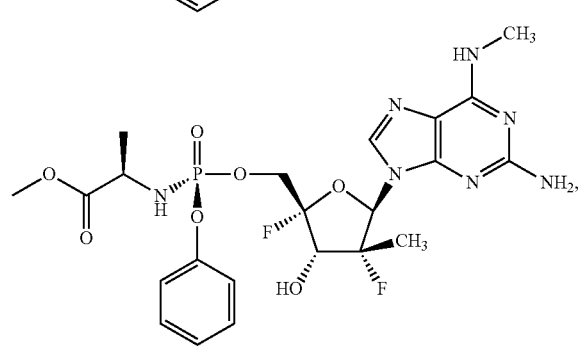
-continued
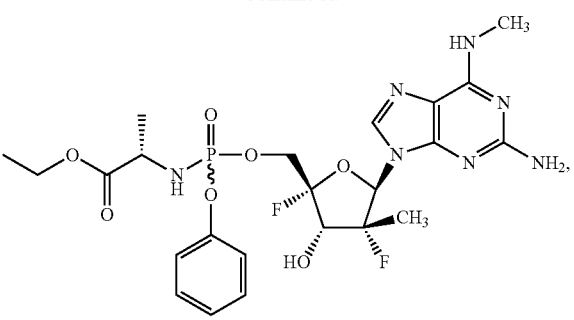
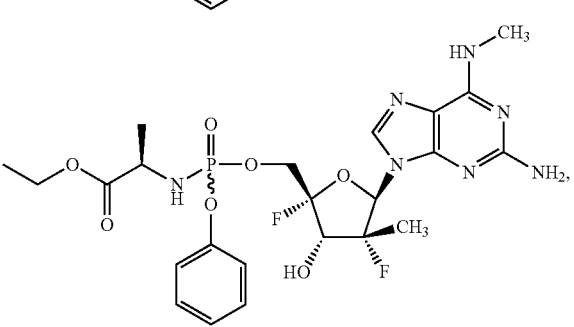
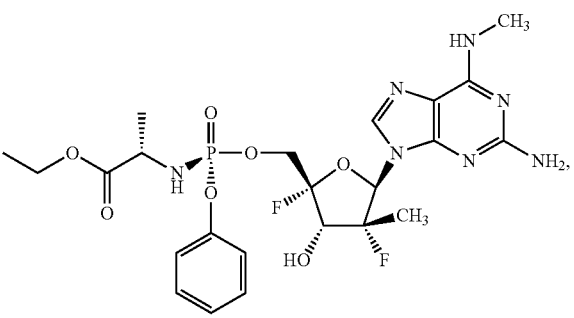
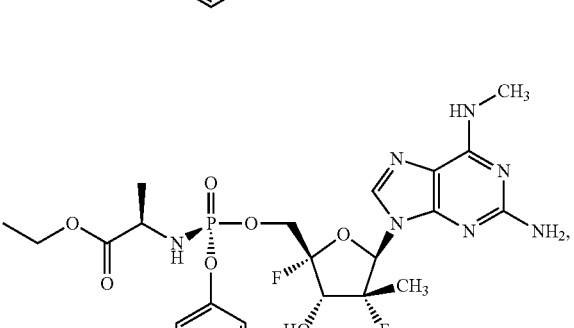
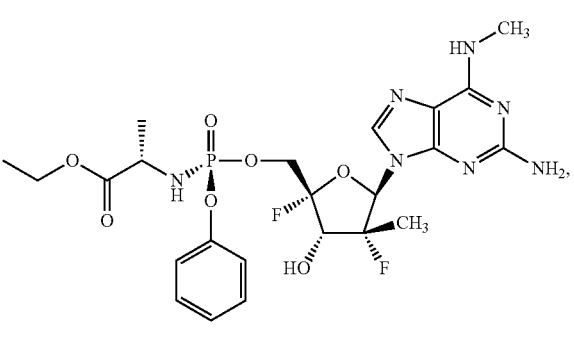

-continued
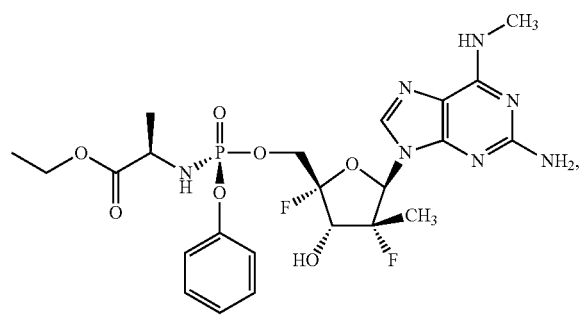
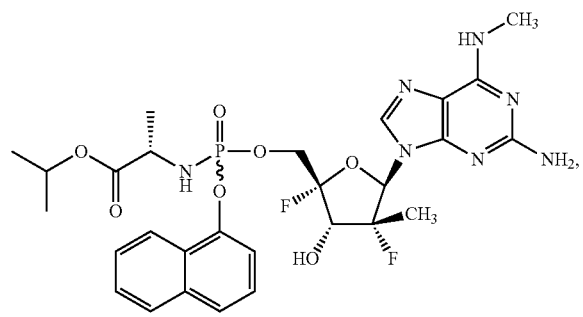
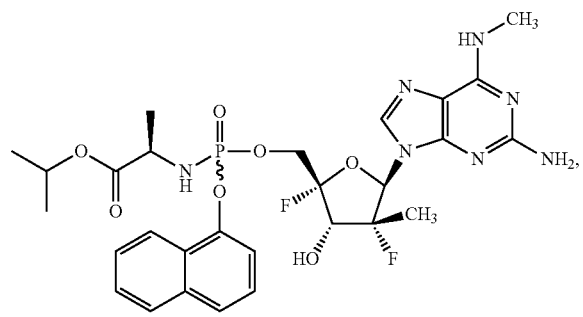
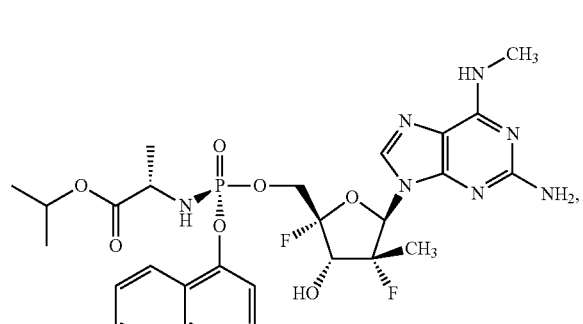
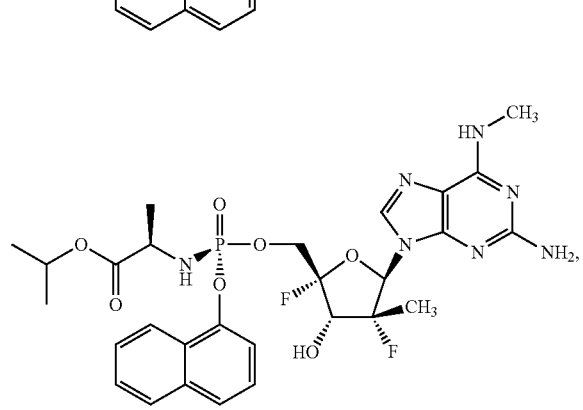
-continued
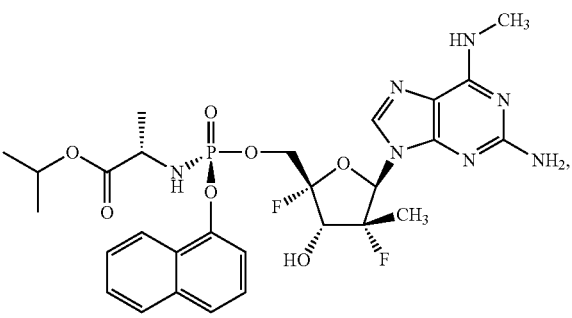
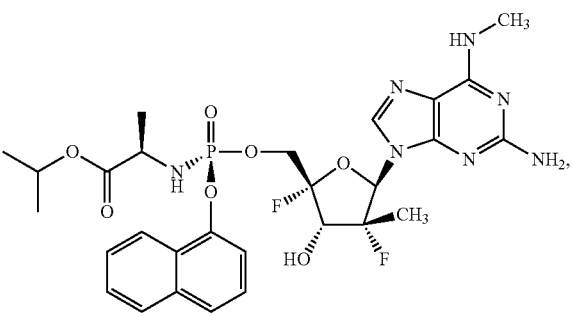
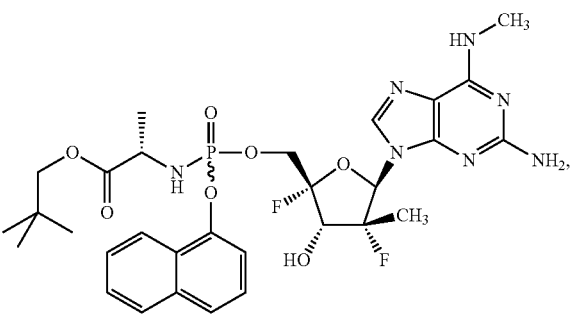
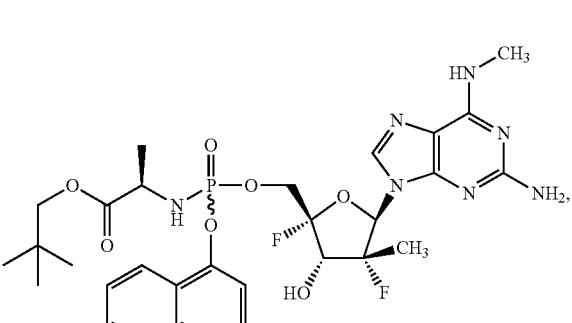
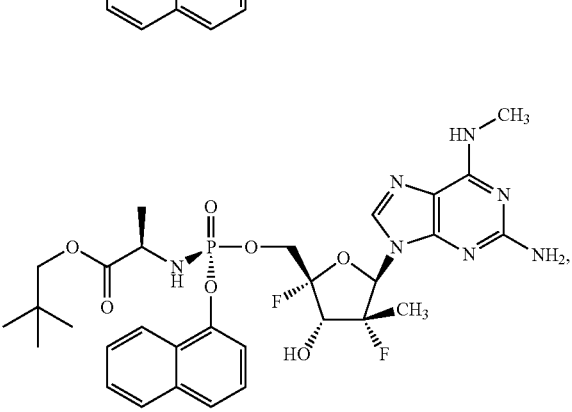

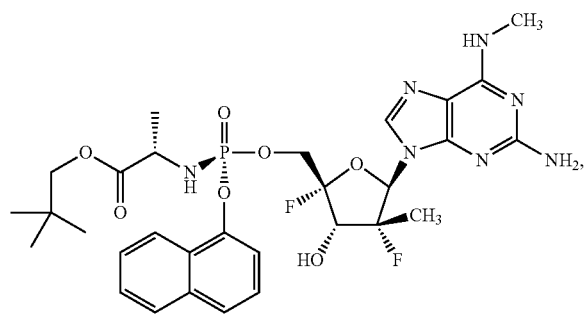
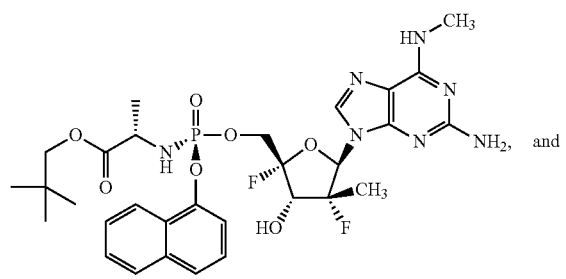 and
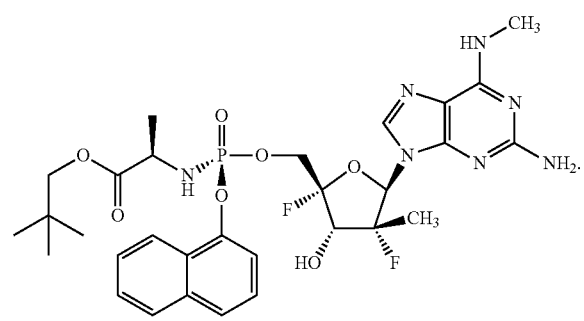
In one embodiment, a thiophosphoramidate of Formula Ia is provided. Non-limiting examples of thiophosphoramidates of Formula Ia include, but are not limited to:
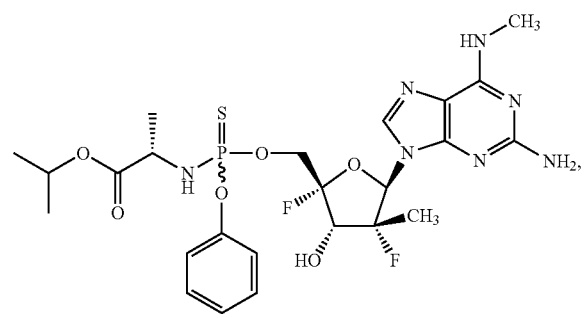
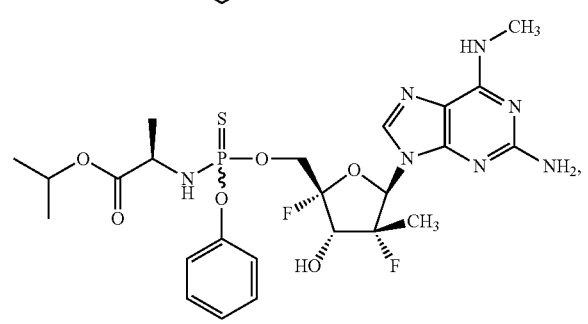
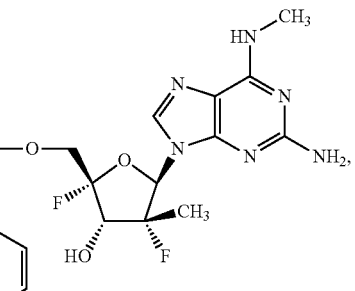
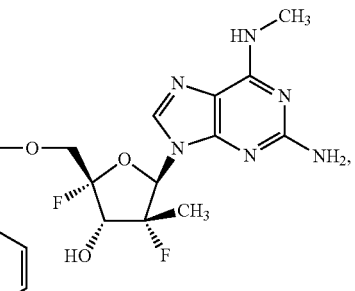
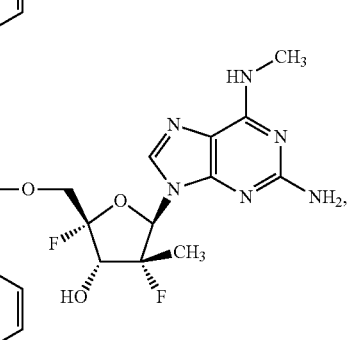
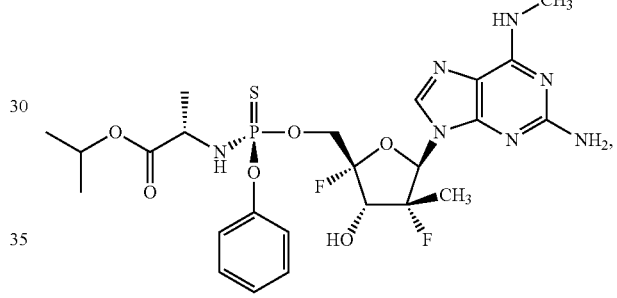

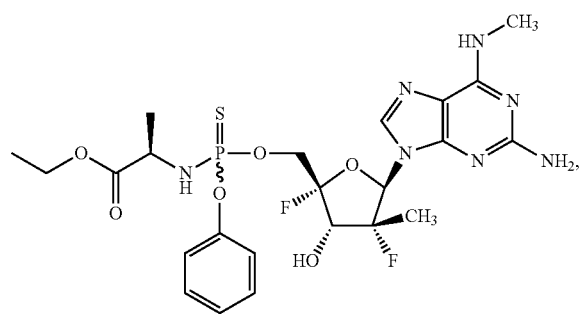
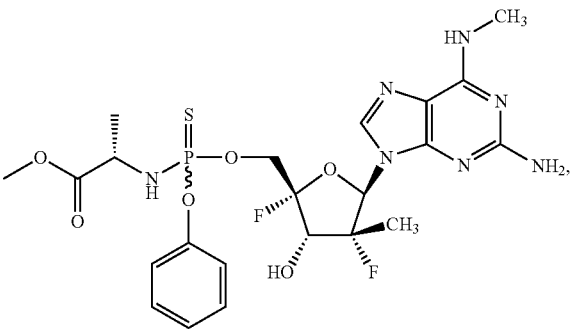
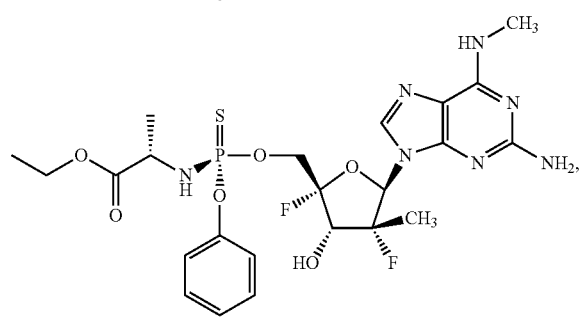
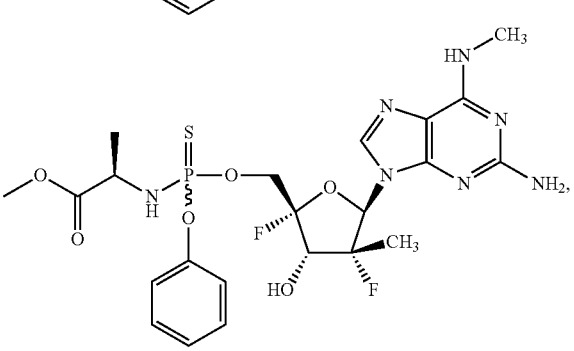
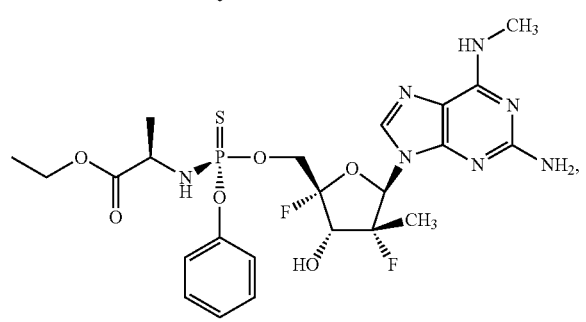
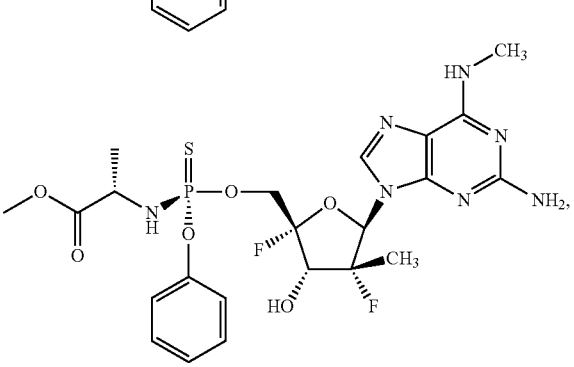
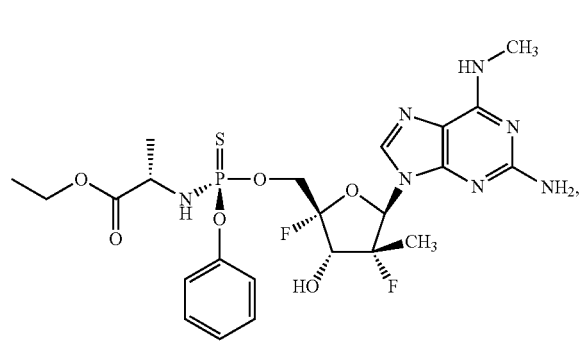
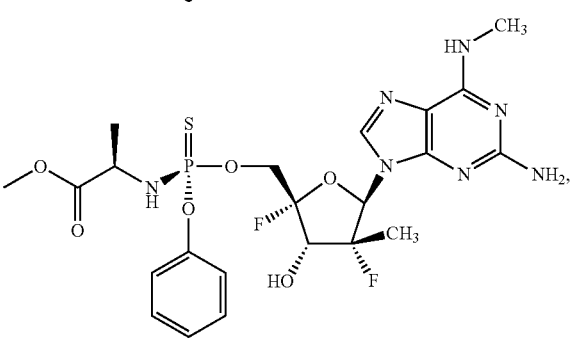
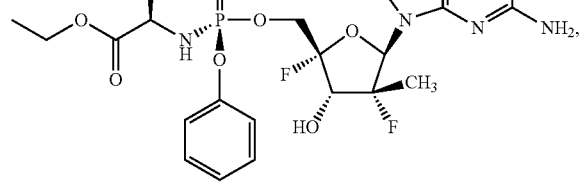
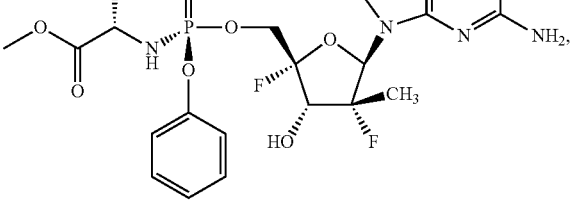

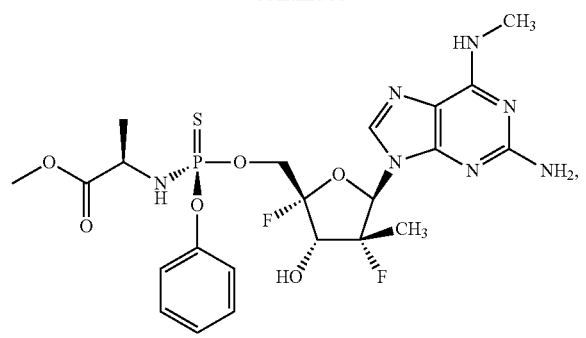
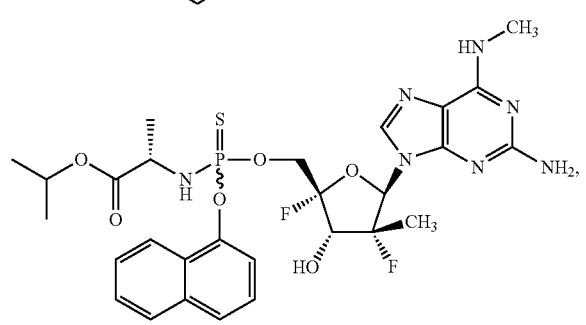
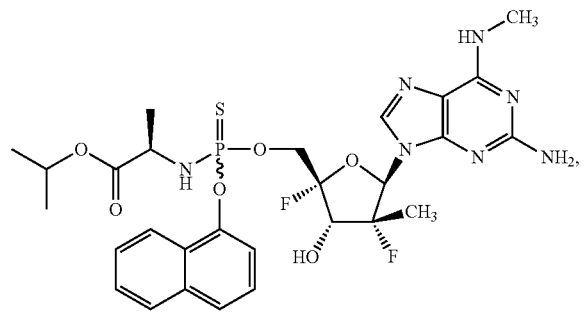
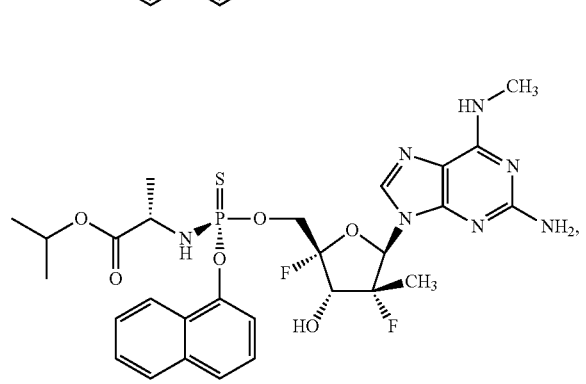
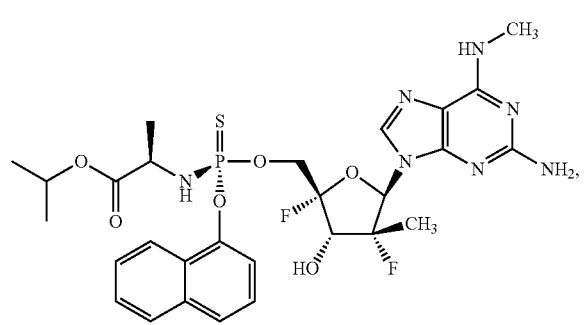
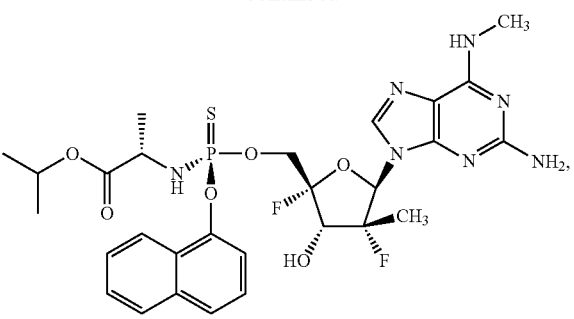
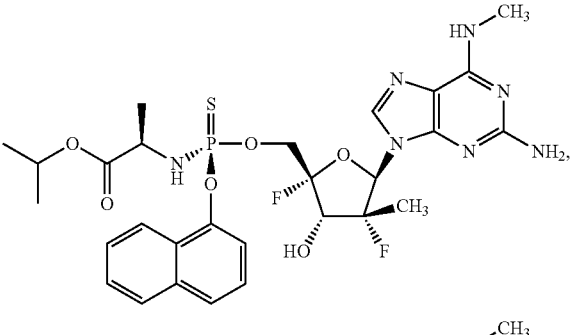
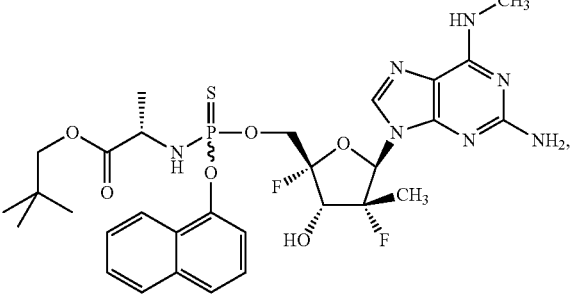
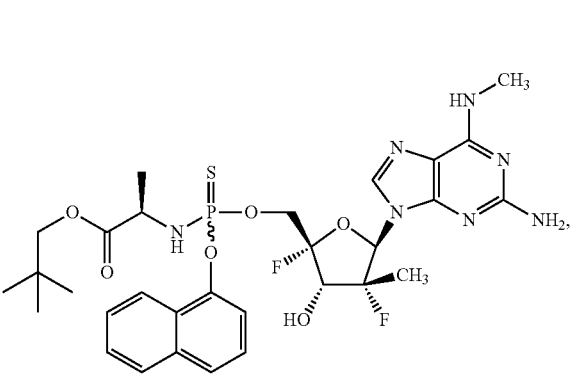
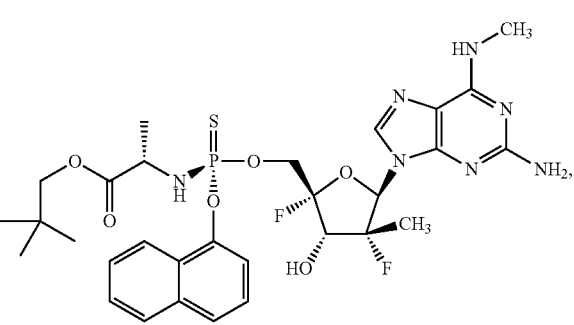

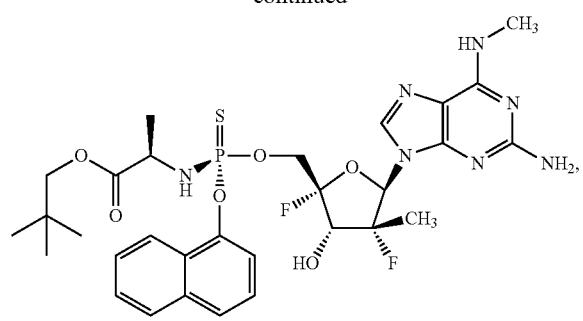
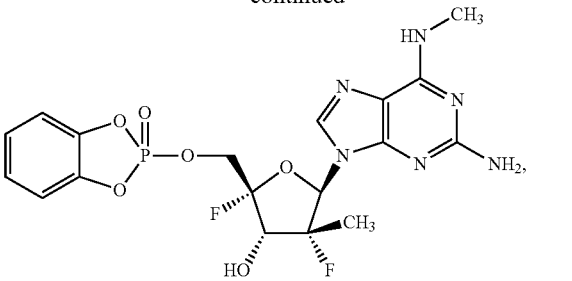
In one embodiment, a stabilized phosphate prodrug of Formula Ia is provided. Non-limiting examples of stabilized phosphate prodrugs of Formula Ia are illustrated below:
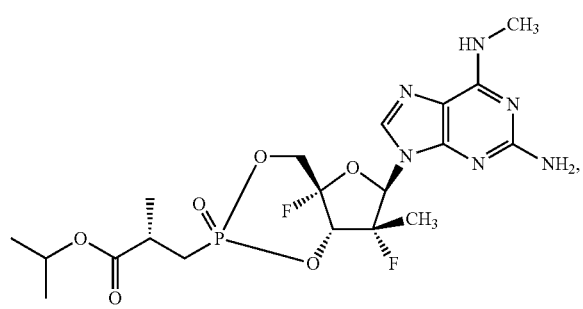
In another embodiment, a compound of Formula Ia is provided. Non-limiting examples of compounds of Formula Ia include:

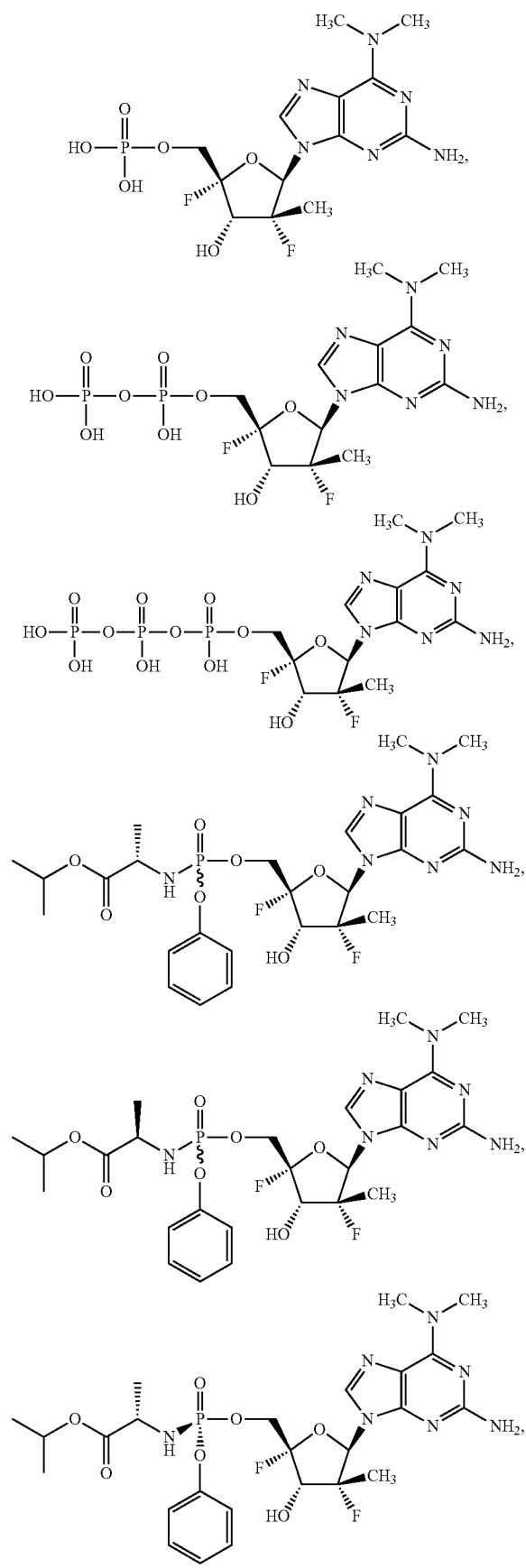
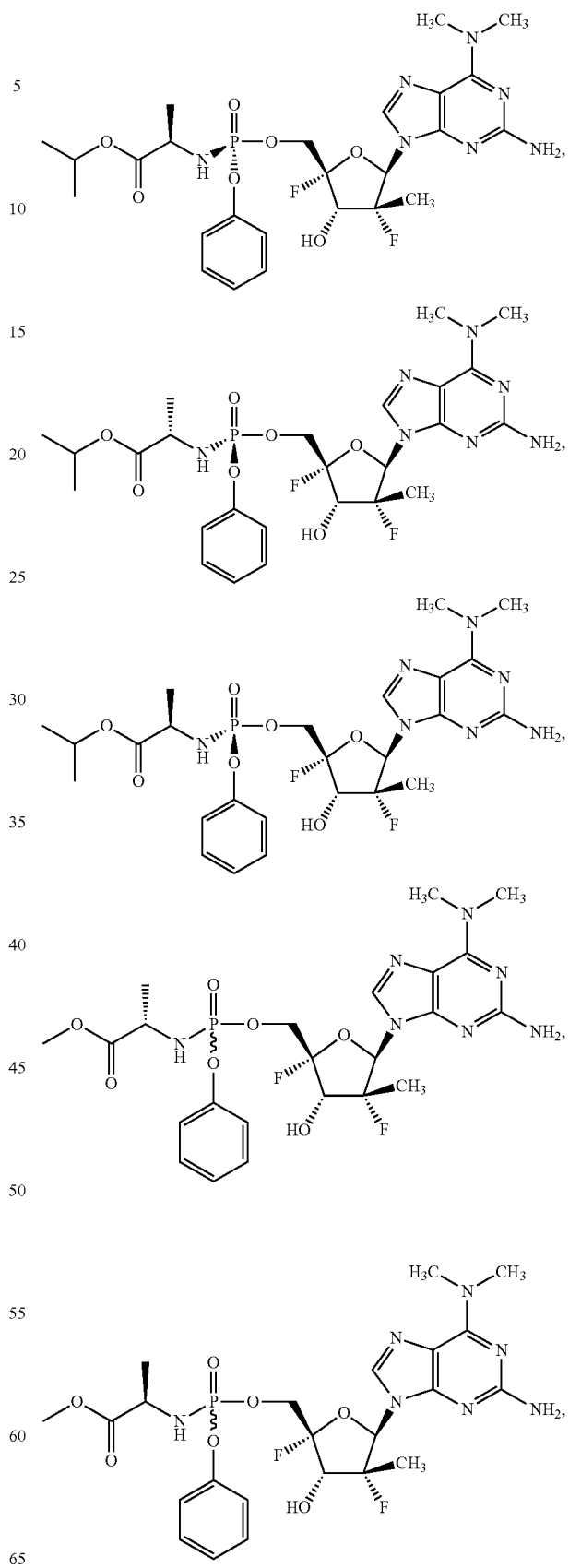

47
-continued
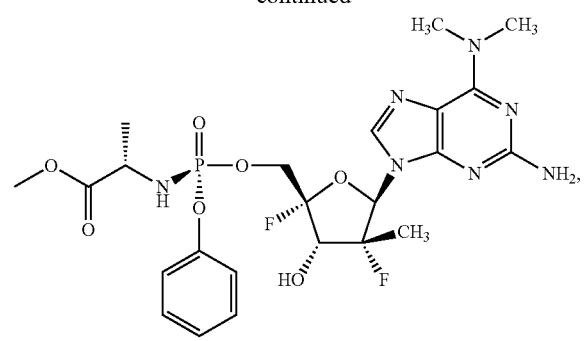
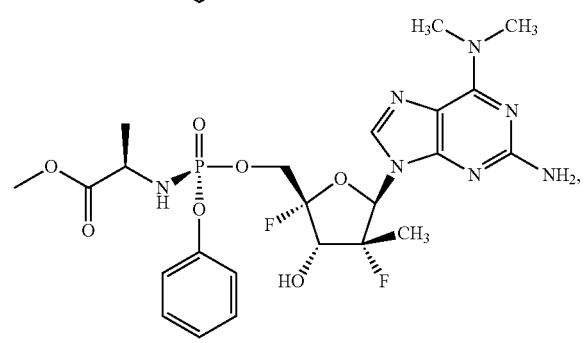
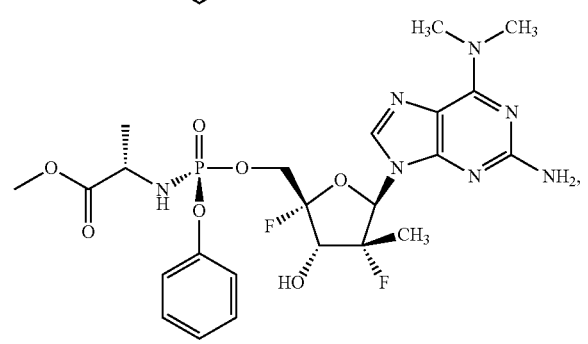
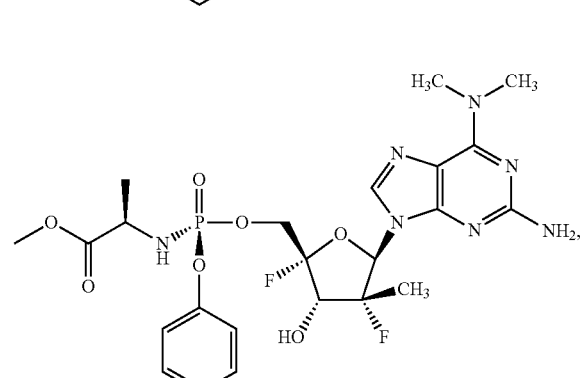
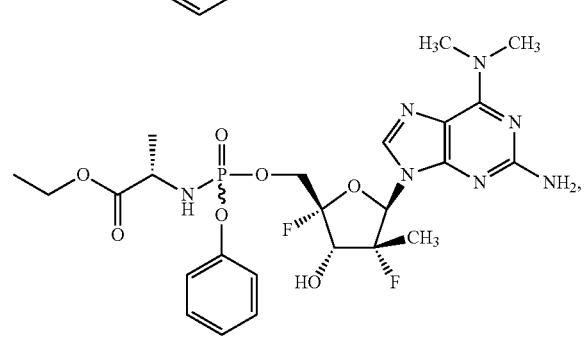
48
-continued
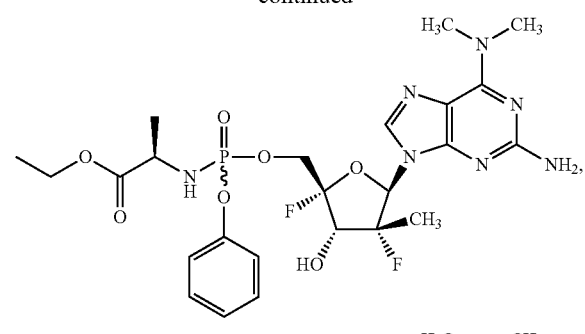
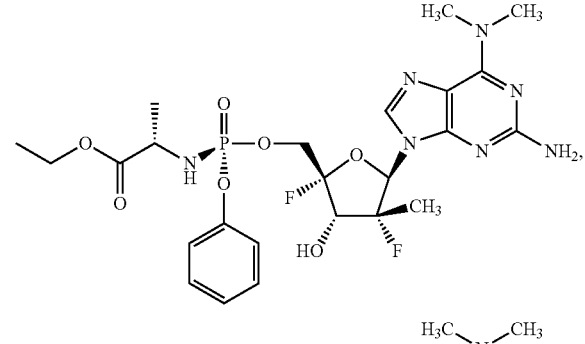
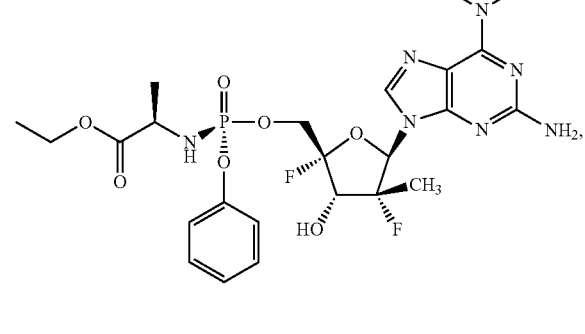
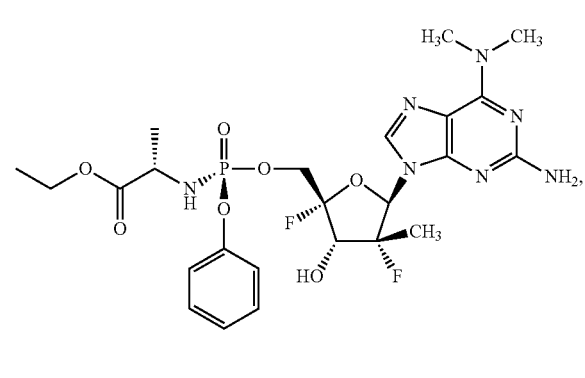
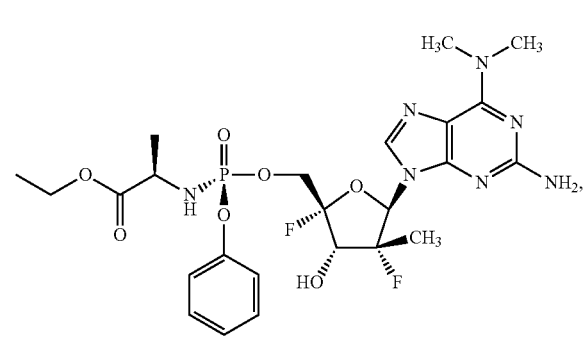

49
-continued
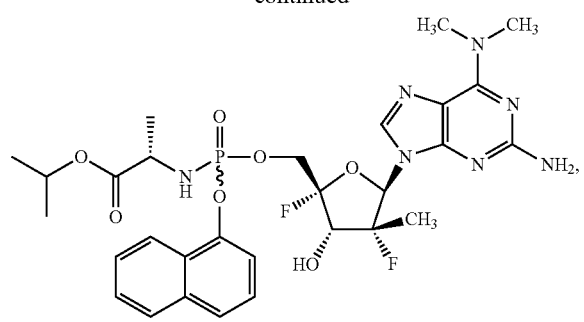
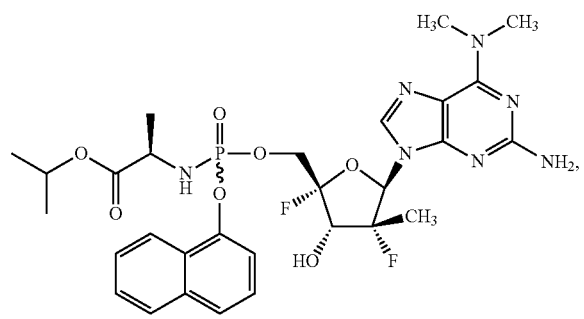
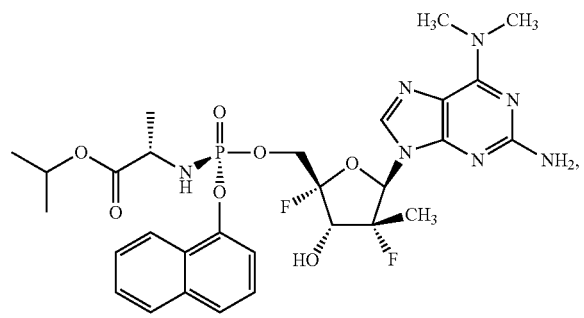
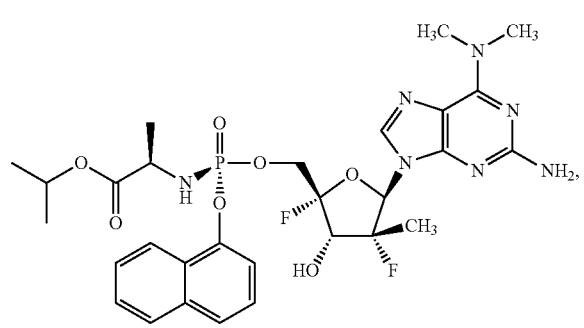
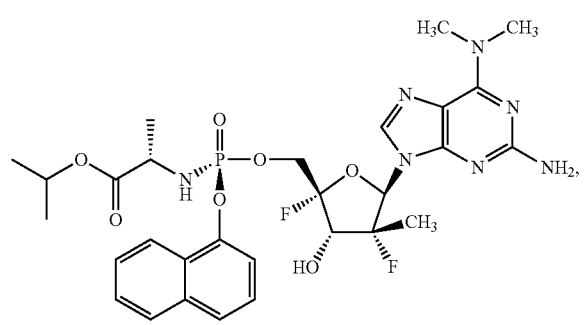
50
-continued
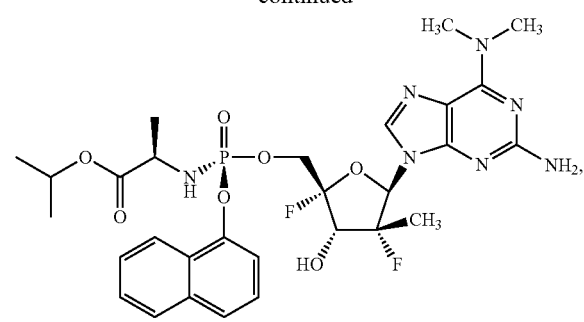
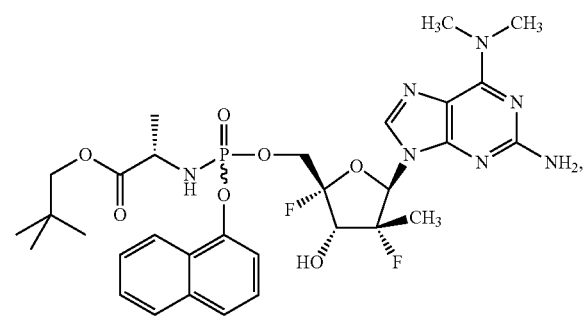
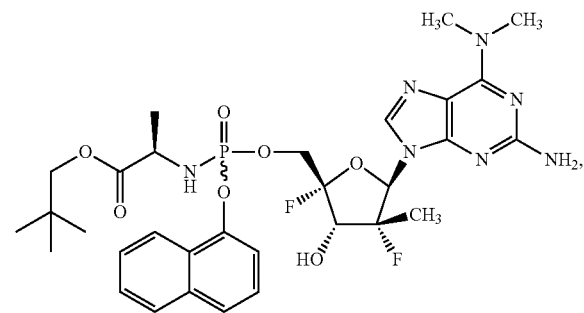
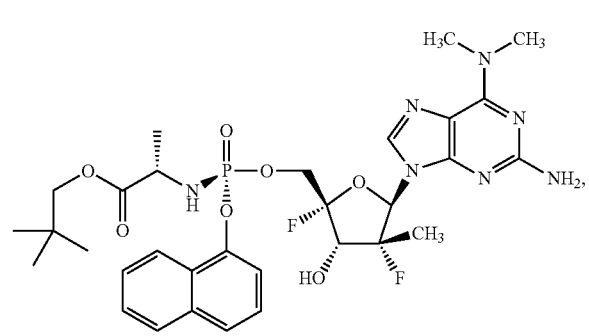
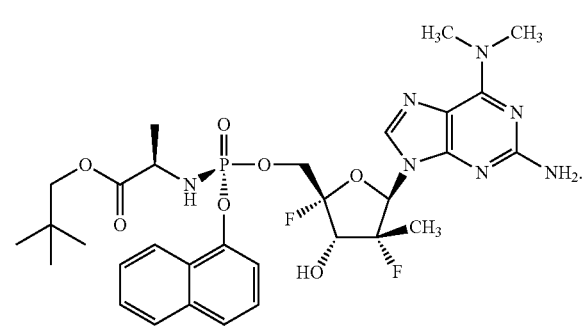

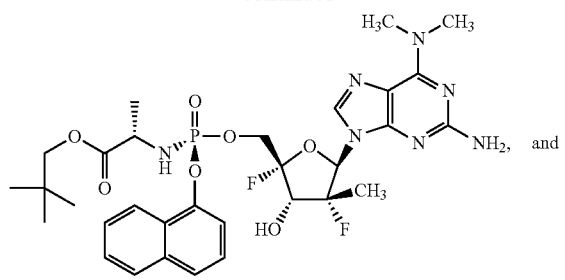
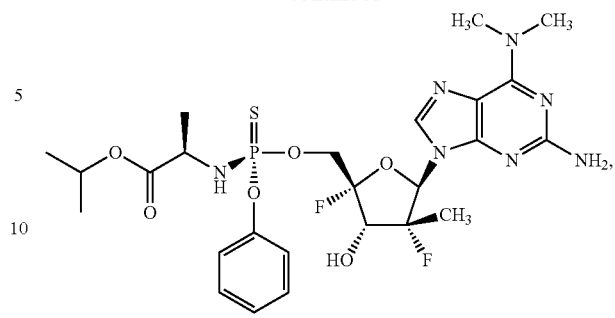  and
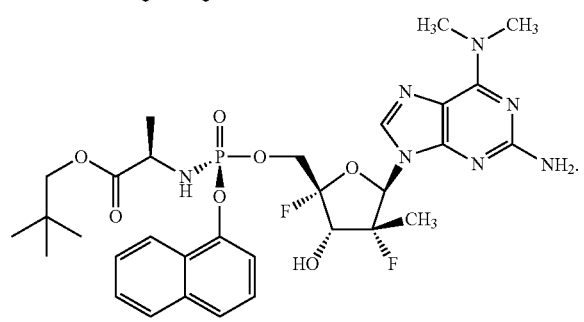
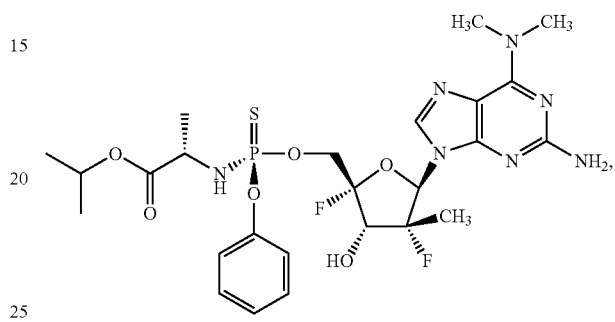
In one embodiment, a thiophosphoramidate of Formula Ia is provided. Non-limiting examples of thiophosphoramidates of Formula Ia include, but are not limited to:
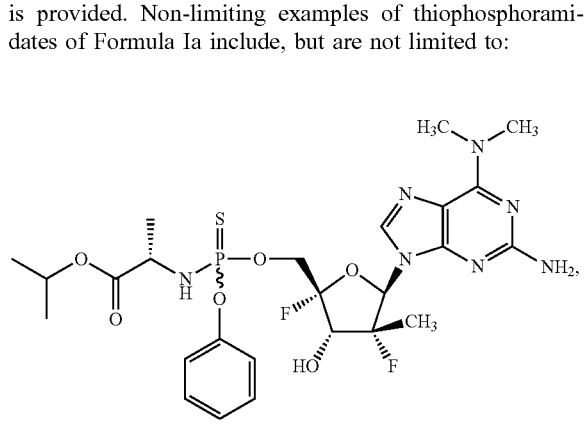
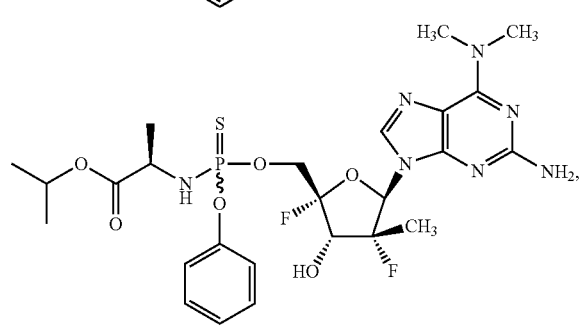
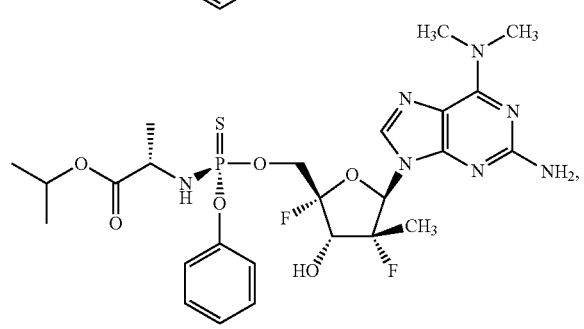
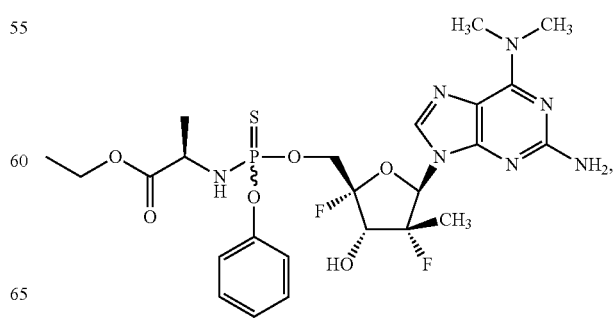

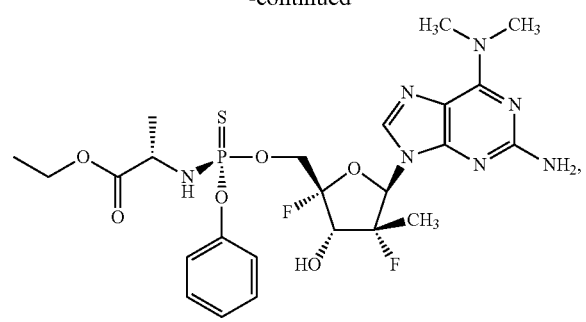
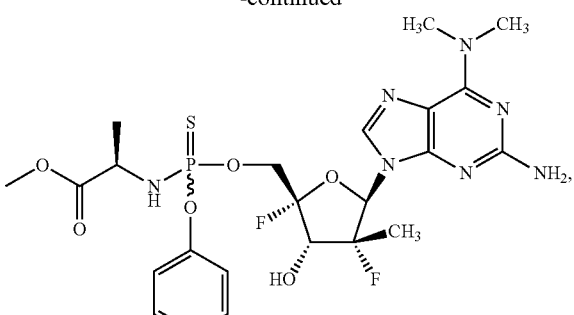
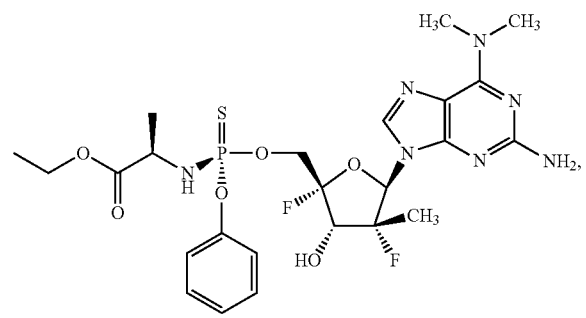
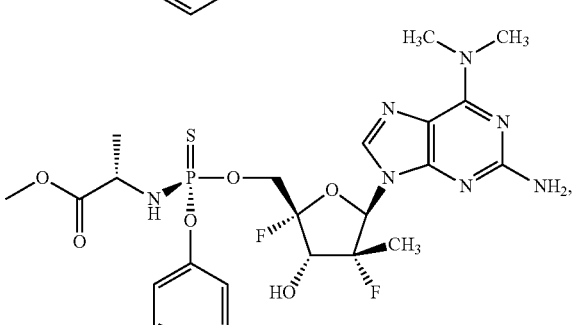
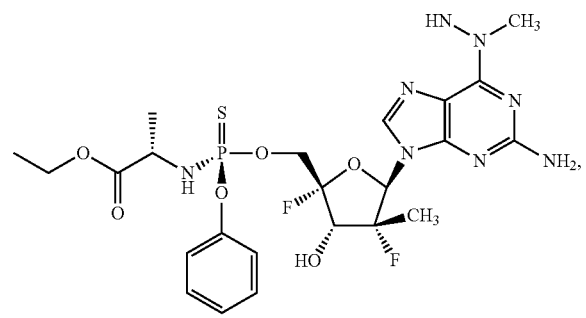
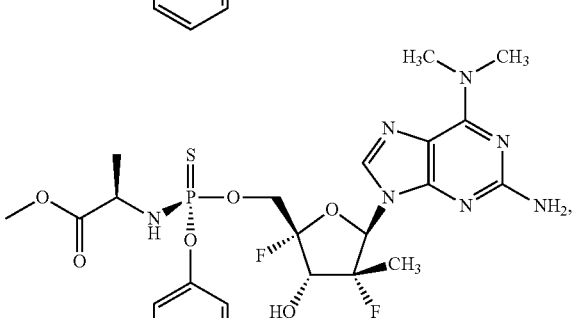
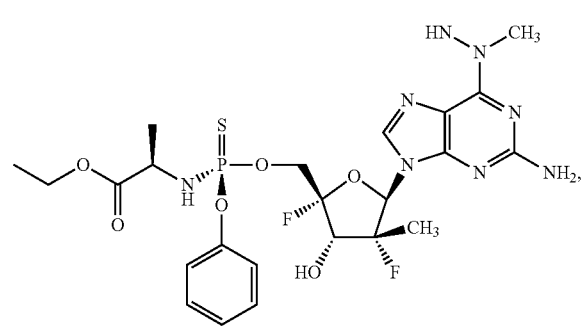
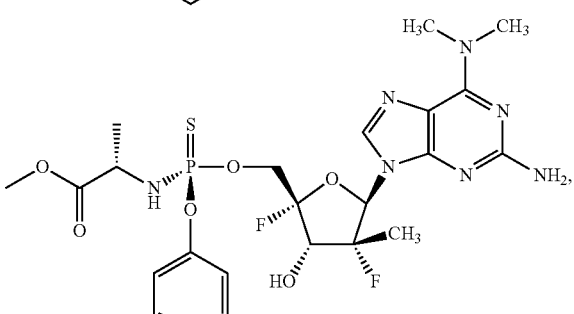
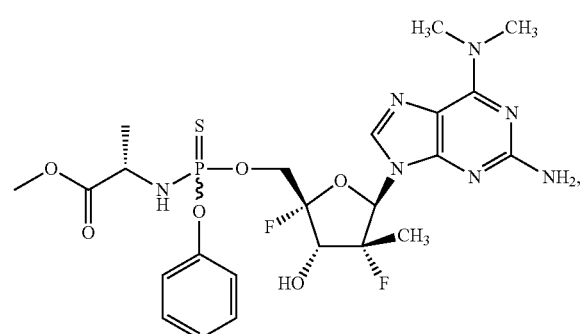
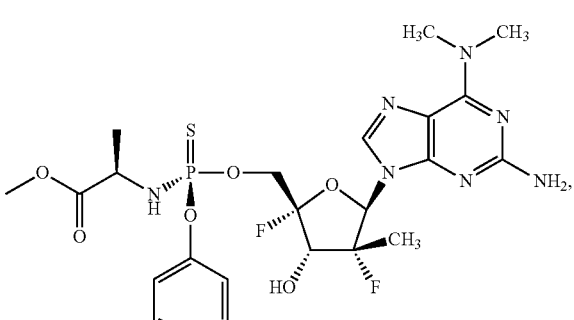

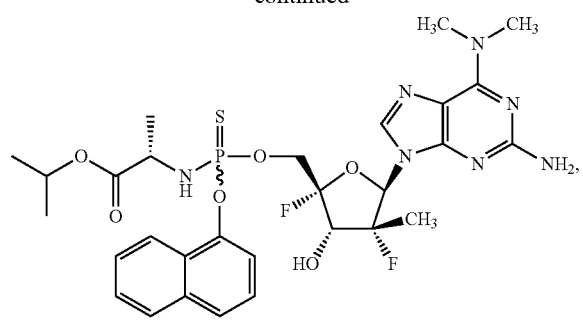
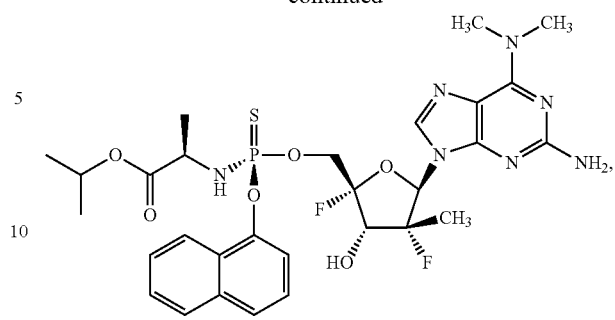

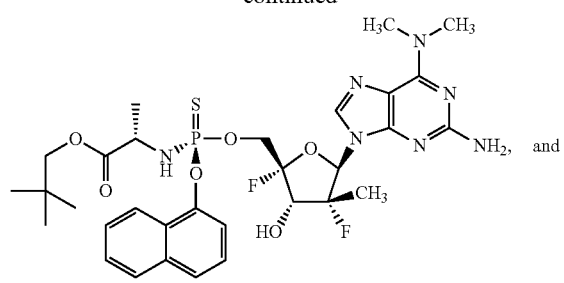
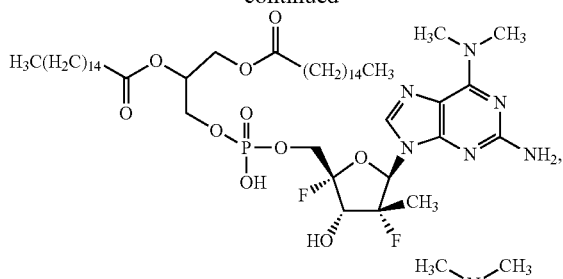
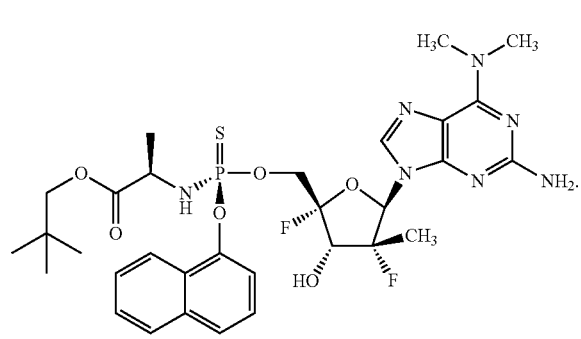
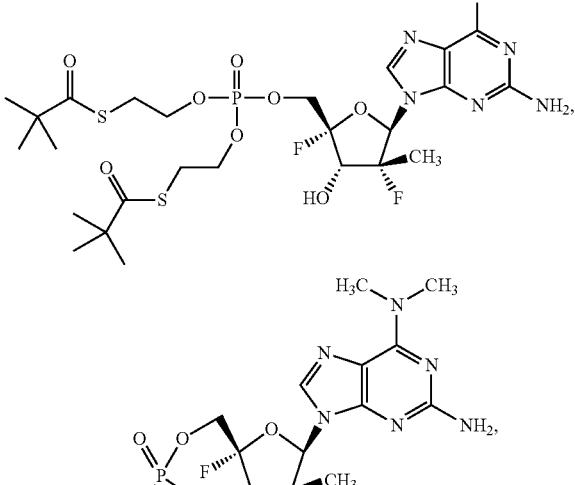
In one embodiment, a stabilized phosphate prodrug of Formula Ia is provided. Non-limiting examples of stabilized phosphate prodrugs of Formula Ia are illustrated below:
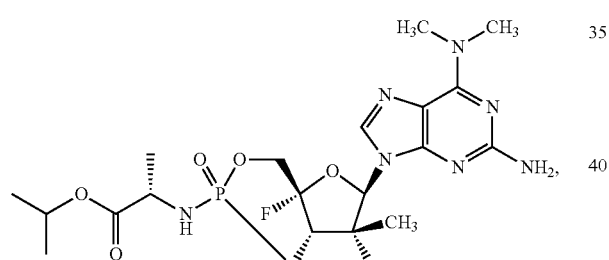
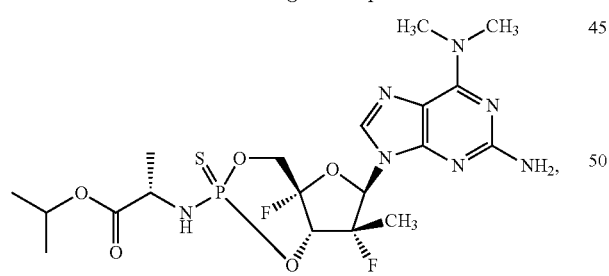
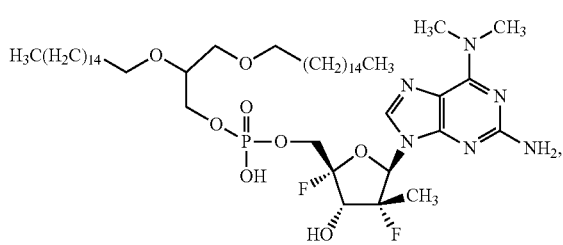
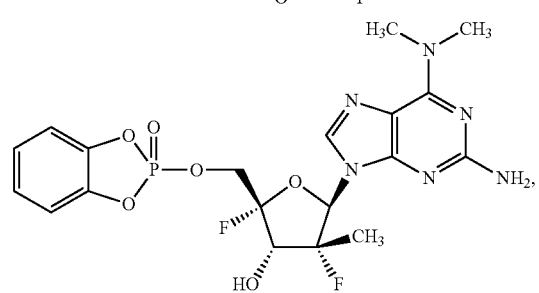
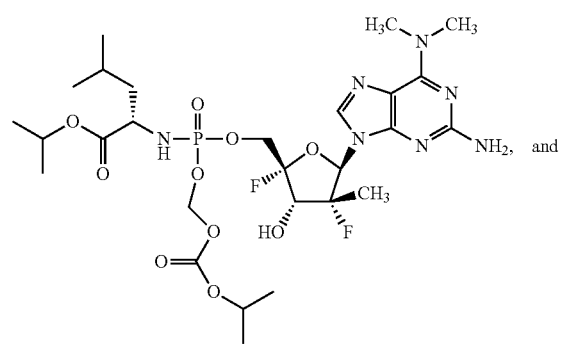

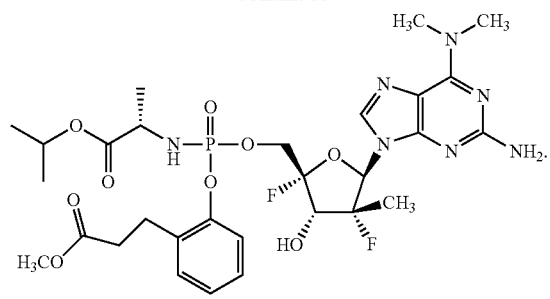
In one embodiment, a compound of Formula II is provided. Non-limiting examples of compounds of Formula II include:
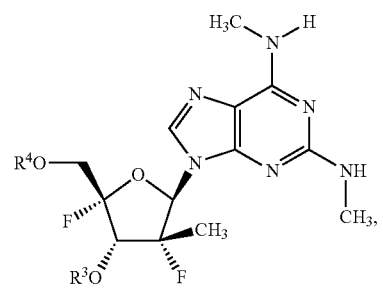
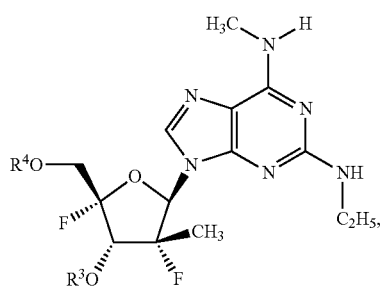
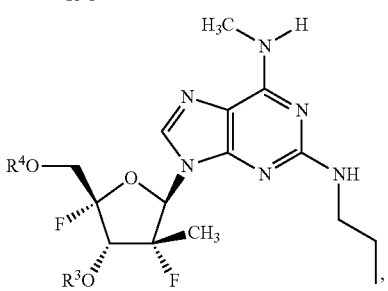
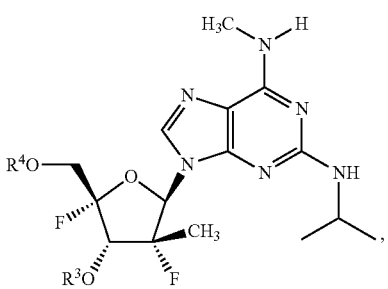
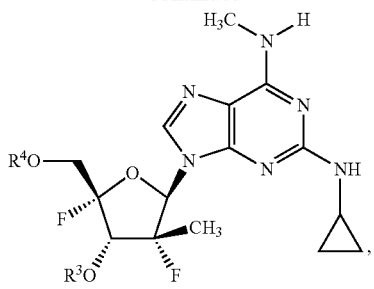
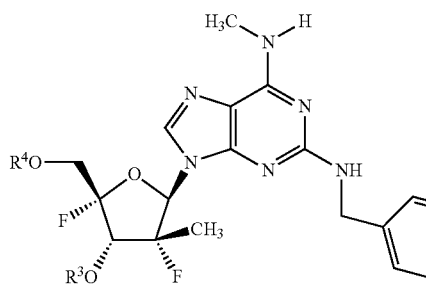
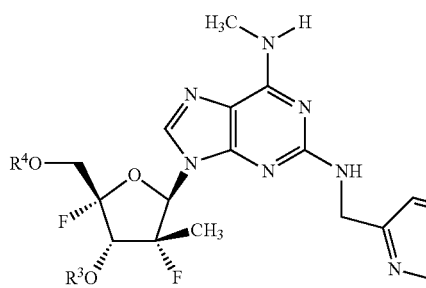
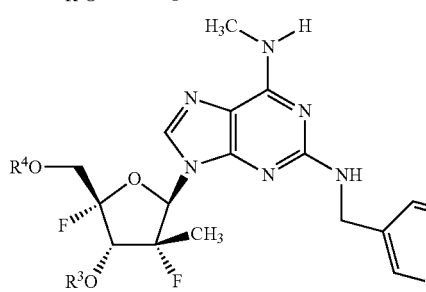
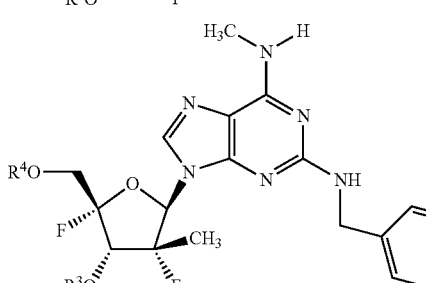
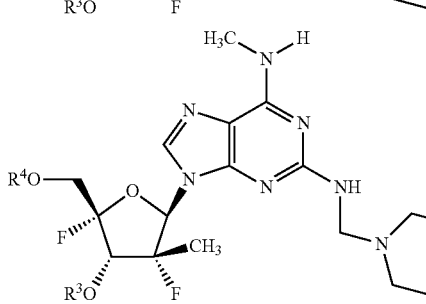

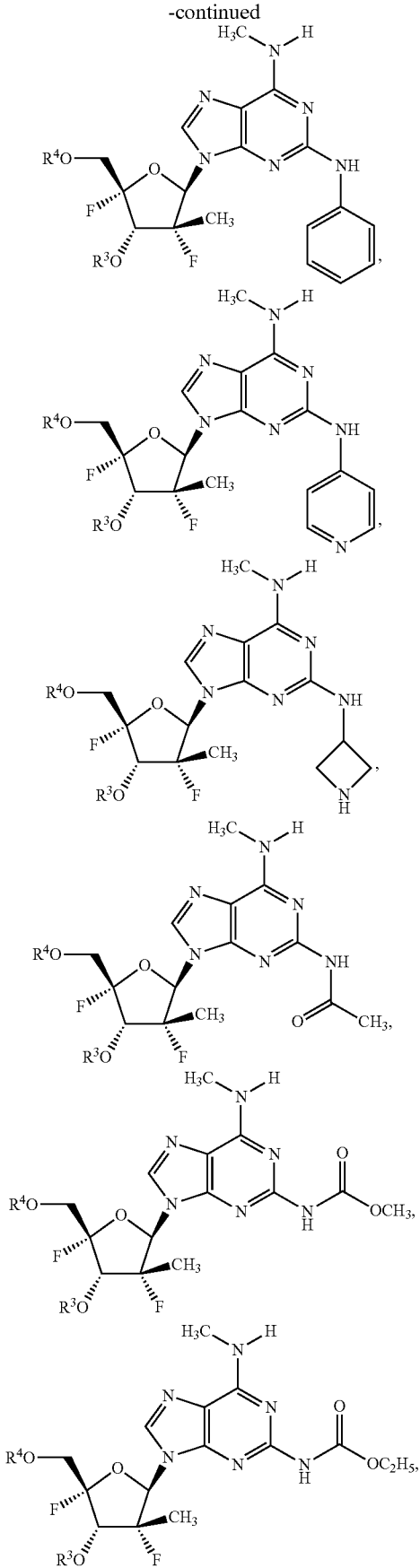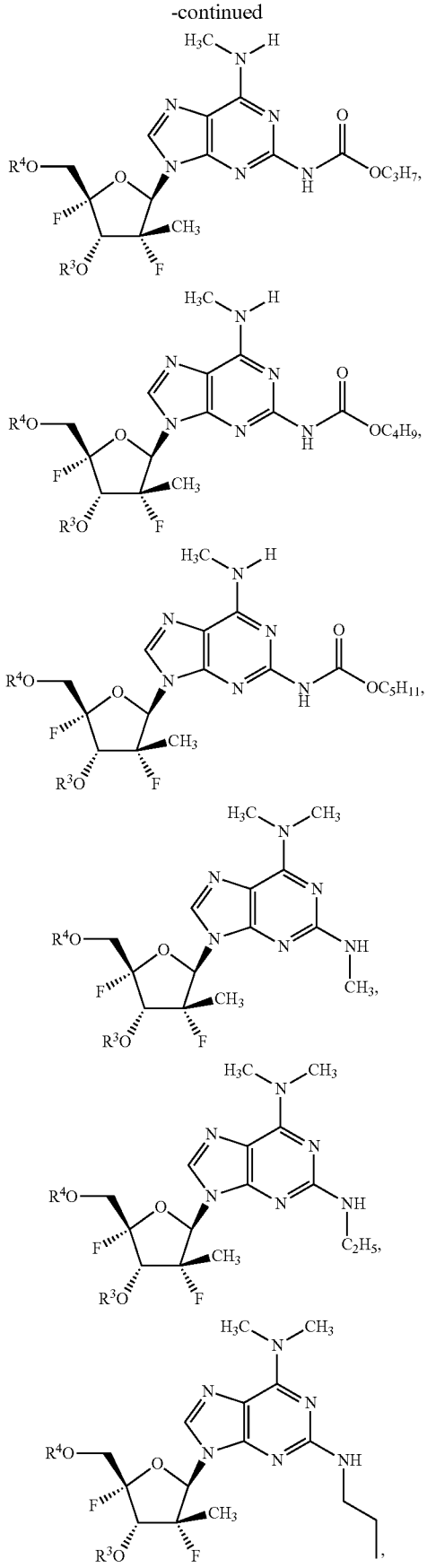

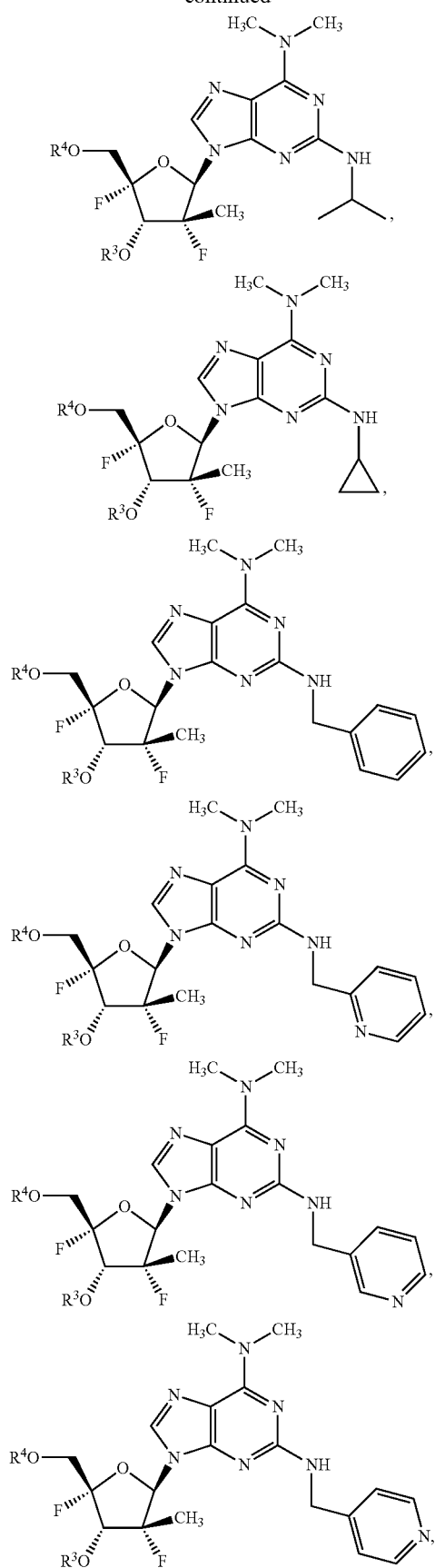
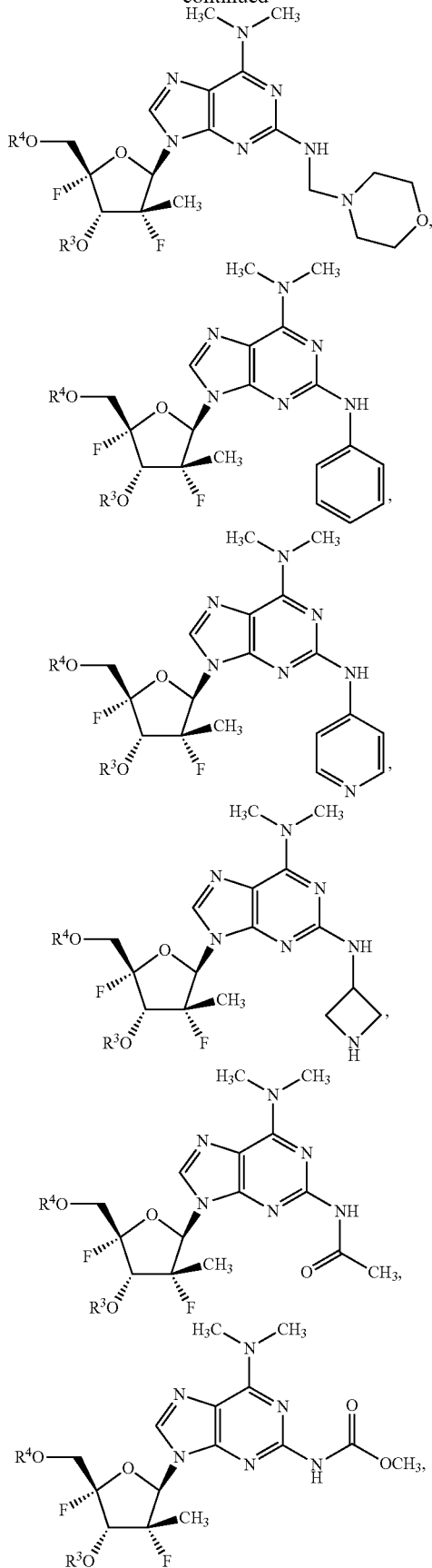

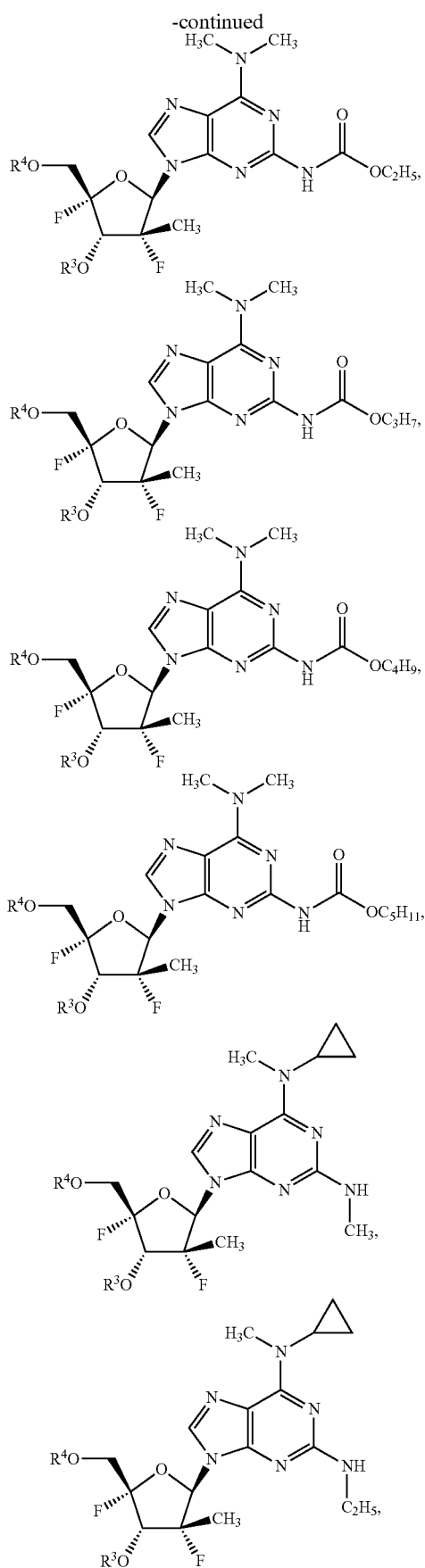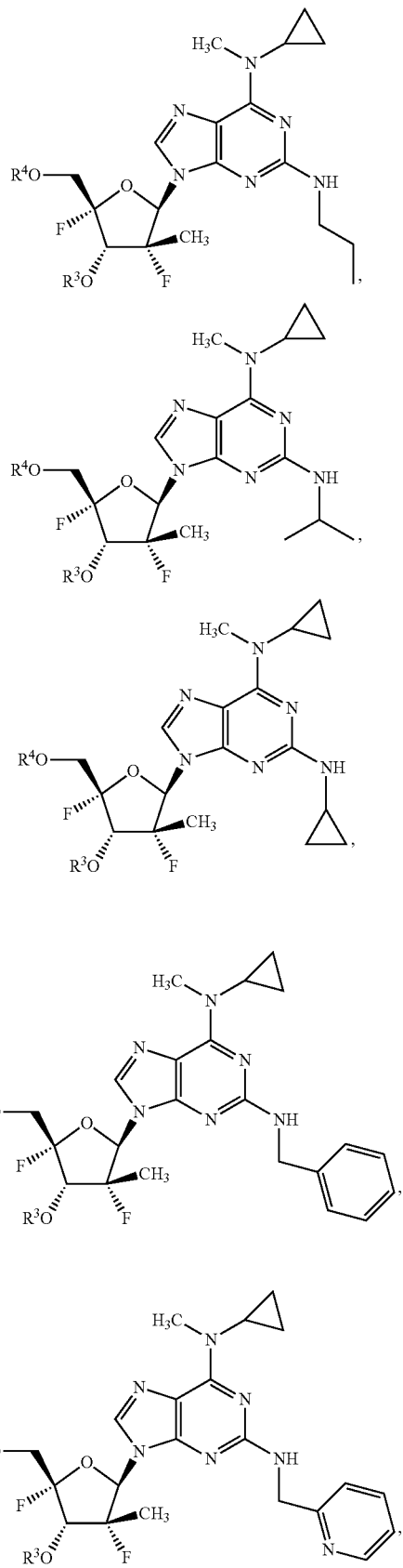

67
-continued
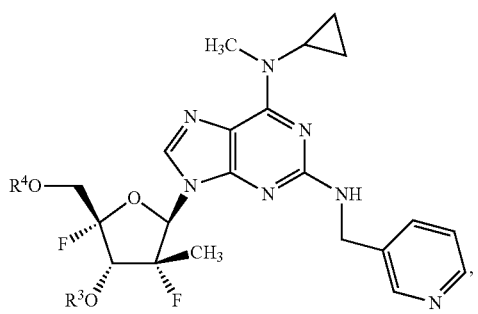
,
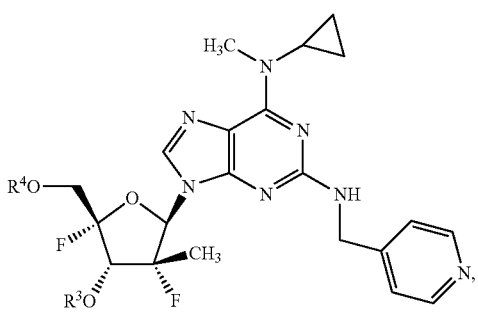
,
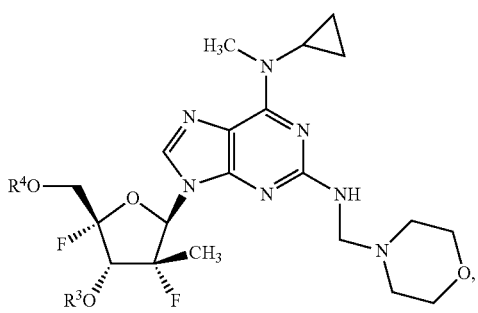
,
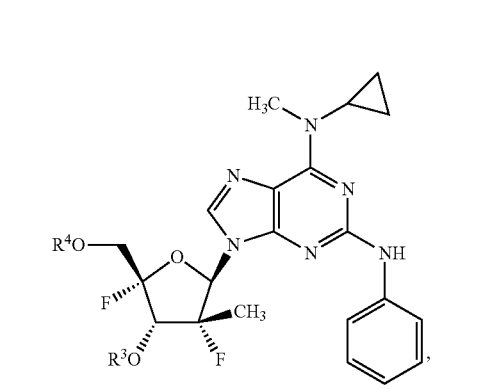
,
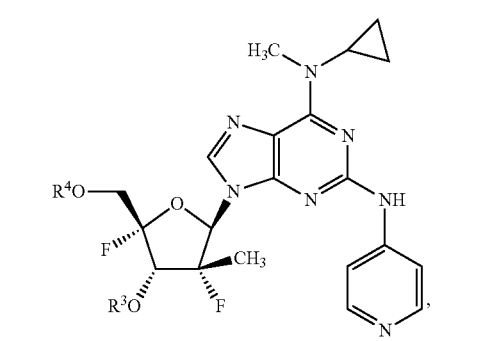
,
68
-continued
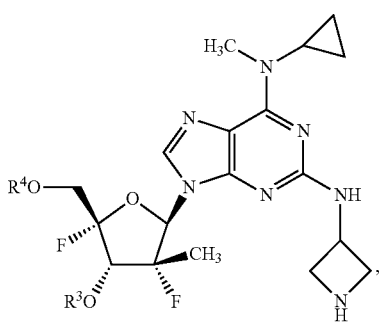
,
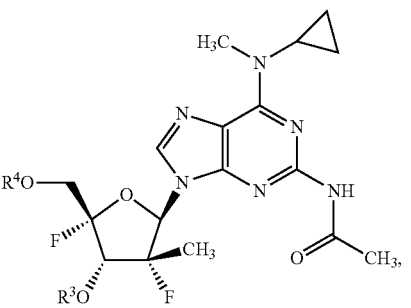
,
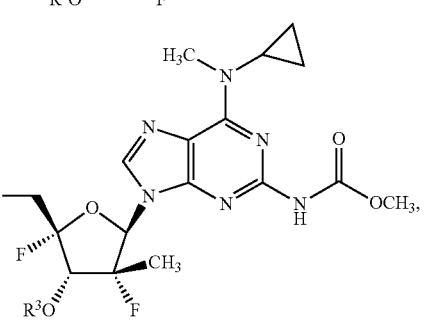
,
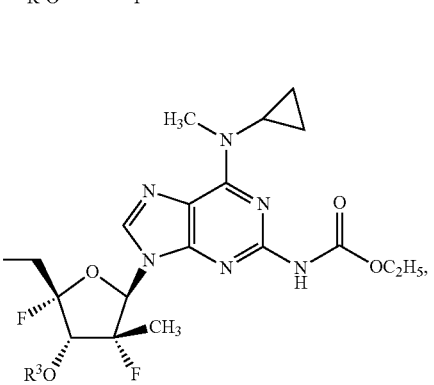
,
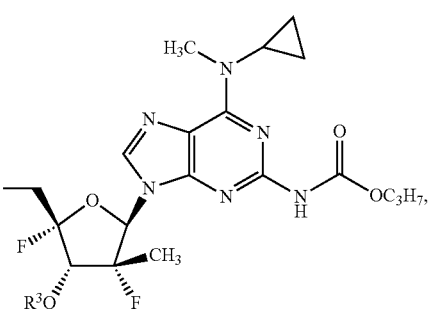
, -continued
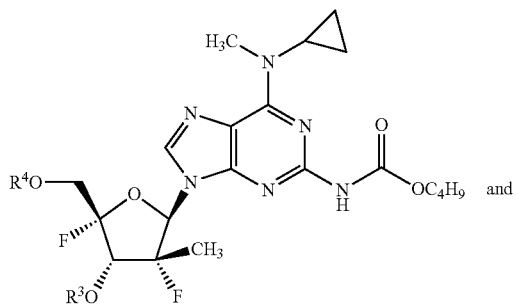
and
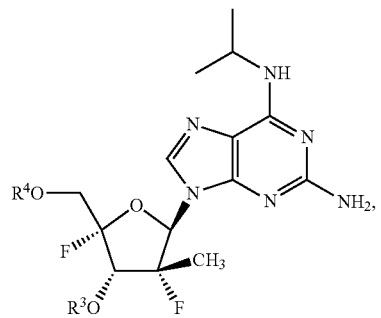
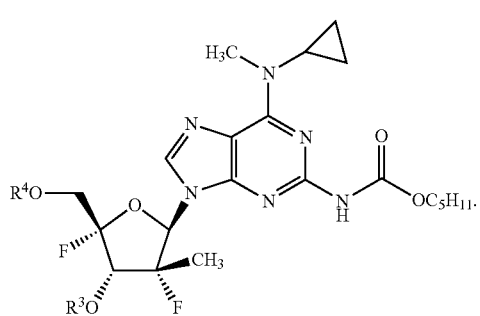
In one embodiment, a compound of Formula I is provided. Non-limiting examples of compounds of Formula I include:
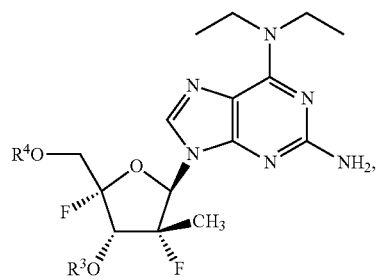
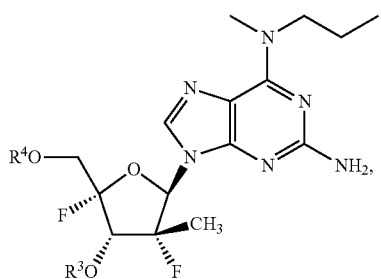
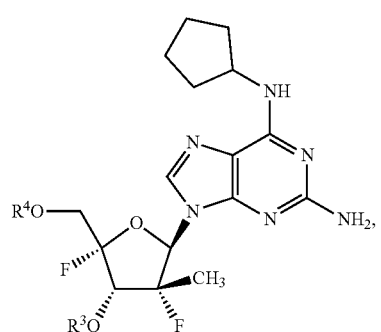
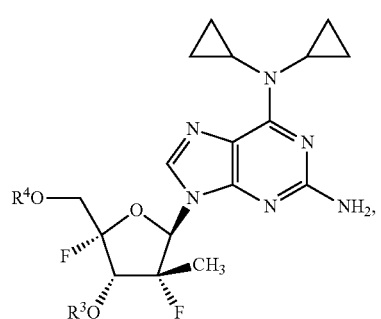

71
-continued
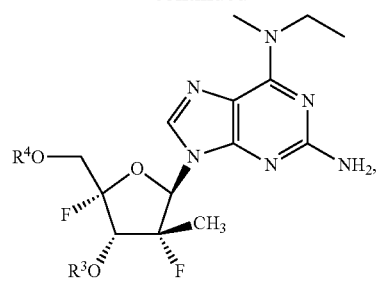
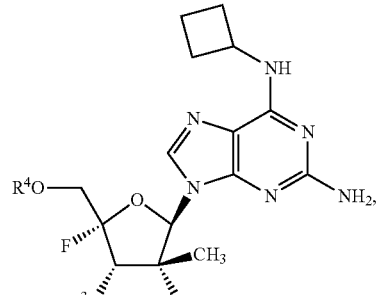
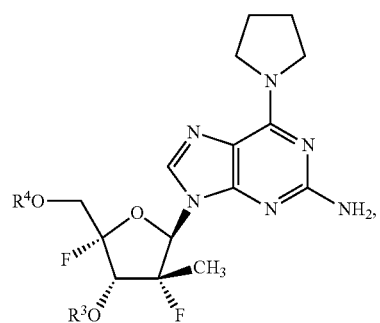
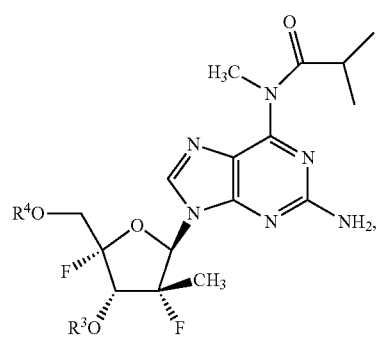
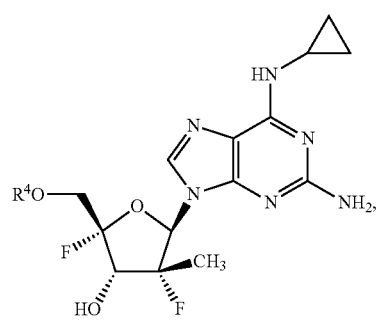
72
-continued
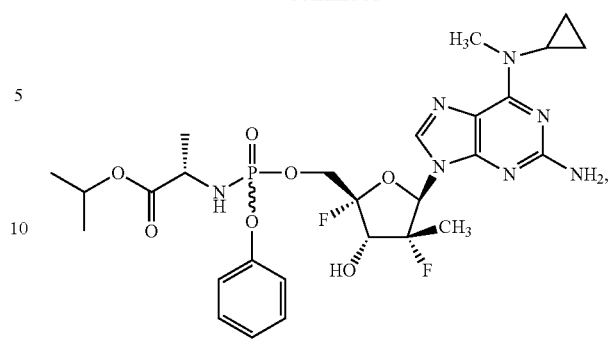
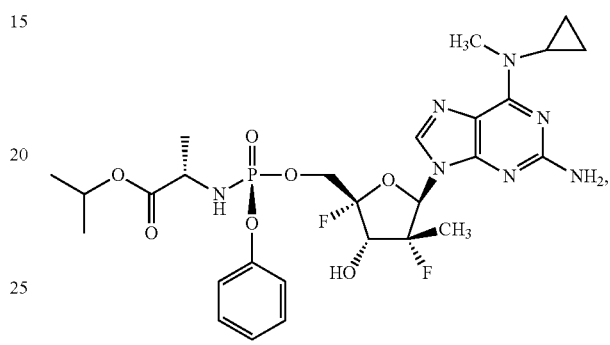
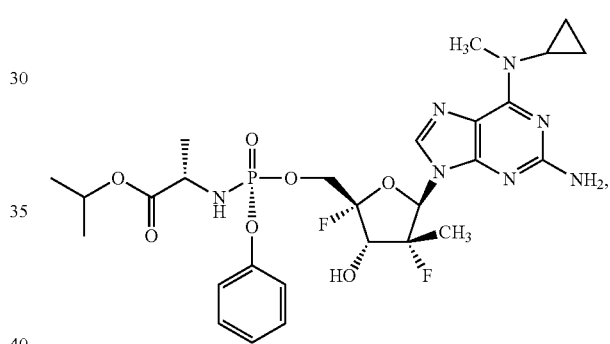
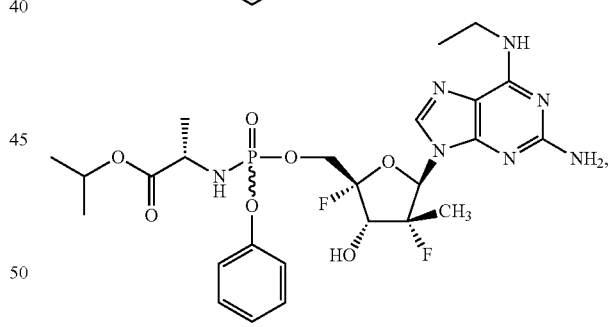
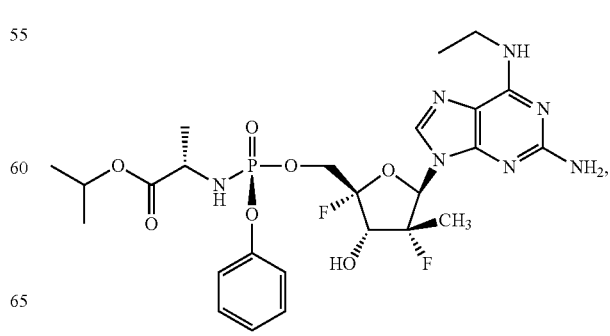

73
-continued
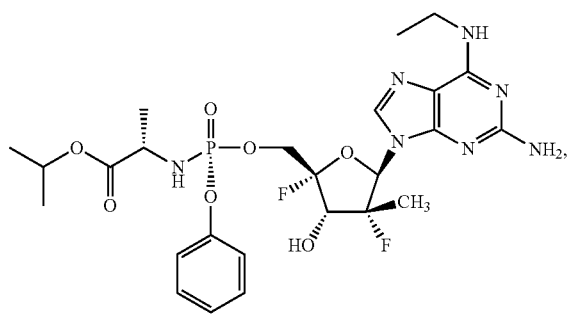
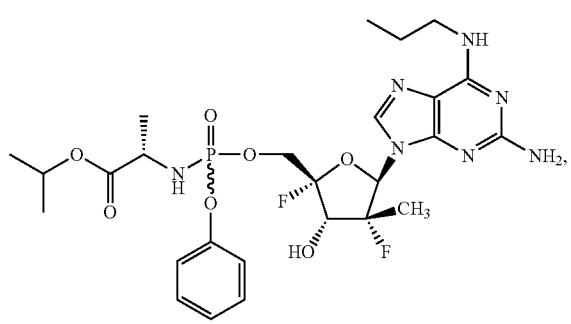
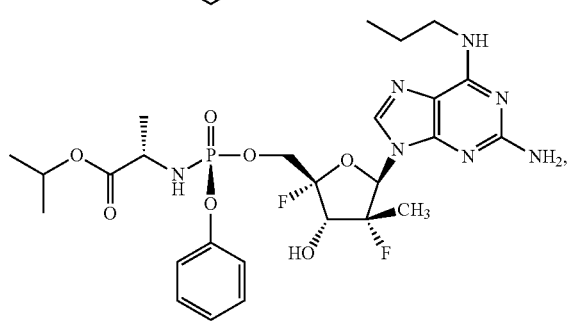
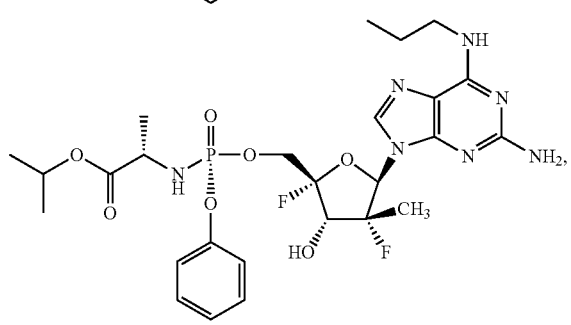
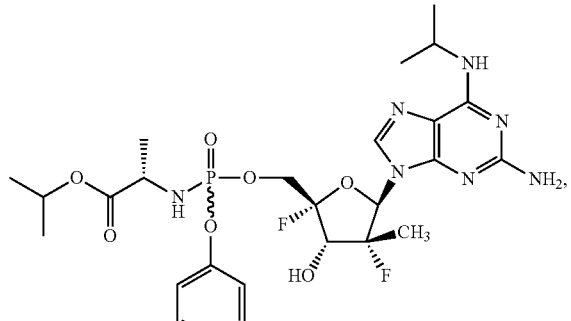
74
-continued
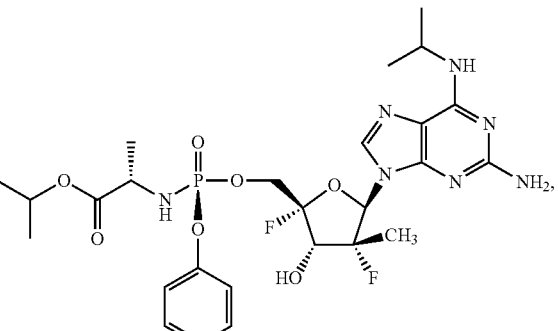
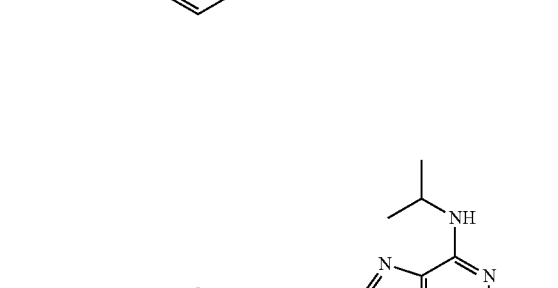
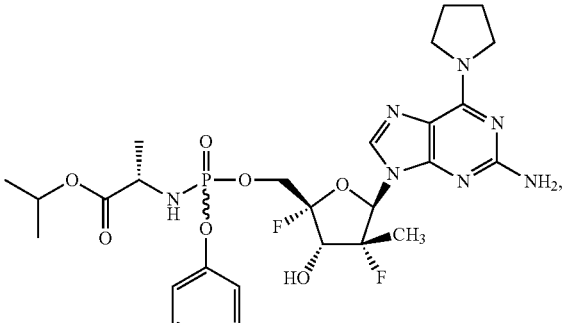
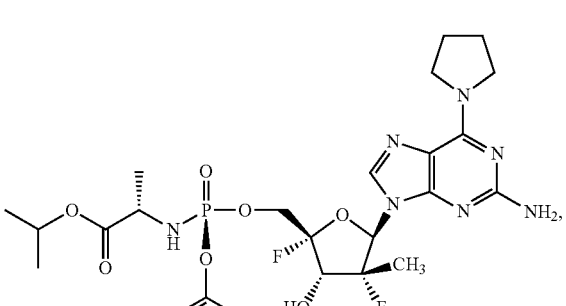

75
-continued
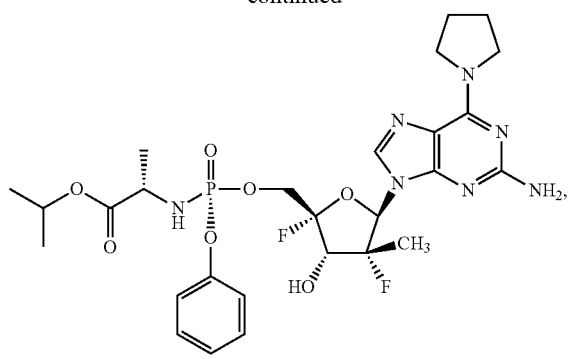
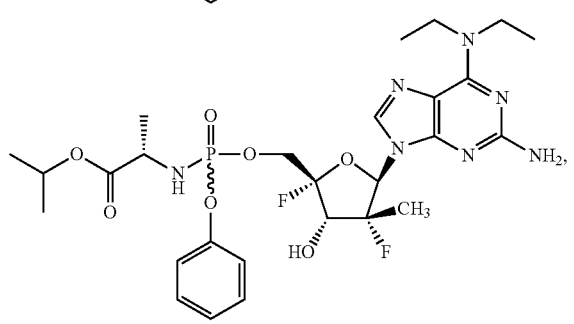
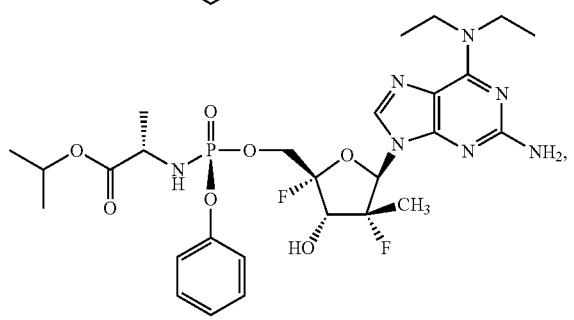
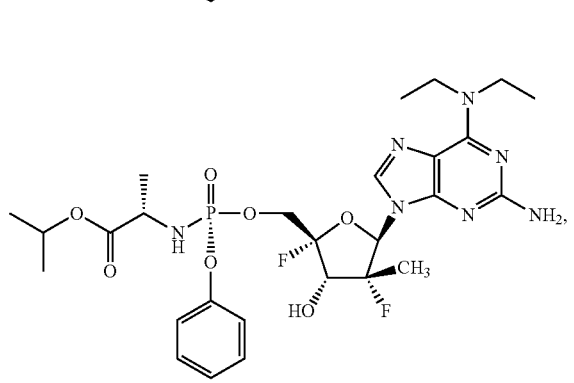
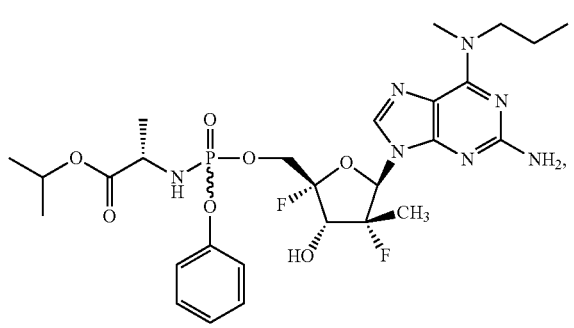
76
-continued
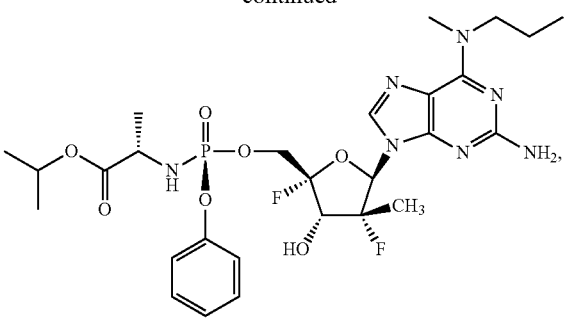
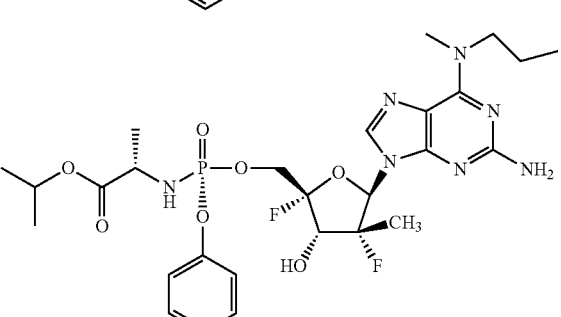
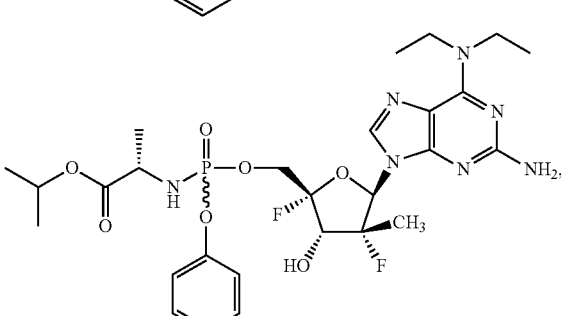
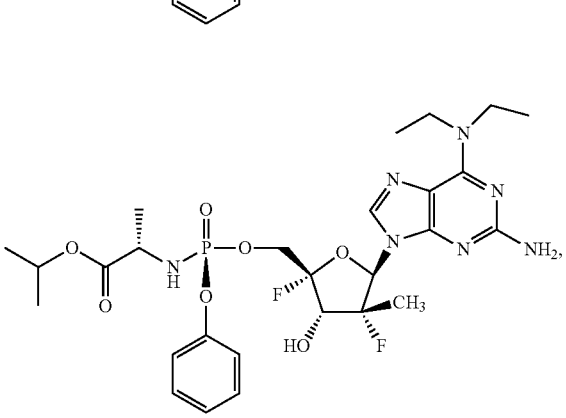
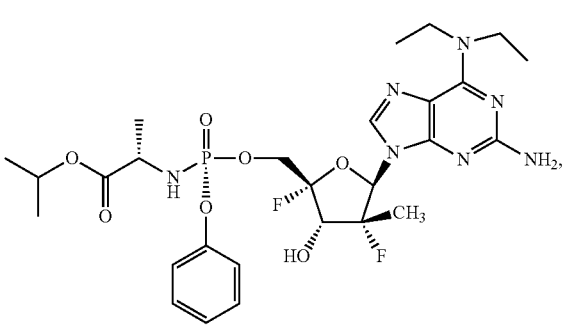

77
-continued
78
-continued
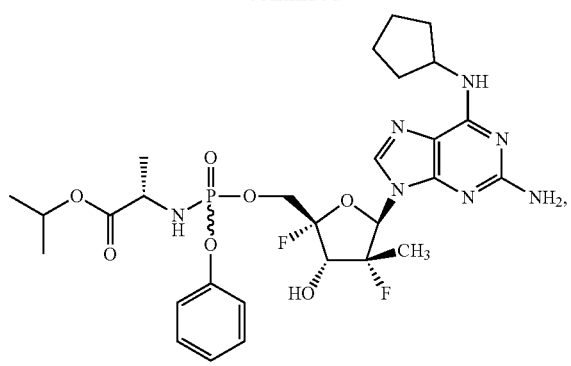
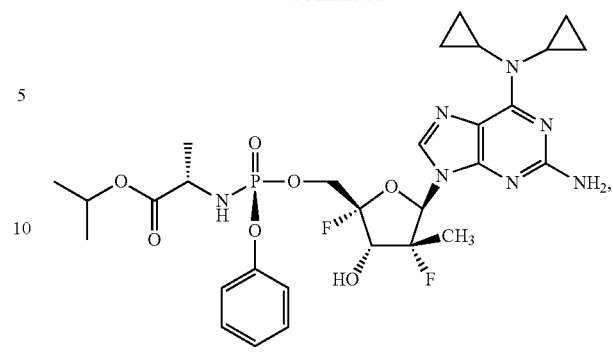

79
-continued
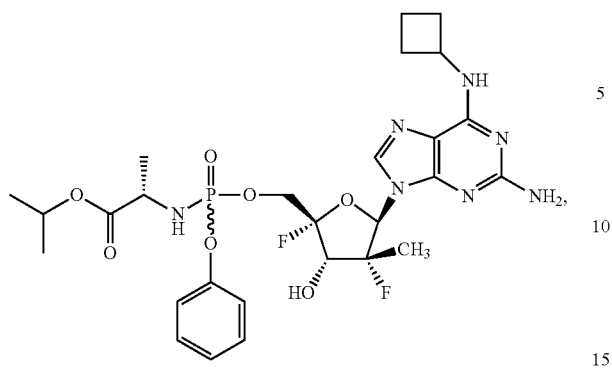
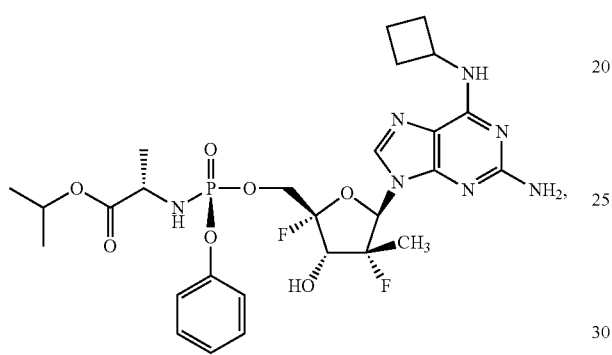
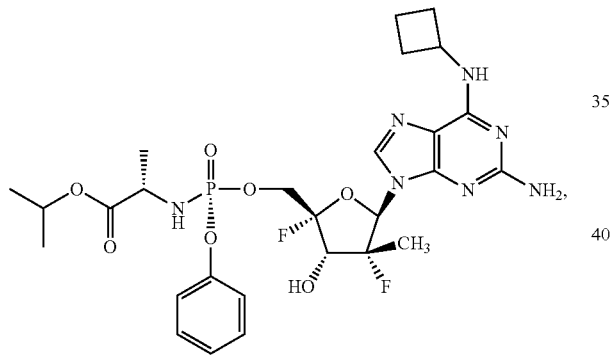
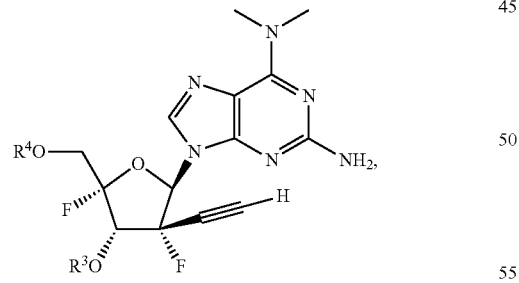
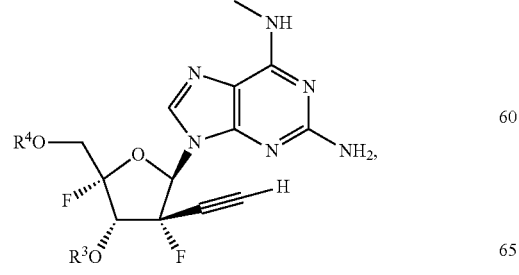
80
-continued
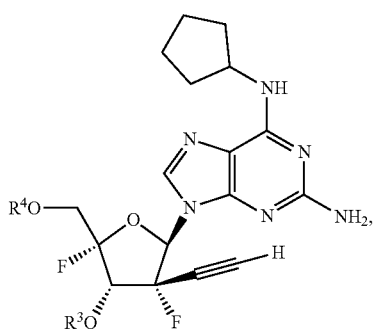
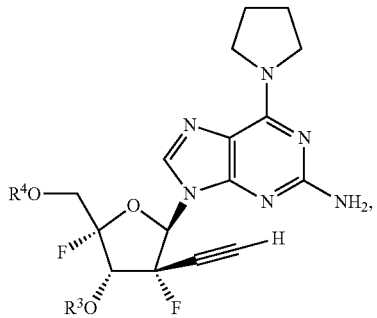
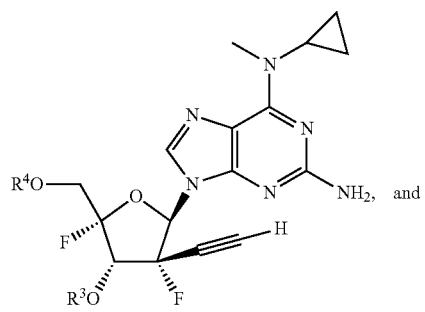
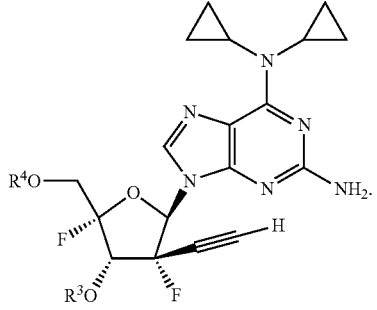
In one embodiment, a compound of Formula II is provided. Non-limiting examples of compounds of Formula II include:
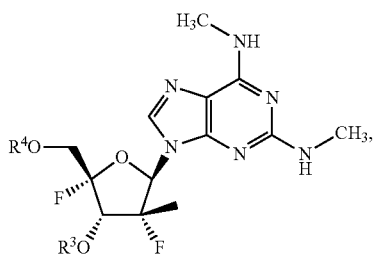

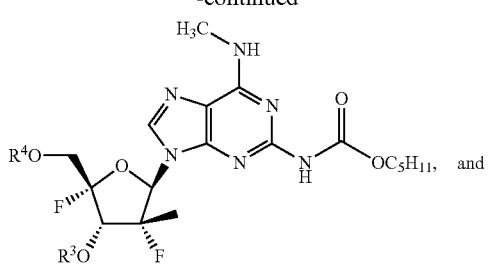
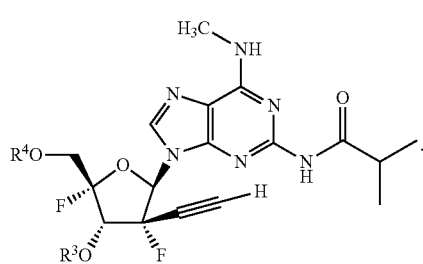
In one embodiment, a compound of Formula IX is provided. Non-limiting examples of compounds of Formula IX include:
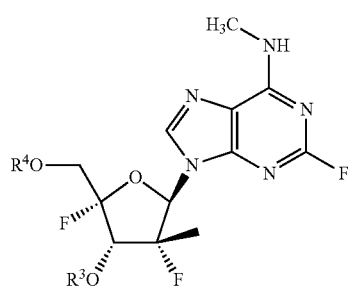
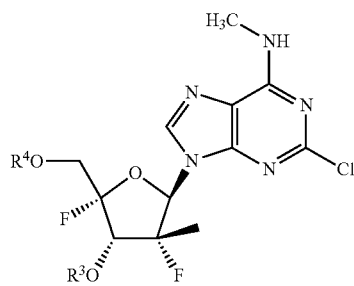
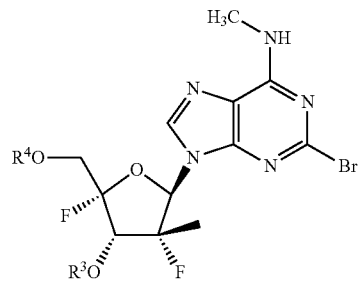
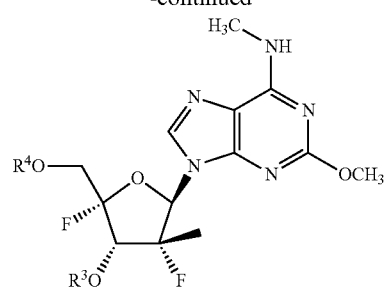
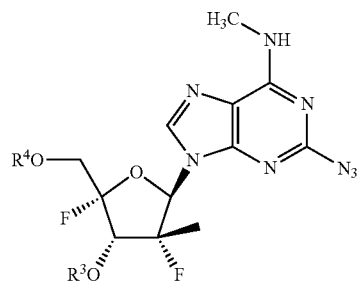
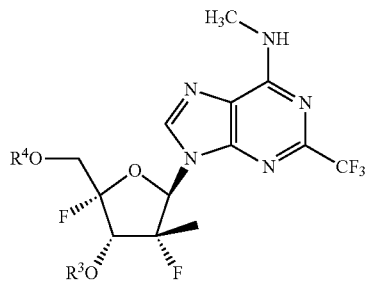
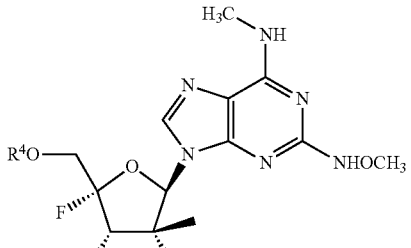
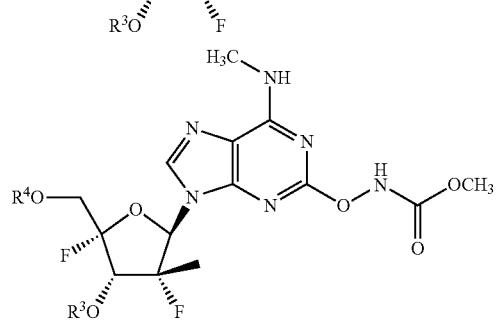
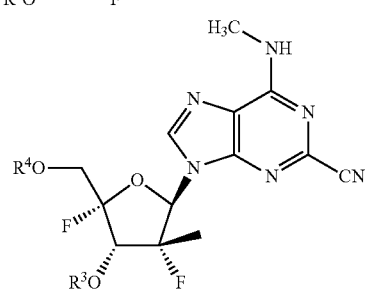

-continued
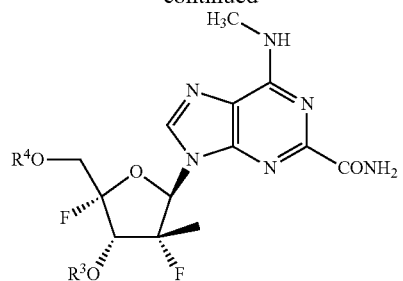
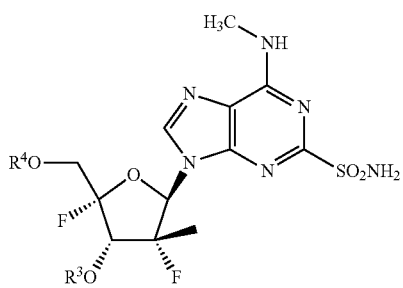
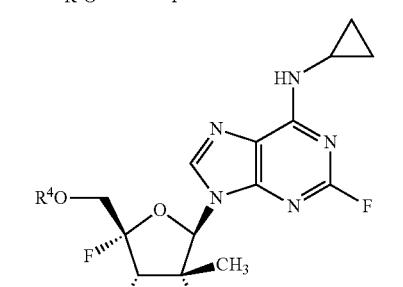
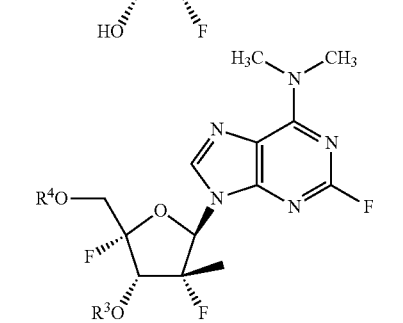
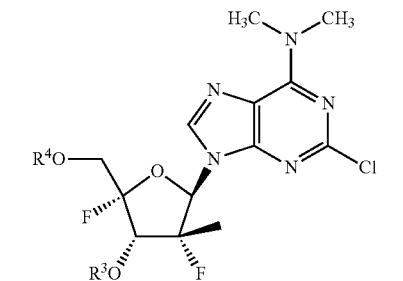
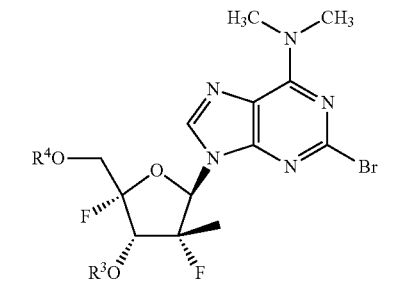
-continued
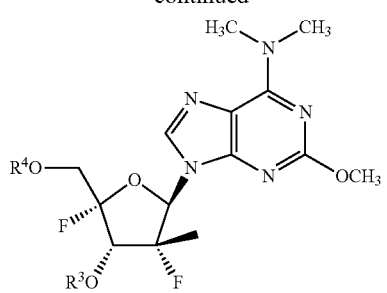
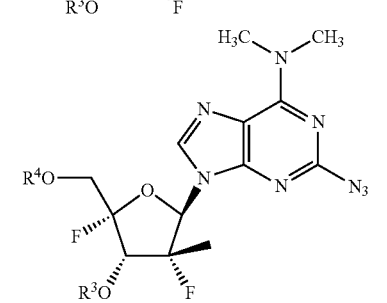
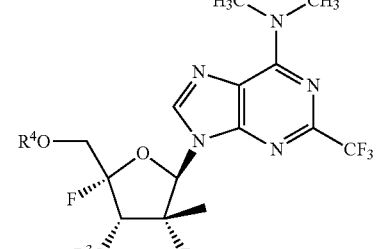
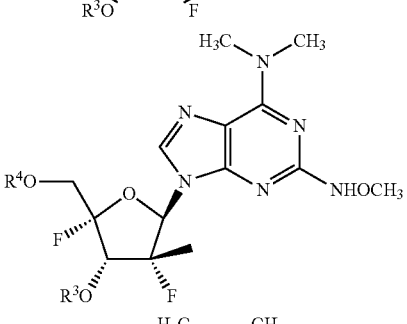
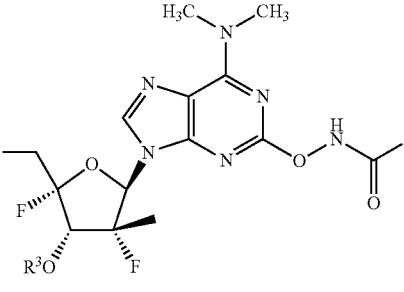
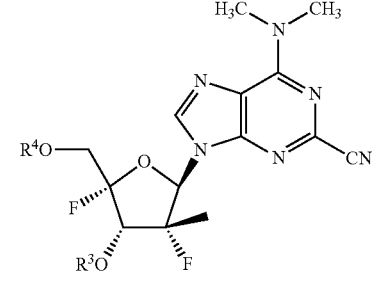

85
-continued
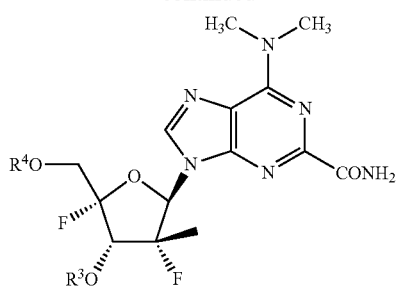
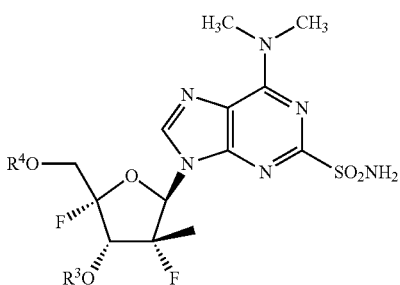
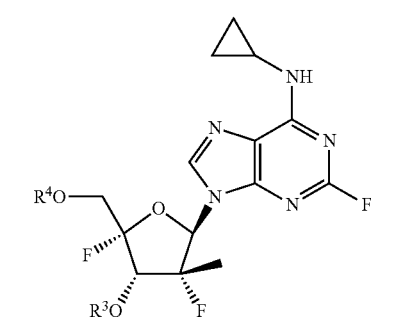
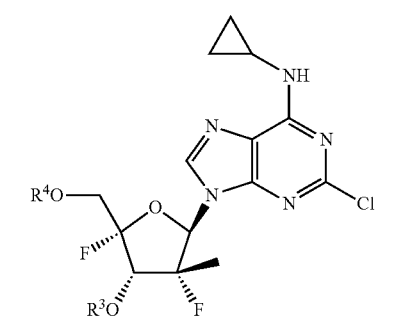
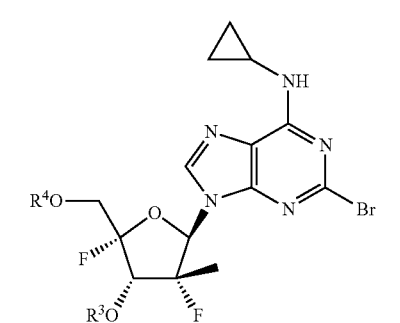
86
-continued
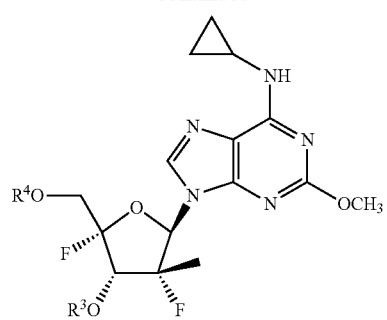
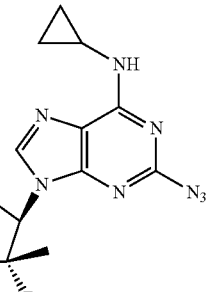
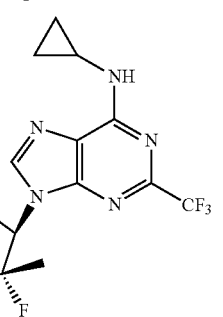
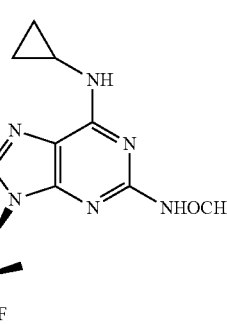
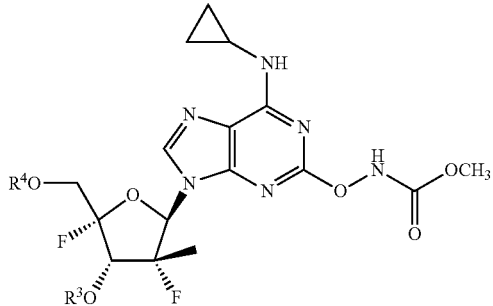

87
-continued
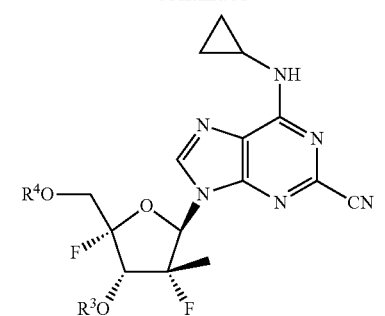
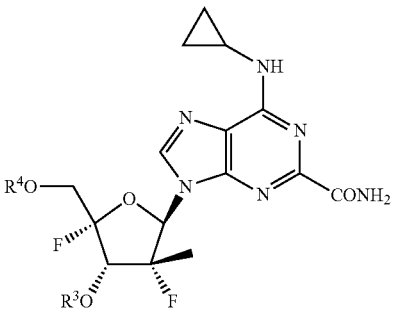
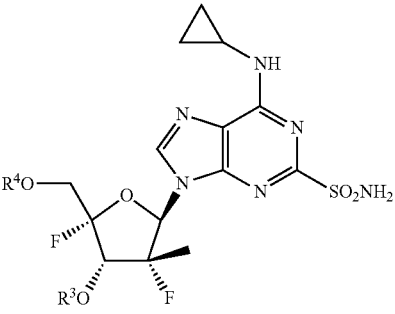
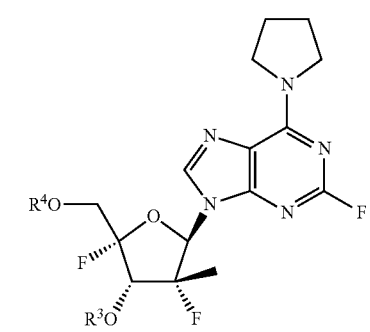
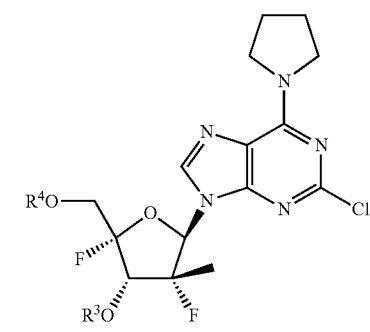
88
-continued
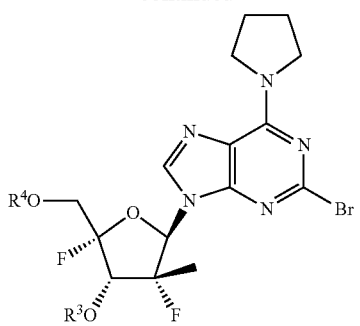
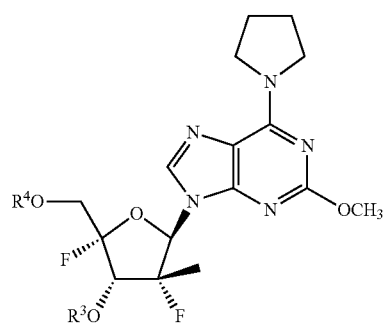
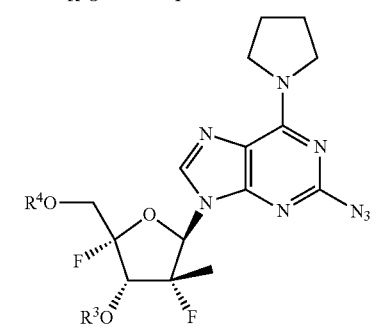
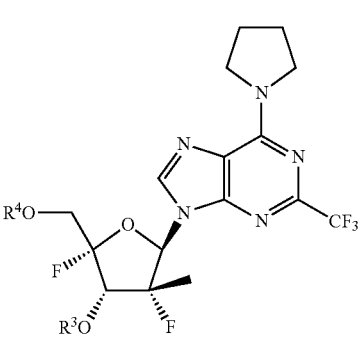
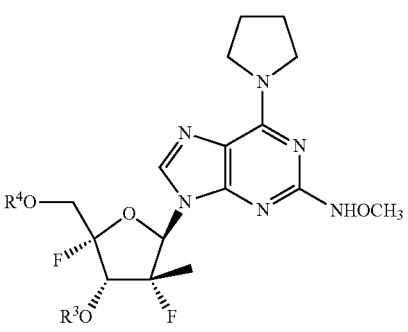

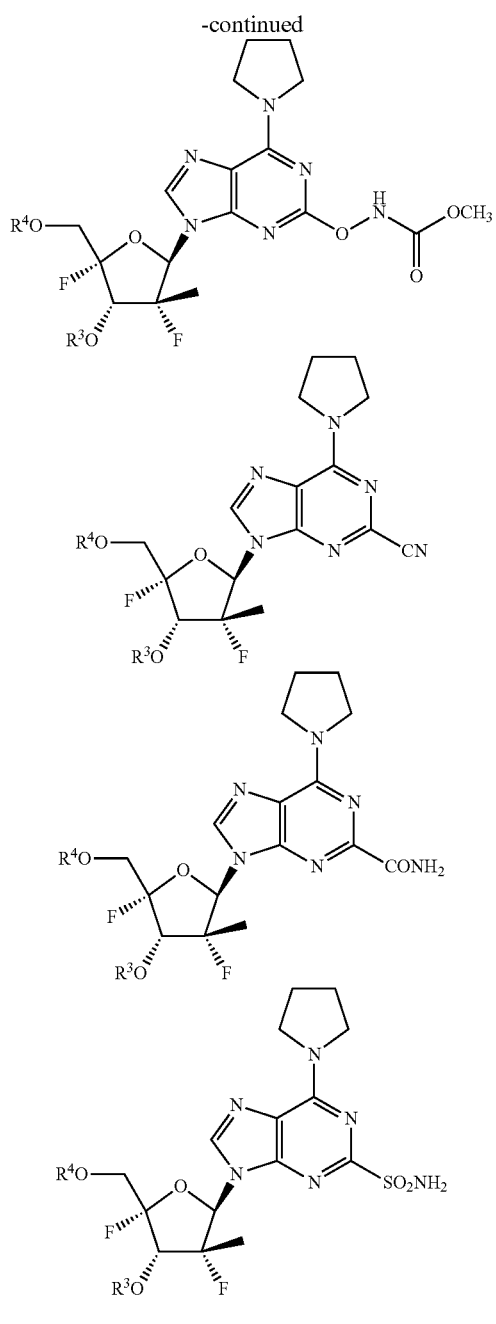
In one embodiment, a compound of Formula IX is provided. Non-limiting examples of compounds of Formula X include:
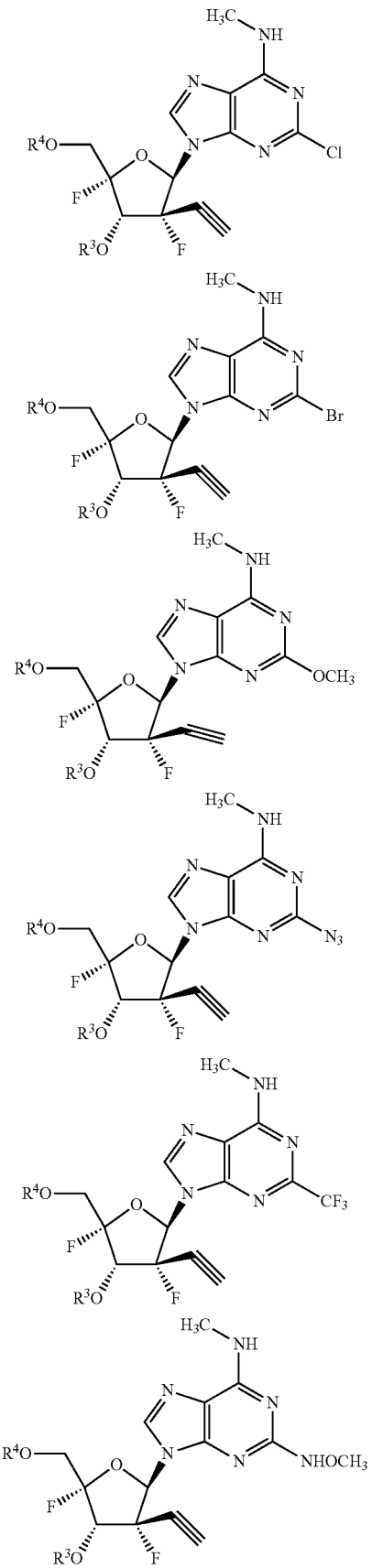

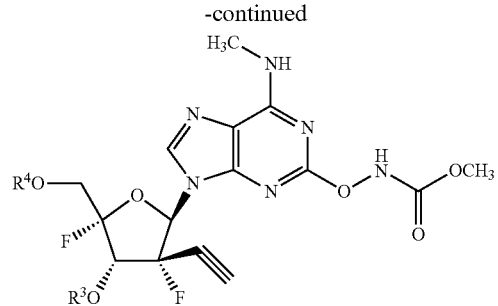
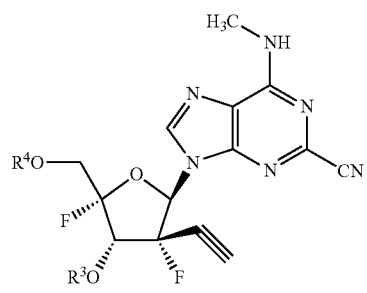
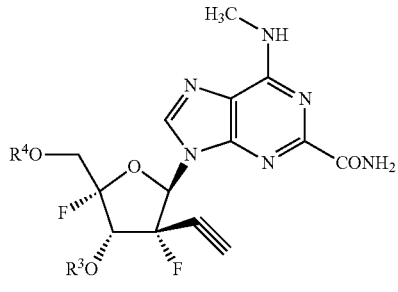
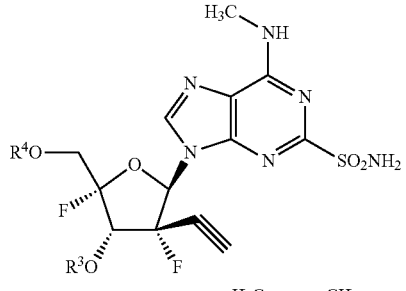
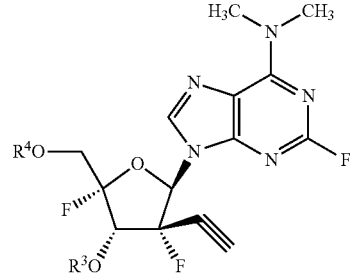
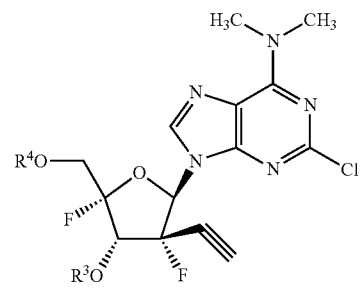
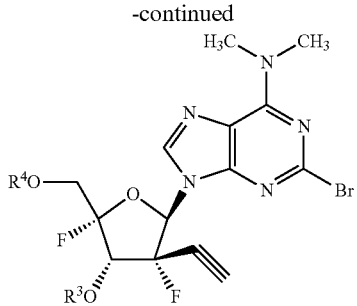
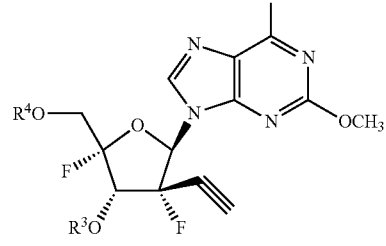
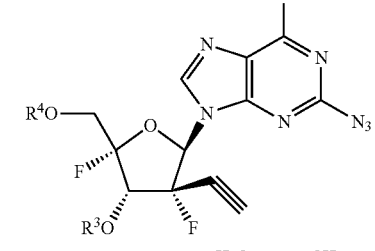
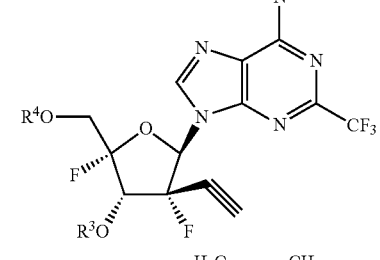
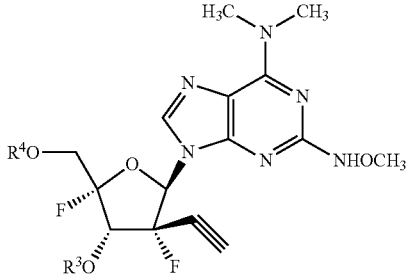
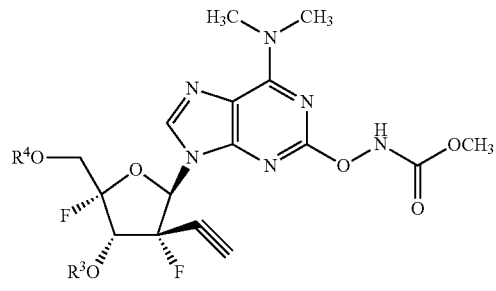

-continued
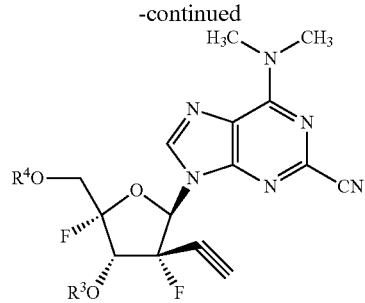
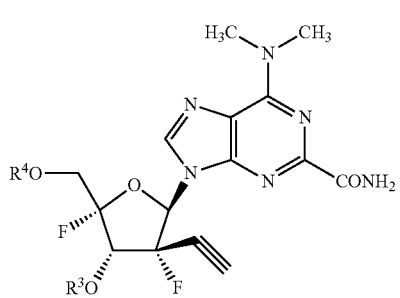
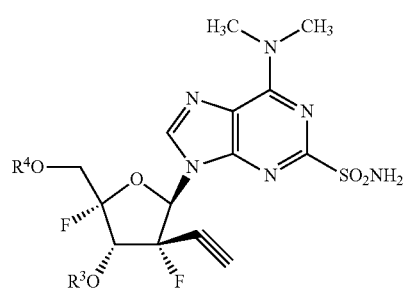
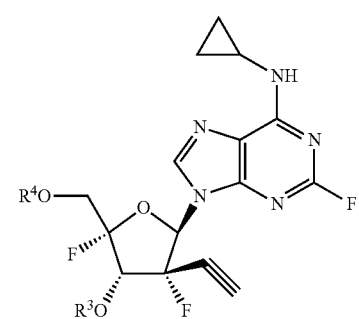
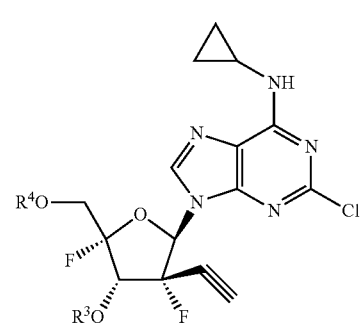
-continued
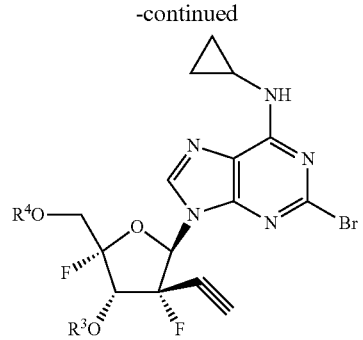
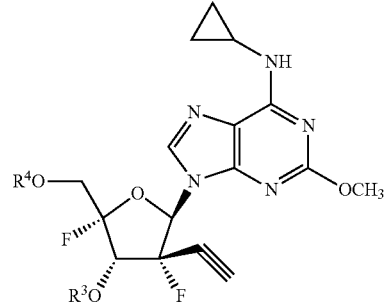
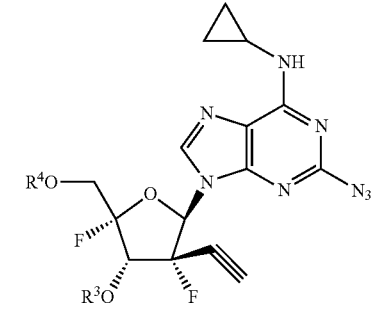
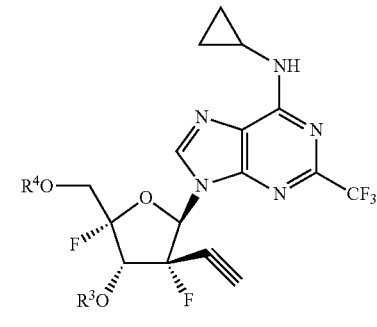
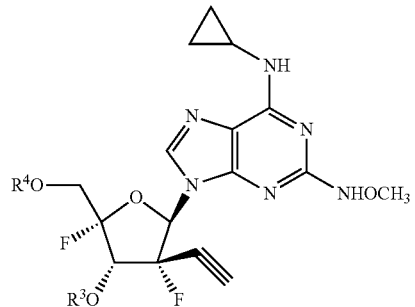

95
-continued
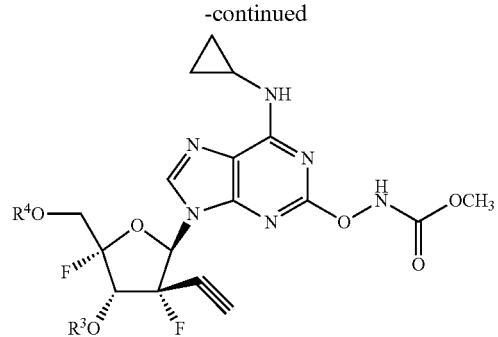
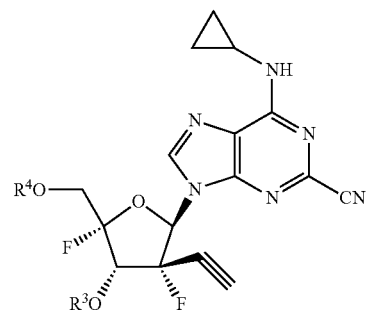
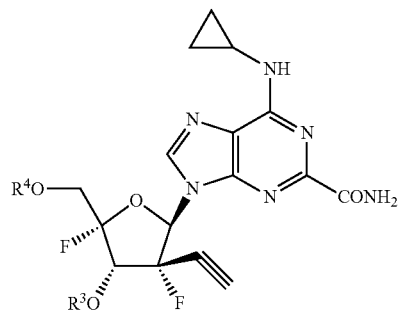
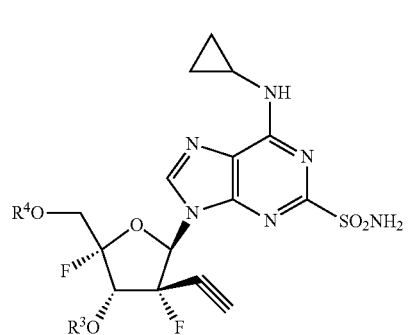
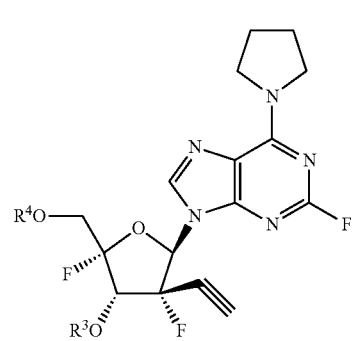
96
-continued
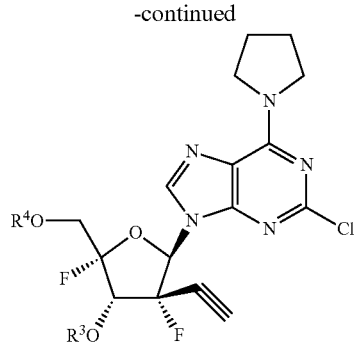
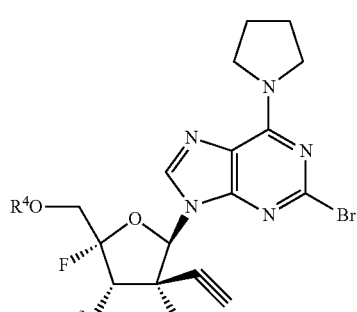
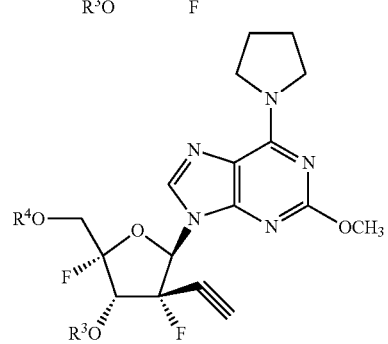
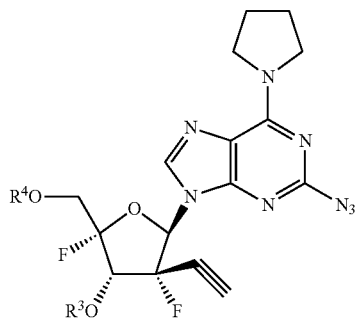
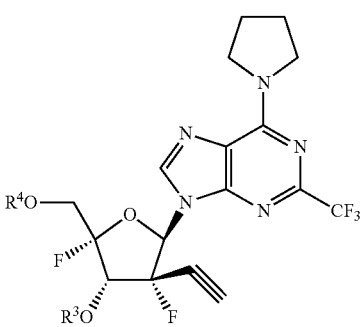

In one embodiment, $R^3$ is hydrogen and

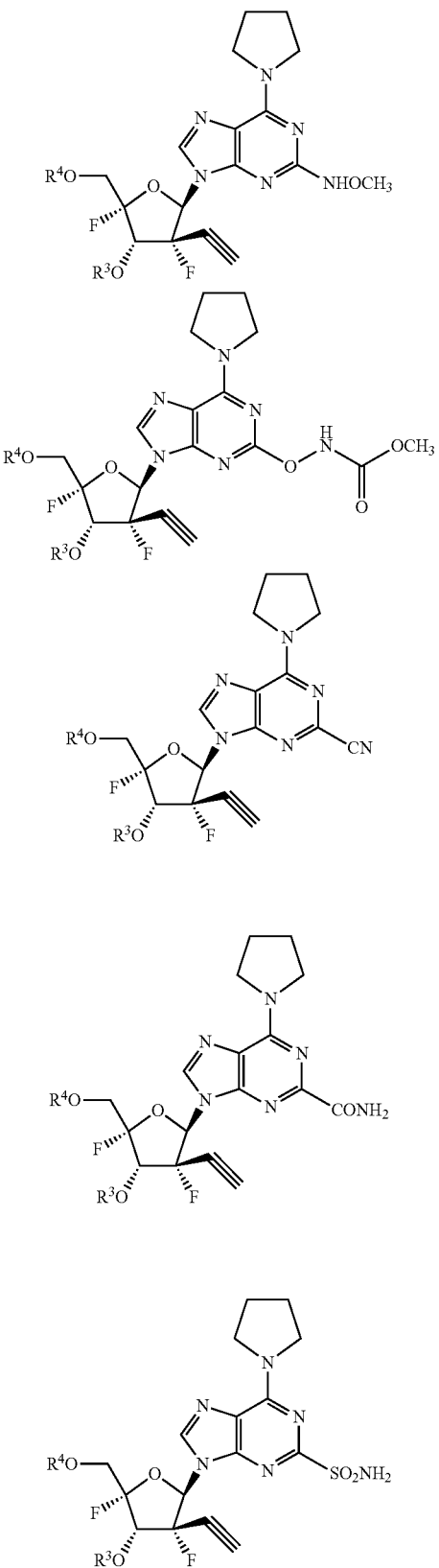

In one embodiment $R^3$ is hydrogen and $R^4$ is

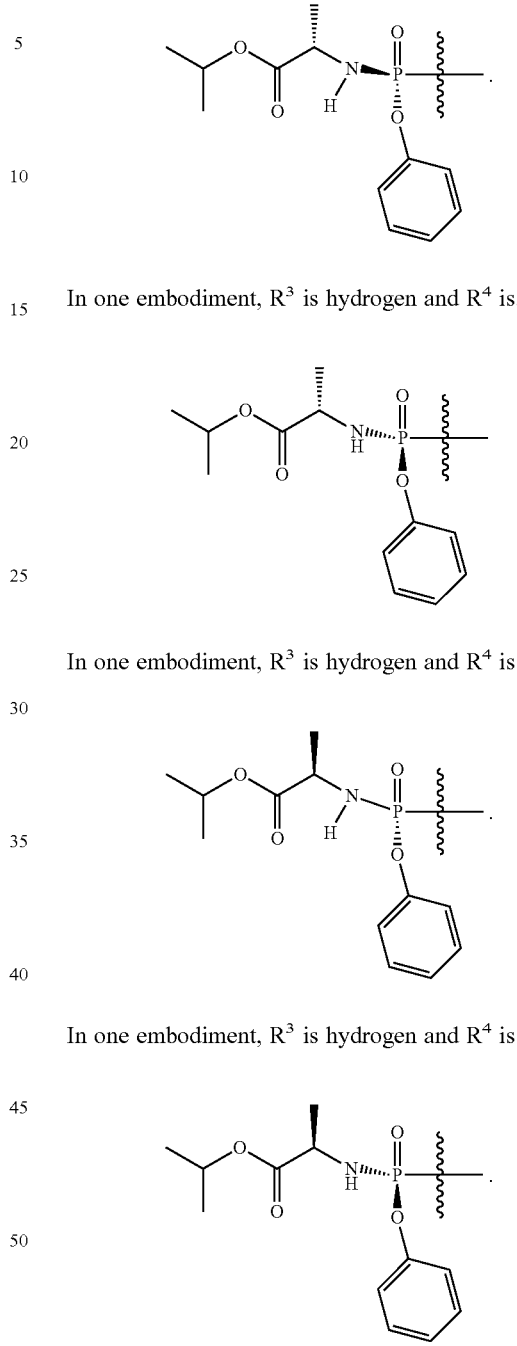

In one embodiment, $R^3$ is hydrogen and $R^4$ is.

In one embodiment, $R^3$ is hydrogen and $R^4$ is

In one embodiment, $R^3$ is hydrogen and $R^4$ is

II. Definitions

The following terms are used to describe the present invention. In instances where a term is not specifically defined herein, that term is given an art-recognized meaning by those of ordinary skill applying that term in context to its use in describing the present invention.

The term "pharmaceutically acceptable salt" or prodrug" is used throughout the specification to describe any pharmaceutically acceptable form (such as an ester, phosphoramidate, thiophosphoramidate, phosphate ester, salt of an ester, or a related group) of a 2'-deoxy-2'-α-fluoro-2'-β-C-substituted-4'-fluoro-$N^6$-substituted-2,6-diaminopurine nucleotide or 2'-deoxy-2'-α-fluoro-2'-β-C-substituted-4'-fluoro-$N^2,N^6$-disubstituted-2,6-diaminopurine nucleotide which, upon administration to a patient, provides the desired active compound. Examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made.

"Pharmaceutically acceptable prodrug" refers to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated, thiophosphoramidated, dethiophosphoramidated, phosphoramidated or dephosphoramidated to produce the active compound. The compounds of this invention possess antiviral activity against HCV, or are metabolized to a compound that exhibits such activity. The β-D-2'-deoxy-2'-α-fluoro-2'-β-C-substituted-4'-fluoro-$N^6$-substituted-2,6-diaminopurine nucleoside can also be administered as a 5'-phosphoether lipid, a bisphosphoramidate, a 3',5'-cyclic phosphoramidate, a 3',5'-cyclic thiophosphoramidate, a DTE conjugate, a mixed phosphoramidate-SATE derivative or a "SATE" derivative.

The term "substituted" or "optionally substituted" indicates that the moiety can have at least one additional substituent, including but not limited to amino, halogen (F, Cl, Br, I), OH, phenyl, benzyl, $N_3$, CN, alkyl, including methyl; alkenyl, alkynyl, alkoxy, haloalkyl; including $CHF_2$, $CH_2F$ and $CF_3$; etc.

The term "alkyl" shall mean within its context, a linear, or branch-chained fully saturated hydrocarbon radical or alkyl group which can be optionally substituted (for example, with halogen, including F). For example, an alkyl group can have 1, 2, 3, 4, 5, 6, 7 or 8 carbon atoms (i.e., $C_1$-$C_8$ alkyl), 1, 2, 3, 4, 5 or 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl, ethyl, n-propyl, iso-propyl, n-butyl, isobutyl, sec-butyl, tert-butyl, pentyl, isopentyl, tert-pentyl, neopentyl, hexyl, 2-methylpentyl, 3-methylpentyl, 2,2-dimethylbutyl and 2,3-dimethylbutyl.

The term "alkenyl" refers to a non-aromatic hydrocarbon group which contains at least one double bond between adjacent carbon atoms and a similar structure to an alkyl group as otherwise described herein. For example, an alkenyl group can have 2 to 8 carbon atoms (i.e., $C_2$-$C_8$ alkenyl), or 2 to 4 carbon atoms (i.e., $C_2$-$C_4$ alkenyl). Examples of suitable alkenyl groups include, but are not limited to, ethenyl or vinyl (—CH=$CH_2$), allyl (—$CH_2$CH=$CH_2$), 1-butenyl (—C=CH—$CH_2CH_3$) and 2-butenyl (—$CH_2$CH=$CHCH_3$). The alkenyl group can be optionally substituted as described herein.

The term "alkynyl" refers to a non-aromatic hydrocarbon group containing at least one triple bond between adjacent carbon atoms and a similar structure to an alkyl group as otherwise described herein. For example, an alkynyl group can have 2 to 8 carbon atoms (i.e., $C_2$-$C_8$ alkyne,), or 2 to 4 carbon atoms (i.e., $C_2$-$C_4$ alkynyl). Examples of alkynyl groups include, but are not limited to, acetylenic or ethynyl and propargyl. The alkynyl group can be optionally substituted as described herein.

The term "aryl" or "aromatic", in context, refers to a substituted (as otherwise described herein) or unsubstituted monovalent aromatic radical having a single ring (e.g., phenyl or benzyl) or condensed rings (e.g., naphthyl, anthracenyl, phenanthrenyl, etc.) and can be bound to the compound according to the present invention at any available stable position on the ring(s) or as otherwise indicated in the chemical structure presented. The aryl group can be optionally substituted as described herein.

"Cycloalkyl", "carbocycle", or "carbocyclyl" refers to a saturated (i.e., cycloalkyl) or partially unsaturated (e.g., cycloalkenyl, cycloalkadienyl, etc.) ring having 3 to 7 carbon atoms as a monocycle. Monocyclic carbocycles have 3 to 7 ring atoms, still more typically 5 or 6 ring atoms. Non-limiting examples of cycloalkyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, a n d 1-cyclo-hex-3-enyl.

A heteroaryl ring system is a saturated or unsaturated ring with one or more nitrogen, oxygen, or sulfur atoms in the ring (monocyclic) including but not limited to imidazole, furyl, pyrrole, furanyl, thiene, thiazole, pyridine, pyrimidine, purine, pyrazine, triazole, oxazole, or fused ring systems such as indole, quinoline, etc., among others, which may be optionally substituted as described above. Heteroaryl groups include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazino-pyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N, or S, and may be aromatic (heteroaryl) or non-aromatic. Exemplary non-aromatic heterocyclic groups for use in the present invention include, for example, pyrrolidinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethylene urea, 1,3-dioxolane, 1,3-dioxane, 1,4-dioxane, phthalimide, and succinimide, among others, all of which may be optionally substituted.

In one embodiment, the term purine or pyrimidine base includes, but is not limited to, adenine, $N^6$-alkylpurines, $N^6$-acylpurines (wherein acyl is —C(O)alkyl, —C(O)(aryl) $C_0$-$C_4$alkyl, or —C(O)($C_0$-$C_4$alkyl)aryl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, optionally substituted 2,6-diaminopurine, and 6-chloropurine. Functional oxygen and nitrogen groups on the base can be protected as necessary or desired. Suitable protecting groups are well known to those skilled in the art, and include benzyl, trimethylsilyl, dimethylhexylsilyl, t-butyldimethylsilyl, t-butyldiphenylsilyl, trityl, alkyl groups, and acyl groups such as acetyl and propionyl; methanesulfonyl, and p-toluenesulfonyl. Alternatively, the purine or pyrimidine base can optionally be substituted such that it forms a viable prodrug, which can be cleaved in vivo. Examples of appropriate substituents include an acyl moiety.

The term "acyl" refers to a the moiety in which the carbonyl moiety, for example, —C(O)alkyl, is selected from alkyl, cycloalkyl, lower alkyl (i.e., $C_1$-$C_4$); alkoxyalkyl, including methoxymethyl; aralkyl-including benzyl, aryloxyalkyl-such as phenoxymethyl; aryl including phenyl optionally substituted with halogen, $C_1$-$C_4$ alkyl or $C_1$-$C_4$ alkoxy. In one embodiment, the term "acyl" refers to a mono, di or triphosphate.

The term "lower acyl" refers to an acyl group in which the carbonyl moiety is lower alkyl (i.e., $C_1$-$C_4$).

The term sulfonate esters, represented by the formula, $R^{14}S(O)_2OR^{15}$, comprise $R^{14}$ wherein $R^{14}$ is alkyl, haloalkyl, aralkyl or aryl. $R^{15}$ is alkyl, aryl or aralkyl.

The term "amino acid" or "amino acid residue" refers to a D- or L-natural or non-naturally occurring amino acid. Representative amino acids include, but are not limited to, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine, among others.

The term "nitrogen-protecting group" as used herein refers to a moiety that is covalently attached to nitrogen and which can be removed, and typically replaced with hydrogen, when appropriate. For example, a nitrogen-protecting group may be a group that is removed in vivo after administration to a host, in vitro by a cell, or it may be removed during a manufacturing process. Suitable nitrogen-protecting groups useful in the present invention are described by Greene and Wuts in Protective Groups in Organic Synthesis (1991) New York, John Wiley and Sons, Inc.

The term "oxygen-protecting group" as used herein refers to a moiety that is covalently attached to oxygen and which can be removed, and typically replaced with hydrogen, when appropriate. For example, an oxygen-protecting group may be a group that is removed in vivo after administration to a host, in vitro by a cell, or it may be removed during a manufacturing process. Suitable oxygen-protecting groups useful in the present invention are described by Greene and Wuts in Protective Groups in Organic Synthesis (1991) New York, John Wiley and Sons, Inc.

Phosphate ester refers to mono, di, and tri phosphates unless otherwise indicated.

The term "phosphoamidate", "phosphoramidate", or "phosphoroamidate" is a moiety that has a phosphorus bound to three oxygen groups and an amine (which may optionally be substituted). Suitable phosphoramidates useful in the present invention are described by Madela, Karolina and McGuigan in 2012, "Progress in the development of anti-hepatitis C virus nucleoside and nucleotide prodrugs", Future Medicinal Chemistry 4(5), pages 625-650 10:1021/jm300074y and Dominique, McGuigan and Balzarini in 2004, "Aryloxy Phosphoramidate Triesters as Pro-Tides", Mini Reviews in Medicinal Chemistry 4(4), pages 371-381. Additional phosphoramidates useful in the present invention are described in U.S. Pat. Nos. 5,233,031, 7,115,590, 7,547, 704, 7,879,815, 7,888,330, 7,902,202, 7,951,789, 7,964,580, 8,071,568; 8,148,349, 8,263,575, 8,324,179, 8,334,270, 8,552,021, 8,563,530, 8,580,765, 8,735,372, 8,759,318; EP 2120565; EP 1143995; U.S. Pat. Nos. 6,455,513; and 8,334, 270. Other phosphoramidates are described in the nucleoside patents described in the Background of the Invention.

Phosphoramidate groups for use in the present invention include those of the structures:

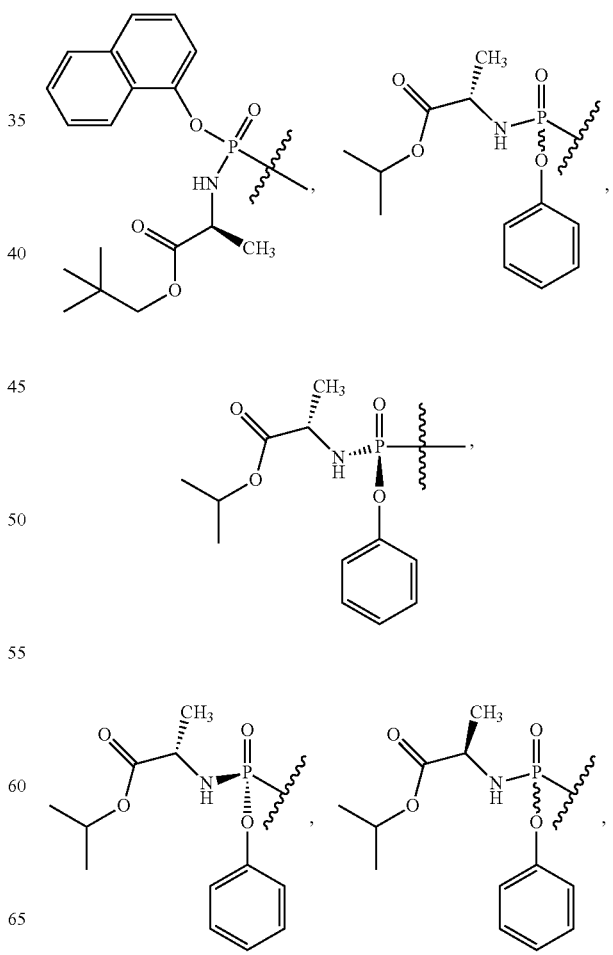

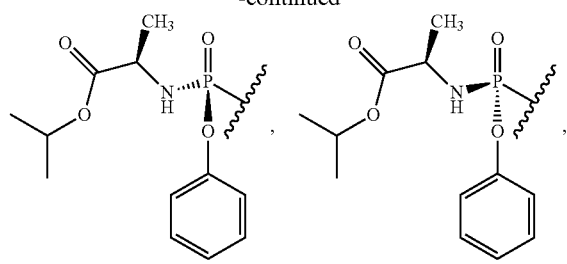

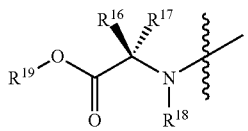

Other phosphoramidates for use in the present invention include those of the structure:

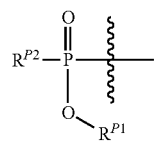

wherein:

$R^{P1}$ is an optionally substituted linear, branched, or cyclic alkyl group, or an optionally substituted aryl, heteroaryl or heterocyclic group or a linked combination thereof; and $R^{P2}$ is a $—NR^{N1}R^{N2}$ group or a B' group;

wherein:

$R^{N1}$ and $R^{N2}$ are each independently H, $C_{1-8}$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; which may be optionally substituted;

$R^{N1}$ and $R^{N2}$ along with the nitrogen atom to which that are attached, join to form a 3 to 7 membered heterocyclic ring;

B' is a group;

wherein:

$R^{16}$ is hydrogen, $(C_1-C_8)$alkyl, $(C_2-C_8)$alkenyl, $(C_2-C_8)$alkynyl, $(C_3-C_8$cycloalkyl)$C_0$-$C_4$alkyl-, (aryl)$C_0$-$C_4$alkyl-, $(C_3-C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);

$R^{17}$ is hydrogen, $(C_1-C_8)$alkyl, $(C_2-C_8)$alkenyl, $(C_2-C_8)$alkynyl, $(C_3-C_8$cycloalkyl)$C_0$-$C_4$alkyl-, (aryl)$C_0$-$C_4$alkyl-, $(C_3-C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);

$R^{18}$ is hydrogen or $C_1$-$C_3$alkyl; or $R^{16}$ and $R^{17}$ can form a $(C_3$-$C_7)$cycloalkyl or $(C_3$-$C_7)$ heterocyclic group; or $R^{18}$ and $R^{16}$ or $R^{17}$ can form $(C_3$-$C_6)$heterocyclic group; and $R^{19}$ is hydrogen, $(C_1-C_6)$alkyl, $(C_3-C_6)$alkenyl, $(C_3-C_6)$ alkynyl, $(C_3-C_8$cycloalkyl)$C_0$-$C_4$alkyl-, (aryl)$C_0$-$C_4$alkyl-, $(C_3-C_6$heterocyclo)$C_0$-$C_4$alkyl-, (heteroaryl)$C_0$-$C_4$alky-; or B' is a

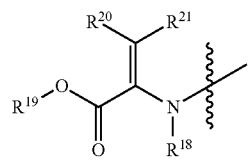

group;

wherein:

$R^{20}$ is hydrogen, $(C_1$-$C_3)$alkyl, $(C_3$-$C_8$cycloalkyl$)C_0$-$C_4$alkyl-, (aryl)$C_0$-$C_4$alkyl-, $(C_3$-$C_6$heterocyclo$)C_0$-$C_4$alkyl-, or (heteroaryl)$C_0$-$C_4$alky-;

$R^{21}$ is hydrogen, $(C_1$-$C_3)$alkyl, $(C_3$-$C_8$cycloalkyl$)C_0$-$C_4$alkyl-, (aryl)$C_0$-$C_4$alkyl-, $(C_3$-$C_6$heterocyclo$)C_0$-$C_4$alkyl-, or (heteroaryl)$C_0$-$C_4$alky-; and $R^{18}$ and $R^{19}$ are as defined above.

Preferred $R^{P1}$ groups include optionally substituted phenyl, naphthyl, and monocyclic heteroaryl groups, especially those groups (particularly lipophilic groups) which enhance bioavailability of the compounds in the cells of the patient and which exhibit reduced toxicity, enhanced therapeutic index and enhanced pharmacokinetics (the compounds are metabolized and excreted more slowly).

The term phosphoramidate is used throughout the specification to describe a group that is found at the 5'- or 3'-position of the furanose ring of the nucleoside compound and forms a prodrug form of the nucleoside compound. In one embodiment, phosphoramidates can be found at both the 5'- and 3'-position of the furanose ring of the nucleoside compound and form a prodrug form of the nucleoside compound. In another embodiment, the phosphoramidate found at the 5' position of the furanose ring of the nucleoside can form a cyclic phosphoramidate compound by forming a bond with the 3'-hydroxyl substituent at the 3' position of the furanose ring of the nucleoside compound and form a prodrug form of the nucleoside compound.

The term "thiophosphoamidate", "thiophosphoramidate", or "thiophosphoroamidate" is a moiety that has a phosphorus bound to sulfur (P=S), two oxygen groups and an amine (which may optionally be substituted). Thiophosphoramidates useful in the present invention are described in U.S. Pat. No. 8,772,474 and WO 2012/040124.

Thiophosphoramidate groups for use in the present invention include those of the structures:

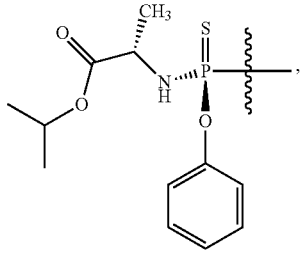

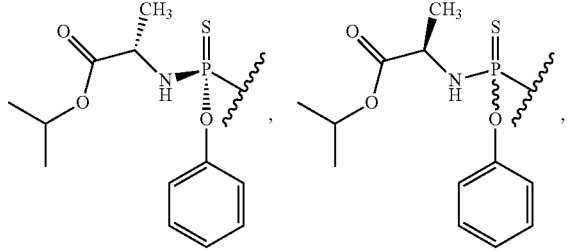

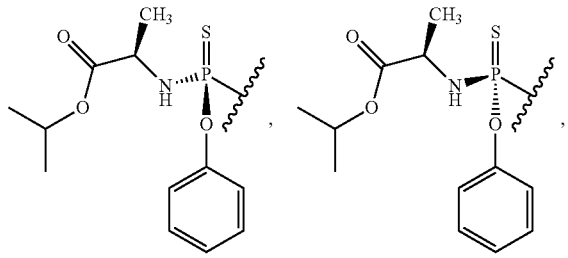

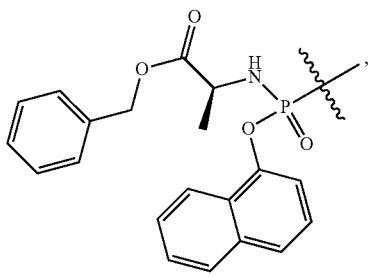

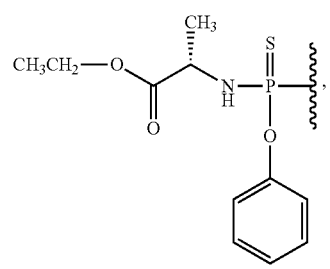

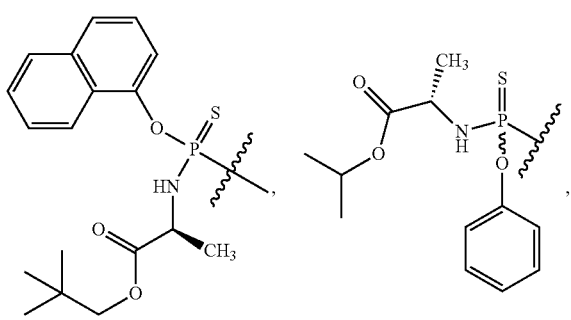

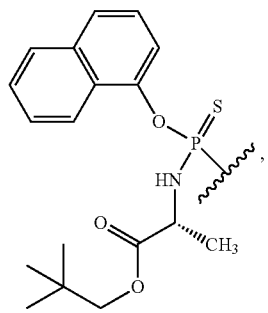

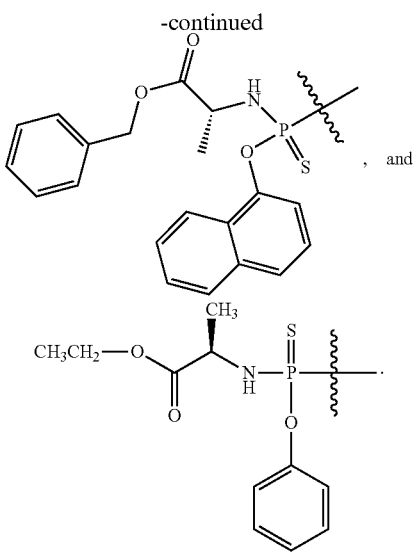
, and

Other thiophosphoramidates include those of the structure:

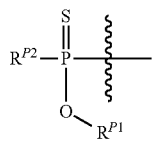

wherein:
$R^{P1}$ is an optionally substituted linear, branched, or cyclic alkyl group, or an optionally substituted aryl, heteroaryl or heterocyclic group or a linked combination thereof; and
$R^{P2}$ is a —$NR^{N1}R^{N2}$ group or a B' group;
wherein:
$R^{N1}$ and $R^{N2}$ are each independently H, $C_1$-$C_8$ alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; or
$R^{N1}$ and $R^{N2}$ along with the nitrogen atom to which that are attached, join to form a 3 to 7 membered heterocyclic ring;
B' is a

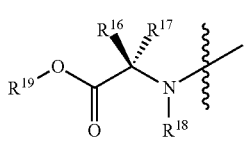

group;
wherein:
$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);

$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);
$R^{18}$ is hydrogen or $C_1$-$C_3$alkyl; or
$R^{16}$ and $R^{17}$ can form a ($C_3$-$C_7$)cycloalkyl or ($C_3$-$C_7$) heterocyclic group; or
$R^{18}$ and $R^{16}$ or $R^{17}$ can form ($C_3$-$C_6$) heterocyclic group; and
$R^{19}$ is hydrogen, ($C_1$-$C_6$)alkyl, ($C_3$-$C_6$)alkenyl, ($C_3$-$C_6$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-; or
B' is a

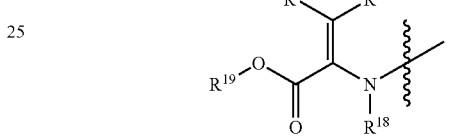

group; and
$R^{18}$, $R^{19}$, $R^{20}$ and $R^{21}$ are as defined above.

Preferred $R^{P1}$ groups include optionally substituted phenyl, naphthyl, and monocyclic heteroaryl groups, especially those groups (particularly lipophilic groups) which enhance bioavailability of the compounds into the cells of the patient and which exhibit reduced toxicity, enhanced therapeutic index and enhanced pharmacokinetics (the compounds are metabolized and excreted more slowly).

The thiophosphoramidate can be at the 5'- or 3'-position of the furanose ring of the nucleoside compound to form a prodrug form of the nucleoside compound. In one embodiment, thiophosphoramidates can be found at both the 5'- and 3'-position of the furanose ring of the nucleoside compound and form a prodrug form of the nucleoside compound. In another embodiment, the thiophosphoramidate found at the 5'-position of the furanose ring of the nucleoside can form a cyclic thiophosphoramidate compound by forming a bond with the 3'-hydroxyl substituent at the 3'-position of the furanose ring of the nucleoside compound and form a prodrug form of the nucleoside compound.

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of at least one of the 2'-deoxy-2'-α-fluoro-2'-β-C-nucleoside-4'-fluoro compounds according to the present invention in combination with at least one other active agent, for example where appropriate at least one additional anti-HCV agent, including other 2'-deoxy-2'-α-fluoro-2'-β-C-methyl-4'-fluoro nucleoside agents which are disclosed herein. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term host, as used herein, refers to a unicellular or multicellular organism in which a HCV virus can replicate, including cell lines and animals, and typically a human. The term host specifically refers to infected cells, cells transfected with all or part of a HCV genome, and animals, in particular, primates (including chimpanzees) and humans. In most animal applications of the present invention, the host is a human patient. Veterinary applications, in certain indications, however, are clearly anticipated by the present invention. The host can be for example, bovine, equine, avian, canine, feline, etc.

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetics or pharmacodynamics, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

III. Methods of Treatment or Prophylaxis

Treatment, as used herein, refers to the administration of an active compound to a host that is infected with a hepatitis C virus.

The term "prophylactic" or preventative, when used, refers to the administration of an active compound to prevent or reduce the likelihood of an occurrence of the viral disorder. The present invention includes both treatment and prophylactic or preventative therapies. In one embodiment, the active compound is administered to a host who has been exposed to and thus at risk of infection by a hepatitis C virus infection.

The invention is directed to a method of treatment or prophylaxis of a hepatitis C virus, including drug resistant and multidrug resistant forms of HCV and related disease states, conditions, or complications of an HCV infection, including such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof an effective amount of at least one β-D-2'-deoxy-2'-α-fluoro-2'-β-C-substituted-4'-fluoro-N$^6$-substituted-2,6-diaminopurine nucleotide as described herein, optionally in combination with at least one additional bioactive agent, for example, an additional anti-HCV agent, further in combination with a pharmaceutically acceptable carrier additive and/or excipient.

In yet another aspect, the present invention is a method for prevention or prophylaxis of a HCV infection or a disease state or related or follow-on disease state, condition or complication of an HCV infection, including such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others, said method comprising administering to a patient at risk with an effective amount of at least one compound according to the present invention as described above in combination with a pharmaceutically acceptable carrier, additive, or excipient, optionally in combination with another anti-HCV agent.

The 5'-stabilized β-D-2'-deoxy-2'-α-fluoro-2'-β-C-substituted-4'-fluoro-N$^6$-substituted-2,6-diaminopurine nucleotide can be administered if desired as any salt or prodrug that upon administration to the recipient is capable of providing directly or indirectly the parent compound, or that exhibits activity itself. Nonlimiting examples are the pharmaceutically acceptable salts and a compound, which has been modified at a function group, such as a hydroxyl or amine function, to modify the biological activity, pharmacokinetics, half-life, controlled delivery, lipophilicity, absorption kinetics, ease of phosphorylation to the active 5'-triphosphate or efficiency of delivery using a desired route of administration of the compound. Methods to modify the properties of an active compound to achieve target properties are known to those of skill in the art or can easily be assessed by standard methods, for example, acylation, phosphorylation, thiophosphoramidation, phosphoramidation, phosphonation, alkylation, or pegylation.

IV. Pharmaceutical Compositions

In an aspect of the invention, pharmaceutical compositions according to the present invention comprise an anti-HCV effective amount of at least one of the 5'-stabilized β-D-2'-deoxy-2'-α-fluoro-2'-β-C-substituted-4'-fluoro-$N^6$-substituted diaminopurine nucleotide compounds described herein, optionally in combination with a pharmaceutically acceptable carrier, additive, or excipient, further optionally in combination or alternation with at least one other active compound.

In an aspect of the invention, pharmaceutical compositions according to the present invention comprise an anti-HCV effective amount of at least one of the active β-D-2'-deoxy-2'-α-fluoro-2'-β-C-substituted-4'-fluoro-$N^6$-substituted-2,6-diaminopurine nucleotide compounds described herein, optionally in combination with a pharmaceutically acceptable carrier, additive, or excipient, further optionally in combination with at least one other antiviral, such as an anti-HCV agent.

The invention includes pharmaceutical compositions that include an effective amount to treat a hepatitis C virus infection, of one of the β-D-2'-deoxy-2'-α-fluoro-2'-β-C-substituted-4'-fluoro-$N^6$-substituted-2,6-diaminopurine nucleotide compounds of the present invention or its salt or prodrug, in a pharmaceutically acceptable carrier or excipient. In an alternative embodiment, the invention includes pharmaceutical compositions that include an effective amount to prevent a hepatitis C virus infection, of one of the β-D-2'-deoxy-2'-α-fluoro-2'-β-C-substituted-4'-fluoro-$N^6$-substituted-2,6-diaminopurine nucleotide compounds of the present invention or its salt or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated, and such therapeutic amount can be determined by the attending physician or specialist.

The 5'-stabilized β-D-2'-deoxy-2'-α-fluoro-2'-β-C-substituted-4'-fluoro-$N^6$-substituted-2,6-diaminopurine nucleotide compounds according to the present invention can be formulated in an admixture with a pharmaceutically acceptable carrier. In general, it is preferable to administer the pharmaceutical composition in orally-administrable form, but certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or other vehicle, for example, this can be easily accomplished by minor modifications (salt formulation, esterification, etc.) which are well known the ordinary skill in the art. It is also well within the routineers' skill to modify the route of administration and dosage regimen of a particular compound in order to manage the pharmacokinetics of the present compounds for maximum beneficial effect in patients.

In certain pharmaceutical dosage forms, the prodrug form of the compounds, especially including acylated (acetylated or other), and ether (alkyl and related) derivatives, phosphate esters, thiophosphoramidates, phosphoramidates, and various salt forms of the present compounds, are preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound.

The amount of compound included within therapeutically active formulations according to the present invention is an effective amount for treating the HCV infection, reducing the likelihood of a HCV infection or the inhibition, reduction, and/or abolition of HCV or its secondary effects, including disease states, conditions, and/or complications which occur secondary to HCV. In general, a therapeutically effective amount of the present compound in pharmaceutical dosage form usually ranges from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. The active nucleoside compound according to the present invention is often administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of an HCV virus infection, or a secondary disease state, condition or complication of HCV, the compositions will be administered in oral dosage form in amounts ranging from about 250 micrograms up to about 500 mg or more at least once a day, for example, at least 25, 50, 100, 150, 250 or 500 milligrams, up to four times a day. The present compounds are often administered orally, but may be administered parenterally, topically, or in suppository form, as well as intranasally, as a nasal spray or as otherwise described herein.

In the case of the co-administration of the present compounds in combination with another anti-HCV compound as otherwise described herein, the amount of the compound according to the present invention to be administered ranges from about 0.01 mg/kg of the patient to about 500 mg/kg. or more of the patient or considerably more, depending upon the second agent to be co-administered and its potency against the virus, the condition of the patient and severity of the disease or infection to be treated and the route of administration. The other anti-HCV agent may for example be administered in amounts ranging from about 0.01 mg/kg to about 500 mg/kg. In certain preferred embodiments, these compounds may be often administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, mannitol, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester prodrug forms of the nucleoside compounds according to the present invention.

In typical embodiments according to the present invention, the compounds and compositions are used to treat, prevent or delay a HCV infection or a secondary disease state, condition or complication of HCV.

V. Combination and Alternation Therapy

It is well recognized that drug-resistant variants of viruses can emerge after prolonged treatment with an antiviral agent. Drug resistance most typically occurs by mutation of a gene that encodes for an enzyme used in viral replication. The efficacy of a drug against an HCV infection, can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed β-D-2'-deoxy-2'-α-fluoro-2'-β-C-substituted-4'-fluoro-$N^6$-substituted-2,6-diaminopurine nucleotides and other described analogs are polymerase inhibitors, it may be useful to administer the compound to a host in combination with, for example a:

(1) Protease inhibitor, such as an NS3/4A protease inhibitor;
(2) NS5A inhibitor;
(3) Another NS5B polymerase inhibitor;
(4) NS5B non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response. Non limiting examples of anti-HCV agents that can be administered in combination with the β-D-2'-D-2'-α-fluoro-2'-β-C-substituted-2-modified-$N^6$-substituted purine nucleotides of the invention are:

(i) protease inhibitors such as telaprevir (Incivek®), boceprevir (Victrelis™), simeprevir (Olysio™), paritaprevir (ABT-450), ACH-2684; AZD-7295; BMS-791325; danoprevir; Filibuvir; GS-9256; GS-9451; MK-5172; Setrobuvir; Sovaprevir; Tegobuvir; VX-135; VX-222 and ALS-220;

(ii) NS5A inhibitor such as ACH-2928, ACH-3102, IDX-719, daclatasvir, ledispasvir and Ombitasvir (ABT-267);

(iii) NS5B inhibitors such as ACH-3422; AZD-7295; Clemizole; ITX-5061; PPI-461; PPI-688, Sovaldi®, MK-3682, and mericitabine;

(iv) NS5B inhibitors such as ABT-333, MBX-700; and, (v) Antibody such as GS-6624.

If the β-D-2'-D-2'-α-fluoro-2'-β-C-substituted-2-modified-$N^6$-substituted purine nucleotide is administered to treat advanced hepatitis C virus leading to liver cancer or cirrhosis, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone deacetylase inhibitors.

V. Process of Preparation of β-D-2'-deoxy-2'-α-fluoro-2'-β-C-substituted-4'-fluoro-$N^6$-substituted 6-amino 2-substituted Purine Nucleotides of the Invention General methods for providing the compounds of the present invention are known in the art or described herein.

The following abbreviations are used in the synthetic schemes.
CBr₄: Carbon tetrabromide
DBU: 1,8-Diazabicyclo[5.4.0]undec-7-ene
DCM: Dichloromethane
THF: Tetrahydrofuran (THF), anhydrous
EtOAc: Ethyl acetate
EtOH: Ethanol
Li(OtBu)₃AlH: Lithium tri-tert-butoxyaluminum hydride
Na₂SO₄: Sodium sulphate (anhydrous)
MeCN: Acetonitrile
MeNH₂: Methylamine
MeOH: Methanol
Na₂SO₄: Sodium sulfate
NaHCO₃: Sodium bicarbonate
NH₄Cl: Ammonium chloride
NH₄OH: Ammonium hydroxide
PE: Petroleum ether
Ph₃P: Triphenylphosphine
Silica gel (230 to 400 mesh, Sorbent)
t-BuMgCl: t-Butyl magnesium chloride
t-BuOK: Sodium tert-butoxide
t-BuOH: Tert-butanol

EXAMPLES

General Methods

¹H, ¹⁹F and ³¹P NMR spectra were recorded on a 300 MHz Fourier transform Brucker spectrometer. Spectra were obtained from samples prepared in 5 mm diameter tubes in CDCl₃, CD₃OD or DMSO-d₆. The spin multiplicities are indicated by the symbols s (singlet), d (doublet), t (triplet), m (multiplet) and, br (broad). Coupling constants (J) are reported in Hz. MS spectra were obtained using electrospray ionization (ESI) on an Agilent Technologies 6120 quadrupole MS apparatus. The reactions were generally carried out under a dry nitrogen atmosphere using Sigma-Aldrich anhydrous solvents. All common chemicals were purchased from commercial sources.

Template for Example Chemistry Below:

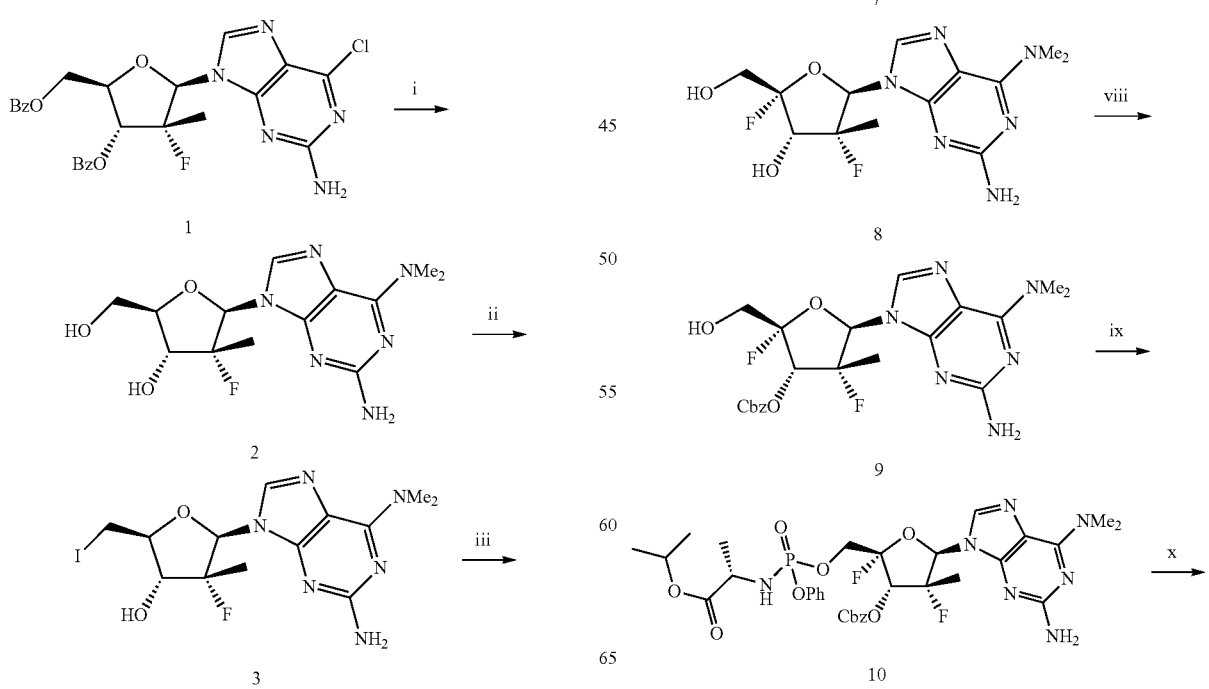

-continued

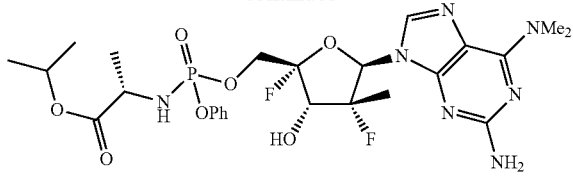

11 i) Me$_2$NH•HCl, DBU, MeOH, 85° C.; ii) I$_2$, PPh$_3$, imidazole, THF; iii) MeONa, MeOH, 60° C.; iv) TMSCl, pyridine, 0° C. then isobutyryl chloride; v) Et$_3$N•3 HF, NIS, MeCN, −20° C.; vi) BzONa, DMSO, 100° C.; vii) MeNH$_2$, EtOH, 75° C.; viii) CbzCl, DMAP, DCM, 0° C.; ix) Isopropyl ((R,S)-(pentafluorophenoxy)-phenoxy-phosphoryl)-L-alaninate, DBU, THF; x) H$_2$, Pd—C, EtOH (2R,3R,4R,5R)-5-(2-Amino-6-(dimethylamino)-9H-purin-9-yl)-4-fluoro-2-(hydroxymethyl)-4-methyltetrahydrofuran-3-ol (2)

To a solution of compound 1 (3.0 g, 5.7 mmol) in MeOH (50 mL) was added dimethylamine hydrochloride (4.7 g, 57.6 mmol) and 1,8-diazabicyclo[5.4.0]undec-7-ene (8.6 mL, 57.6 mmol). The reaction mixture was heated at 85° C. in a sealed container for 6 h, cooled down to room temperature (RT) and concentrated. The residue was purified by column chromatography (silica gel, DCM/MeOH 100:0 to 85:15). Product 2 (1.6 g, 86%) was obtained as a white solid.

(2R,3R,4R,5R)-5-(2-Amino-6-(dimethylamino)-9H-purin-9-yl)-4-fluoro-2-(iodomethyl)-4-methyltetrahydrofuran-3-ol (3)

To a solution of compound 2 (1.67 g, 5.1 mmol) in dry THF (30 mL) was added triphenylphosphine (1.60 g, 6.1 mmol) and imidazole (420 mg, 6.1 mmol). Then, a solution of iodine (1.42 g, 5.6 mmol) in dry THF (10 mL) was added drop-wise. The mixture was stirred at RT for 3 h. The solution was then filtered over Celite and concentrated. The dark residue containing 3 was used as such in the next step.

(3R,4R,5R)-5-(2-Amino-6-(dimethylamino)-9H-purin-9-yl)-4-fluoro-4-methyl-2-methylenetetrahydrofuran-3-ol (4)

To a solution of 3 in MeOH (40 mL) was added MeONa (1.38 g, 25.5 mmol). The reaction mixture was heated at 60° C. for 15 h and then, cooled down to RT and concentrated. EtOAc (100 mL) was added and the solution was washed with satd. NH$_4$Cl aq. solution (80 mL) and brine (80 mL). The organics were dried over anhydrous Na$_2$SO$_4$ and concentrated. The residue was purified by column chromatography (silica gel, PE/EtOAc 0 to 100%). Product 4 (0.87 g, 55% yield over 2 steps) was obtained as a yellow solid.

N-(6-(Dimethylamino)-9-((2R,3R,4R)-3-fluoro-4-hydroxy-3-methyl-5-methylenetetrahydrofuran-2-yl)-9H-purin-2-yl)isobutyramide (5)

To a solution of 4 (500 mg, 1.6 mmol) in dry pyridine (8 mL) was added chlorotrimethylsilane (410 µL, 3.2 mmol) drop-wise at 0° C. The reaction mixture was stirred at 0° C. for 10 mins and then isobutyryl chloride (250 µL, 2.4 mmol) was added drop-wise. The orange solution was stirred at RT for 4 h. After cooling down to 0° C., the reaction was quenched by addition of H$_2$O (2 mL) and 30% NH$_4$OH (3 mL). The mixture was then stirred for 1 h at 0° C. EtOAc (50 mL) was added and the solution was washed with satd. NH$_4$Cl aq. solution (40 mL) and brine (40 mL). The organics were dried over anhydrous Na$_2$SO$_4$ and concentrated. The residue was co-evaporated with toluene (2×50 mL) and purified by column chromatography (silica gel, PE/EtOAc 0 to 100%). Product 5 (460 mg, 75% yield) was obtained as a colorless oil.

N-(9-((2R,3R,4S,5R)-3,5-Difluoro-4-hydroxy-5-(iodomethyl)-3-methyltetrahydrofuran-2-yl)-6-(dimethylamino)-9H-purin-2-yl)isobutyramide (6)

To a solution of 5 (176 mg, 0.47 mmol) in dry MeCN (8 mL) was added Et$_3$N.3HF (90 µL, 0.56 mmol). A solution of N-iodosuccinimide (146 mg, 0.65 mmol) in dry MeCN (8 mL) was added drop-wise over 45 mins at −20° C. The resulting orange solution was stirred for 2 h at 0° C. and for 1 h at RT. The reaction was then diluted with EtOAc (50 mL) and quenched by addition of satd. (1:1) NaHCO$_3$/Na$_2$S$_2$O$_3$ aq. solution (30 mL). The phases were separated and the organic layer was washed with brine (40 mL), dried over anhydrous Na$_2$SO$_4$ and concentrated. The residue was purified by column chromatography (silica gel, PE/EtOAc 0 to 100%). Product 6 (129 mg, 53% yield) was obtained as a yellow solid.

((2S,3S,4R,5R)-5-(6-(Dimethylamino)-2-isobutyramido-9H-purin-9-yl)-2,4-difluoro-3-hydroxy-4-methyltetrahydrofuran-2-yl)methyl benzoate (7)

To a solution of 6 (548 mg, 1.05 mmol) in dry DMSO (40 mL) was added sodium benzoate (1.51 g, 10.5 mmol). The resulting milky suspension was stirred for 3 days at 100° C. The mixture was then cooled down, partitioned between H$_2$O (30 mL) and EtOAc (50 mL) and the phases were separated. The aqueous layer was back-extracted with EtOAc (3×30 mL). The combined organics were washed with satd. NH$_4$Cl aq. solution (2×50 mL) and brine (50 mL). The organic solution was dried over anhydrous Na$_2$SO$_4$ and concentrated. The residue was purified by column chromatography (silica gel, PE/EtOAc 0 to 100%). Product 7 (410 mg, 75% yield) was obtained as a white solid.

(2S,3S,4R,5R)-5-(2-Amino-6-(dimethylamino)-9H-purin-9-yl)-2,4-difluoro-2-(hydroxymethyl)-4-methyltetrahydrofuran-3-ol (8)

A solution of 7 (330 mg, 0.64 mmol) in methylamine (33% in EtOH) (25 mL) in a sealed container was stirred for 2 days at 75° C. The mixture was then cooled down and concentrated. The residue was purified by column chromatography (silica gel, DCM/MeOH 0 to 10%). Product 8 (180 mg, 82% yield) was obtained as a white solid. $^1$H NMR (300 MHz, CD$_3$OD) δ 7.93 (s, 1H), 6.43 (d, J=22.4 Hz, 1H), 4.62 (d, J=20.7 Hz, 1H), 3.86-3.84 (m, 2H), 3.41 (m, 6H), 1.20 (d, J=22.2 Hz, 3H). MS (ESI) m/z calcd. for C$_{13}$H$_{19}$F$_2$N$_6$O$_3$ [M+H]$^+$ 345.1; found 345.2.

(2S,3S,4R,5R)-5-(2-Amino-6-(dimethylamino)-9H-purin-9-yl)-2,4-difluoro-2-(hydroxymethyl)-4-methyltetrahydrofuran-3-yl benzyl carbonate (9)

To a solution of 8 (93 mg, 0.27 mmol) and DMAP (37 mg, 0.30 mmol) in dry DCM (5 mL) was added benzyl chloroformate (43 µL, 0.30 mmol) drop-wise at 0° C. The reaction mixture was stirred for 45 mins at RT and diluted with DCM (5 mL). The solution was washed with H$_2$O (5 mL), brine (5 mL), dried over anhydrous Na$_2$SO$_4$ and concentrated. The residue was purified by column chromatography (silica gel, PE/EtOAc 0 to 100%). Product 9 (70 mg, 55% yield) was obtained as a white solid.

(2S)-Isopropyl 2-(((((2S,3S,4R,5R)-5-(2-amino-6-(dimethylamino)-9H-purin-9-yl)-3-(((benzyloxy)carbonyl)oxy)-2,4-difluoro-4-methyltetrahydrofuran-2-yl)methoxy) (phenoxy)phosphoryl)amino) propanoate (10)

To a solution of compound 9 (51 mg, 0.11 mmol) and isopropyl ((R,S)-(pentafluorophenoxy)-phenoxy-phosphoryl)-L-alaninate (73 mg, 0.16 mmol) in dry THF (3 mL) was added DBU (33 μL, 0.22 mmol) drop-wise at 0° C. The reaction mixture was stirred for 18 h at RT. The solution was then diluted with EtOAc (10 mL) and satd. NH$_4$Cl aq. solution (8 mL). The phases were separated and the aqueous layer was back-extracted with EtOAc (3×5 mL). The combined organics were washed with brine (15 mL), dried over Na$_2$SO$_4$ and concentrated. The residue was purified by reverse phase column chromatography (C-18 silica, H$_2$O/MeOH 100:0 to 0:100). Product 10 (50 mg, 63%) was obtained as a white solid.

(2S)-Isopropyl 2-(((((2S,3S,4R,5R)-5-(2-amino-6-(dimethylamino)-9H-purin-9-yl)-2,4-difluoro-3-hydroxy-4-methyltetrahydrofuran-2-yl)methoxy)(phenoxy)phosphoryl) amino)propanoate (11)

To a solution of compound 10 (50 mg, 0.07 mmol) in EtOH (3 mL) was added palladium (10% on charcoal) (8 mg). The flask was flushed with hydrogen and the suspension was stirred under a hydrogen atmosphere for 3 h at RT. The mixture was then filtered over Celite and concentrated. The residue was purified by reverse phase column chromatography (C-18 silica, H$_2$O/MeOH 100:0 to 0:100). Product 11 (33 mg, 77%) was obtained as a white solid. $^1$H NMR (300 MHz, CD$_3$OD) δ 7.80 (s, 0.5H), 7.79 (s, 0.5H), 7.35-7.16 (m, 5H), 6.42 (d, J=17.6 Hz, 0.5H), 6.40 (d, J=17.6 Hz, 0.5H), 4.96-4.86 (overlapped with H$_2$O, m, 1H), 4.62-4.38 (m, 2H), 3.92-3.88 (m, 1H), 3.39 (m, 6H), 1.30-1.18 (m, 12H). $^{31}$P NMR (121 MHz, CD$_3$OD) δ 4.01 (s), 3.89 (s). MS (ESI) m/z calcd. for C$_{25}$H$_{35}$F$_2$N$_7$O$_7$P [M+H]$^+$ 614.2; found 614.2.

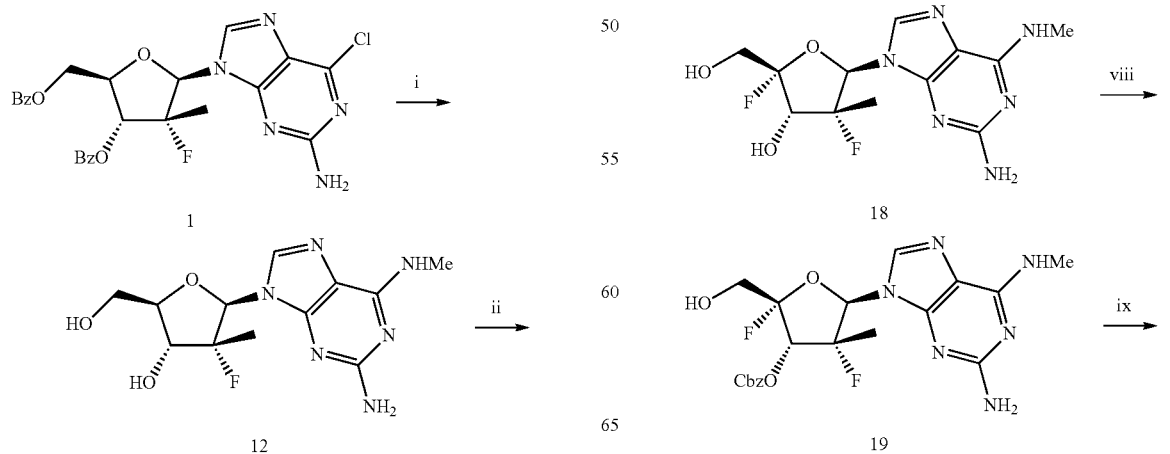

-continued

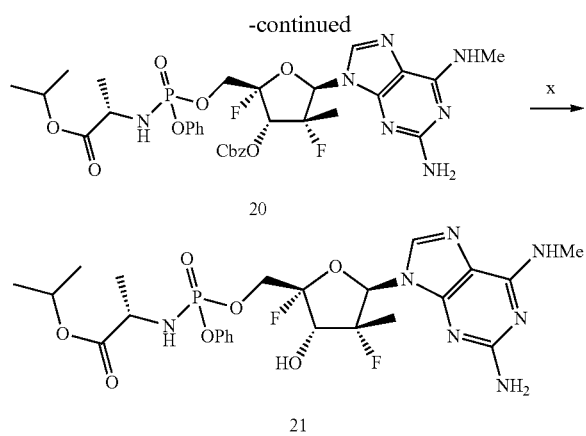

20

21 i) MeNH₂, EtOH, 100° C.; ii) I₂, PPh₃, imidazole, THF; iii) MeONa, MeOH, 60° C.; iv) TMSCl, pyridine, 0° C. then isobutyryl chloride; v) Et₃N•3 HF, NIS, MeCN, -20° C.; vi) BzONa, DMSO, 100° C.; vii) MeNH₂, EtOH, 75° C.; viii) CbzCl, DMAP, DCM, 0° C.; ix) Isopropyl ((R,S)-(pentafluorophenoxy)-phenoxy-phosphoryl)-L-alaninate, DBU, THF; x) H₂, Pd—C, EtOH (2R,3R,4R,5R)-5-(2-Amino-6-(methylamino)-9H-purin-9-yl)-4-fluoro-2-(hydroxymethyl)-4-methyltetrahydrofuran-3-ol (12)

A solution of compound 1 (2.3 g, 4.4 mmol) in methylamine (33% in EtOH) (50 mL) in a sealed container was stirred for 3 h at 100° C. The mixture was then cooled down to RT and concentrated. The residue was purified by column chromatography (silica gel, DCM/MeOH 100:0 to 75:25). Product 12 (1.4 g, 100%) was obtained as an off-white solid.

(2R,3R,4R,5R)-5-(2-Amino-6-(methylamino)-9H-purin-9-yl)-4-fluoro-2-(iodomethyl)-4-methyltetrahydrofuran-3-ol (13)

To a solution of compound 12 (1.36 g, 4.40 mmol) in dry THF (30 mL) was added triphenylphosphine (1.38 g, 5.28 mmol) and imidazole (360 mg, 5.28 mmol). Then, a solution of iodine (1.23 g, 4.84 mmol) in dry THF (10 mL) was added drop-wise. The mixture was stirred at RT for 15 h. The solution was then filtered over Celite and concentrated. The dark residue containing 13 was used as such in the next step.

(3R,4R,5R)-5-(2-Amino-6-(methylamino)-9H-purin-9-yl)-4-fluoro-4-methyl-2-methylenetetrahydrofuran-3-ol (14)

To a solution of 13 in MeOH (40 mL) was added MeONa (1.19 g, 22.0 mmol). The reaction mixture was heated at 60° C. for 15 h and then, cooled down to RT and concentrated. EtOAc (100 mL) was added and the solution was washed with satd. NH₄Cl aq. solution (80 mL) and brine (80 mL). The organics were dried over anhydrous Na₂SO₄ and concentrated. The residue was purified by column chromatography (silica gel, PE/EtOAc 0 to 100%). Product 14 (0.58 g, 45% yield over 2 steps) was obtained as a yellow solid.

N-(6-(Methylamino)-9-((2R,3R,4R)-3-fluoro-4-hydroxy-3-methyl-5-methylenetetrahydrofuran-2-yl)-9H-purin-2-yl)isobutyramide (15)

To a solution of 14 (300 mg, 1.02 mmol) in dry pyridine (5 mL) was added chlorotrimethylsilane (320 μL, 2.54 mmol) drop-wise at 0° C. The reaction mixture was stirred at 0° C. for 10 mins and then isobutyryl chloride (160 μL, 1.54 mmol) was added drop-wise. The orange solution was stirred at RT for 4 h. After cooling down to 0° C., the reaction was quenched by addition of H₂O (2 mL) and 30% NH₄OH (3 mL). The mixture was then stirred for 1 h at 0° C. EtOAc (50 mL) was added and the solution was washed with satd. NH₄Cl aq. solution (40 mL) and brine (40 mL). The organics were dried over anhydrous Na₂SO₄ and concentrated. The residue was co-evaporated with toluene (2×50 mL) and purified by column chromatography (silica gel, PE/EtOAc 0 to 100%). Product 15 (240 mg, 65% yield) was obtained as a colorless oil.

N-(9-42R,3R,4S,5R)-3,5-Difluoro-4-hydroxy-5-(iodomethyl)-3-methyltetrahydrofuran-2-yl)-6-(methylamino)-9H-purin-2-yl)isobutyramide (16)

To a solution of 15 (120 mg, 0.33 mmol) in dry MeCN (6 mL) was added Et₃N.3HF (65 μL, 0.40 mmol). A solution of N-iodosuccinimide (103 mg, 0.46 mmol) in dry MeCN (6 mL) was added drop-wise over 30 mins at -20° C. The resulting orange solution was stirred for 2 h at 0° C. and for 1 h at RT. The reaction was then diluted with EtOAc (40 mL) and quenched by addition of satd. (1:1) NaHCO₃/Na₂S₂O₃ aq. solution (25 mL). The phases were separated and the organic layer was washed with brine (30 mL), dried over anhydrous Na₂SO₄ and concentrated. The residue was purified by column chromatography (silica gel, PE/EtOAc 0 to 100%). Product 16 (85 mg, 50% yield) was obtained as a yellow solid.

((2S,3S,4R,5R)-5-(6-(Methylamino)-2-isobutyramido-9H-purin-9-yl)-2,4-difluoro-3-hydroxy-4-methyltetrahydrofuran-2-yl)methyl benzoate (17)

To a solution of 16 (85 mg, 0.17 mmol) in dry DMSO (5 mL) was added sodium benzoate (245 mg, 1.70 mmol). The resulting milky suspension was stirred for 5 days at 100° C. The mixture was then cooled down, partitioned between H₂O (15 mL) and EtOAc (25 mL) and the phases were separated. The aqueous layer was back-extracted with EtOAc (3×10 mL). The combined organics were washed with satd. NH₄Cl aq. solution (2×20 mL) and brine (20 mL). The organic solution was dried over anhydrous Na₂SO₄ and concentrated. The residue was purified by column chromatography (silica gel, PE/EtOAc 0 to 100%). Product 17 (60 mg, 70% yield) was obtained as a white solid.

(2S,3S,4R,5R)-5-(2-Amino-6-(methylamino)-9H-purin-9-yl)-2,4-difluoro-2-(hydroxymethyl)-4-methyltetrahydrofuran-3-ol (18)

A solution of 17 (60 mg, 0.12 mmol) in methylamine (33% in EtOH) (6 mL) in a sealed container was stirred for 3 days at 75° C. The mixture was then cooled down and concentrated. The residue was purified by column chromatography (silica gel, DCM/MeOH 0 to 10%). Product 18 (29 mg, 72% yield) was obtained as a white solid. $^1$H NMR (300 MHz, CD₃OD) δ 7.94 (s, 1H), 6.42 (d, J=16.9 Hz, 1H), 4.76-4.59 (m, 1H), 3.91-3.81 (m, 2H), 3.04 (s, 3H), 1.22 (d, J=22.3 Hz, 3H). MS (ESI) m/z calcd. for $C_{12}H_{17}F_2N_6O_3$ [M+H]⁺331.1; found 331.2.

(2S,3S,4R,5R)-5-(2-Amino-6-(methylamino)-9H-purin-9-yl)-2,4-difluoro-2-(hydroxymethyl)-4-methyltetrahydrofuran-3-yl benzyl carbonate (19)

To a solution of 18 (27 mg, 0.08 mmol) and DMAP (11 mg, 0.08 mmol) in dry DCM (1 mL) was added benzyl chloroformate (7 µL, 0.08 mmol) at 0° C. The reaction mixture was stirred for 1.5 h at RT and diluted with DCM (4 mL). The solution was washed with H$_2$O (3 mL), brine (3 mL), dried over anhydrous Na$_2$SO$_4$ and concentrated. The residue was purified by column chromatography (silica gel, PE/EtOAc 0 to 100%). Product 19 was obtained along with diprotected species (ratio: 7:3; 20 mg in total) as a colorless solid and used as such in the next step.

(2S)-Isopropyl 2-(((((2S,3S,4R,5R)-5-(2-amino-6-(methylamino)-9H-purin-9-yl)-3-(((benzyloxy)carbonyl)oxy)-2,4-difluoro-4-methyltetrahydrofuran-2-yl)methoxy) (phenoxy)phosphoryl)amino) propanoate (20)

To a solution of the mixture containing compound 19 (20 mg) and isopropyl ((R,S)-(pentafluorophenoxy)-phenoxyphosphoryl)-L-alaninate (22 mg, 0.05 mmol) in dry THF (1 mL) was added DBU (9 µL, 0.06 mmol) at 0° C. The reaction mixture was stirred for 4 h at RT. The solution was then diluted with EtOAc (5 mL) and satd. NH$_4$Cl aq. solution (3 mL). The phases were separated and the aqueous layer was back-extracted with EtOAc (3×3 mL). The combined organics were washed with brine (10 mL), dried over Na$_2$SO$_4$ and concentrated. The residue containing product 20 was used as such in the next step.

(2S)-Isopropyl 2-(((((2S,3S,4R,5R)-5-(2-amino-6-(methylamino)-9H-purin-9-yl)-2,4-difluoro-3-hydroxy-4-methyltetrahydrofuran-2-yl)methoxy)(phenoxy)phosphoryl) amino)propanoate (21)

To a solution of the mixture containing compound 20 in EtOH (1 mL) was added palladium (10% on charcoal) (3 mg). The flask was flushed with hydrogen and the suspension was stirred under a hydrogen atmosphere for 3 h at RT. The mixture was then filtered over Celite and concentrated. The residue was purified by column chromatography (silica gel, DCM/MeOH 0 to 10%) and then by reverse phase column chromatography (C-18 silica, H$_2$O/MeOH 100:0 to 0:100). Product 21 (5 mg, 10% over 3 steps) was obtained as a white solid. $^1$H NMR (300 MHz, CD$_3$OD) δ 7.78, 7.76 (s+s, 1H), 7.35-7.16 (m, 5H), 6.41 (d, J=17.4 Hz) and 6.39 (d, J=17.5 Hz, 1H), 4.98-4.90 (overlapped with H$_2$O, m, 1H), 4.69-4.53 (m, 1H), 447-4.35 (m, 1H), 3.95-3.85 (m, 1H), 3.03 (s, 3H), 1.31-1.17 (m, 12H). $^{31}$P NMR (121 MHz, CD$_3$OD) δ 2.63 (s), 2.50 (s). MS (ESI) m/z calcd. for C$_{24}$H$_{33}$F$_2$N$_7$O$_7$P [M+H]$^+$ 600.2; found 600.2.

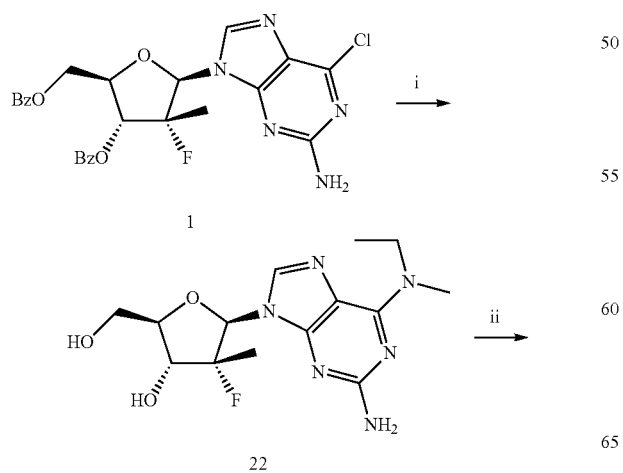

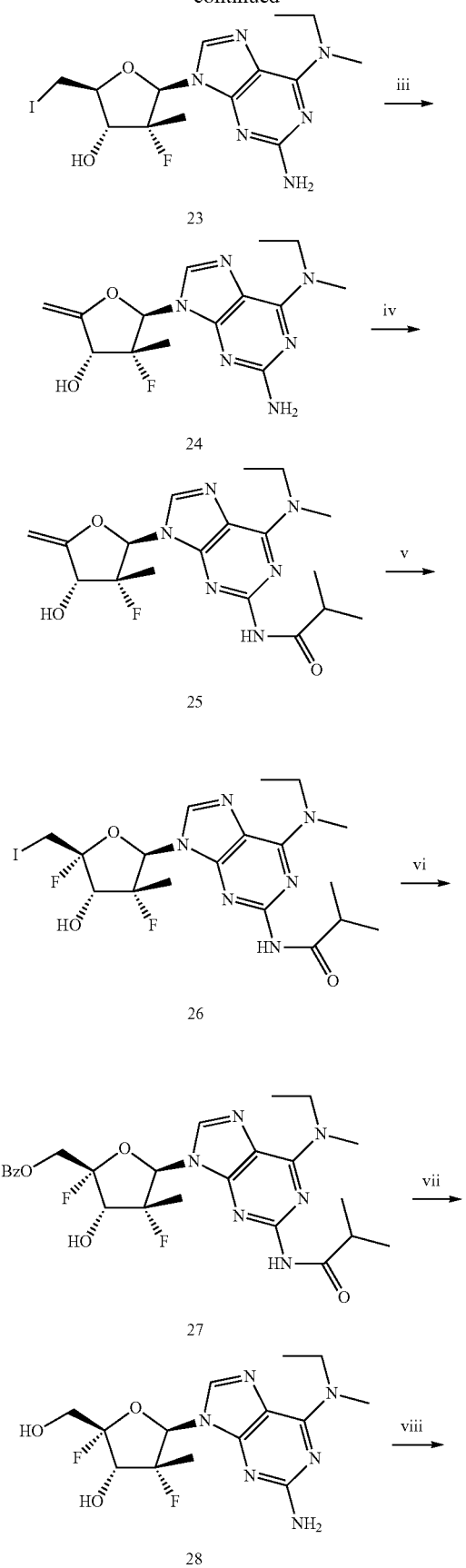

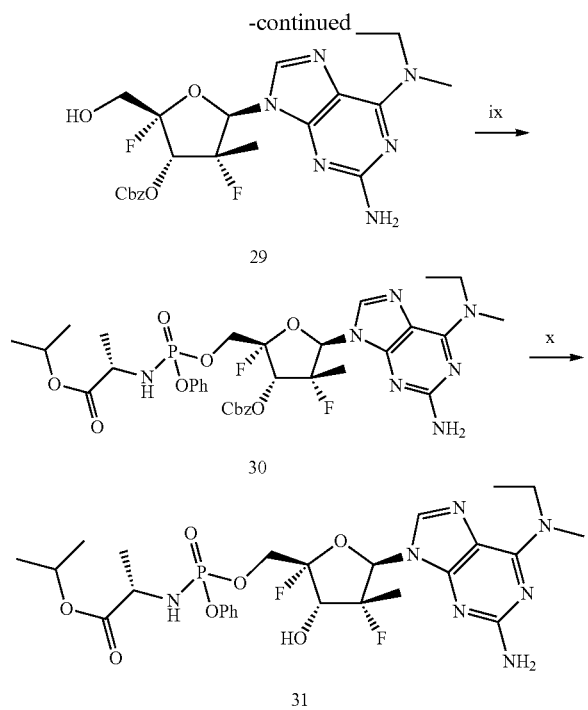

i) N-Methyl-ethylamine, EtOH, 100° C.; ii) I₂, PPh₃, imidazole, THF; iii) MeONa, MeOH, 60° C.; iv) TMSCl, pyridine, 0° C. then isobutyryl chloride; v) Et₃N·3 HF, NIS, MeCN, -20° C.; vi) BzONa, DMSO, 100° C.; vii) MeNH₂, EtOH, 75° C.; viii) CbzCl, DMAP, DCM, 0° C.; ix) Isopropyl ((R,S)-(pentafluorophenoxy)-phenoxy-phosphoryl)-L-alaninate, DBU, THF; x) H₂, Pd—C, EtOH (2R,3R,4R,5R)-5-(2-Amino-6-(ethyl(methyl)amino)-9H-purin-9-yl)-4-fluoro-2-(hydroxymethyl)-4-methyltetrahydrofuran-3-ol (22)

To a solution of compound 1 (2.9 g, 5.5 mmol) in EtOH (60 mL) was added N-methyl-ethylamine (1.4 mL, 16.5 mmol). The reaction mixture was heated at 100° C. in a sealed container for 15 h, cooled down to RT and 30% NH₄OH (20 mL) was added. The reaction mixture was heated at 100° C. in a sealed container for 4 h and cooled down to RT. The residue was purified by column chromatography (silica gel, DCM/MeOH 100:0 to 90:10). Product 22 (1.7 g, 90%) was obtained as a white solid.

(2R,3R,4R,5R)-5-(2-Amino-6-(ethyl(methyl)amino)-9H-purin-9-yl)-4-fluoro-2-(iodomethyl)-4-methyltetrahydrofuran-3-ol (23)

To a solution of compound 22 (1.56 g, 4.6 mmol) in dry THF (30 mL) was added triphenylphosphine (2.90 g, 11.0 mmol) and imidazole (750 mg, 11.1 mmol). Then, a solution of iodine (2.57 g, 10.1 mmol) in dry THF (15 mL) was added drop-wise. The mixture was stirred at RT for 3 h. The solution was then filtered over Celite and concentrated. The dark residue containing 23 was used as such in the next step.

(3R,4R,5R)-5-(2-Amino-6-(ethyl(methyl)amino)-9H-purin-9-yl)-4-fluoro-4-methyl-2-methylenetetrahydrofuran-3-ol (24)

To a solution of 23 in MeOH (50 mL) was added MeONa (3.73 g, 69.0 mmol). The reaction mixture was heated at 60° C. for 15 h and then, cooled down to RT and concentrated. EtOAc (100 mL) was added and the solution was washed with satd. NH₄Cl aq. solution (80 mL) and brine (80 mL). The organics were dried over anhydrous Na₂SO₄ and concentrated. The residue was purified by column chromatography (silica gel, PE/EtOAc 0 to 100%). Product 24 (0.82 g, 55% yield over 2 steps) was obtained as a yellow solid.

N-(6-(Ethyl)methyl)amino)-9-((2R,3R,4R)-3-fluoro-4-hydroxy-3-methyl-5-methylenetetrahydrofuran-2-yl)-9H-purin-2-yl)isobutyramide (25)

To a solution of 24 (500 mg, 1.55 mmol) in dry pyridine (8 mL) was added chlorotrimethylsilane (400 µL, 3.1 mmol) drop-wise at 0° C. The reaction mixture was stirred at 0° C. for 10 mins and then isobutyryl chloride (240 µL, 2.3 mmol) was added drop-wise. The orange solution was stirred at RT for 4 h. After cooling down to 0° C., the reaction was quenched by addition of H₂O (2 mL) and 30% NH₄OH (3 mL). The mixture was then stirred for 1 h at 0° C. EtOAc (50 mL) was added and the solution was washed with satd. NH₄Cl aq. solution (40 mL) and brine (40 mL). The organics were dried over anhydrous Na₂SO₄ and concentrated. The residue was co-evaporated with toluene (2×50 mL) and purified by column chromatography (silica gel, PE/EtOAc 0 to 100%). Product 25 (440 mg, 72% yield) was obtained as a white solid.

N-(9-((2R,3R,4S,5R)-3,5-Difluoro-4-hydroxy-5-(iodomethyl)-3-methyltetrahydrofuran-2-yl)-6-(ethyl(methyl)amino)-9H-purin-2-yl)isobutyramide (26)

To a solution of 25 (275 mg, 0.70 mmol) in dry MeCN (15 mL) was added Et₃N.3HF (140 µL, 0.84 mmol). A solution of N-iodosuccinimide (220 mg, 0.98 mmol) in dry MeCN (12 mL) was added drop-wise over 45 mins at -20° C. The resulting orange solution was stirred for 2 h at 0° C. and for 1 h at RT. The reaction was then diluted with EtOAc (50 mL) and quenched by addition of satd. (1:1) NaHCO₃/Na₂S₂O₃ aq. solution (30 mL). The phases were separated and the organic layer was washed with brine (40 mL), dried over anhydrous Na₂SO₄ and concentrated. The residue was purified by column chromatography (silica gel, PE/EtOAc 0 to 100%). Product 26 (245 mg, 65% yield) was obtained as a white solid.

((2S,3S,4R,5R)-5-(6-(Ethyl)methyl)amino)-2-isobutyramido-9H-purin-9-yl)-2,4-difluoro-3-hydroxy-4-methyltetrahydrofuran-2-yl)methyl benzoate (27)

To a solution of 26 (245 mg, 0.46 mmol) in dry DMSO (15 mL) was added sodium benzoate (787 mg, 6.9 mmol). The resulting milky suspension was stirred for 5 days at 100° C. The mixture was then cooled down, partitioned between H₂O (40 mL) and EtOAc (50 mL) and the phases were separated. The aqueous layer was back-extracted with EtOAc (3×30 mL). The combined organics were washed with satd. NH₄Cl aq. solution (2×50 mL) and brine (50 mL). The organic solution was dried over anhydrous Na₂SO₄ and concentrated. The residue was purified by column chromatography (silica gel, PE/EtOAc 0 to 100%). Product 27 (206 mg, 84% yield) was obtained as an off-white solid.

(2S,3S,4R,5R)-5-(2-Amino-6-(ethyl(methyl)amino)-9H-purin-9-yl)-2,4-difluoro-2-(hydroxymethyl)-4-methyltetrahydrofuran-3-ol (28)

A solution of 27 (205 mg, 0.38 mmol) in methylamine (33% in EtOH) (20 mL) in a sealed container was stirred for 2 days at 80° C. The mixture was then cooled down and concentrated. The residue was purified by column chromatography (silica gel, DCM/MeOH 0 to 10%). Product 28 (110 mg, 80% yield) was obtained as a white solid. $^1$H NMR (300 MHz, CD$_3$OD) δ 7.93 (s, 1H), 6.43 (d, J=16.0 Hz, 1H), 4.73-4.58 (m, 1H), 4.04-3.94 (m, 2H), 3.90-3.80 (m, 2H), 3.34 (s, 3H), 1.26-1.17 (m, 6H). MS (ESI) m/z calcd. for C$_{14}$H$_{21}$F$_2$N$_6$O$_3$ [M+H]$^+$ 359.2; found 359.2.

(2S,3S,4R,5R)-5-(2-Amino-6-(ethyl(methyl)amino)-9H-purin-9-yl)-2,4-difluoro-2-(hydroxymethyl)-4-methyltetrahydrofuran-3-yl benzyl carbonate (29)

To a solution of 28 (30 mg, 0.08 mmol) and DMAP (12 mg, 0.10 mmol) in dry DCM (2 mL) was added benzyl chloroformate (17 µL, 0.12 mmol) at 0° C. The reaction mixture was stirred for 2 h at RT and diluted with DCM (5 mL). The solution was washed with H$_2$O (5 mL), brine (5 mL), dried over anhydrous Na$_2$SO$_4$ and concentrated. The residue was purified by column chromatography (silica gel, PE/EtOAc 0 to 100%). Product 29 (25 mg, 60% yield) was obtained as a white solid.

(2S)-Isopropyl 2-4-(((((2S,3S,4R,5R)-5-(2-amino-6-(ethyl(methyl)amino)-9H-purin-9-yl)-3-(((benzyloxy)carbonyl)oxy)-2,4-difluoro-4-methyltetrahydrofuran-2-yl)methoxy) (phenoxy)phosphoryl)amino) propanoate (30)

To a solution of compound 29 (25 mg, 0.05 mmol) and isopropyl ((R,S)-(pentafluorophenoxy)-phenoxy-phosphoryl)-L-alaninate (36 mg, 0.08 mmol) in dry THF (2 mL) was added DBU (16 µL, 0.11 mmol) at 0° C. The reaction mixture was stirred for 18 h at RT. The solution was then diluted with EtOAc (5 mL) and satd. NH$_4$Cl aq. solution (4 mL). The phases were separated and the aqueous layer was back-extracted with EtOAc (3×3 mL). The combined organics were washed with brine (10 mL), dried over Na$_2$SO$_4$ and concentrated. The residue containing product 30 was used as such in the next step.

(2S)-Isopropyl 2-((((((2S,3S,4R,5R)-5-(2-amino-6-(ethyl(methyl)amino)-9H-purin-9-yl)-2,4-difluoro-3-hydroxy-4-methyltetrahydrofuran-2-yl)methoxy) (phenoxy)phosphoryl) amino)propanoate (31)

To a solution of the mixture containing compound 30 in EtOH (2 mL) was added palladium (10% on charcoal) (4 mg). The flask was flushed with hydrogen and the suspension was stirred under a hydrogen atmosphere for 3 h at RT. The mixture was then filtered over Celite and concentrated. The residue was purified by column chromatography (silica gel, DCM/MeOH 0 to 10%) and then by reverse phase column chromatography (C-18 silica, H$_2$O/MeOH 100:0 to 0:100). Product 31 (14 mg, 44% over 2 steps) was obtained as a white solid. $^1$H NMR (300 MHz, CD$_3$OD) δ 7.75, 7.72 (s+s, 1H), 7.34-7.13 (m, 5H), 6.42 (d, J=17.6 Hz) and 6.40 (d, J=17.7 Hz, 1H), 4.98-4.90 (overlapped with H$_2$O, m, 1H), 4.66-4.51 (m, 1H), 4.47-4.35 (m, 1H), 4.05-3.86 (m, 3H), 3.35-3.32 (overlapped with MeOH, m, 4H), 1.31-1.17 (m, 15H). $^{31}$P NMR (121 MHz, CD$_3$OD) δ 4.10 (s), 4.00 (s). MS (ESI) m/z calcd. for C$_{26}$H$_{37}$F$_2$N$_7$O$_7$P [M+H]$^+$ 628.2; found 628.4.

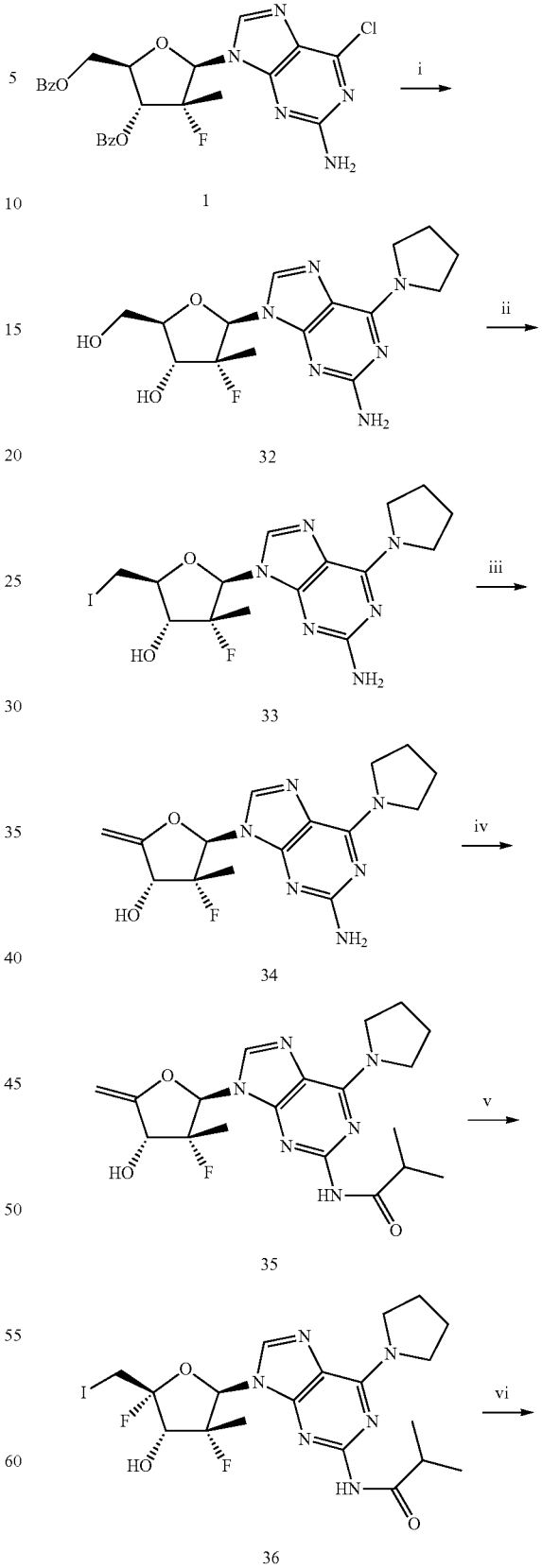

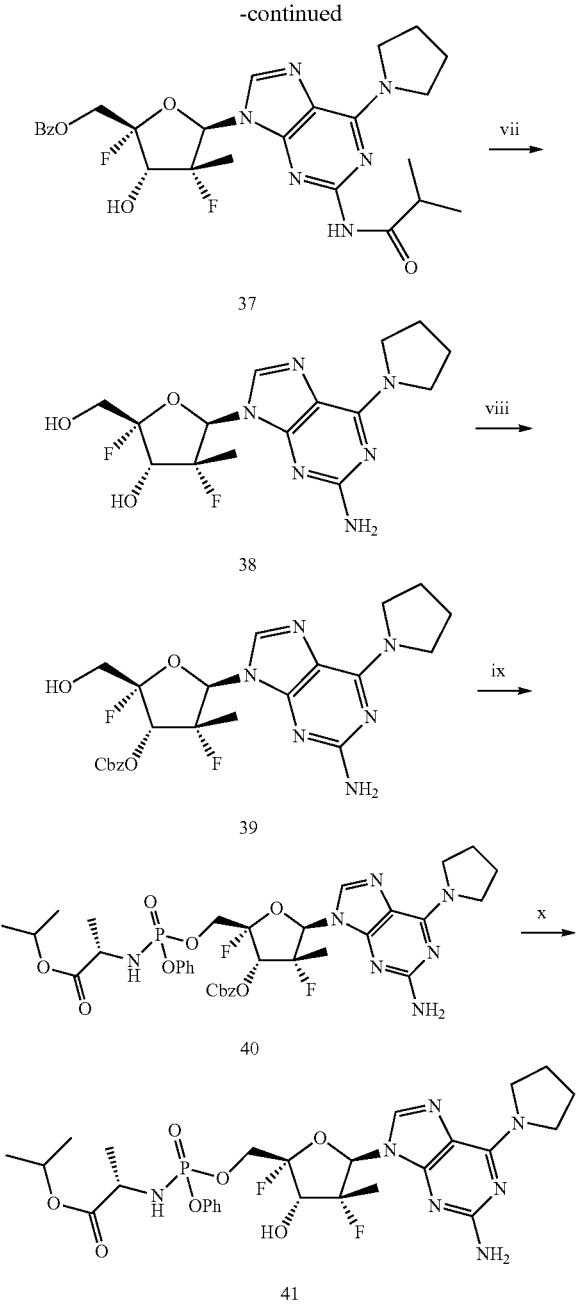

37

38

39

40

41 i) Pyrrolidine, EtOH, 100° C.; ii) I₂, PPh₃, imidazole, THF; iii) MeONa, MeOH, 60° C.; iv) TMSCl, pyridine, 0° C. then isobutyryl chloride; v) Et₃N•3 HF, NIS, MeCN, -20° C.; vi) BzONa, DMSO, 100° C.; vii) MeNH₂, EtOH, 75° C.; viii) CbzCl, DMAP, DCM, 0° C.; ix) Isopropyl ((R,S)-(pentafluorophenoxy)-phenoxy-phosphoryl)-L-alaninate, DBU, THF; x) H₂, Pd—C, EtOH (2R,3R,4R,5R)-5-(2-Amino-6-(pyrrolidin-1-yl)-9H-purin-9-yl)-4-fluoro-2-(hydroxymethyl)-4-methyltetrahydrofuran-3-ol (32)

To a solution of compound 1 (3.0 g, 5.7 mmol) in EtOH (60 mL) was added pyrrolidine (1.45 mL, 17.0 mmol). The reaction mixture was heated at 100° C. in a sealed container for 3 h, cooled down to RT and 30% NH₄OH (25 mL) was added. The reaction mixture was heated at 80° C. in a sealed container for 15 h and cooled down to RT. The residue was purified by column chromatography (silica gel, DCM/MeOH 100:0 to 90:10). Product 32 (1.9 g, 95%) was obtained as a white solid.

(2R,3R,4R,5R)-5-(2-Amino-6-(pyrrolidin-1-yl)-9H-purin-9-yl)-4-fluoro-2-(iodomethyl)-4-methyltetrahydrofuran-3-ol (33)

To a solution of compound 32 (1.90 g, 5.5 mmol) in dry THF (30 mL) was added triphenylphosphine (3.60 g, 13.7 mmol) and imidazole (930 mg, 13.7 mmol). Then, a solution of iodine (3.18 g, 12.5 mmol) in dry THF (30 mL) was added drop-wise. The mixture was stirred at RT for 4 h. The solution was then filtered over Celite and concentrated. The dark residue containing 33 was used as such in the next step.

(3R,4R,5R)-5-(2-Amino-6-(pyrrolidin-1-yl)-9H-purin-9-yl)-4-fluoro-4-methyl-2-methylenetetrahydrofuran-3-ol (34)

To a solution of 33 in MeOH (60 mL) was added MeONa (4.60 g, 85.3 mmol). The reaction mixture was heated at 60° C. for 15 h and then, cooled down to RT and concentrated. EtOAc (150 mL) was added and the solution was washed with satd. NH₄Cl aq. solution (100 mL) and brine (100 mL). The organics were dried over anhydrous Na₂SO₄ and concentrated. The residue was purified by column chromatography (silica gel, PE/EtOAc 0 to 100%). Product 34 (0.94 g, 52% yield over 2 steps) was obtained as a yellow solid.

N-(6-(Pyrrolidin-1-yl)-9-((2R,3R,4R)-3-fluoro-4-hydroxy-3-methyl-5-methylenetetrahydrofuran-2-yl)-9H-purin-2-yl)isobutyramide (35)

To a solution of 34 (900 mg, 2.69 mmol) in dry pyridine (15 mL) was added chlorotrimethylsilane (700 μL, 5.40 mmol) drop-wise at 0° C. The reaction mixture was stirred at 0° C. for 10 mins and then isobutyryl chloride (420 μL, 4.03 mmol) was added drop-wise. The orange solution was stirred at RT for 4 h. After cooling down to 0° C., the reaction was quenched by addition of H₂O (4 mL) and 30% NH₄OH (5 mL). The mixture was then stirred for 1 h at 0° C. EtOAc (100 mL) was added and the solution was washed with satd. NH₄Cl aq. solution (80 mL) and brine (80 mL). The organics were dried over anhydrous Na₂SO₄ and concentrated. The residue was co-evaporated with toluene (2×100 mL) and purified by column chromatography (silica gel, PE/EtOAc 0 to 100%). Product 35 (705 mg, 65% yield) was obtained as a white solid.

N-(9-((2R,3R,4S,5R)-3,5-Difluoro-4-hydroxy-5-(iodomethyl)-3-methyltetrahydrofuran-2-yl)-6-(pyrrolidin-1-yl)-9H-purin-2-yl)isobutyramide (36)

To a solution of 35 (446 mg, 1.10 mmol) in dry MeCN (18 mL) was added Et₃N.3HF (220 μL, 1.32 mmol). A solution of N-iodosuccinimide (346 mg, 1.54 mmol) in dry MeCN (18 mL) was added drop-wise over 45 mins at -20° C. The resulting orange solution was stirred for 2 h at 0° C. and for 1 h at RT. The reaction was then diluted with EtOAc (60 mL) and quenched by addition of satd. (1:1) NaHCO₃/Na₂S₂O₃ aq. solution (40 mL). The phases were separated and the organic layer was washed with brine (40 mL), dried over anhydrous Na₂SO₄ and concentrated. The residue was purified by column chromatography (silica gel, PE/EtOAc 0 to 100%). Product 36 (340 mg, 56% yield) was obtained as a white solid.

((2S,3S,4R,5R)-5-(6-(pyrrolidin-1-yl)-2-isobutyramido-9H-purin-9-yl)-2,4-difluoro-3-hydroxy-4-methyltetrahydrofuran-2-yl)methyl Benzoate (37)

To a solution of 36 (290 mg, 0.53 mmol) in dry DMSO (18 mL) was added sodium benzoate (1.14 g, 7.9 mmol). The resulting milky suspension was stirred for 5 days at 100° C. The mixture was then cooled down, partitioned between H$_2$O (50 mL) and EtOAc (60 mL) and the phases were separated. The aqueous layer was back-extracted with EtOAc (3×30 mL). The combined organics were washed with satd. NH$_4$Cl aq. solution (2×60 mL) and brine (60 mL). The organic solution was dried over anhydrous Na$_2$SO$_4$ and concentrated. The residue was purified by column chromatography (silica gel, PE/EtOAc 0 to 100%). Product 37 (190 mg, 66% yield) was obtained as an off-white solid.

(2S,3S,4R,5R)-5-(2-Amino-6-(pyrrolidin-1-yl)-9H-purin-9-yl)-2,4-difluoro-2-(hydroxymethyl)-4-methyltetrahydrofuran-3-ol (38)

A solution of 37 (190 mg, 0.35 mmol) in methylamine (33% in EtOH) (20 mL) in a sealed container was stirred for 2 days at 80° C. The mixture was then cooled down and concentrated. The residue was purified by column chromatography (silica gel, DCM/MeOH 0 to 10%). Product 38 (90 mg, 70% yield) was obtained as a white solid. $^1$H NMR (300 MHz, CD$_3$OD) δ 7.96 (s, 1H), 6.43 (d, J=22.8 Hz, 1H), 4.71-4.61 (m, 1H), 3.85 (lm, 6H), 2.00 (large, 4H), 1.20 (d, J=29.6 Hz, 3H). MS (ESI) m/z calcd. for C$_{15}$H$_{21}$F$_2$N$_6$O$_3$ [M+H]$^+$ 371.2; found 371.2.

(2S,3S,4R,5R)-5-(2-Amino-6-(pyrrolidin-1-yl)-9H-purin-9-yl)-2,4-difluoro-2-(hydroxymethyl)-4-methyltetrahydrofuran-3-yl benzyl carbonate (39)

To a solution of 38 (30 mg, 0.08 mmol) and DMAP (12 mg, 0.10 mmol) in dry DCM (2 mL) was added benzyl chloroformate (17 μL, 0.12 mmol) at 0° C. The reaction mixture was stirred for 2 h at RT and diluted with DCM (5 mL). The solution was washed with H$_2$O (5 mL), brine (5 mL), dried over anhydrous Na$_2$SO$_4$ and concentrated. The residue was purified by column chromatography (silica gel, PE/EtOAc 0 to 100%). Product 39 (25 mg, 62% yield) was obtained as a white solid.

(2S)-Isopropyl 2-(((((2S,3S,4R,5R)-5-(2-amino-6-(pyrrolidin-1-yl)-9H-purin-9-yl)-3-(((benzyloxy)carbonyl)oxy)-2,4-difluoro-4-methyltetrahydrofuran-2-yl)methoxy) (phenoxy)phosphoryl)amino) propanoate (40)

To a solution of compound 39 (25 mg, 0.05 mmol) and isopropyl ((R,S)-(pentafluorophenoxy)-phenoxy-phosphoryl)-L-alaninate (36 mg, 0.08 mmol) in dry THF (2 mL) was added DBU (16 μL, 0.11 mmol) at 0° C. The reaction mixture was stirred for 5 h at RT. The solution was then diluted with EtOAc (5 mL) and satd. NH$_4$Cl aq. solution (4 mL). The phases were separated and the aqueous layer was back-extracted with EtOAc (3×3 mL). The combined organics were washed with brine (10 mL), dried over Na$_2$SO$_4$ and concentrated. The residue was roughly purified by column chromatography (silica gel, PE/EtOAc 0 to 100%). The product-containing fractions were pooled and 40 was used as such in the next step.

(2S)-Isopropyl 2-(((((2S,3S,4R,5R)-5-(2-amino-6-(pyrrolidin-1-yl)-9H-purin-9-yl)-2,4-difluoro-3-hydroxy-4-methyltetrahydrofuran-2-yl)methoxy)(phenoxy)phosphoryl) amino)propanoate (41)

To a solution of the mixture containing compound 40 in EtOH (2 mL) was added palladium (10% on charcoal) (4 mg). The flask was flushed with hydrogen and the suspension was stirred under a hydrogen atmosphere for 3 h at RT. The mixture was then filtered over Celite and concentrated. The residue was purified by column chromatography (silica gel, DCM/MeOH 0 to 10%) and then by reverse phase column chromatography (C-18 silica, H$_2$O/MeOH 100:0 to 0:100). Product 41 (7 mg, 22% over 2 steps) was obtained as a white solid. $^1$H NMR (300 MHz, CD$_3$OD) δ 7.79 (s, 0.7H), 7.77 (s, 0.3H), 7.36-7.17 (m, 5H), 6.43 (d, J=23.6 Hz, 0.3H), 6.41 (d, J=23.6 Hz, 0.7H), 4.99-4.92 (overlapped with H$_2$O, m, 1H), 4.60.4.40 (m, 2H), 4.93 (lm, 6H), 2.00 (m, 2H), 1.32-1.19 (m, 12H). $^{31}$P NMR (121 MHz, CD$_3$OD) δ 4.15 (s), 4.01 (s). MS (ESI) m/z calcd. for C$_{27}$H$_{37}$F$_2$N$_7$O$_7$P [M+H]$^+$ 640.2; found 640.2.

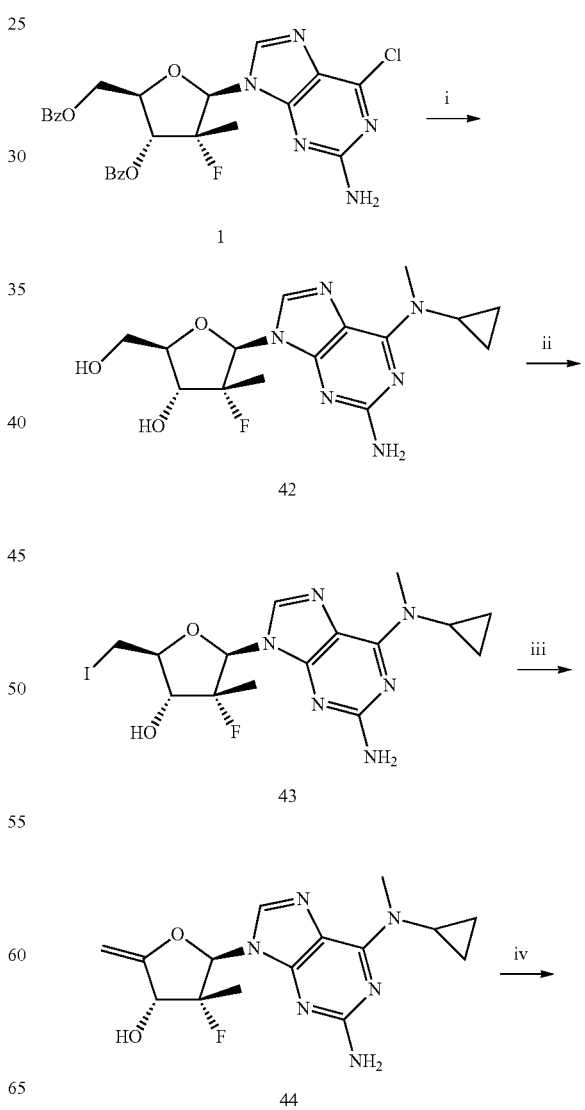

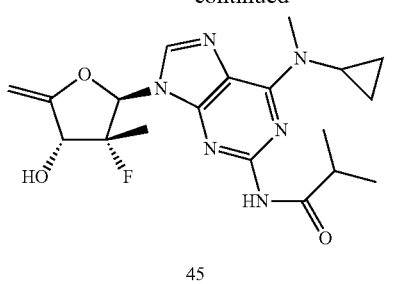

45

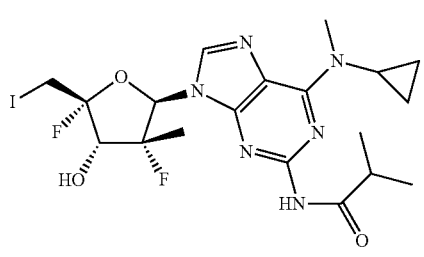

46

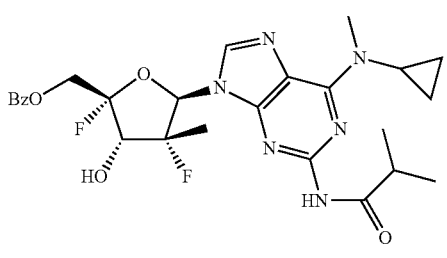

47

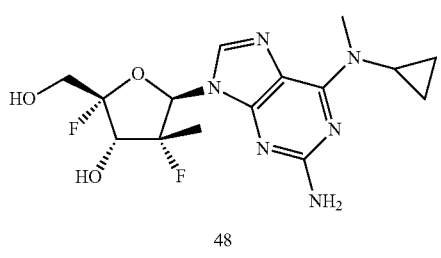

48

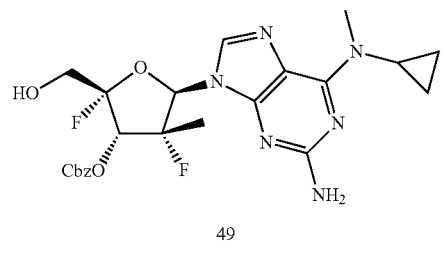

49

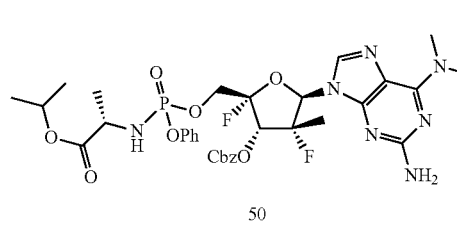

50

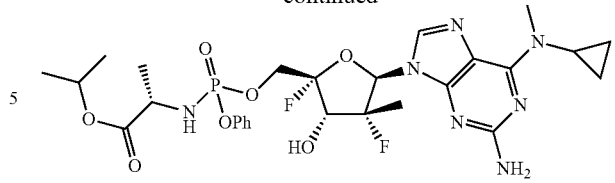

51 i) N-Methyl-cyclopropylamine•HCl, Et₃N, EtOH, 100° C.; ii) I₂, PPh₃, imidazole, THF; iii) MeONa, MeOH, 60° C.; iv) TMSCl, pyridine, 0° C. then isobutyryl chloride; v) Et₃N•3 HF, NIS, MeCN, -20° C.; vi) BzONa, DMSO, 100° C.; vii) MeNH₂, EtOH, 75° C.; viii) CbzCl, DMAP, DCM, 0° C.; ix) Isopropyl ((R,S)-(pentafluorophenoxy)-phenoxy-phosphoryl)-L-alaninate, DBU, THF; x) H₂, Pd—C, EtOH (2R,3R,4R,5R)-5-(2-Amino-6-(cyclopropyl)methyl) amino)-9H-purin-9-yl)-4-fluoro-2-(hydroxymethyl)-4-methyltetrahydrofuran-3-ol (42)

To a solution of compound 1 (3.0 g, 5.7 mmol) in EtOH (60 mL) was added N-methyl-cyclopropylamine hydrochloride (1.2 g, 11.4 mmol). The reaction mixture was heated at 100° C. in a sealed container for 3 h, cooled down to RT and 30% NH₄OH (30 mL) was added. The reaction mixture was heated at 80° C. in a sealed container for 15 h and cooled down to RT. The residue was purified by column chromatography (silica gel, DCM/MeOH 100:0 to 90:10). Product 42 (1.9 g, 94%) was obtained as a white solid.

(2R,3R,4R,5R)-5-(2-Amino-6-(cyclopropyl)methyl) amino)-9H-purin-9-yl)-4-fluoro-2-(iodomethyl)-4-methyltetrahydrofuran-3-ol (43)

To a solution of compound 42 (1.86 g, 5.28 mmol) in dry THF (35 mL) was added triphenylphosphine (3.32 g, 12.68 mmol) and imidazole (862 mg, 12.68 mmol). Then, a solution of iodine (2.57 g, 10.1 mmol) in dry THF (15 mL) was added drop-wise. The mixture was stirred at RT for 3 h. The solution was then filtered over Celite and concentrated. The dark residue containing 43 was used as such in the next step.

(3R,4R,5R)-5-(2-Amino-6-(cyclopropyl)methyl) amino)-9H-purin-9-yl)-4-fluoro-4-methyl-2-methylenetetrahydrofuran-3-ol (44)

To a solution of 43 in MeOH (50 mL) was added MeONa (2.85 g, 52.8 mmol). The reaction mixture was heated at 60° C. for 15 h and then, cooled down to RT and concentrated. EtOAc (100 mL) was added and the solution was washed with satd. NH₄Cl aq. solution (80 mL) and brine (80 mL). The organics were dried over anhydrous Na₂SO₄ and concentrated. The residue was purified by column chromatography (silica gel, PE/EtOAc 0 to 100%). Product 44 (0.57 g, 32% yield over 2 steps) was obtained as a yellow solid.

N-(6-(Cyclopropyl(methyl)amino)-9-((2R,3R,4R)-3-fluoro-4-hydroxy-3-methyl-5-methylenetetrahydrofuran-2-yl)-9H-purin-2-yl)isobutyramide (45)

To a solution of 44 (560 mg, 1.67 mmol) in dry pyridine (10 mL) was added chlorotrimethylsilane (530 μL, 4.19 mmol) drop-wise. The reaction mixture was stirred at 0° C. for 10 mins and then isobutyryl chloride (350 μL, 3.35 mmol) was added drop-wise. The orange solution was stirred at RT for 3 h. After cooling down to 0° C., the reaction was quenched by addition of H₂O (2 mL) and 30% NH₄OH (3 mL). The mixture was then stirred for 1 h at 0° C. EtOAc (50 mL) was added and the solution was washed with satd. NH₄Cl aq. solution (40 mL) and brine (40 mL). The organics were dried over anhydrous Na₂SO₄ and concentrated. The residue was co-evaporated with toluene (2×50 mL) and purified by column chromatography (silica gel, PE/EtOAc 0 to 100%). Product 45 (505 mg, 75% yield) was obtained as a white solid.

N-(9-((2R,3R,4S,5R)-3,5-Difluoro-4-hydroxy-5-(iodomethyl)-3-methyltetrahydrofuran-2-yl)-6-(cyclopropyl(methyl)amino)-9H-purin-2-yl)isobutyramide (46)

To a solution of 45 (359 mg, 0.89 mmol) in dry MeCN (15 mL) was added Et₃N.3HF (175 μL, 1.07 mmol). A solution of N-iodosuccinimide (280 mg, 1.24 mmol) in dry MeCN (15 mL) was added drop-wise over 45 mins at −20° C. The resulting orange solution was stirred for 2 h at 0° C. and for 1 h at RT. The reaction was then diluted with EtOAc (50 mL) and quenched by addition of satd. (1:1) NaHCO₃/Na₂S₂O₃ aq. solution (30 mL). The phases were separated and the organic layer was washed with brine (40 mL), dried over anhydrous Na₂SO₄ and concentrated. The residue was purified by column chromatography (silica gel, PE/EtOAc 0 to 100%). Product 46 (278 mg, 57% yield) was obtained as a white solid.

((2S,3S,4R,5R)-5-(6-(Cyclopropyl(methyl)amino)-2-isobutyramido-9H-purin-9-yl)-2,4-difluoro-3-hydroxy-4-methyltetrahydrofuran-2-yl)methyl benzoate (47)

To a solution of 46 (278 mg, 0.51 mmol) in dry DMSO (25 mL) was added sodium benzoate (1.09 g, 7.65 mmol). The resulting milky suspension was stirred for 3 days at 100° C. The mixture was then cooled down, partitioned between H₂O (460 mL) and EtOAc (80 mL) and the phases were separated. The aqueous layer was back-extracted with EtOAc (3×50 mL). The combined organics were washed with satd. NH₄Cl aq. solution (2×80 mL) and brine (80 mL). The organic solution was dried over anhydrous Na₂SO₄ and concentrated. The residue was purified by column chromatography (silica gel, PE/EtOAc 0 to 100%). Product 47 (222 mg, 80% yield) was obtained as an off-white solid.

(2S,3S,4R,5R)-5-(2-Amino-6-(cyclopropyl(methyl)amino)-9H-purin-9-yl)-2,4-difluoro-2-(hydroxymethyl)-4-methyltetrahydrofuran-3-ol (48)

A solution of 47 (220 mg, 0.40 mmol) in methylamine (33% in EtOH) (20 mL) in a sealed container was stirred for 20 h at 80° C. The mixture was then cooled down and concentrated. The residue was purified by column chromatography (silica gel, DCM/MeOH 0 to 10%). Product 48 (118 mg, 79% yield) was obtained as a white solid. ¹H NMR (300 MHz, CD₃OD) δ 8.00 (s, 1H), 6.45 (d, J=12.6 Hz, 1H), 4.66 (m, 1H), 3.86 (m, 2H), 3.32 (overlapped with MeOH, m, 3H), 3.15 (m, 1H), 1.22 (d, J=16.8 Hz, 3H), 0.92 (m, 2H), 0.72 (m, 2H). MS (ESI) m/z calcd. for C₁₅H₂₁F₂N₆O₃ [M+H]⁺ 371.2; found 371.2.

(2S,3S,4R,5R)-5-(2-Amino-6-(cyclopropyl(methyl)amino)-9H-purin-9-yl)-2,4-difluoro-2-(hydroxymethyl)-4-methyltetrahydrofuran-3-yl benzyl carbonate (49)

To a solution of 48 (38 mg, 0.10 mmol) and DMAP (13 mg, 0.11 mmol) in dry DCM (2 mL) was added benzyl chloroformate (17 μL, 0.12 mmol) at 0° C. The reaction mixture was stirred for 3 h at RT and diluted with DCM (5 mL). The solution was washed with H₂O (5 mL), brine (5 mL), dried over anhydrous Na₂SO₄ and concentrated. The residue was purified by column chromatography (silica gel, PE/EtOAc 0 to 100%). Product 49 (35 mg, 68% yield) was obtained as a white solid.

(2S)-Isopropyl 2-(((((2S,3S,4R,5R)-5-(2-amino-6-(cyclopropyl(methyl)amino)-9H-purin-9-yl)-3-(((benzyloxy)carbonyl)oxy)-2,4-difluoro-4-methyltetrahydrofuran-2-yl)methoxy) (phenoxy) phosphoryl)amino)propanoate (50)

To a solution of compound 49 (35 mg, 0.07 mmol) and isopropyl ((R,S)-(pentafluorophenoxy)-phenoxy-phosphoryl)-L-alaninate (50 mg, 0.11 mmol) in dry THF (3 mL) was added DBU (21 μL, 0.14 mmol) at 0° C. The reaction mixture was stirred for 16 h at RT. The solution was then diluted with EtOAc (6 mL) and satd. NH₄Cl aq. solution (4 mL). The phases were separated and the aqueous layer was back-extracted with EtOAc (3×3 mL). The combined organics were washed with brine (10 mL), dried over Na₂SO₄ and concentrated. The residue containing product 50 was used as such in the next step.

(2S)-Isopropyl 2-(((((2S,3S,4R,5R)-5-(2-amino-6-(cyclopropyl(methyl)amino)-9H-purin-9-yl)-2,4-difluoro-3-hydroxy-4-methyltetrahydrofuran-2-yl) methoxy)(phenoxy)phosphoryl) amino)propanoate (51)

To a solution of the mixture containing compound 50 in EtOH (3 mL) was added palladium (10% on charcoal) (6 mg). The flask was flushed with hydrogen and the suspension was stirred under a hydrogen atmosphere for 3 h at RT. The mixture was then filtered over Celite and concentrated. The residue was purified by column chromatography (silica gel, DCM/MeOH 0 to 10%) and then by reverse phase column chromatography (C-18 silica, H₂O/MeOH 100:0 to 0:100). Product 51 (13 mg, 29% over 2 steps) was obtained as a white solid. ¹H NMR (300 MHz, CD₃OD) δ 7.79 (m, 1H), 7.34-7.14 (m, 5H), 6.43 (d, J=17.4 Hz) and 6.41 (d, J=18.0 Hz, 1H), 4.95-4.86 (overlapped with H₂O, m, 1H), 4.63-4.52 (m, 1H), 4.47-4.34 (m, 1H), 3.96-3.85 (m, 1H), 3.32-3.30 (overlapped with MeOH, m, 4H), 3.16-3.07 (m, 1H), 1.32-1.18 (m, 12H), 0.92 (m, 2H), 0.71 (m, 2H). ³¹P NMR (121 MHz, CD₃OD) δ 4.16 (s), 4.05 (s). MS (ESI) m/z calcd. for C₂₇H₃₇F₂N₇O₇P [M+H]⁺ 640.2; found 640.4.

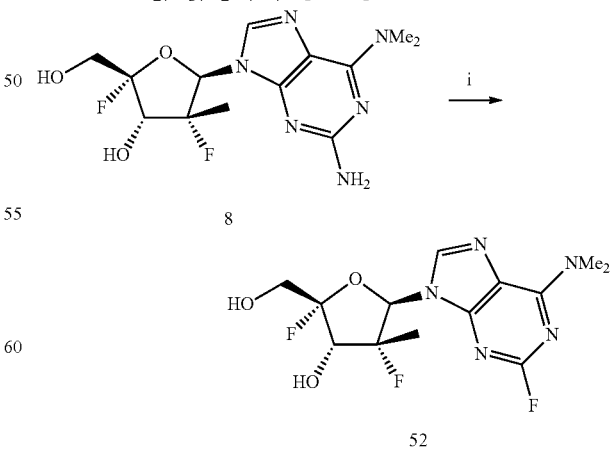

i) tBuONO, pyridine•HF, pyridine, -15° C.

(2S,3S,4R,5R)-5-(2-Fluoro-6-(dimethylamino)-9H-purin-9-yl)-2,4-difluoro-2-(hydroxymethyl)-4-methyltetrahydrofuran-3-ol (52)

A solution of 8 (80 mg, 0.23 mmol) in dry pyridine (500 μL) was cooled down to −15° C. pyridine hydrofluoride (300 μL) was added. Then, tert-butyl nitrite (61 μL, 0.46 mmol) was added drop-wise over 5 mins. The mixture was stirred at 10° C. for 4 h and quenched by the addition of a suspension of $CaCO_3$ (800 mg) in $H_2O$ (2 mL). The resulting suspension was stirred at RT for 15 mins and extracted with EtOAc (5×5 mL). The combined organics were dried over anhydrous $Na_2SO_4$ and concentrated. The residue was purified by column chromatography (silica gel, DCM/MeOH 0 to 10%). Product 52 (52 mg, 65% yield) was obtained as an off-white solid. $^1$H NMR (300 MHz, $CD_3OD$) δ 8.25 (s, 1H), 6.48 (d, J=16.4 Hz, 1H), 4.59 (dd, J=24.8, 20.0 Hz, 1H), 3.90-3.82 (m, 2H), 3.74 (br s, 3H), 3.27 (br s, 3H), 1.20 (d, J=22.4 Hz, 3H). MS (ESI) m/z calcd. for $C_{13}H_{17}F_3N_5O_3$ [M+H]$^+$ 348.1; found 348.2.

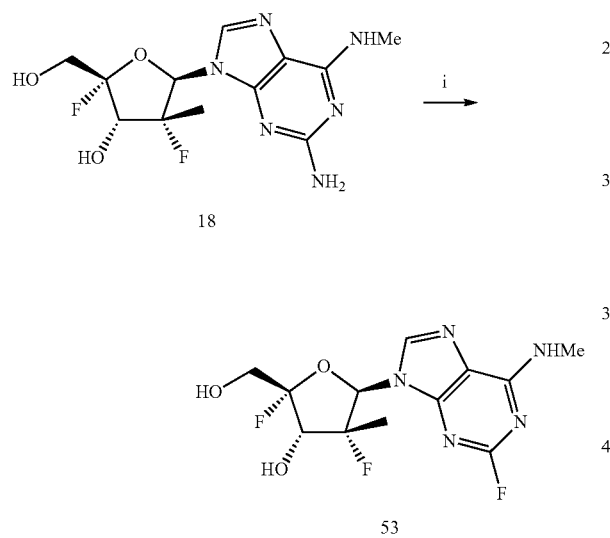

i) tBuONO, pyridine·HF, pyridine, −15° C.

(2S,3S,4R,5R)-5-(2-Fluoro-6-(methylamino)-9H-purin-9-yl)-2,4-difluoro-2-(hydroxymethyl)-4-methyltetrahydrofuran-3-ol (53)

A solution of 18 (70 mg, 0.21 mmol) in dry pyridine (500 μL) was cooled down to −15° C. pyridine hydrofluoride (280 μL) was added. Then, tert-butyl nitrite (57 μL, 0.42 mmol) was added drop-wise over 5 mins. The mixture was stirred at 10° C. for 4 h and quenched by the addition of a suspension of $CaCO_3$ (800 mg) in $H_2O$ (2 mL). The resulting suspension was stirred at RT for 15 mins and extracted with EtOAc (5×5 mL). The combined organics were dried over anhydrous $Na_2SO_4$ and concentrated. The residue was purified by column chromatography (silica gel, DCM/MeOH 0 to 10%). Product 53 (43 mg, 62% yield) was obtained as an off-white solid. $^1$H NMR (300 MHz, $CD_3OD$) δ 8.26 (s, 1H), 6.45 (d, J=16.5 Hz, 1H), 4.61 (m, 1H), 3.86 (m, 2H), 3.06 (s, 3H), 1.21 (d, J=22.2 Hz, 3H). MS (ESI) m/z calcd. for $C_{12}H_{15}F_3N_5O_3$ [M+H]$^+$ 334.1; found 334.2.

Synthesis of Intermediate 1

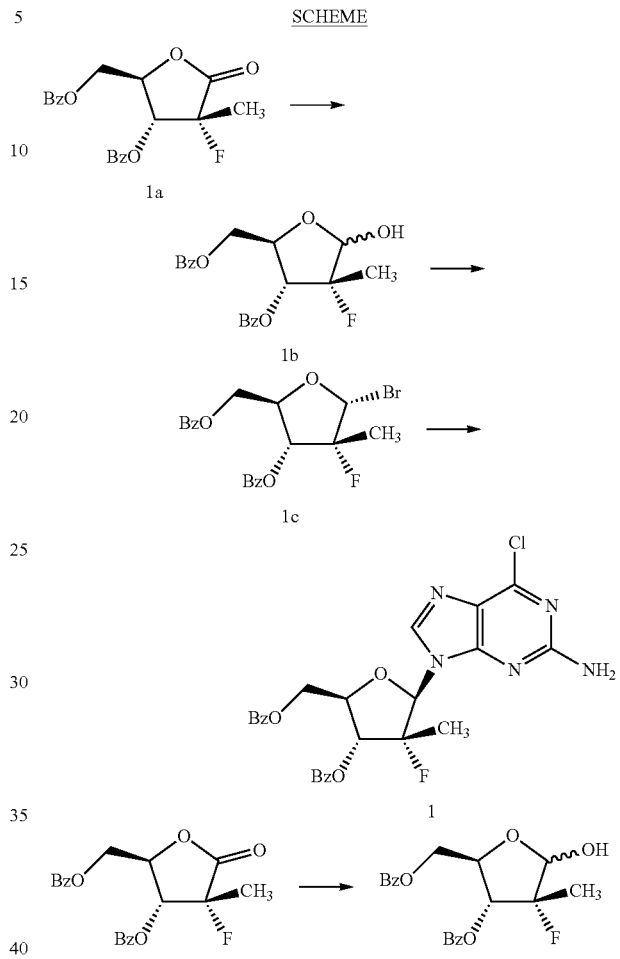

To a suspension of 1a (111 g, 300 mmol) in toluene (200 mL) was added $NaAlH_2(OCH_2CH_2OCH_3)_2$ (81 mL, 300 mmol) at −20° C. and mixture stirred for 20 min. TLC analysis indicated that starting material was consumed. The reaction mixture was poured into cooled aq. HCl solution (1M, 330 mL). The separated organic layer was washed with water, brine and concentrated. The crude product was purified by column chromatography (EtOAc:PE, 1:8 to 1:4) to give crude 1b as an oil (80 g). Crude 1b dissolved in MeOH (300 mL) and $H_2O$ (1 mL) and solution stirred for 1 h where product precipitated. After filtration, the filter cake was dried to give 1a as an off-white solid.

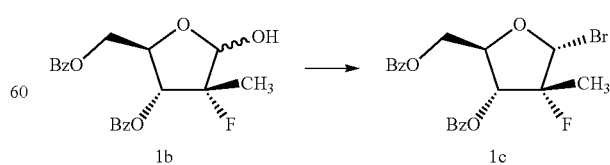

To a solution of 1b (75 g, 185 mmol) in MeCN (20 mL) was added $PPh_3$ (120 g, 455 mmol). $CBr_4$ (120 g, 361 mmol) was added to the mixture in portions (temperature kept below −20° C.). After stirring at RT for 1 h, TLC indicated consumption of starting material. Water (20 mL) was added, and the mixture stirred for 5 min. After filtration, the filter cake was triturated with MeOH to give 1c (66 g, 75%).

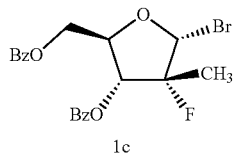

1c

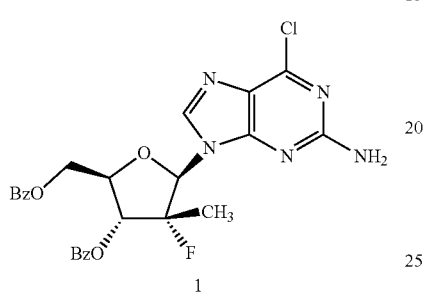

1

To a suspension of 2-amino-6-chloropurine (69 g, 414 mmol) in t-BuOH (600 mL) was added t-BuOK (46 g). MeCN and T384-0 (65 g, 138 mmol) were then added at 50° C. After stirring at 60-65° C. for 20 h, TLC indicated the consumption of starting material. After cooling the mixture to RT and filtration, the filtrate was adjusted to pH=7 using conc. HCl solution. The mixture was filtered and concentrated. The residue was purified by column chromatography ($CH_2Cl_2$) to give 1 (35 g).

APPENDIX

| Code No. | Structure | H NMR/MS |
|---|---|---|
| 1 | (structure shown) | $^1$H NMR (400 MHz, CDCl$_3$) δ 8.07-8.04 (, m, 5H), 7.62-7.29 (m, 6H), 6.44 (dd, J = 22.8. 8.0 Hz, 1H), 6.15 (d, J = 18.0 Hz, 1H), 5.05-5.01 (m, 1H), 4.80-4.76 (m, 1H), 4.64-4.60 (m, 1H), 1.36 (d, J = 22.8 Hz, 3H). [M + H]$^+$ = 526.2 |

Biological Data

Example X. Assay Methodology and Biological Data

Huh-7 luc/neo ET cells bearing a discistronic HCV genotype 1b luciferase reporter replicon were plated at 7.5×10$^3$ cells/ml in duplicate 96-well plates for the parallel determination of antiviral efficacy (EC$_{50}$) and cytotoxicity (TC$_{50}$). The plates were cultured for 24 hours prior to the addition of compounds. Six serial one half log dilutions of the test articles (high test concentration of 100.0 μM. or high test concentration of 1.0 μM) and human interferon-alpha2b (high test 10.0 U/ml) were prepared in cell culture medium and added to the cultured cells in triplicate wells for each dilution. Six wells in the test plates received medium alone as an untreated control. Following 72 hours of culture in the presence of compound, one of the plates was used for the determination of cytotoxicity by staining with STT and the other for antiviral efficacy by determination of luciferase reporter activity. Cytotoxicity and efficacy data were collected and imported into a customized Excel workbook for determination of the TC$_{50}$ and EC$_{50}$ values.

TABLE XXX

Replicon Assay Results for Compounds Tested.

| Cmpd No. | Structure | HCV Replicon EC$_{50}$/EC$_{95}$ (µM) | HCV Replicon CC$_{50}$ (µM) | Fold increase in activity compared to parent nucleoside |
|---|---|---|---|---|
| 1 | 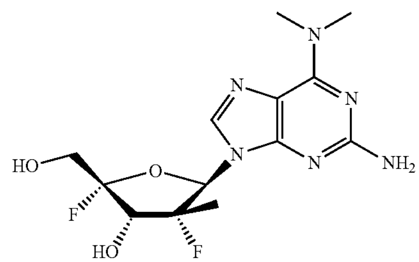 | 84.1 | >100 | |
| 2 | 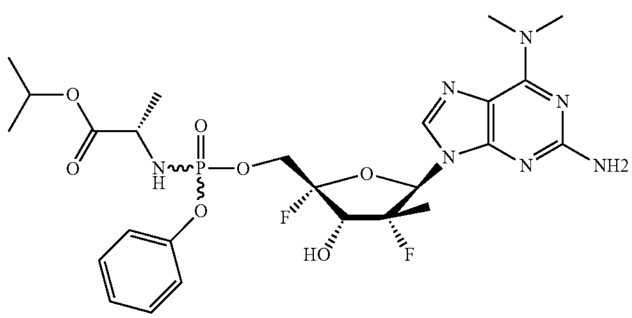 | 0.034 | >10 | 2,941 |
| 3 | 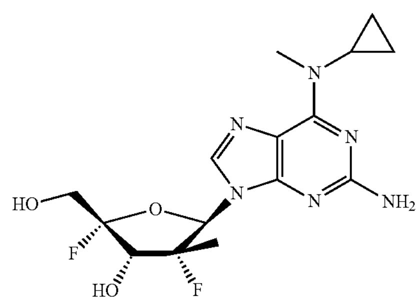 | 72.4 | >100 | |
| 4 | 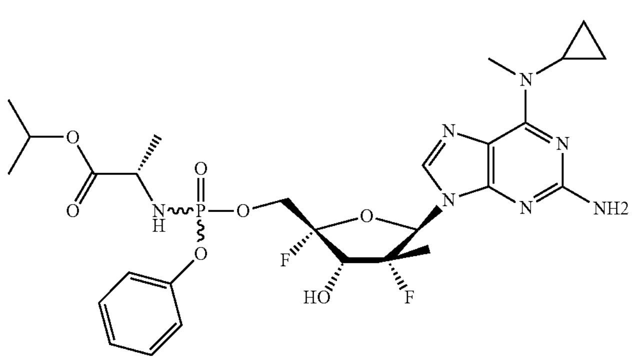 | 0.015 | >10 | 667 |

TABLE XXX-continued

Replicon Assay Results for Compounds Tested.

| Cmpd No. | Structure | HCV Replicon EC$_{50}$/EC$_{95}$ (μM) | HCV Replicon CC$_{50}$ (μM) | Fold increase in activity compared to parent nucleoside |
|---|---|---|---|---|
| 5 | 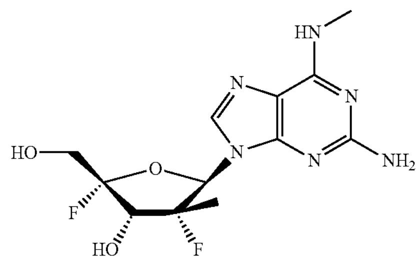 | >100 | >100 | |
| 6 | 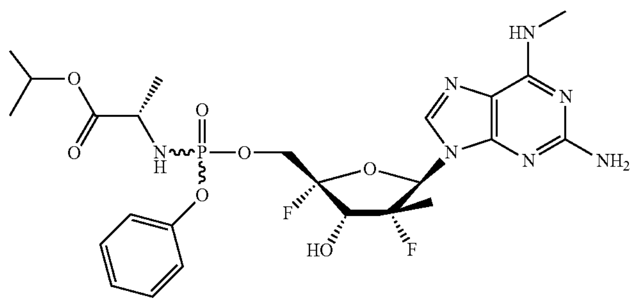 | 0.001 | >10 | 10,000 |
| 8 | 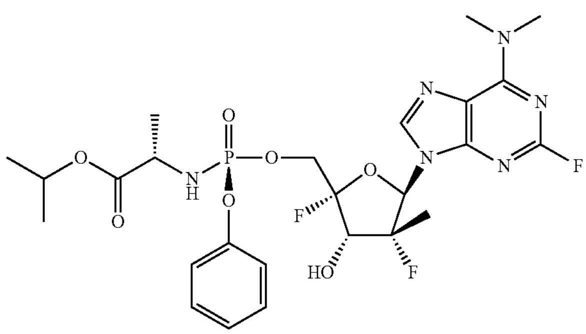 [SMILES: CC(C)OC(=O)[C@H](C)N[P@](=O)(OC[C@@]1(F)O[C@@H](n2cnc3c(N(C)C)nc(F)nc32)[C@](C)(F)[C@@H]1O)Oc1ccccc1] | 0.014 | 35.3 | 2521 |
| 10 | 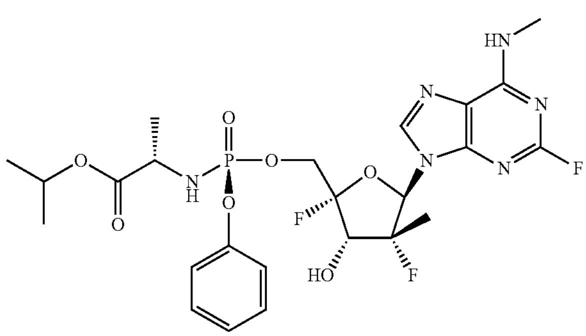 [SMILES: CNc1nc(F)nc2c1ncn2[C@@H]1O[C@](F)(CO[P@@](=O)(N[C@@H](C)C(=O)OC(C)C)Oc2ccccc2)[C@@H](O)[C@@]1(C)F] | 11.4 | 54 | 4.7 |

TABLE XXX-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 11 | 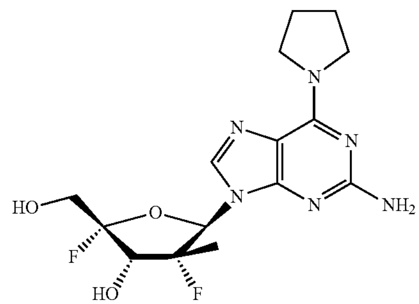 | 63.0 | >100 | |
| 12 | 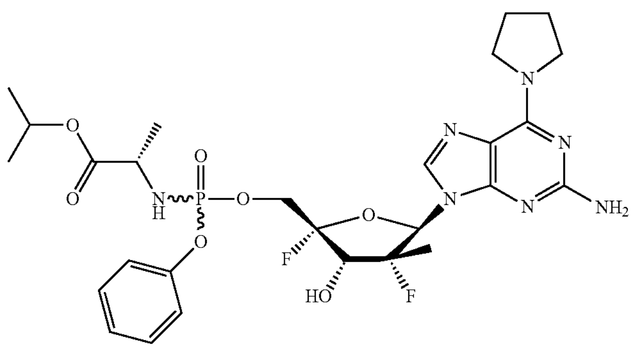 | 0.108 | >10 | >31.3 |
| 13 | 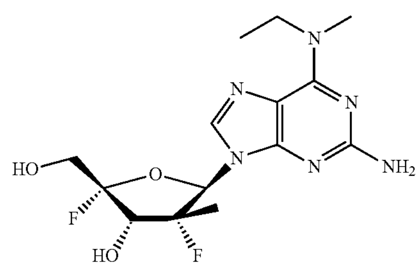 | 79.5 | >100 | |
| 14 | 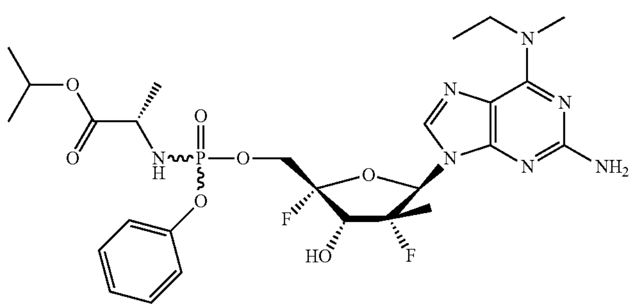 | 0.023 | >10 | 434 |

TABLE XXX-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 15 | 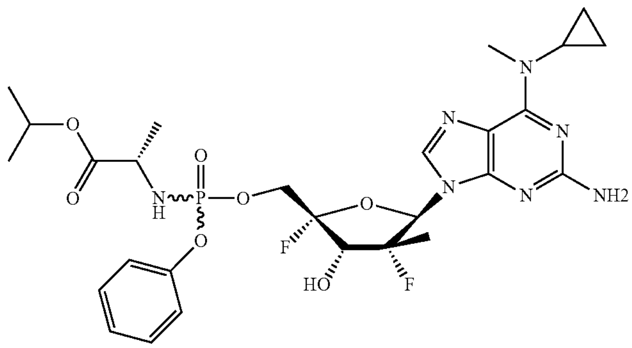 | 0.015 | >50 | 3332 |
| 16 | 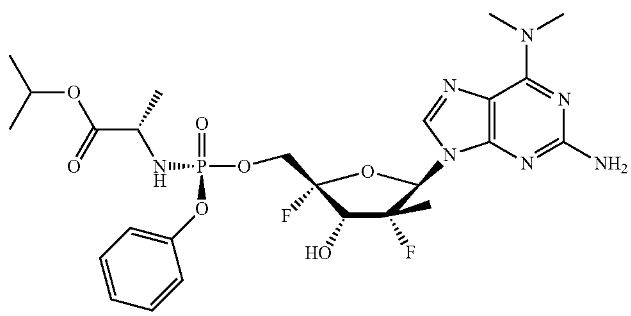 | 1.24 | >50 | 40 |
| 17 | 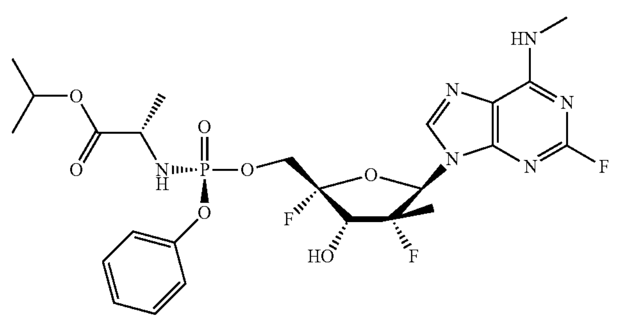 | 11.4 | >50 | 4.3 |

As used herein, the terms about and approximately should be interpreted to include any values which are within 5% of the recited value. Furthermore, recitation of the term about and approximately with respect to a range of values should be interpreted to include both the upper and lower end of the recited range. As used herein, the terms first, second, third and the like should be interpreted to uniquely identify elements and do not imply or restrict to any particular sequencing of elements or steps.

Concentrations, amounts, and other numerical data may be presented here in a range format (e.g., from about 5% to about 20%). It is to be understood that such range format is used merely for convenience and brevity, and should be interpreted flexibly to include not only the numerical values explicitly recited as the limits of the range, but also to include all the individual numerical values or sub-ranges encompassed within that range, as if each numerical value and sub-range is explicitly recited unless otherwise indicated. For example, a range of from about 5% to about 20% should be interpreted to include numerical values such as, but not limited to 5%, 5.5%, 9.7%, 10.3%, 15%, etc., and sub-ranges such as, but not limited to 5% to 10%, 10% to 15%, 8.9% to 18.9%, etc.

While the invention has been shown or described in only some of its embodiments, it should be apparent to those skilled in the art that it is not so limited, but is susceptible to various changes without departing from the spirit and scope of the invention. Furthermore, it is to be understood that the form of the invention shown and described is to be taken as presently preferred embodiments. Various modifications and changes may be made to each and every processing step as would be obvious to a person skilled in the art having the benefit of this disclosure. It is intended that the following claims be interpreted to embrace all such modifications and changes and, accordingly, the specification is to be regarded in an illustrative rather than a restrictive sense.

Moreover, it is intended that the appended claims be construed to include alternative embodiments.

We claim:
1. A compound having formula I or formula II:

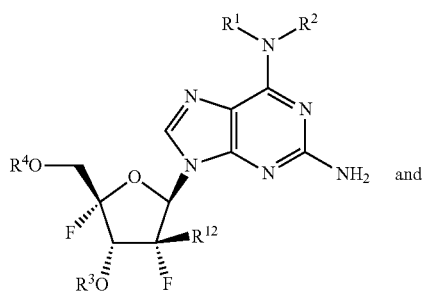

Formula I

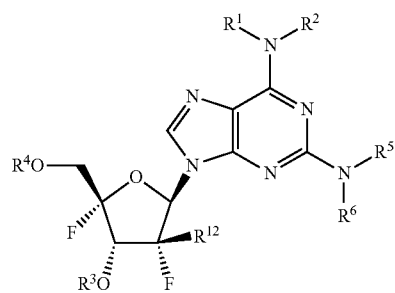

Formula II wherein:
R$^1$ is C$_1$-C$_6$alkyl or (C$_0$-C$_2$alkyl)(C$_3$-C$_6$cycloalkyl);
R$^2$ is hydrogen, C$_1$-C$_6$alkyl, CHF$_2$, CH$_2$F, CF$_3$, (C$_0$-C$_2$alkyl) (C$_3$-C$_6$cycloalkyl), —C(O)R$^{3C}$, —C(S)R$^{3C}$, —(C$_0$-C$_2$alkyl)(aryl), —(C$_0$-C$_2$alkyl)(heterocycle), or —(C$_0$-C$_2$alkyl)(heteroaryl); or
R$^1$ and R$^2$ together with the nitrogen to which they are bonded can form a heterocycle;
R$^3$ is hydrogen,

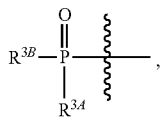

diphosphate, triphosphate, an optionally substituted carbonyl linked amino acid, —C(S)R$^{3C}$, —C(S)R$^{3C}$, or —C(O)R$^{3C}$;
R$^{3A}$ is O$^-$, OH, an —O-optionally substituted aryl, an —O-optionally substituted heteroaryl, or an optionally substituted heterocyclyl;
R$^{3B}$ is O$^-$, OH, an optionally substituted N-linked amino acid or an optionally substituted N-linked amino acid ester;
R$^{3C}$ is optionally substituted alkyl, optionally substituted alkenyl, optionally substituted alkynyl, optionally substituted —(C$_0$-C$_2$)(cycloalkyl), optionally substituted —(C$_0$-C$_2$)(heterocyclo), optionally substituted —(C$_0$-C$_2$)(aryl), optionally substituted —(C$_0$-C$_2$)(heteroaryl), optionally substituted —O-alkyl, optionally substituted —O-alkenyl, optionally substituted —O-alkynyl, optionally substituted —O—(C$_0$-C$_2$)(cycloalkyl), optionally substituted —O—(C$_0$-C$_2$)(heterocyclo), optionally substituted —O—(C$_0$-C$_2$)(aryl), optionally substituted —O—(C$_0$-C$_2$)(heteroaryl), optionally substituted —S-alkyl, optionally substituted —S-alkenyl, optionally substituted —S-alkynyl, optionally substituted —S—(C$_0$-C$_2$)(cycloalkyl), optionally substituted —S—(C$_0$-C$_2$)(heterocyclo), optionally substituted —S—(C$_0$-C$_2$)(aryl), or optionally substituted —S—(C$_0$-C$_2$)(heteroaryl);
R$^4$ is a monophosphate, diphosphate, triphosphate; or
R$^3$ and R$^4$ together with the oxygens that they are bonded to can form a 3',5'-cyclic ring;
R$^5$ is hydrogen, C$_1$-C$_6$alkyl, or —(C$_0$-C$_2$alkyl)(C$_3$-C$_6$cycloalkyl);
R$^6$ is C$_1$-C$_6$alkyl, —(C$_0$-C$_2$alkyl)(C$_3$-C$_6$cycloalkyl), —(C$_{0-6}$alkyl)(aryl), —(C$_{0-6}$alkyl)(heteroaryl), —(C$_{0-6}$alkyl)(heterocycle), —C(S)R$^{3C}$ or —C(O)R$^{3C}$;
R$^{12}$ is CH$_3$, CH$_2$F, CHF$_2$, CF$_3$, or ethynyl; or
a racemate, an enantiomer, a diastereomer, an isotopically-labelled analog, or a pharmaceutically acceptable salt thereof.

2. The compound of claim 1, wherein R$^4$ is a stabilized phosphate, a phosphoramidate, or a thiophosphoramidate.

3. The compound of claim 2, wherein the compound is:

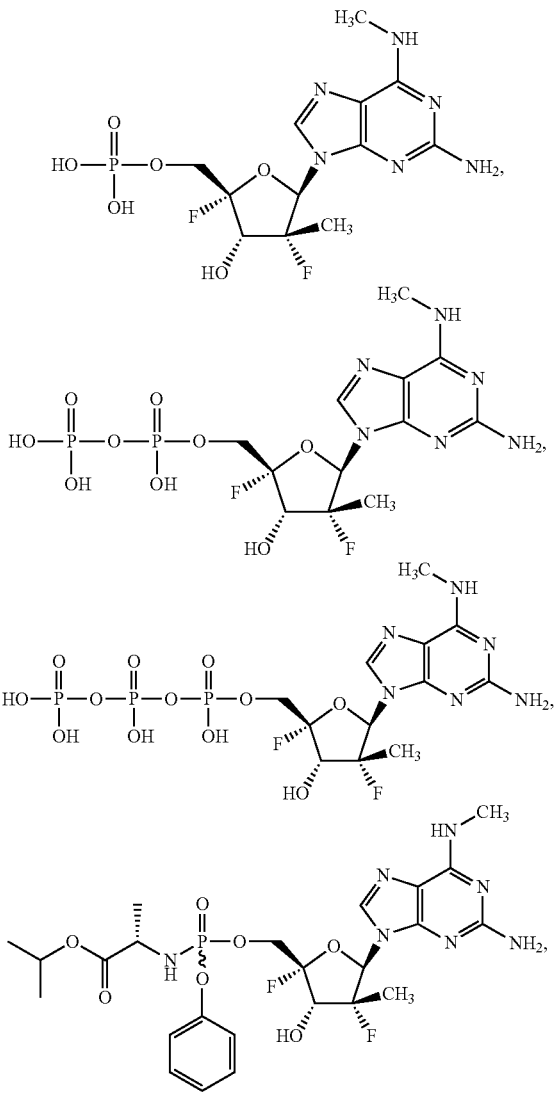

151
-continued
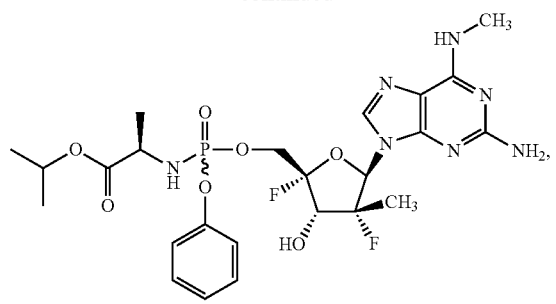
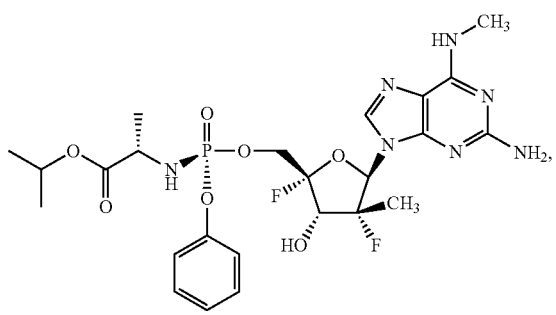
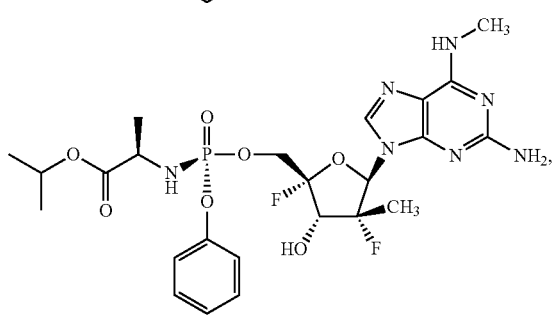
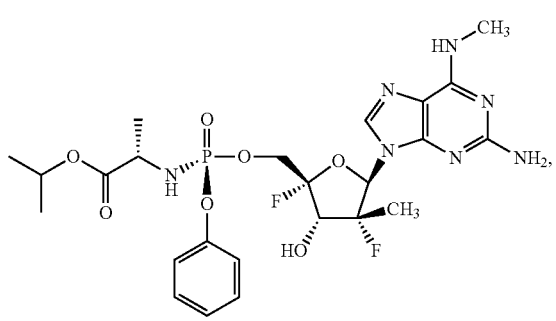
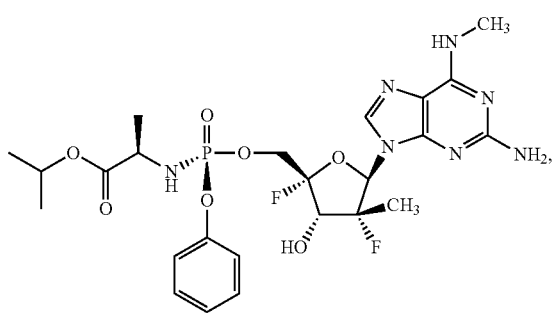
152
-continued
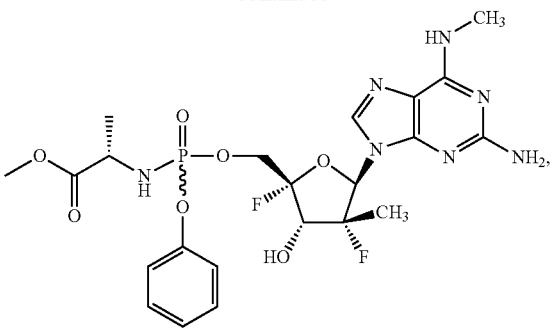
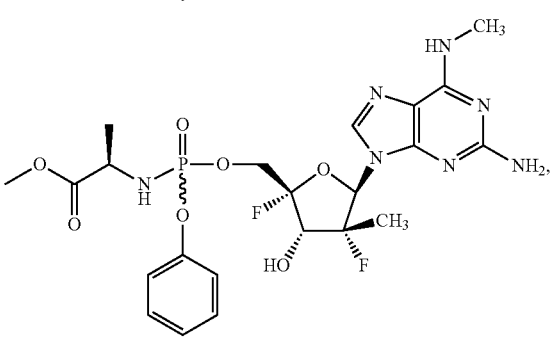
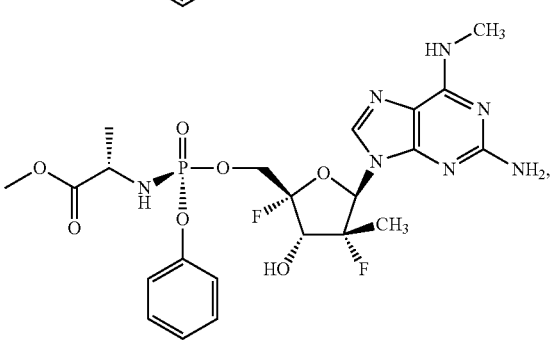
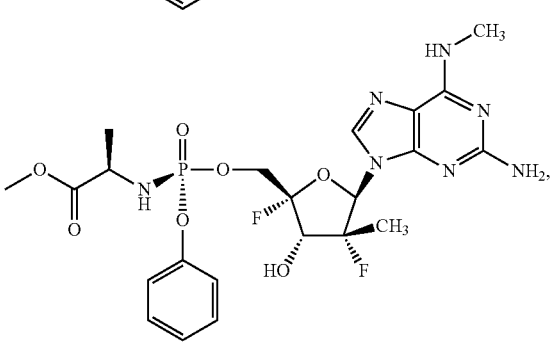
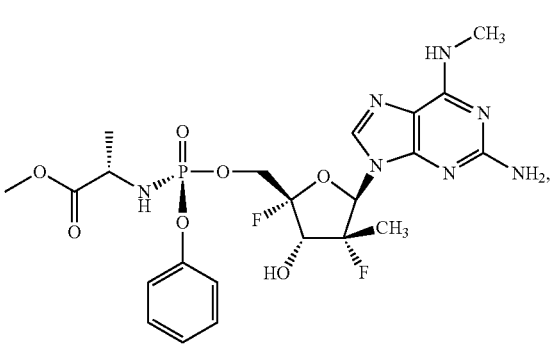

153
-continued
154
-continued
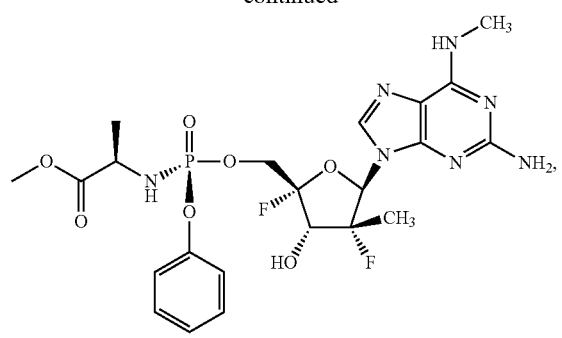
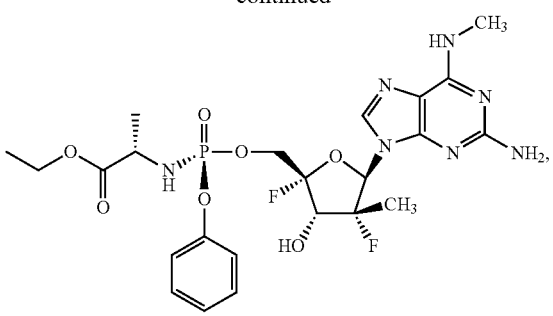

155
-continued
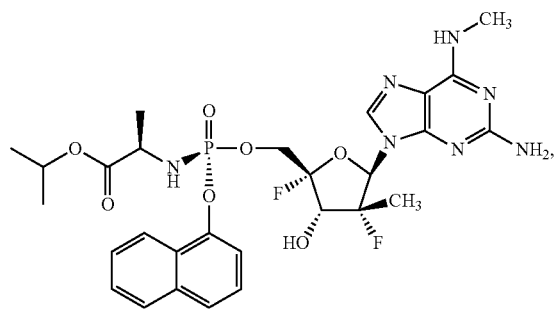
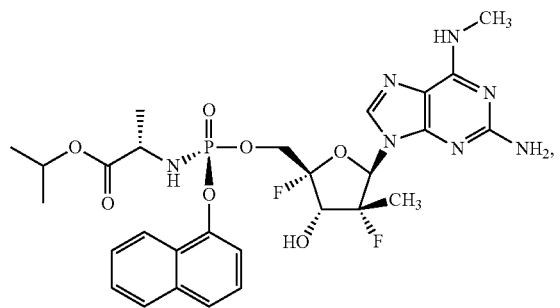
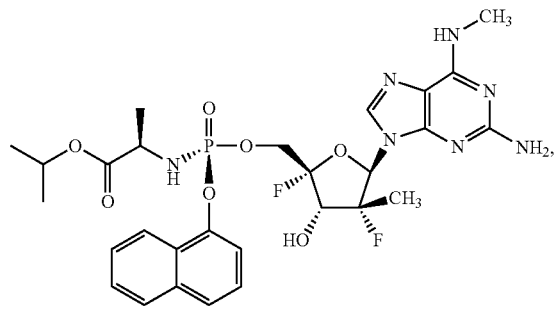
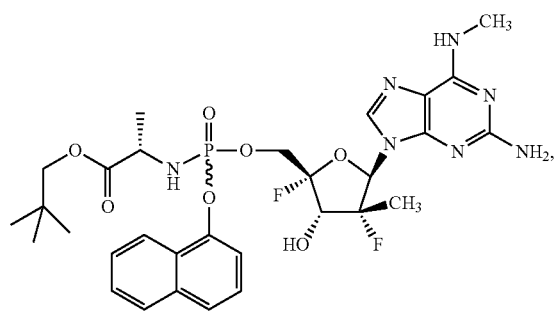
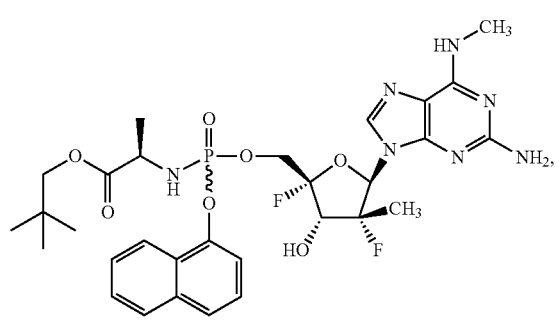
156
-continued
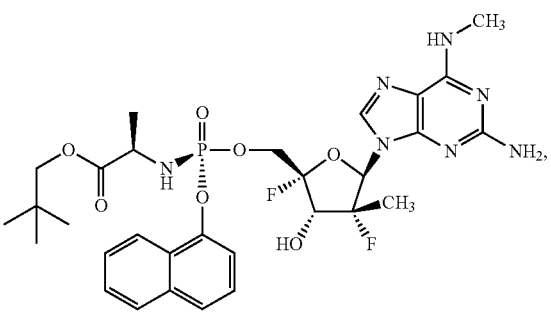
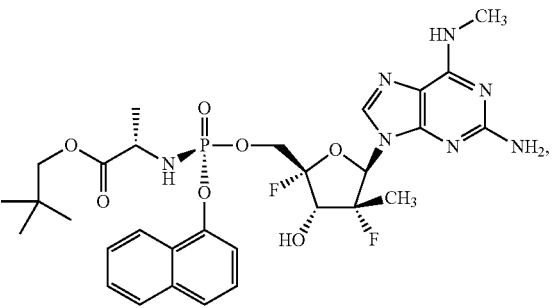
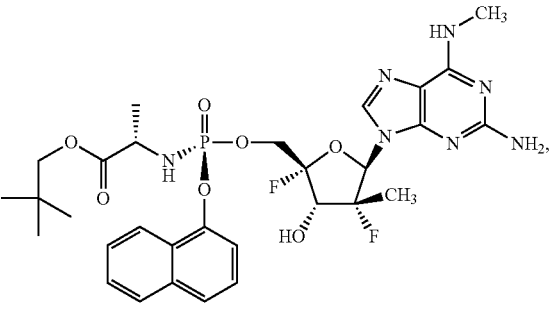
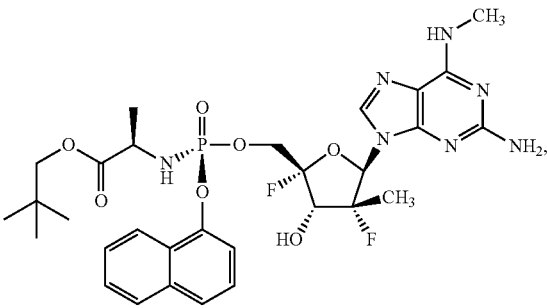
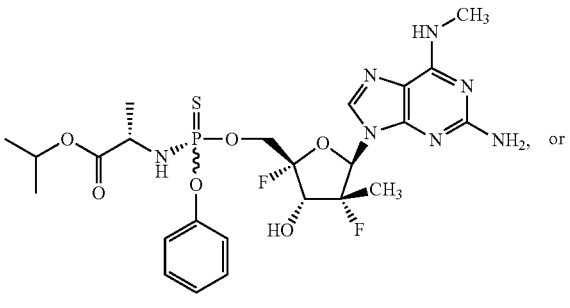 or 157
-continued
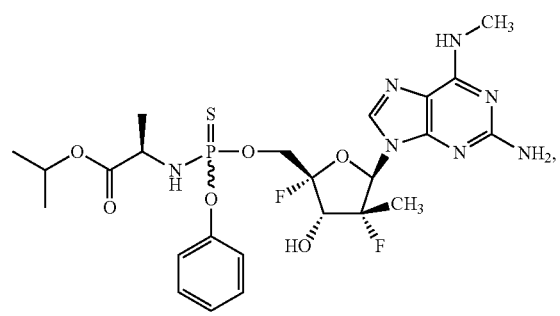
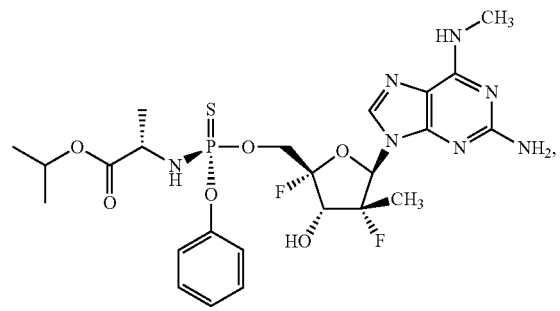
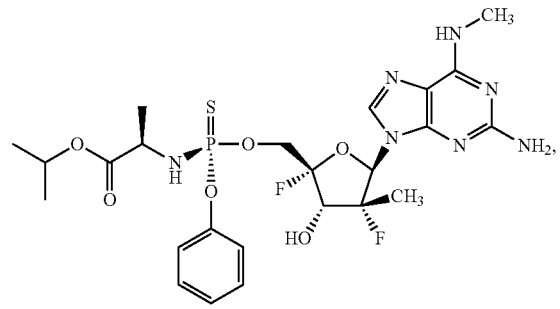
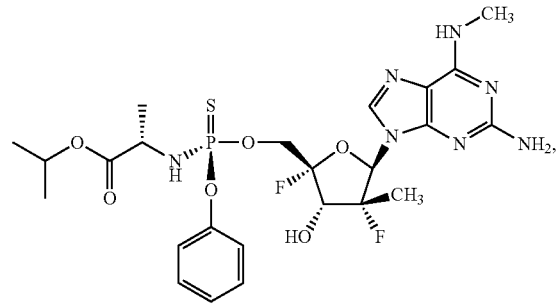
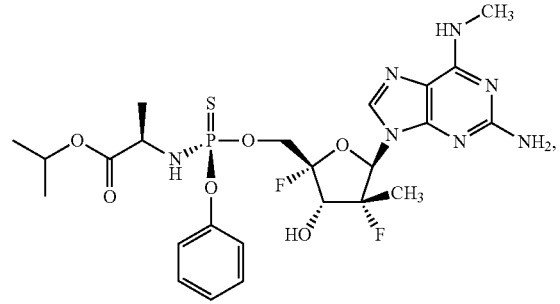
158
-continued
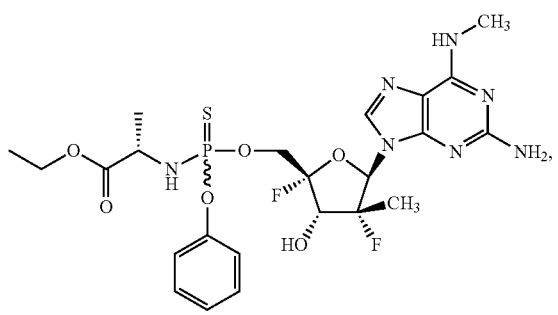
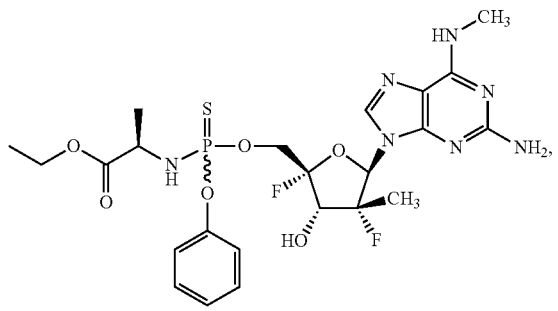
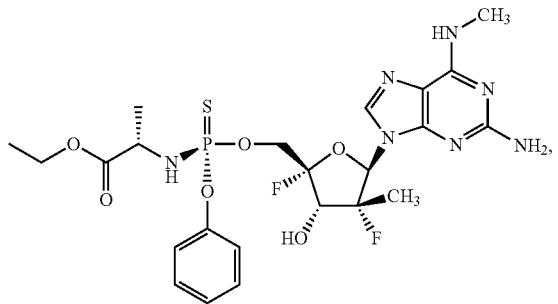
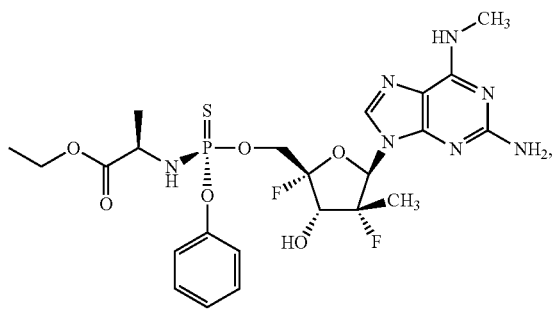
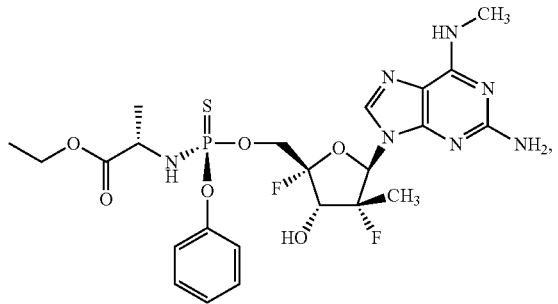

159
-continued
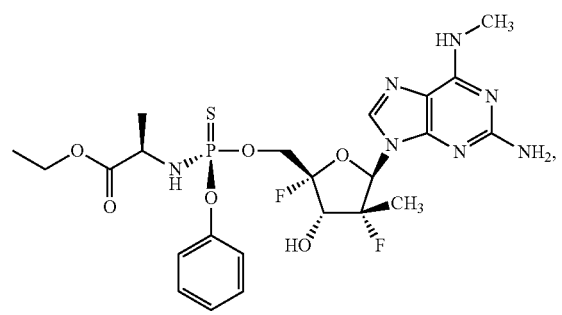
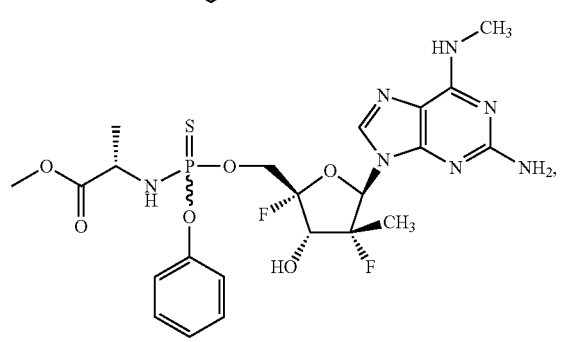
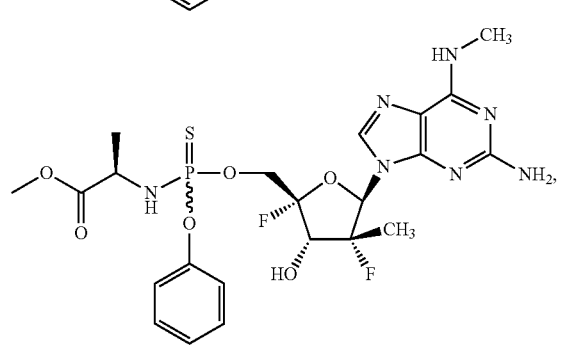
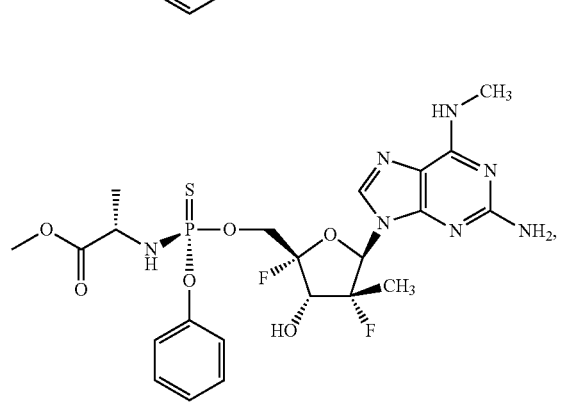
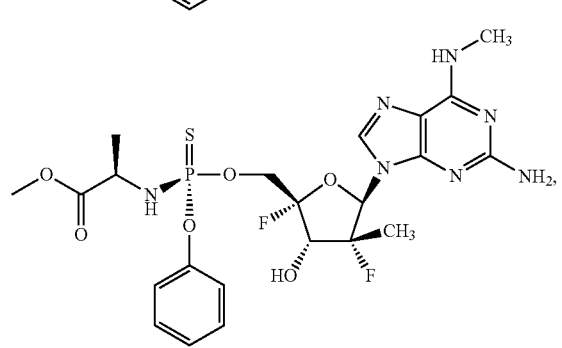
160
-continued
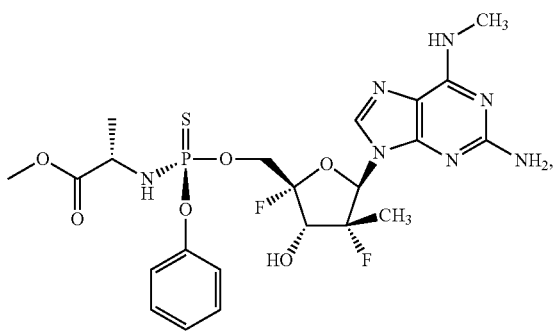
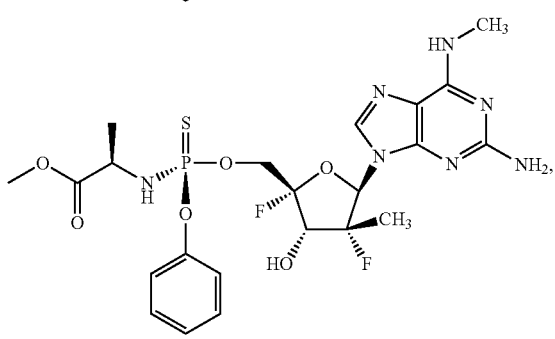
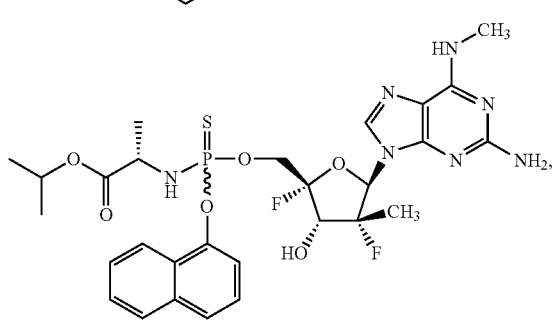
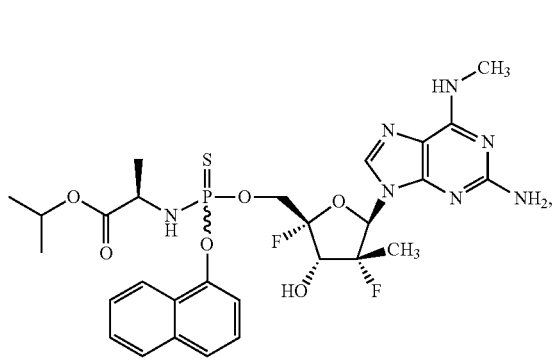
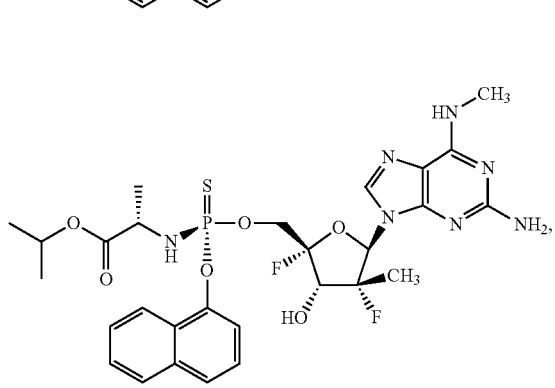

161
-continued
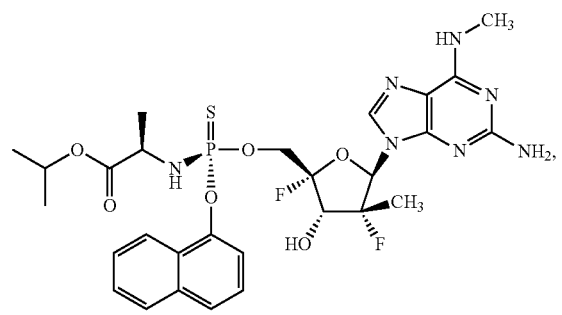
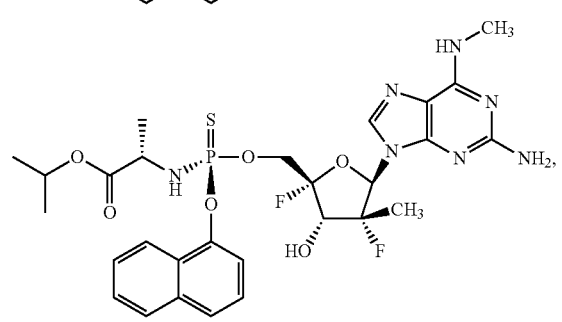
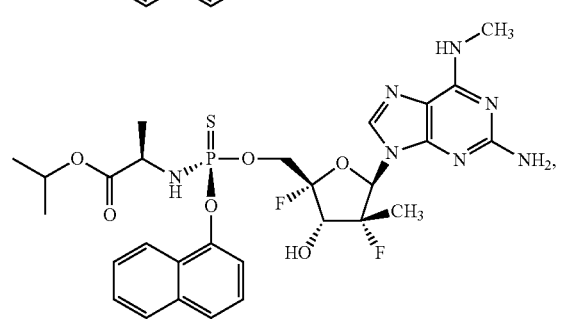
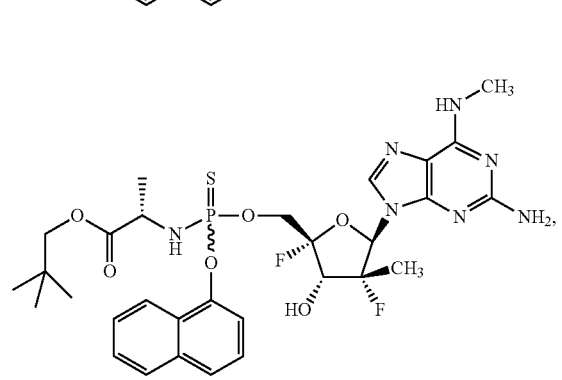
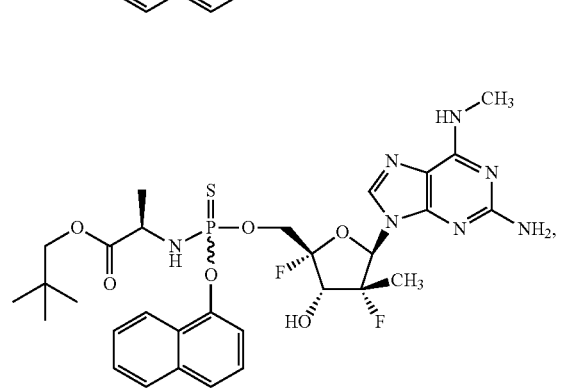
162
-continued
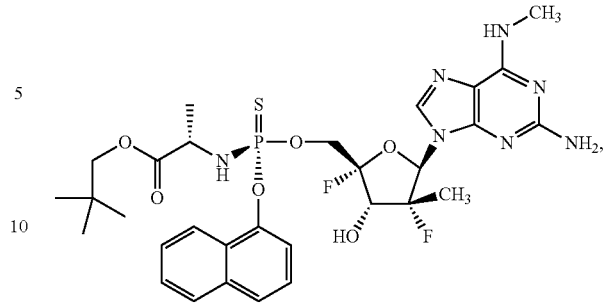
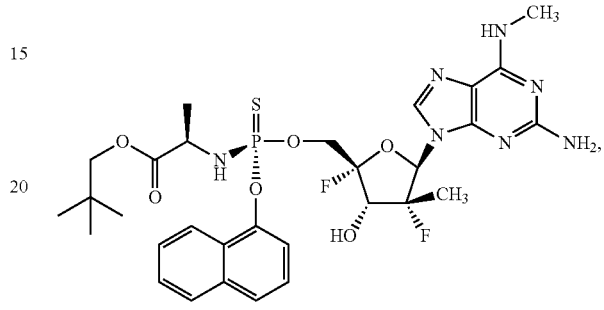
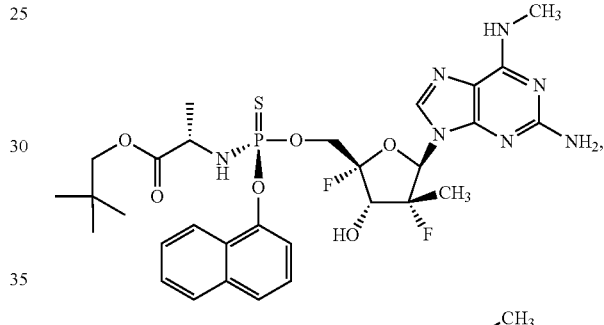
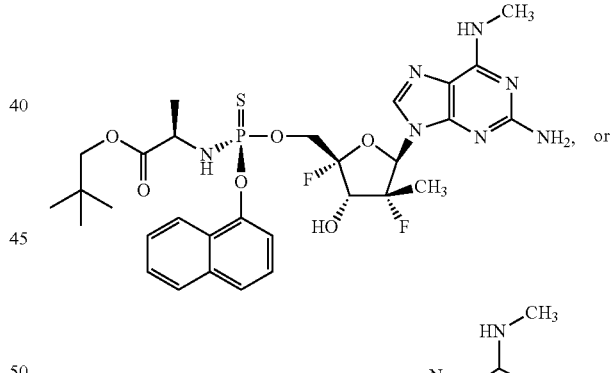
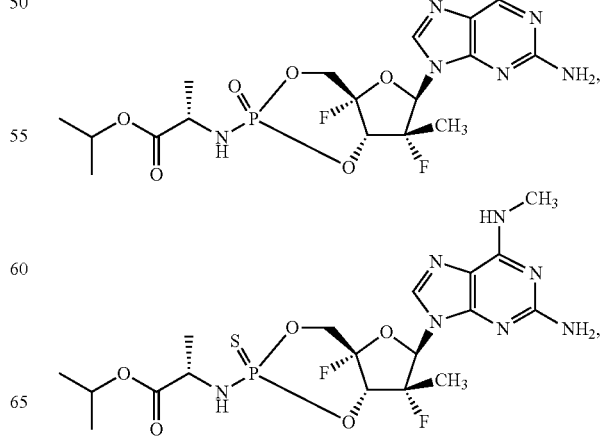

163
-continued
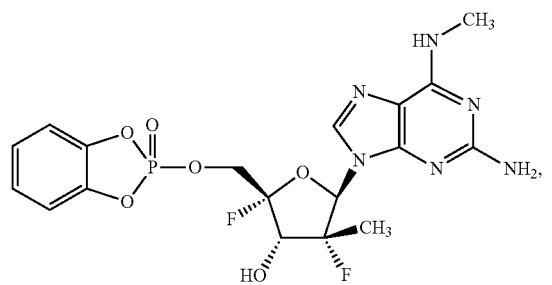
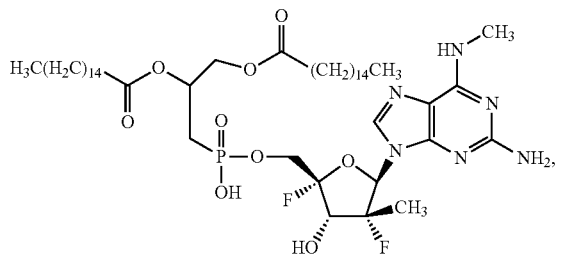
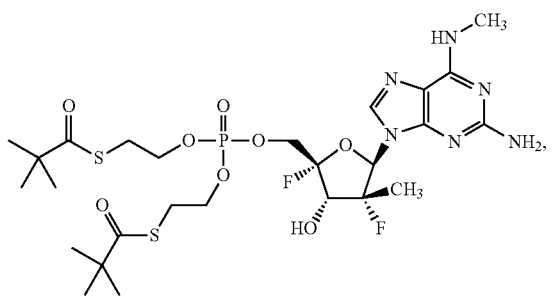
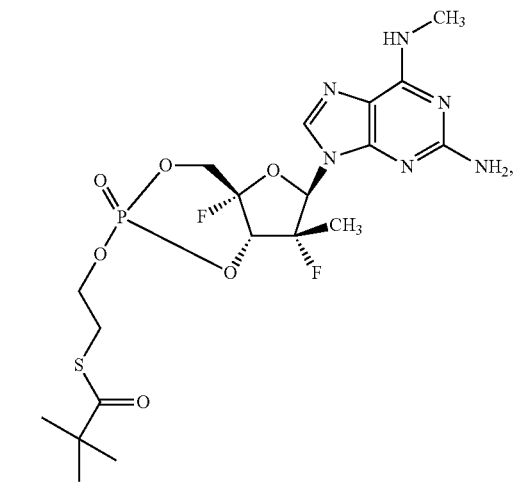
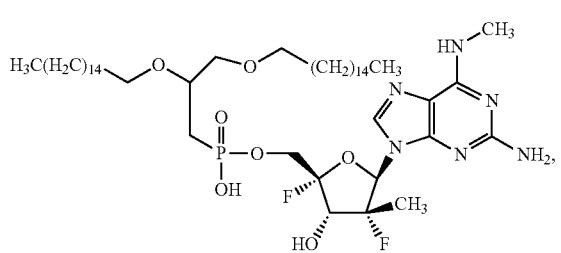
164
-continued
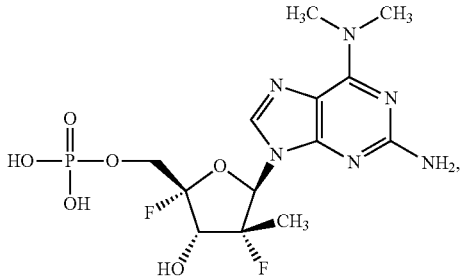
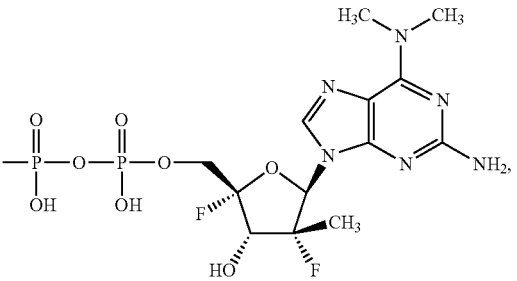
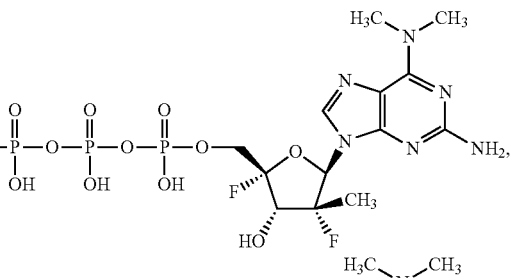
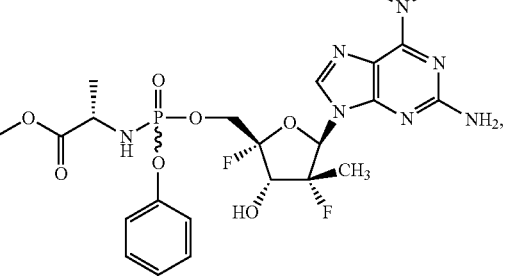
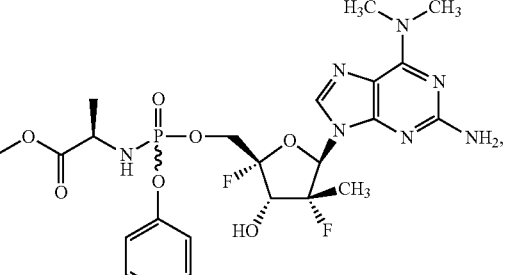
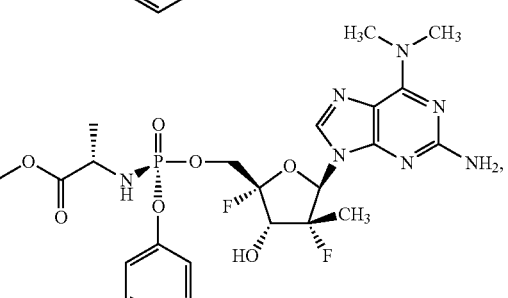

165
-continued
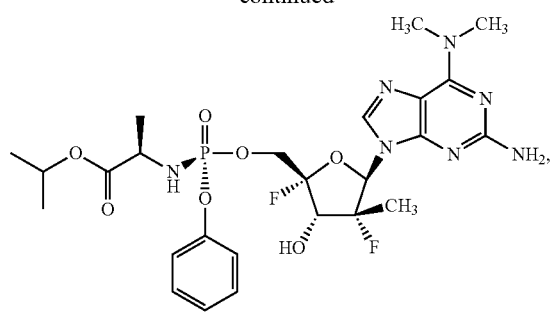
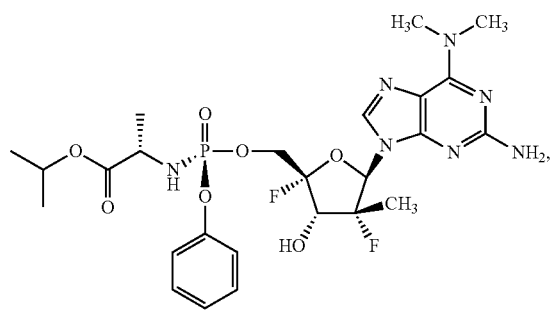
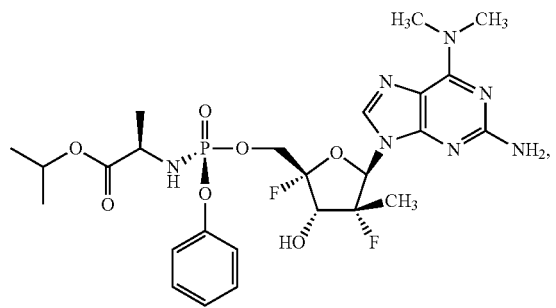
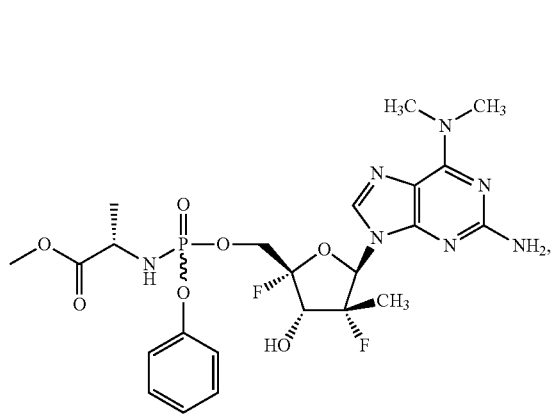
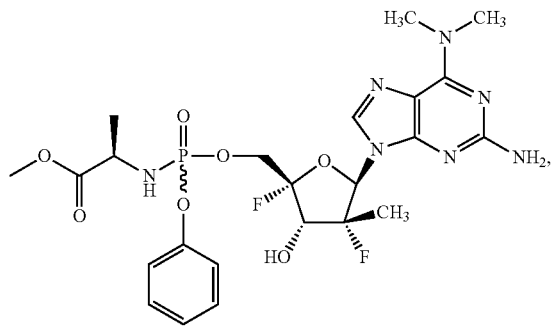
166
-continued
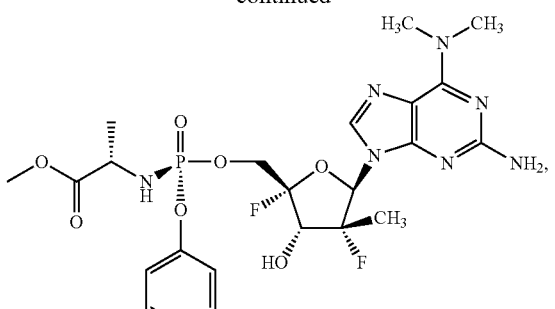
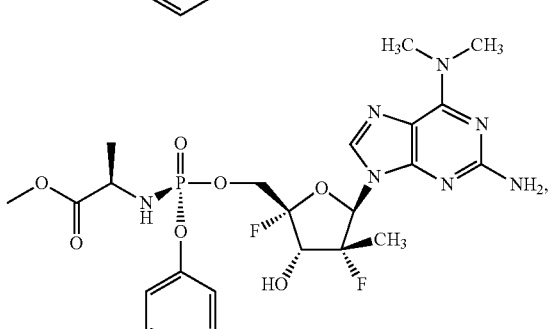
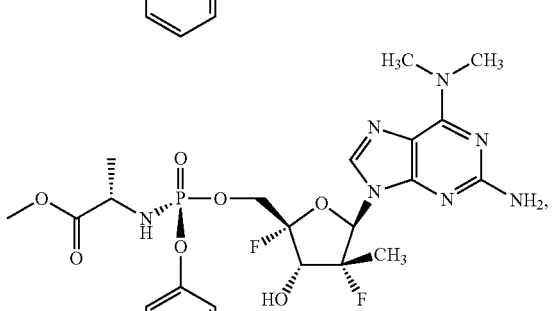
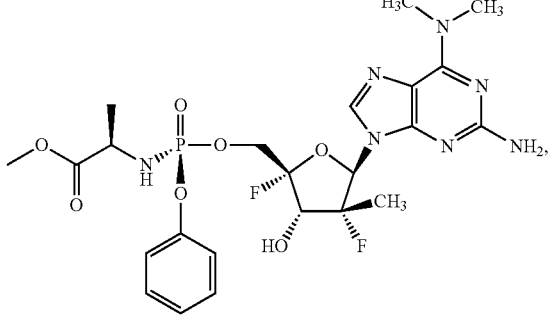
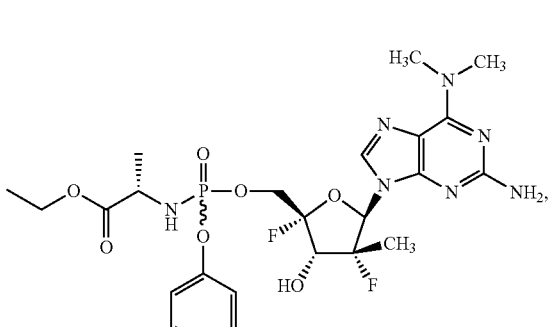

167
-continued
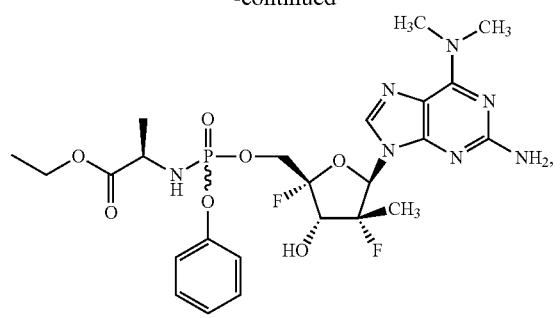
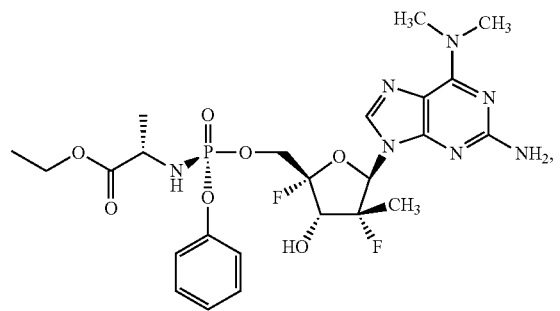
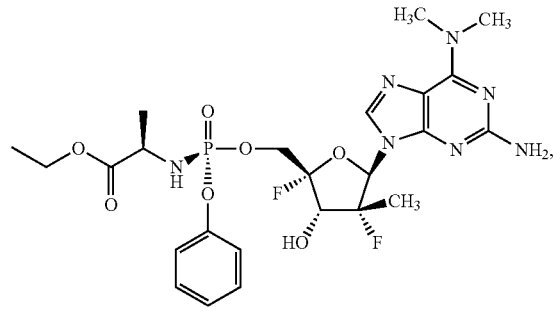
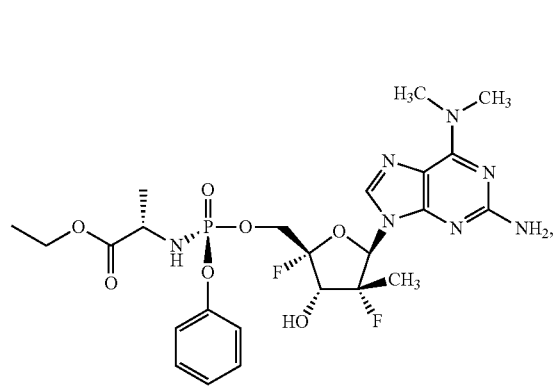
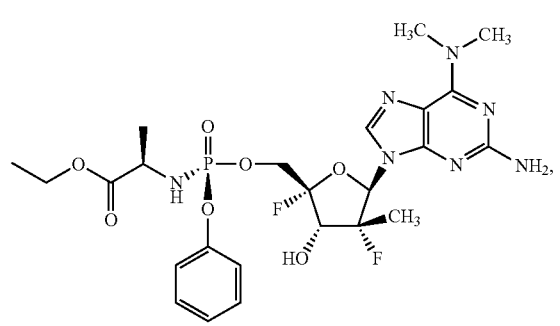
168
-continued
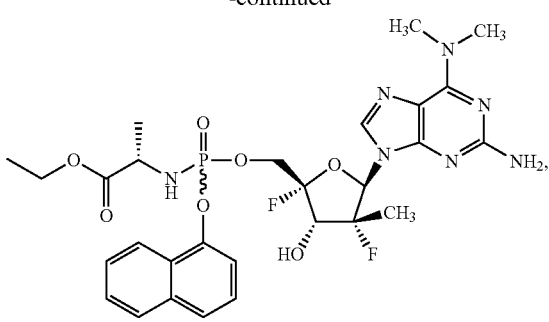
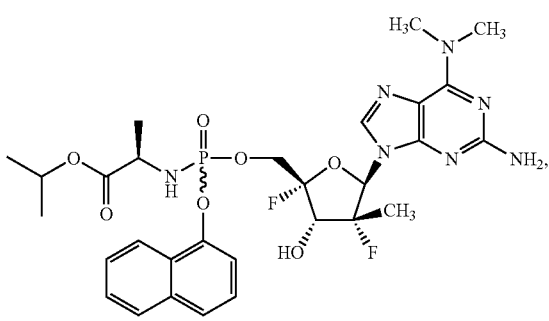
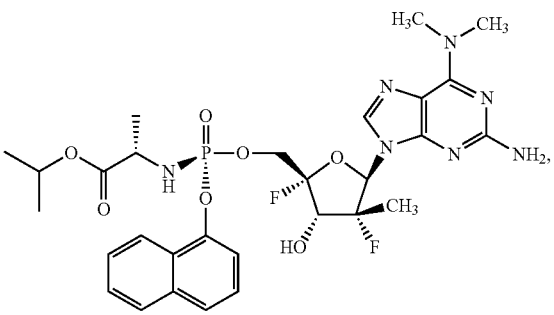
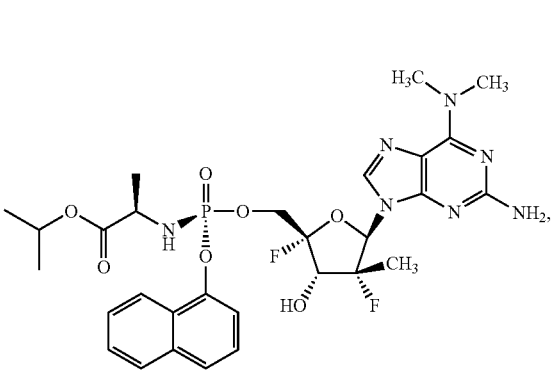
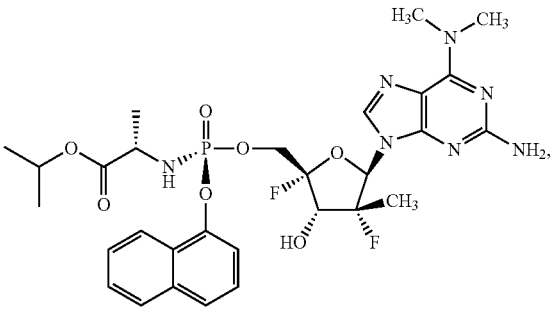

169
-continued
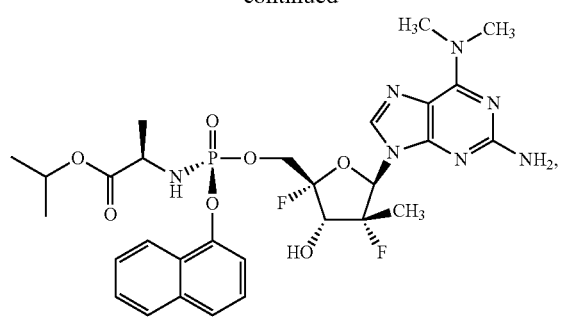
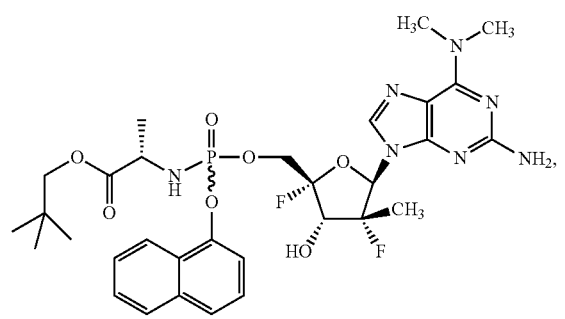
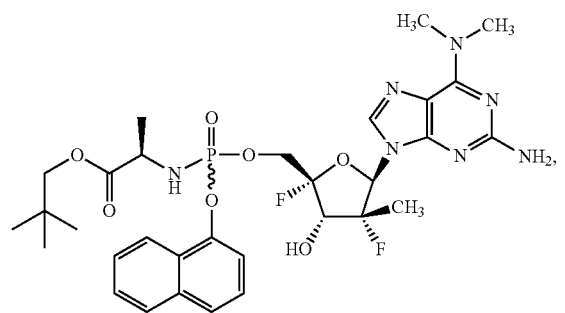
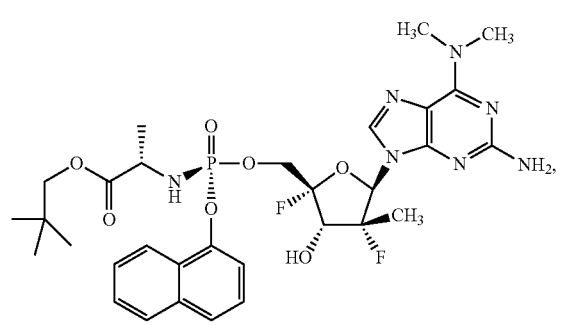
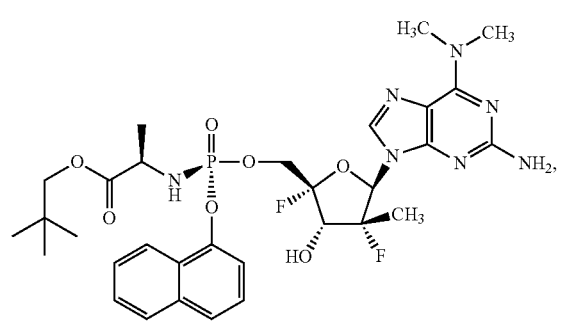
170
-continued
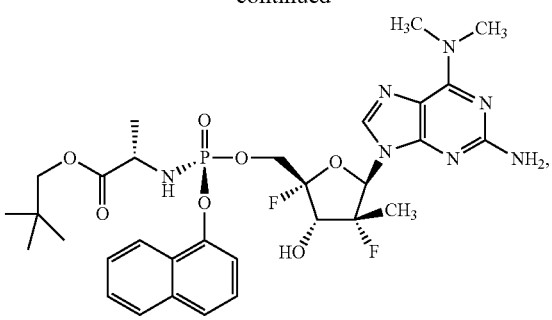
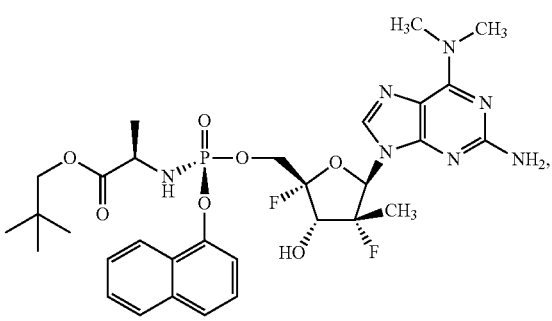
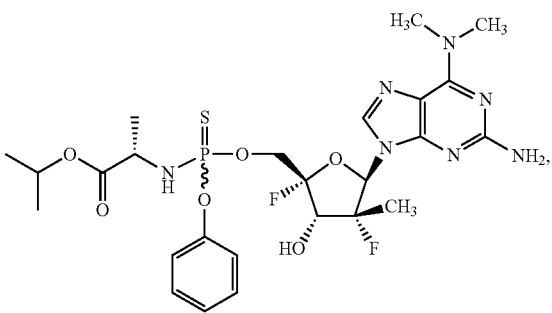
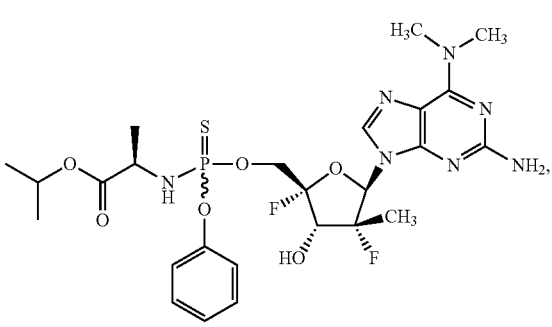
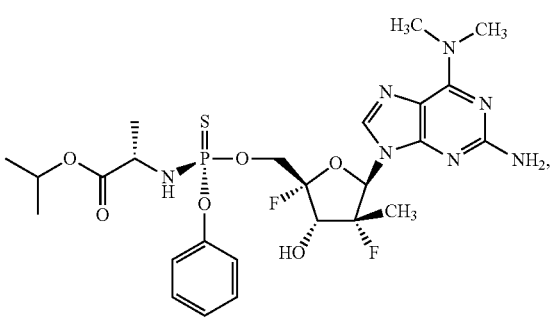

171
-continued
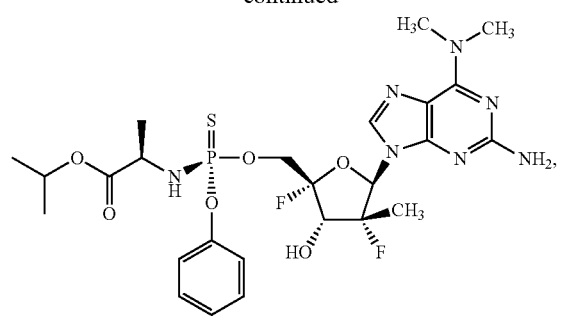
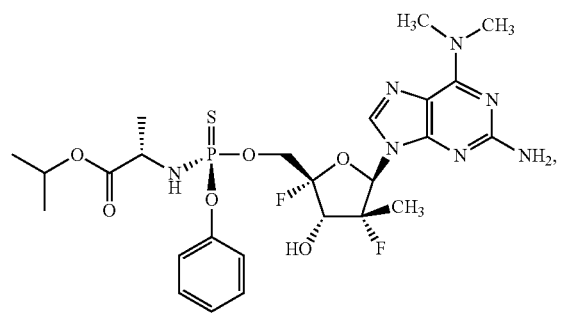
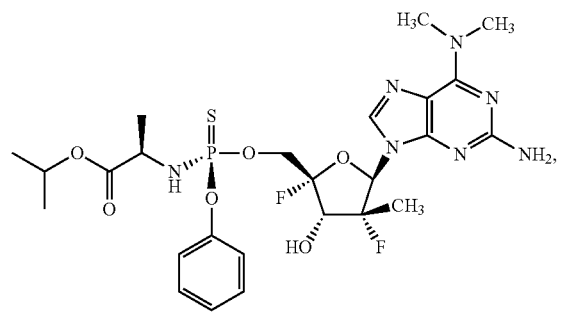
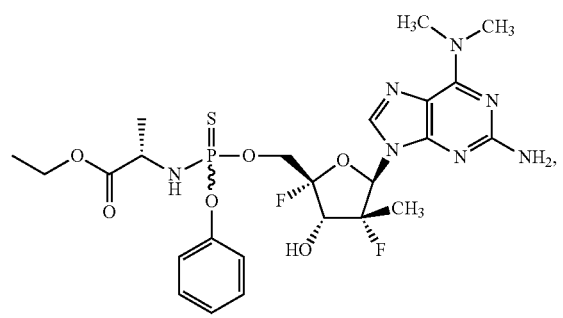
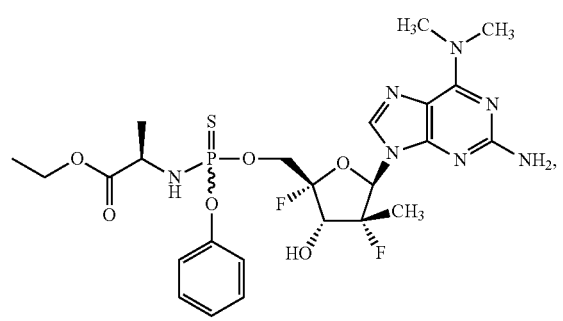
172
-continued
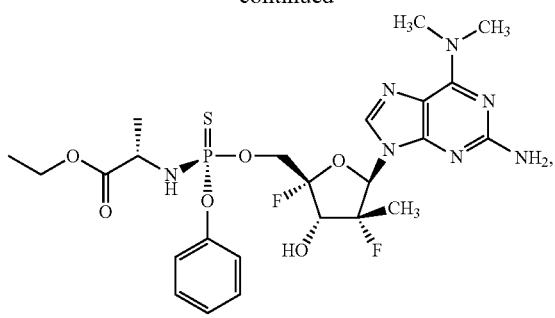
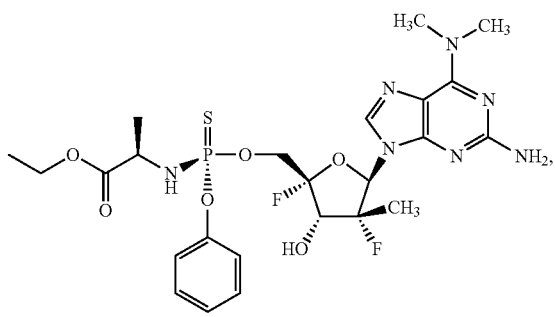
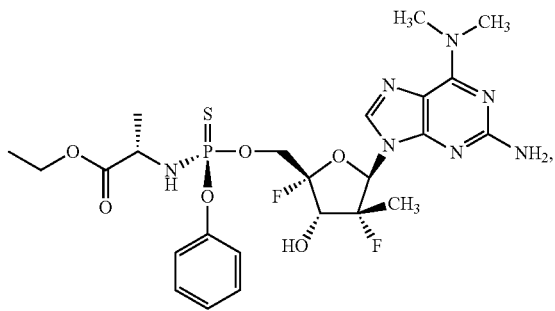
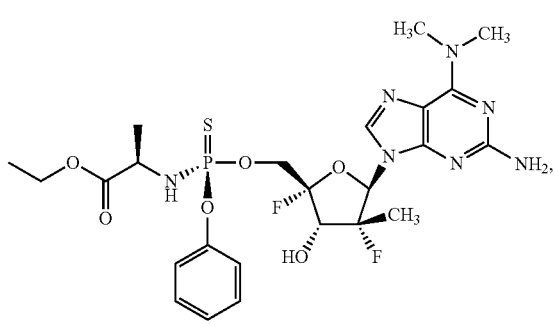
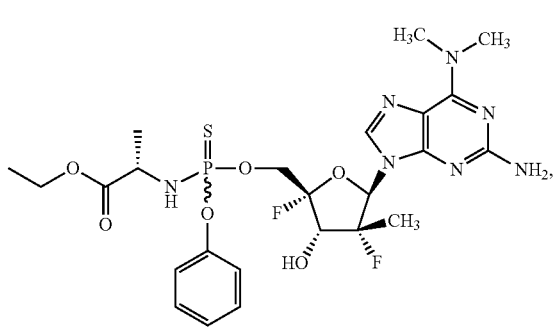

173
-continued
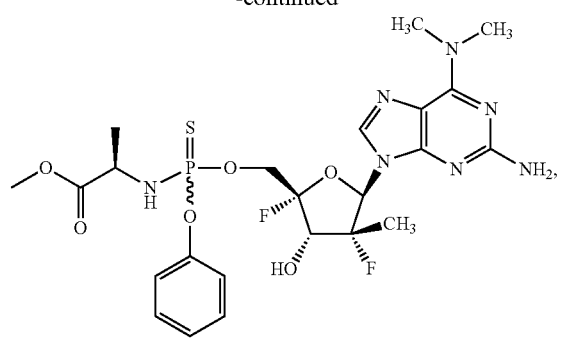
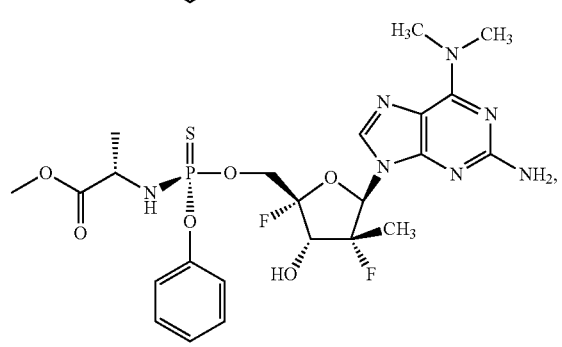
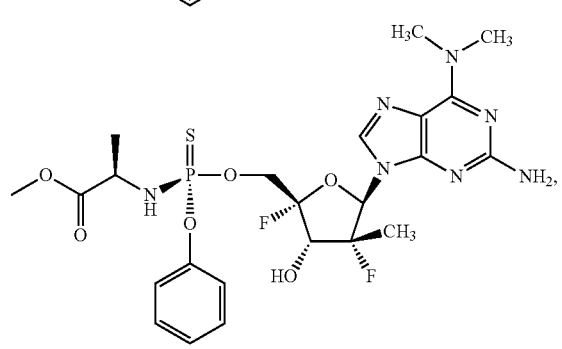
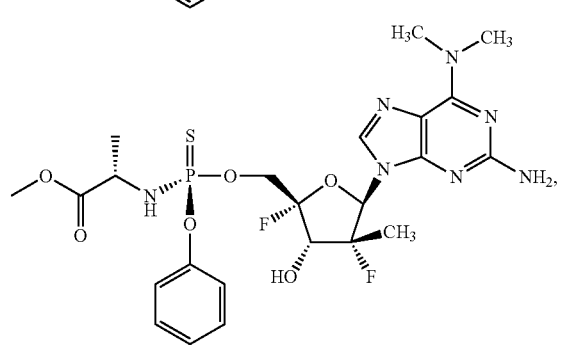
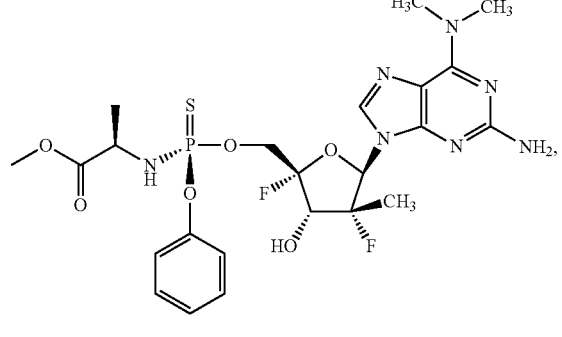
174
-continued
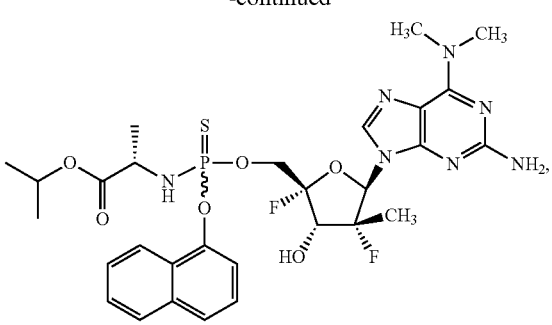
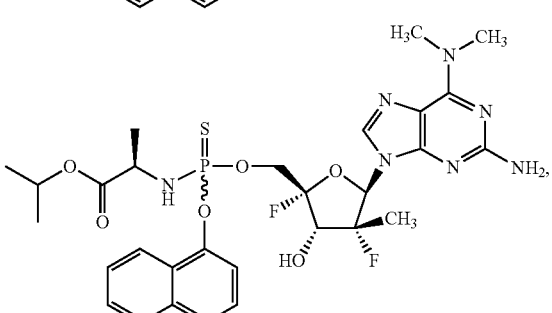
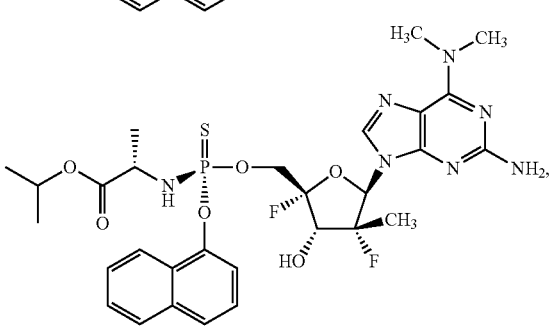
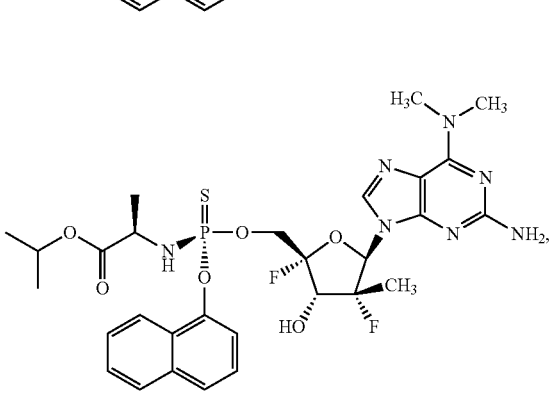
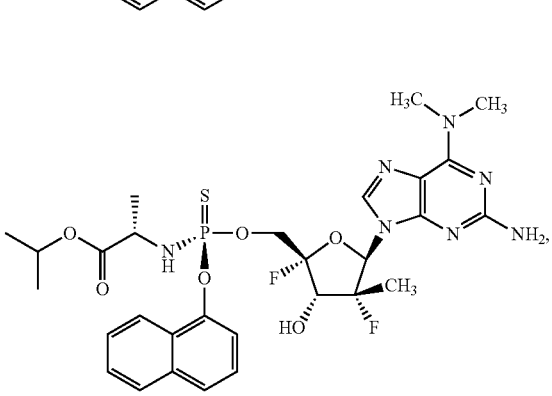

175
-continued
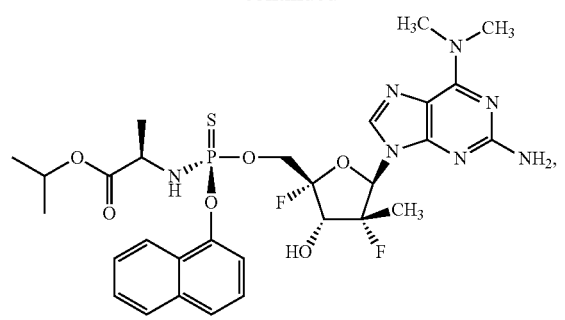
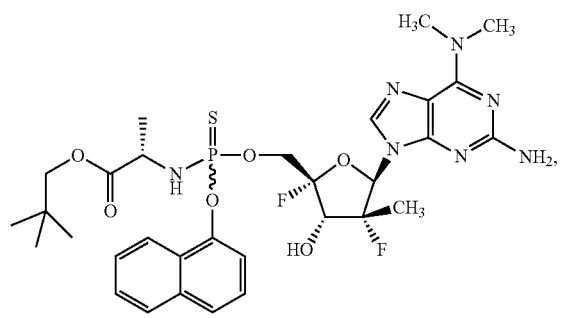
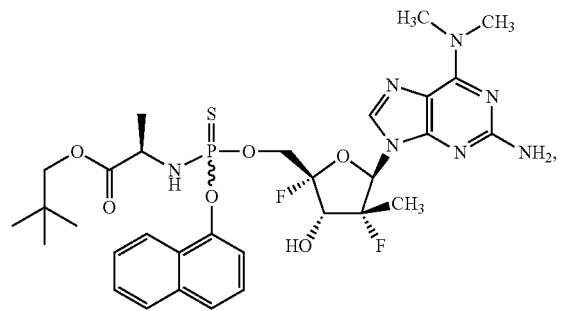
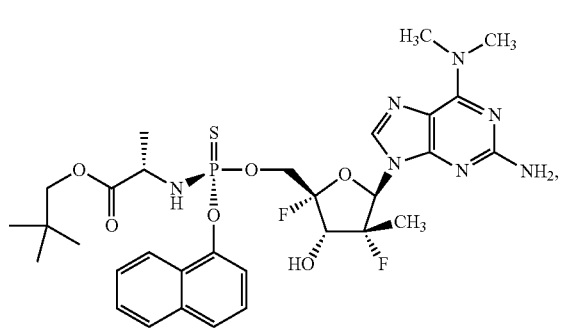
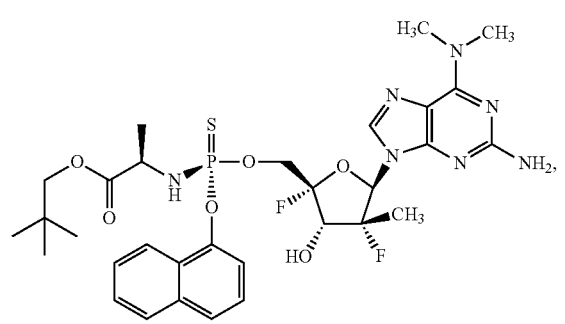
176
-continued
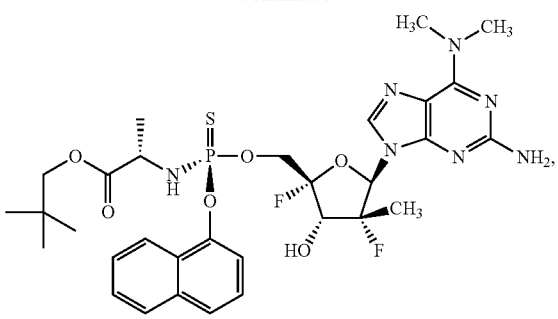
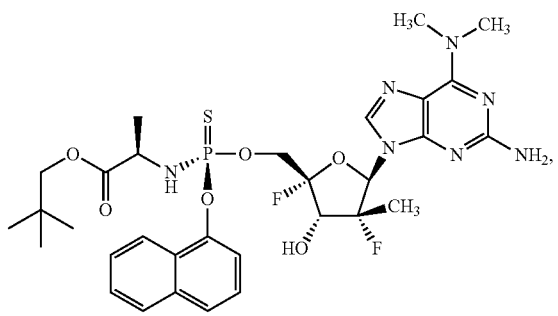
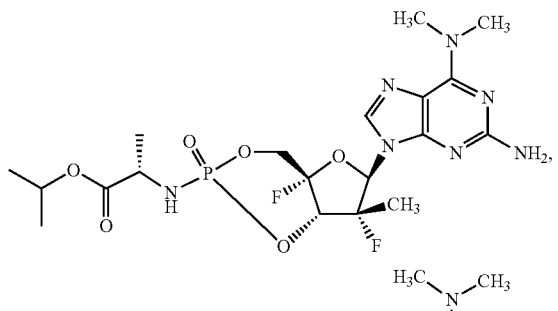
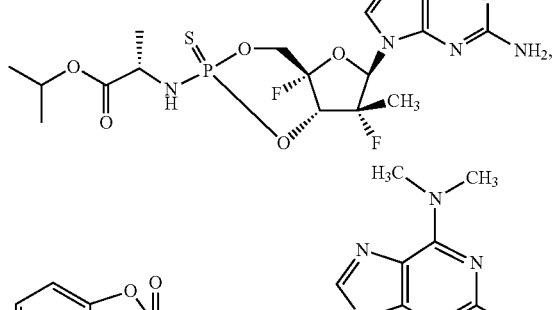
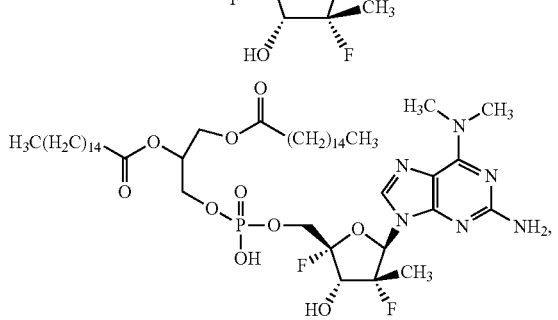

-continued

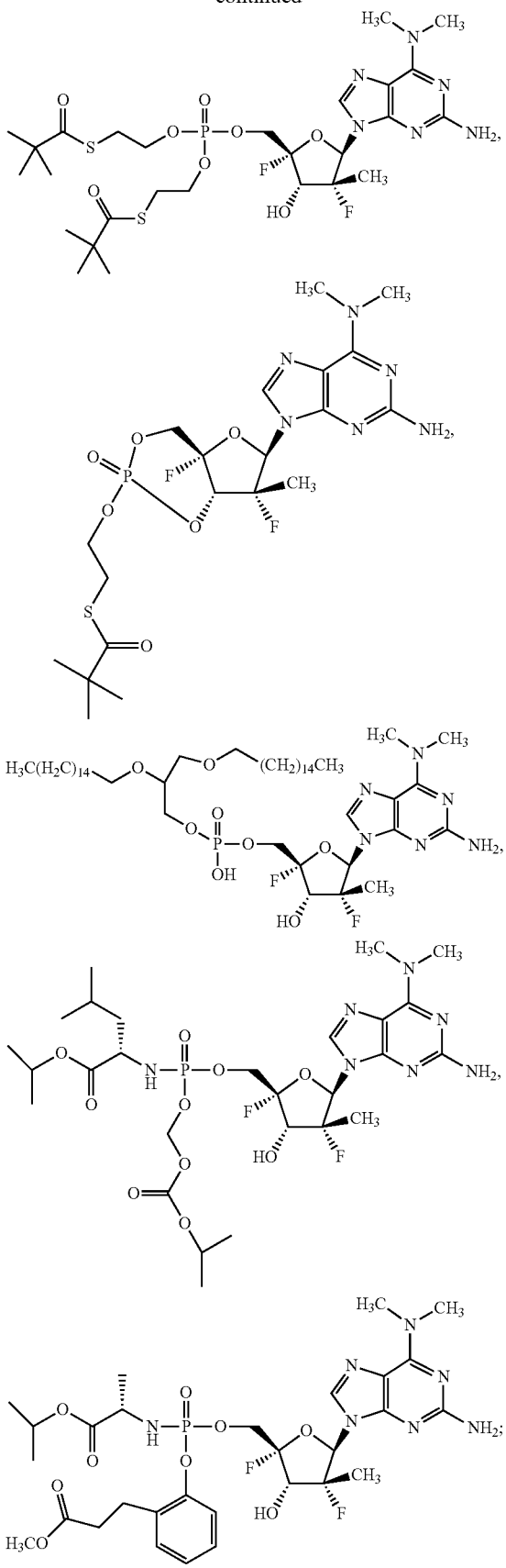

or a racemate, an enantiomer, a diastereomer, an isotopically-labelled analog, or a pharmaceutically acceptable salt thereof.

4. The compound of claim 1, wherein the compound is a compound of Formula Ia:

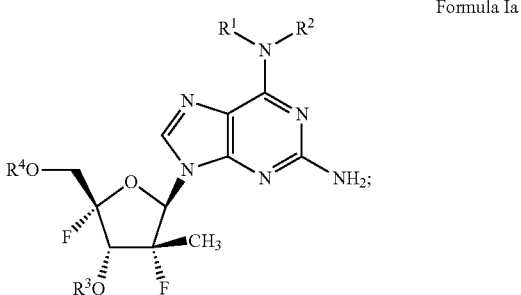

Formula Ia or a racemate, an enantiomer, a diastereomer, an isotopically-labelled analog, or
a pharmaceutically acceptable salt thereof.

5. The compound of claim 1, wherein the compound is a compound of Formula Ib:

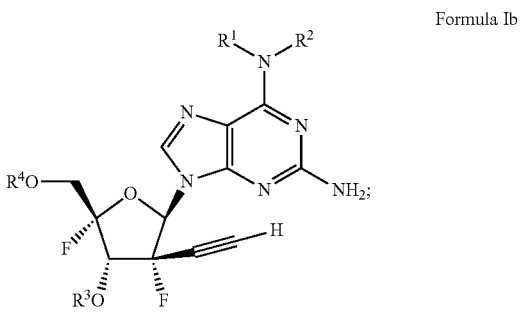

Formula Ib or a racemate, an enantiomer, a diastereomer, an isotopically-labelled analog, or
a pharmaceutically acceptable salt thereof.

6. The compound of claim 1, wherein $R^3$ is hydrogen.

7. The compound of claim 1, wherein $R^1$ is methyl and $R^2$ is hydrogen.

8. The compound of claim 1, wherein both $R^1$ and $R^2$ are methyl.

9. The compound of claim 1, wherein $R^1$ is methyl and $R^2$ is cyclopropyl.

10. The compound of claim 1, wherein the compound is

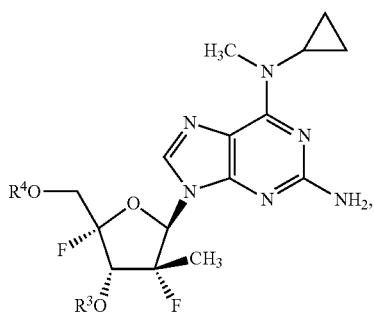

-continued
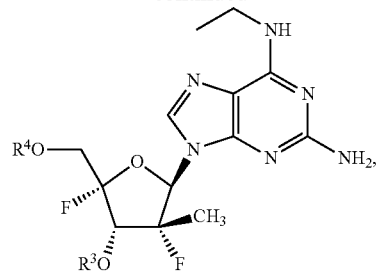
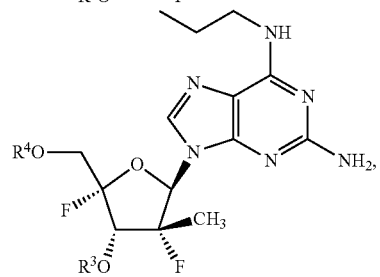
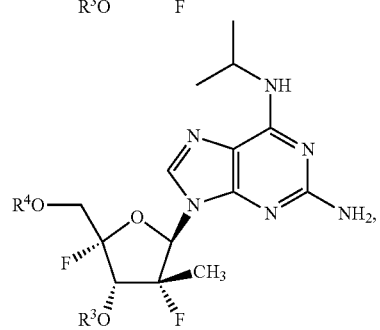
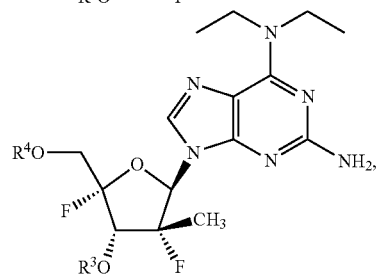
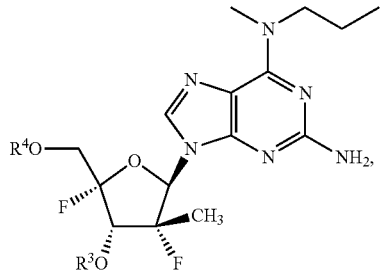
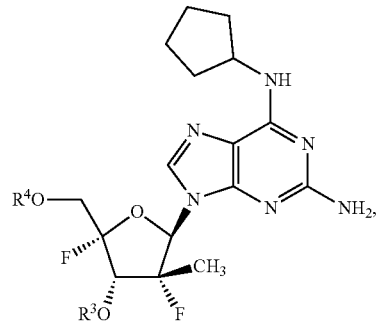
-continued
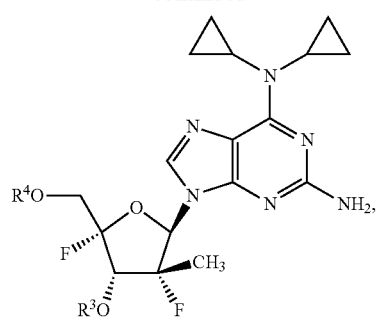
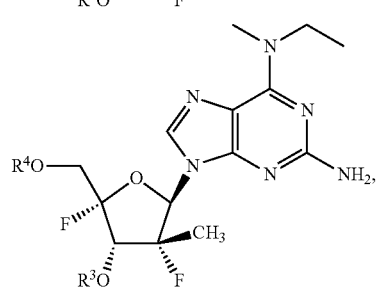
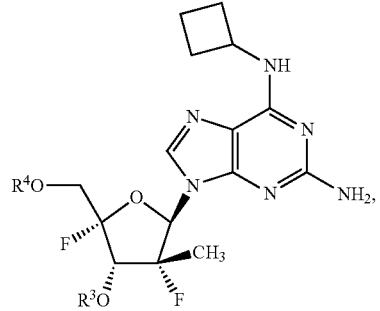
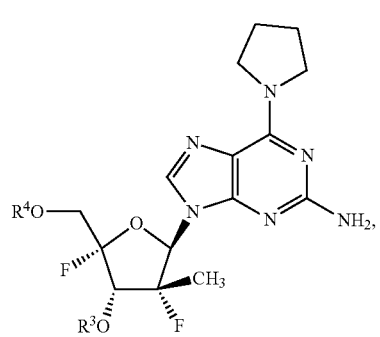
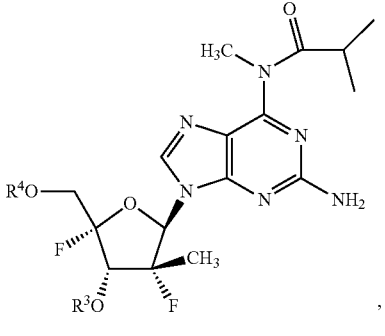
, 181
-continued
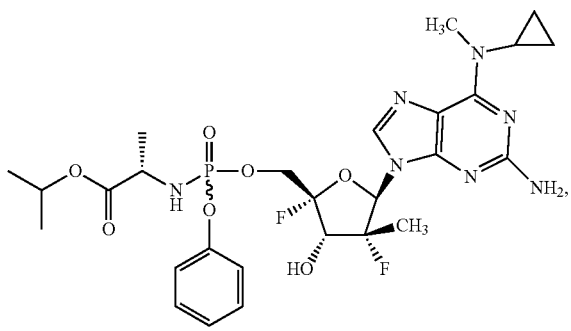
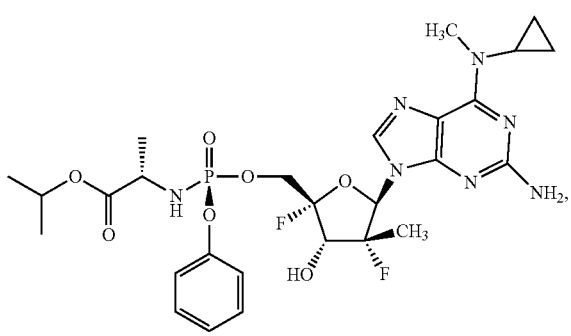
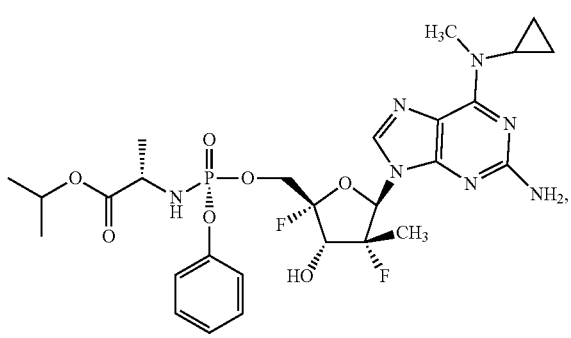
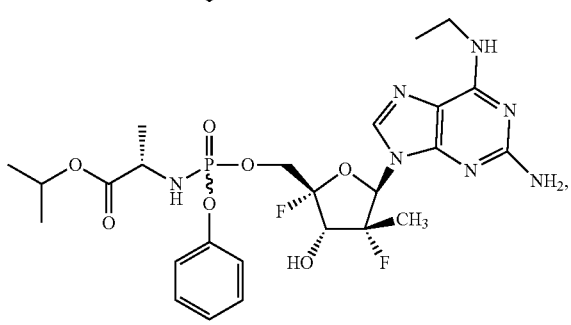
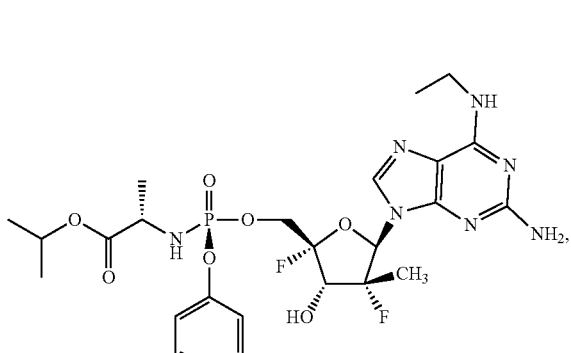
182
-continued
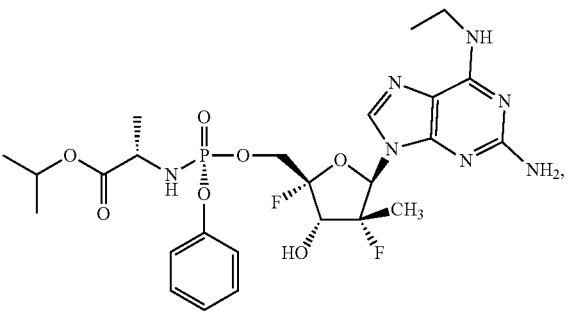
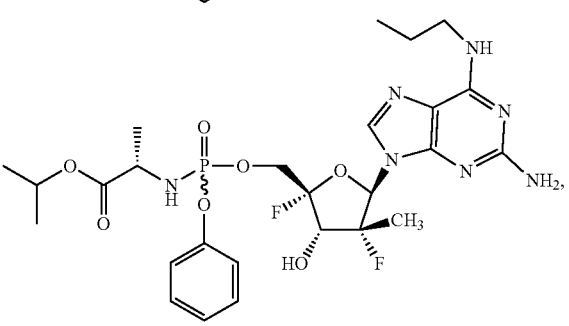
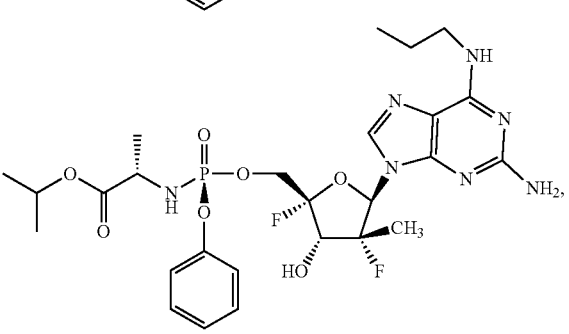
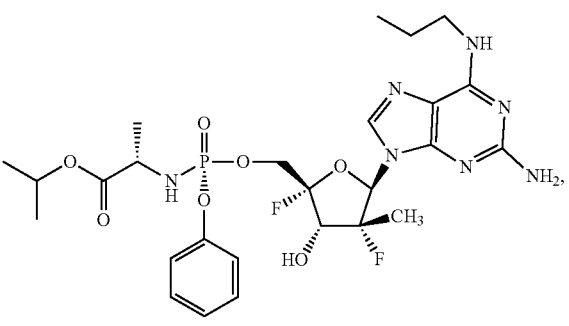
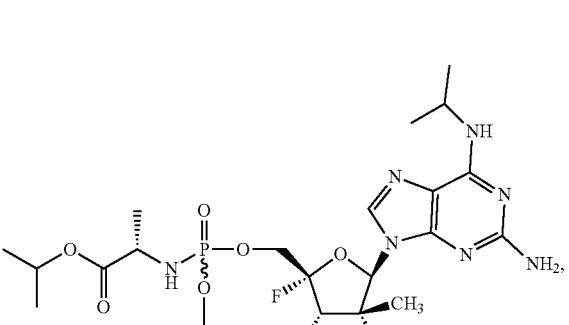

-continued
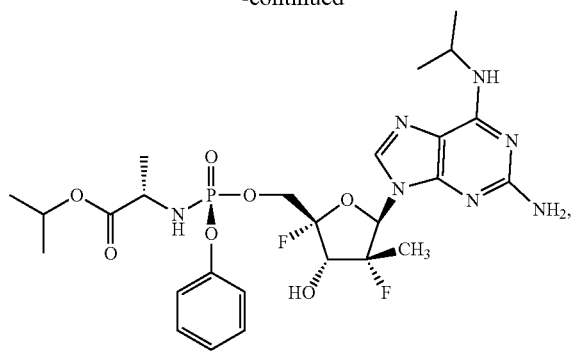
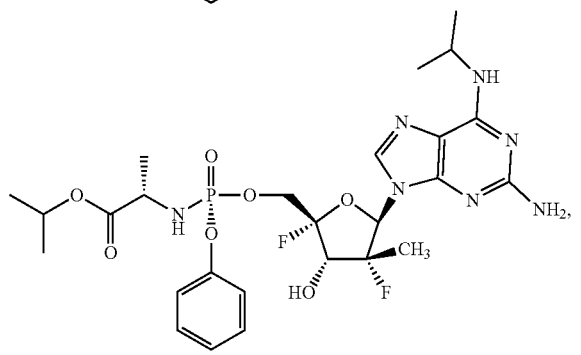
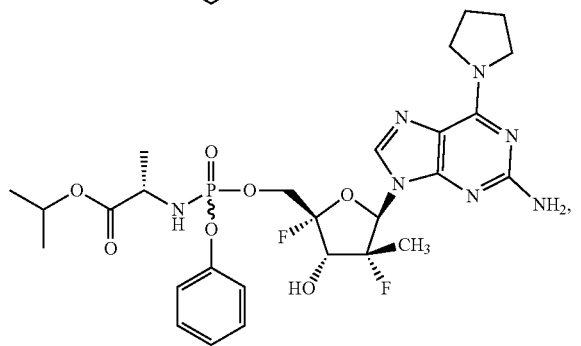
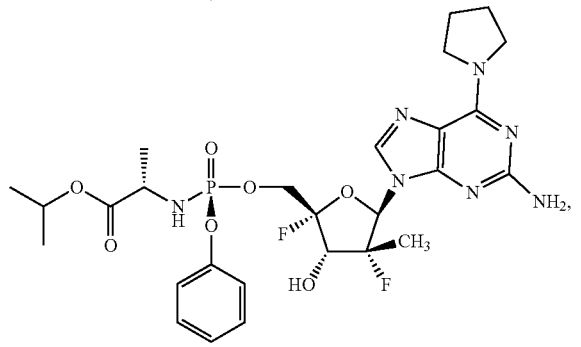
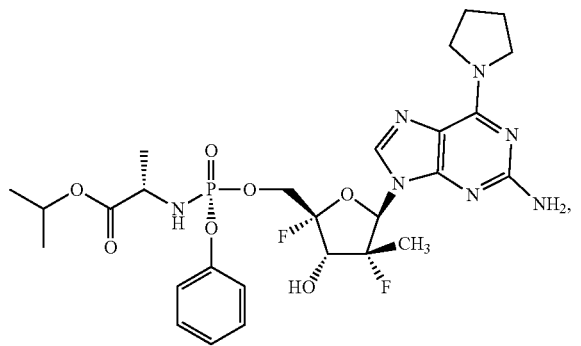
-continued
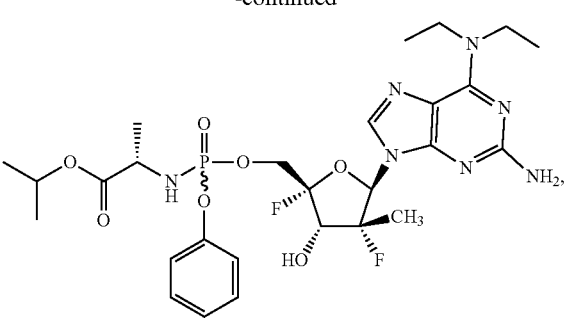
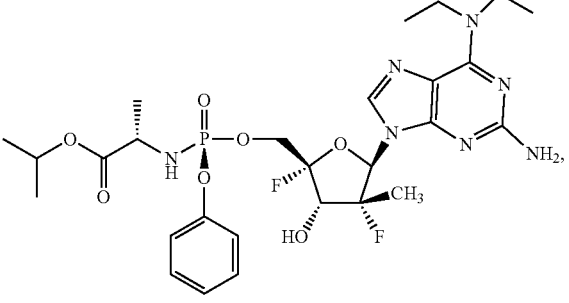
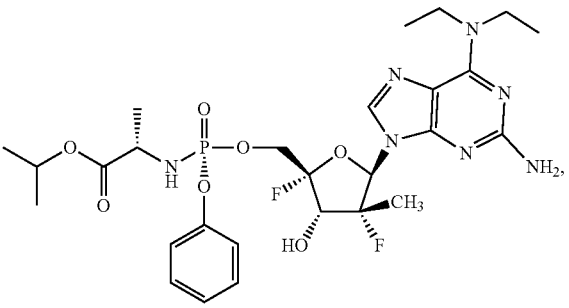
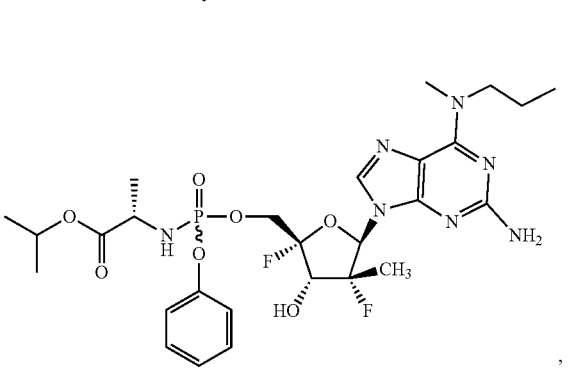
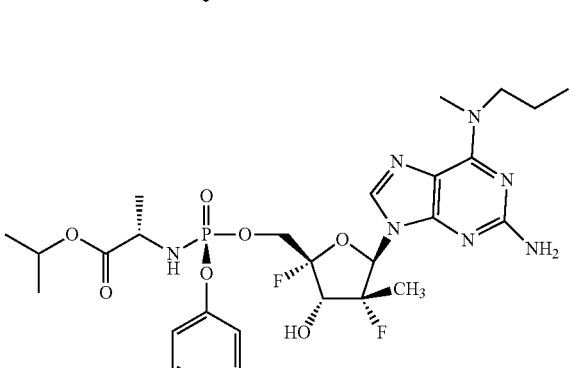

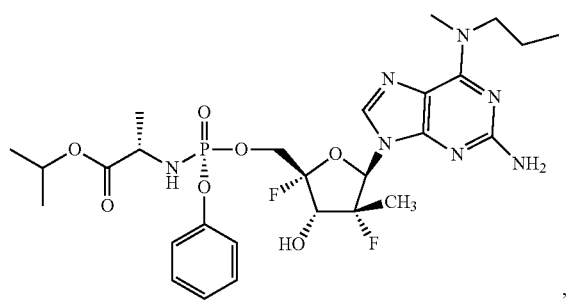
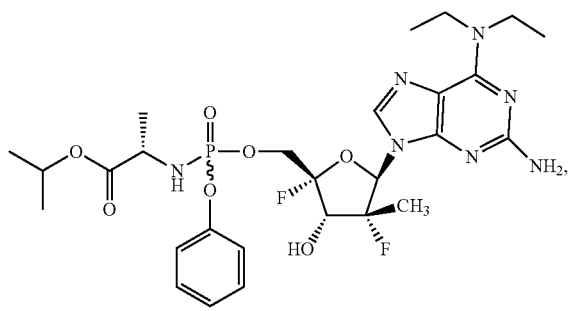
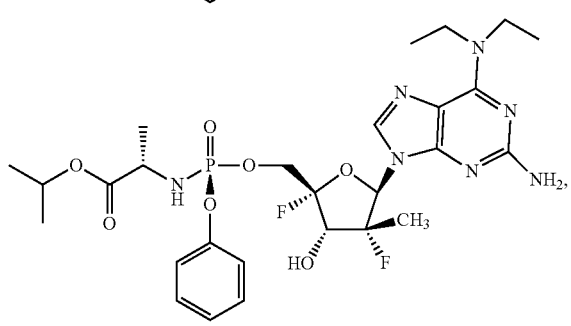
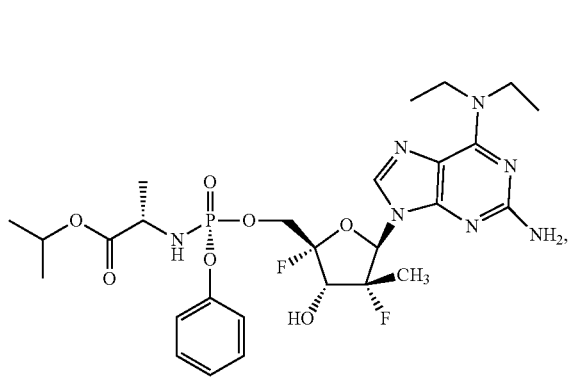
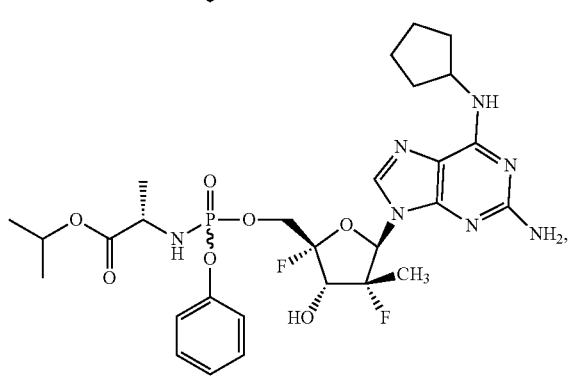
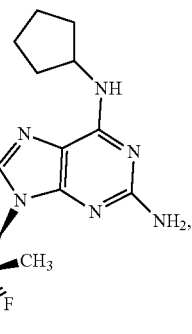
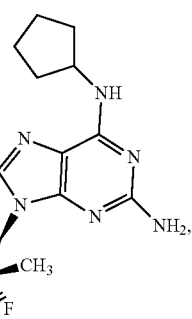
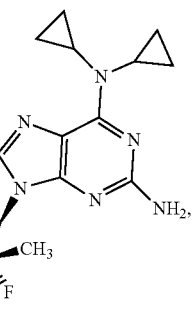
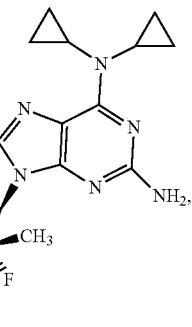

187
-continued
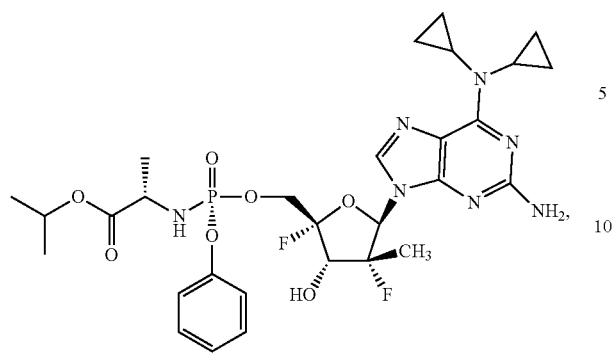
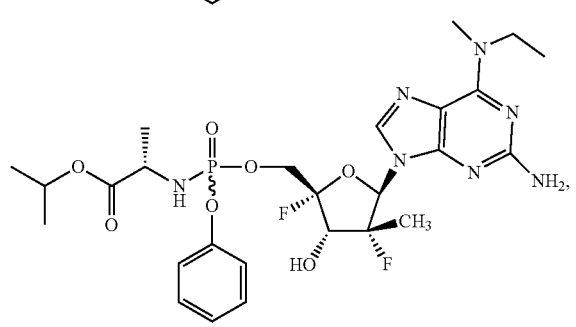
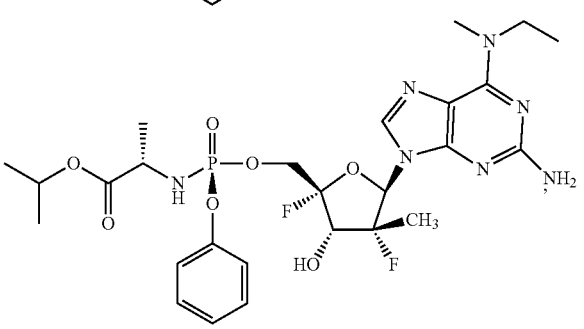
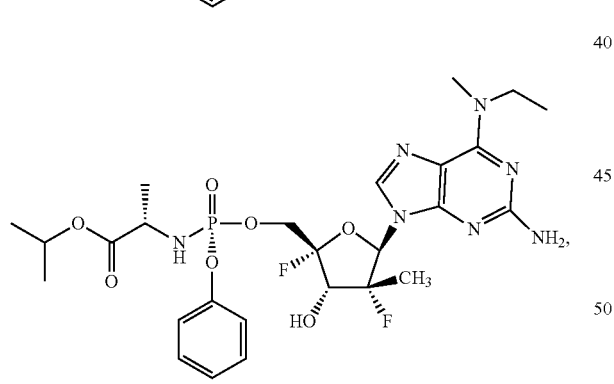
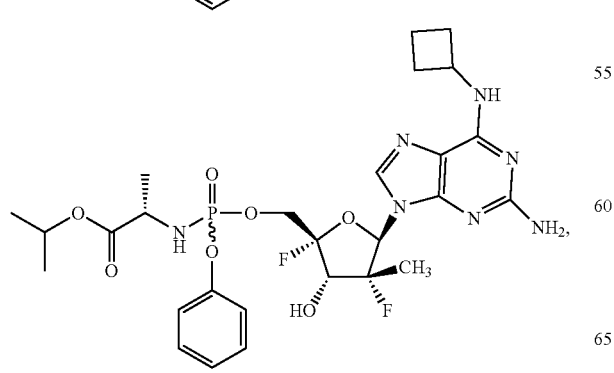
188
-continued
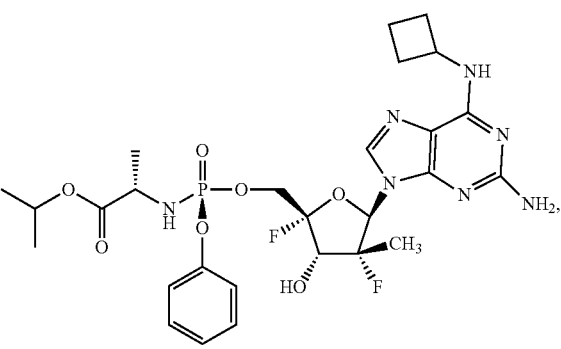
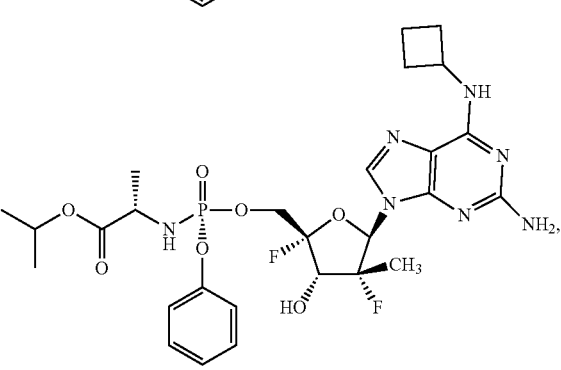
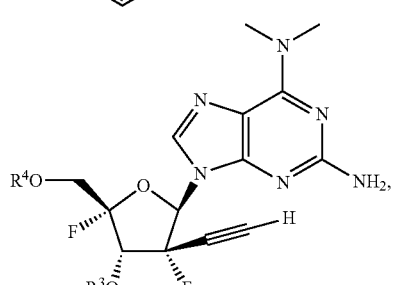
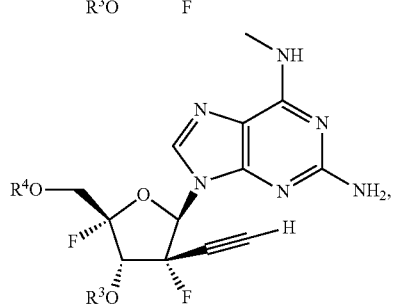
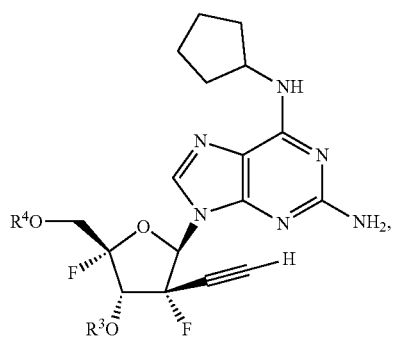

-continued

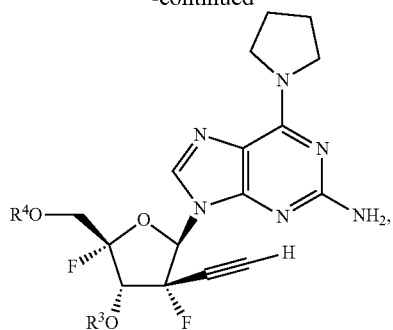

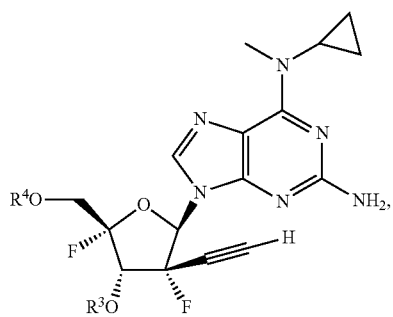

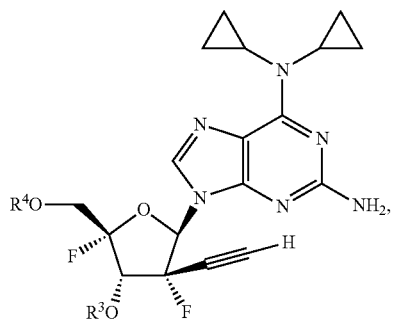

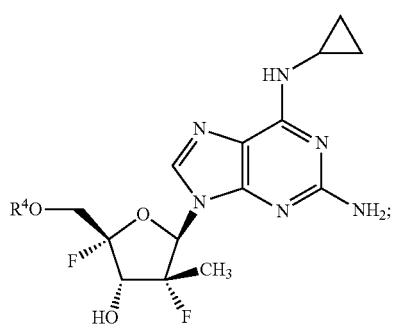

or a racemate, an enantiomer, a diastereomer, an isotopically-labelled analog, or a pharmaceutically acceptable salt thereof.

11. The compound of claim 1, wherein the compound is a compound of Formula II:

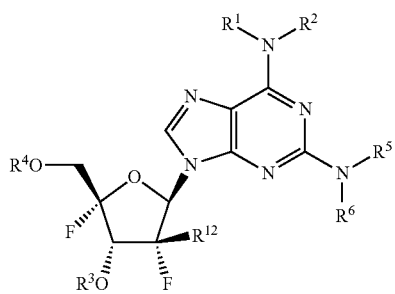

Formula II wherein:
$R^5$ is hydrogen, $C_1$-$C_6$alkyl, or —($C_0$-$C_2$alkyl)($C_3$-$C_6$cycloalkyl);

$R^6$ is $C_1$-$C_6$alkyl, —($C_0$-$C_2$alkyl)($C_3$-$C_6$cycloalkyl), —($C_{0\text{-}6}$alkyl)(aryl), —($C_{0\text{-}6}$alkyl)(heteroaryl), —($C_{0\text{-}6}$alkyl)(heterocycle) or —C(O)$R^{3C}$;

or a racemate, an enantiomer, a diastereomer, an isotopically-labelled analog, or a pharmaceutically acceptable salt thereof.

12. The compound of claim 11, wherein the compound is

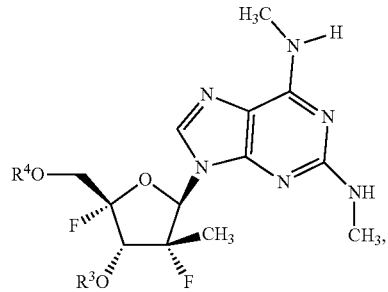

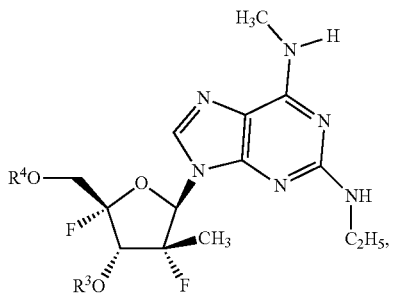

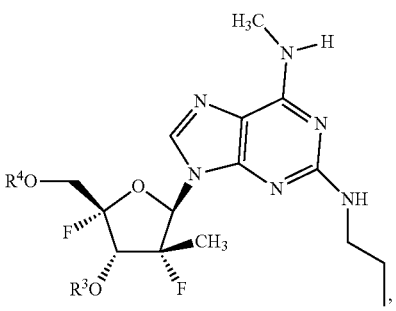

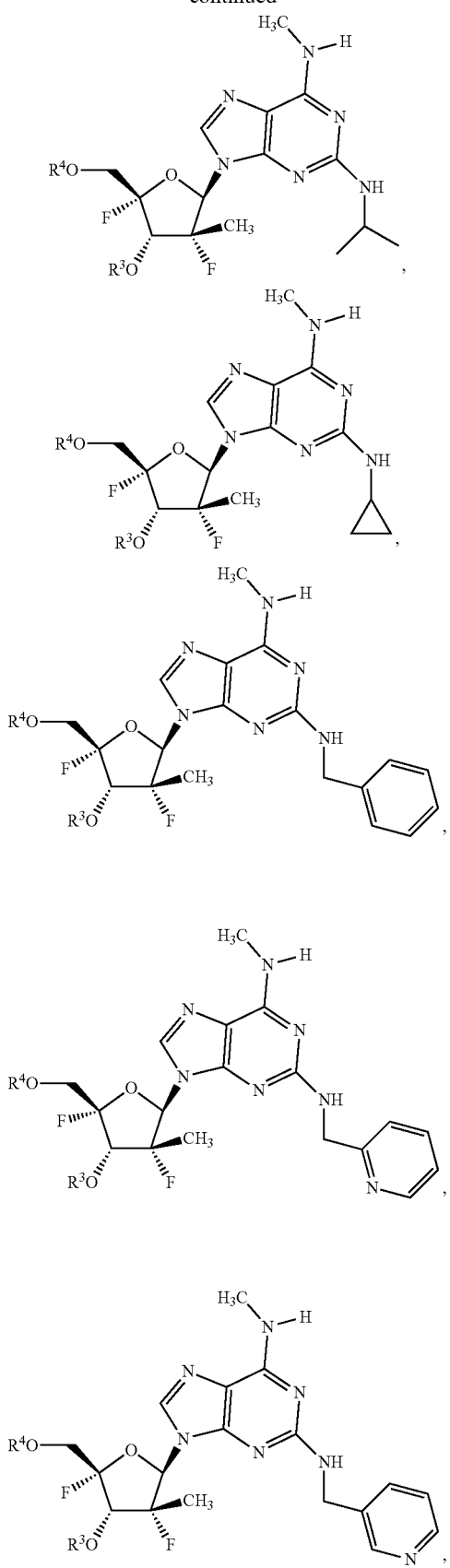
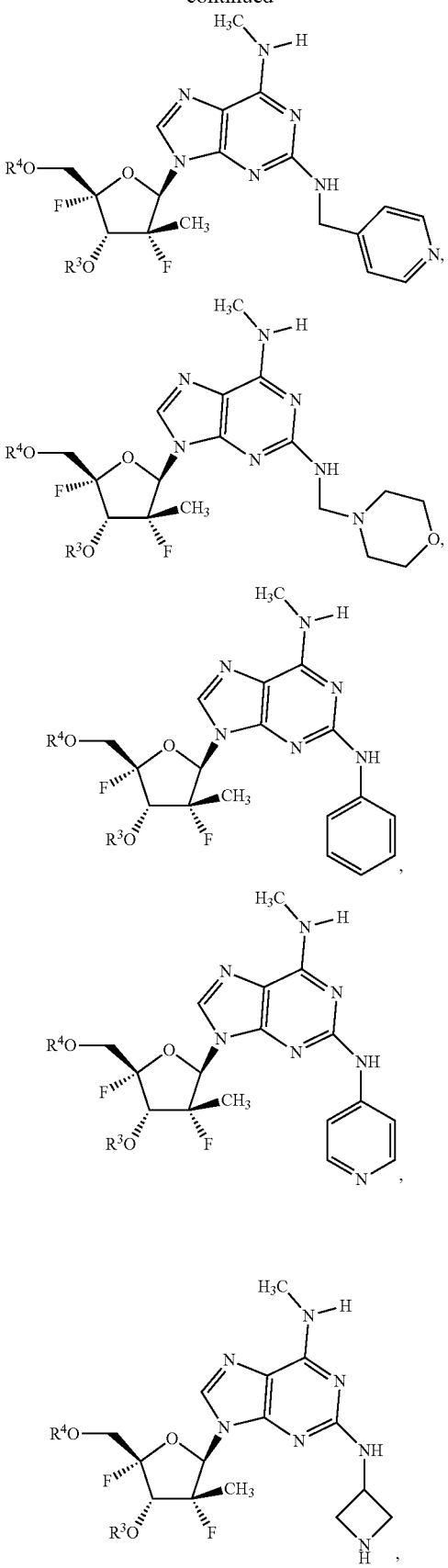

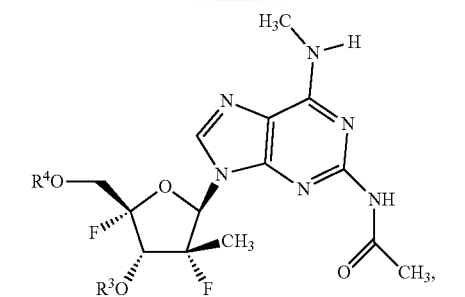
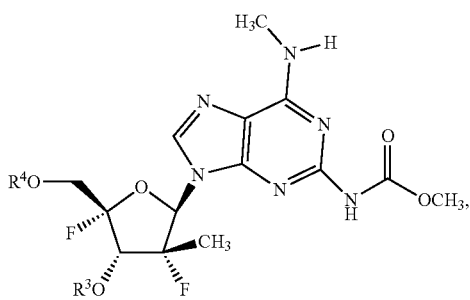
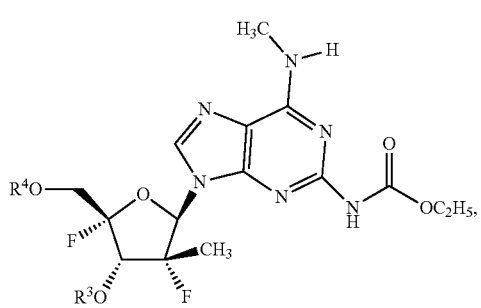
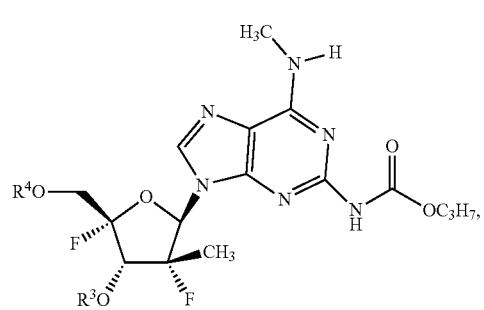
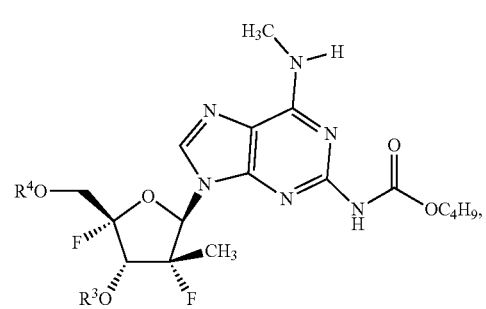
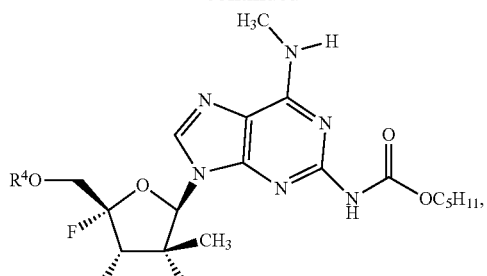
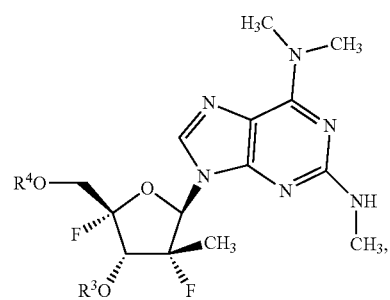
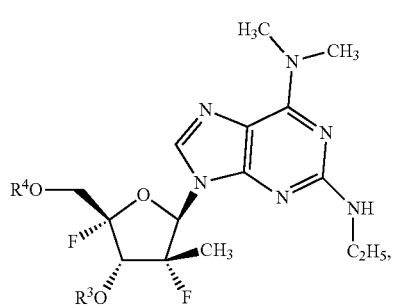
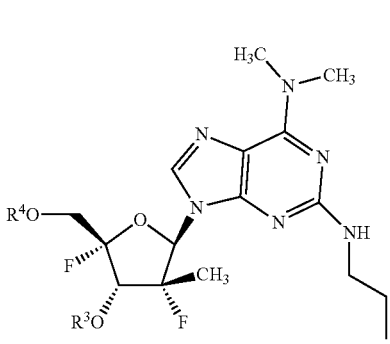
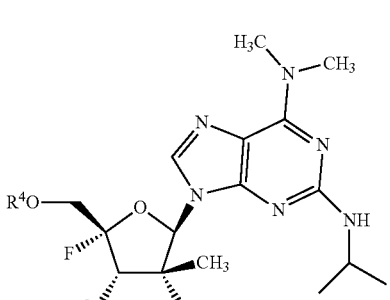

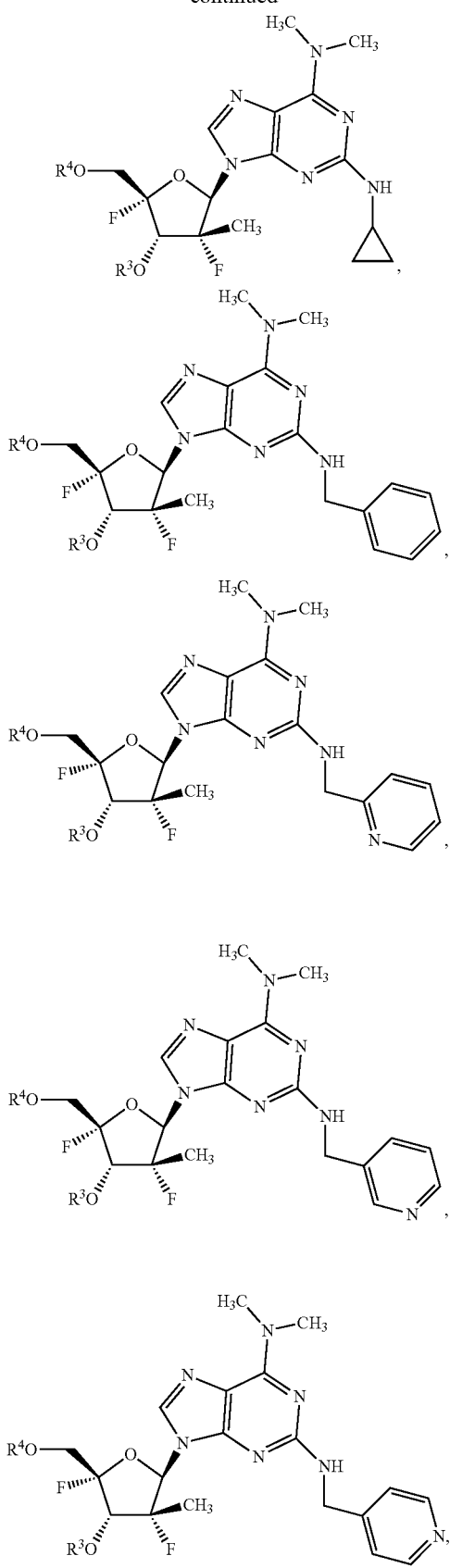
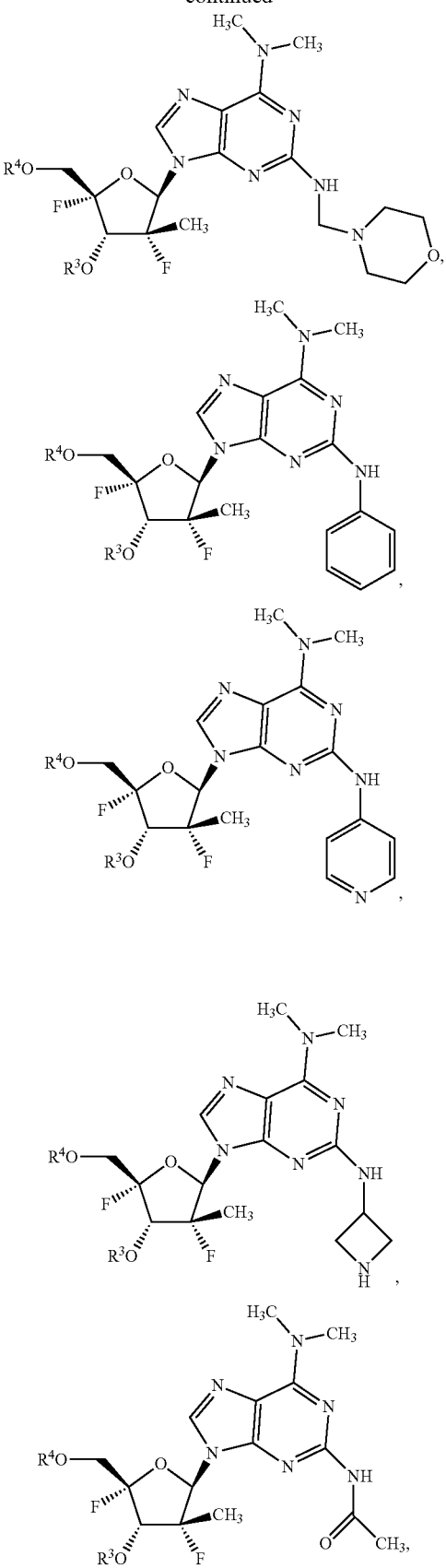

197
-continued
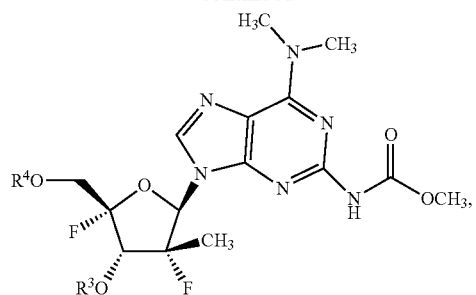
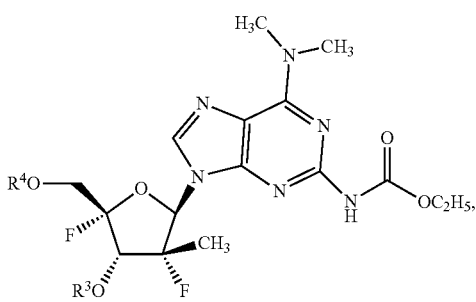
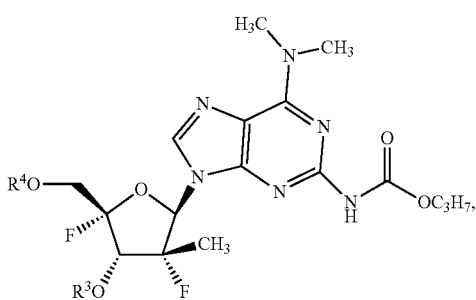
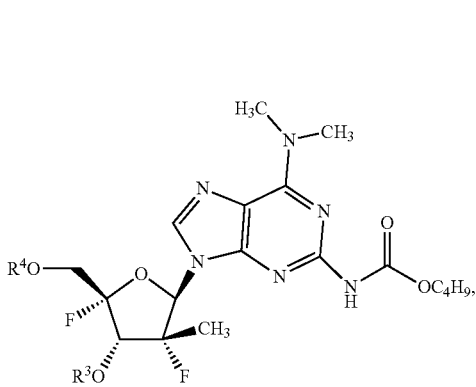
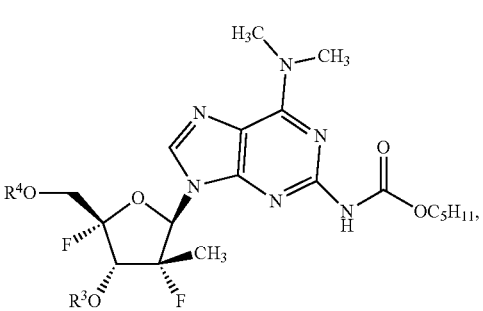
198
-continued
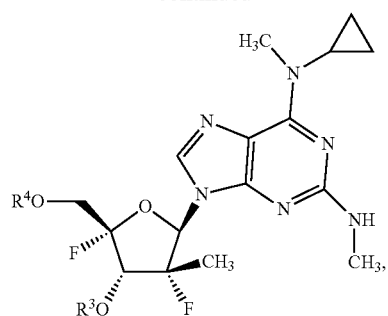
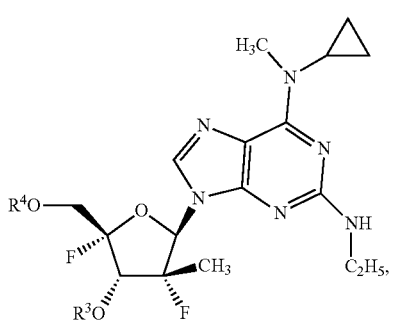
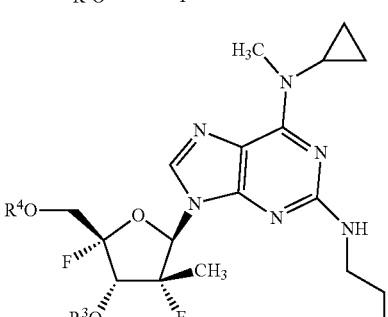
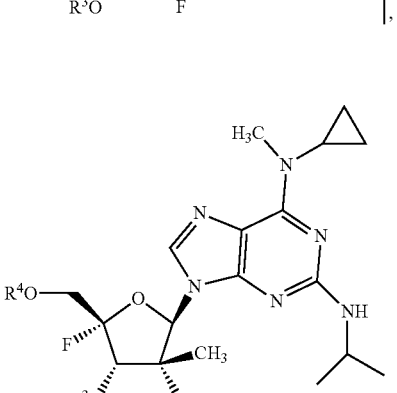
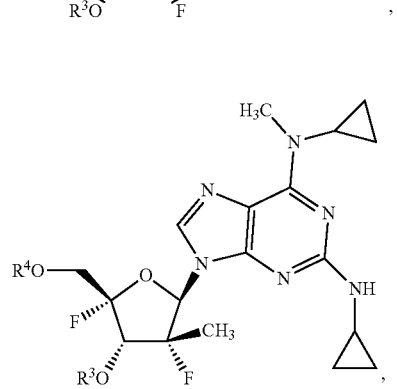

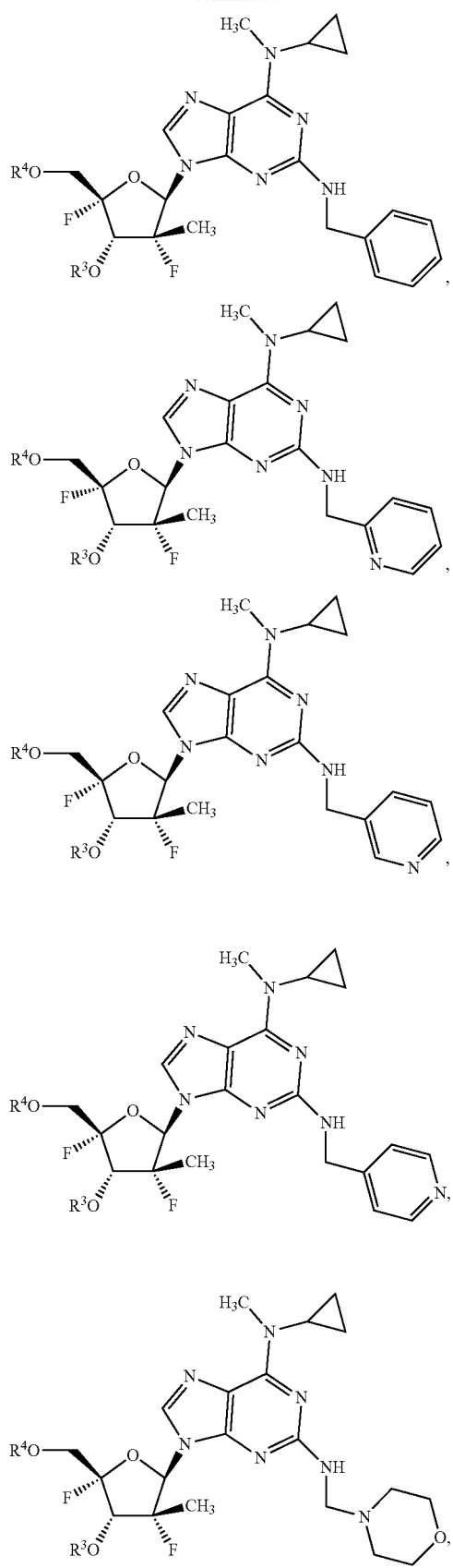
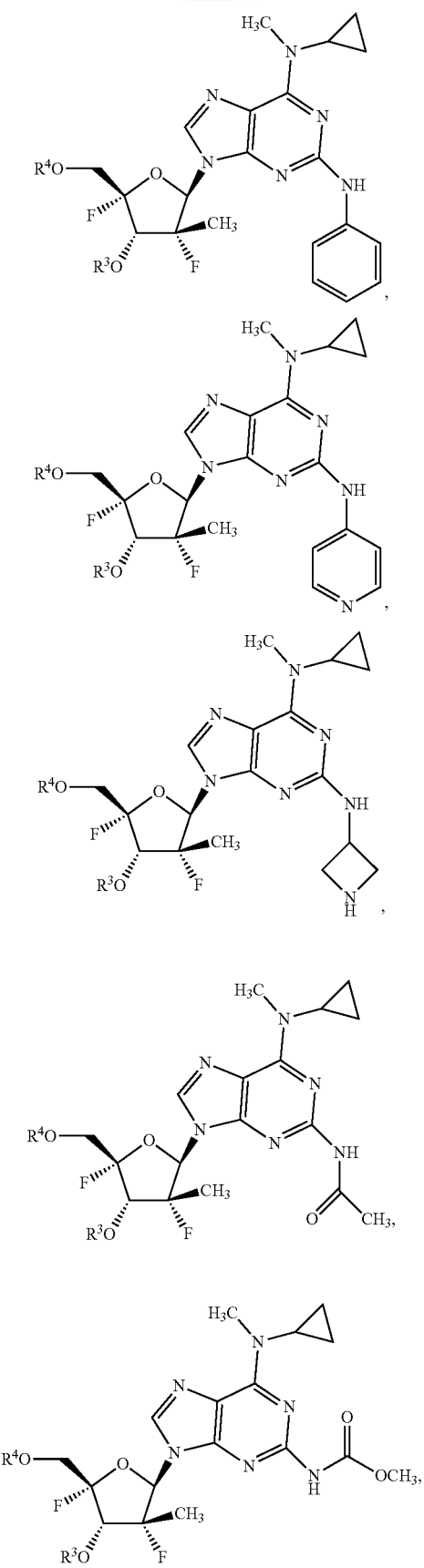

-continued

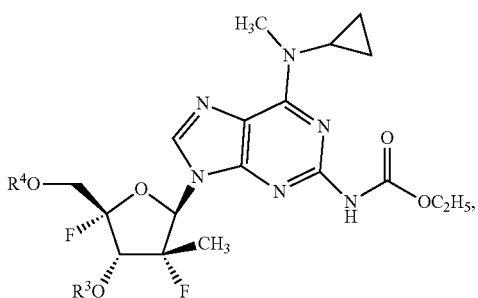

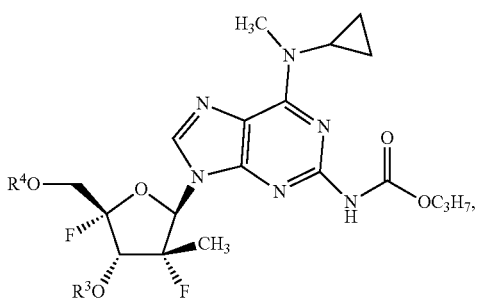

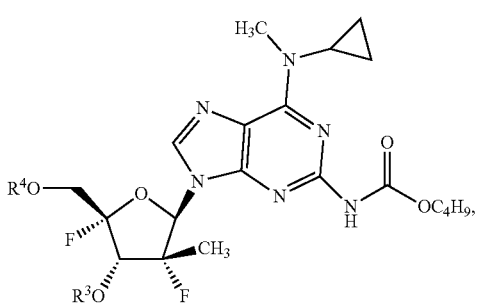

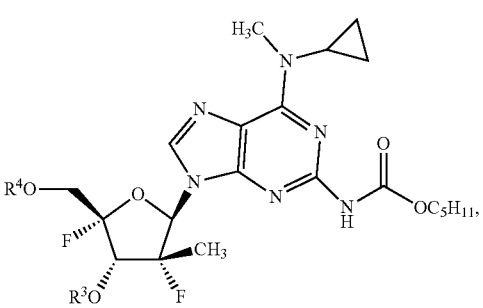

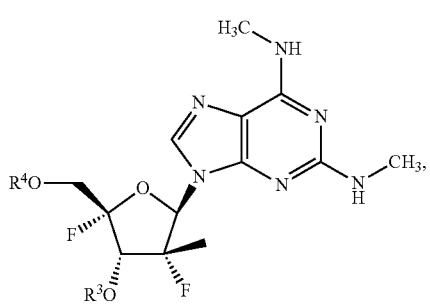

-continued

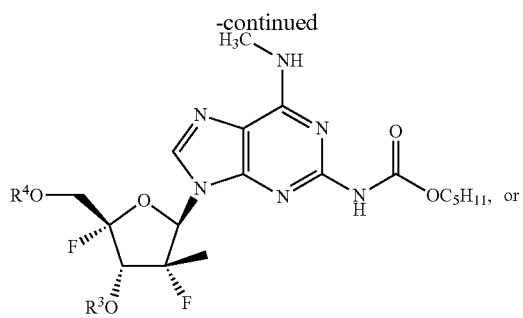

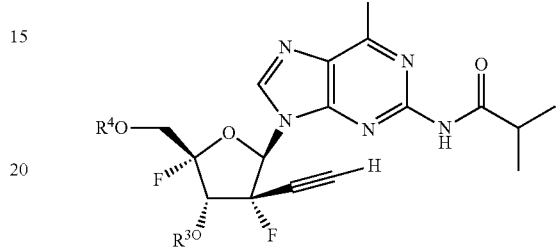

or a racemate, an enantiomer, a diastereomer, an isotopically-labelled analog, or a pharmaceutically acceptable salt thereof.

13. The compound of claim 11, wherein the compound is a compound of Formula IIa:

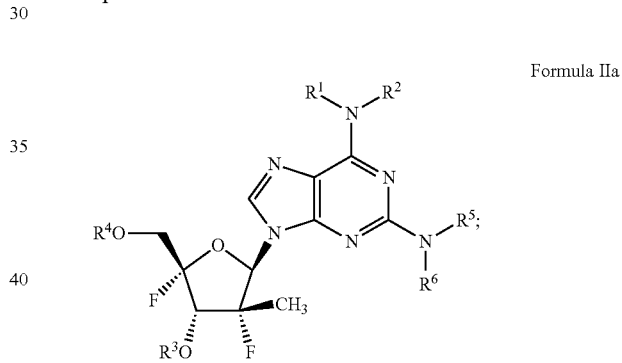

Formula IIa or a racemate, an enantiomer, a diastereomer, an isotopically-labelled analog, or
a pharmaceutically acceptable salt thereof.

14. The compound of claim 11, wherein the compound is a compound of Formula IIb:

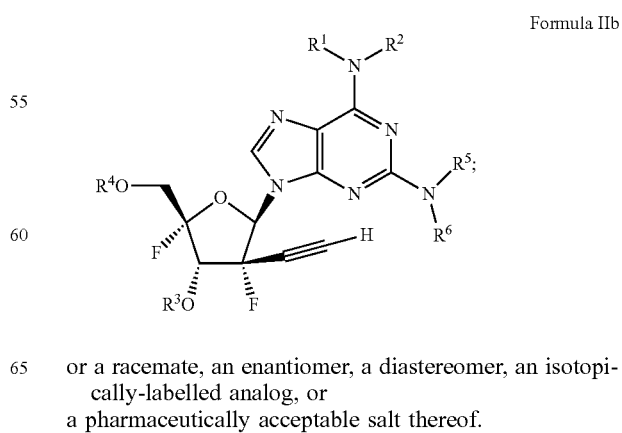

Formula IIb or a racemate, an enantiomer, a diastereomer, an isotopically-labelled analog, or
a pharmaceutically acceptable salt thereof.

15. The compound of claim 1, wherein the compound is a compound of Formula III:

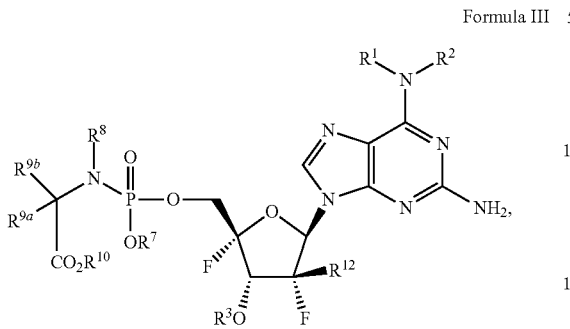

Formula III wherein $R^7$ is hydrogen, $C_{1-6}$alkyl; $C_{3-7}$cycloalkyl; heteroaryl, heterocyclic, or aryl, optionally substituted with $C_{1-6}$alkyl, $C_{2-6}$alkenyl, $C_{2-6}$ alkynyl, $C_{1-6}$alkoxy, F, Cl, Br, I, nitro, cyano, $C_{1-6}$haloalkyl, —N(R$^{7'}$)$_2$, $C_{1-6}$acylamino, NHSO$_2$C$_{1-6}$alkyl, —SO$_2$N(R$^{7'}$)$_2$, COR$^{7''}$, and —SO$_2$C$_{1-6}$alkyl; (R$^{7'}$ is independently hydrogen or $C_{1-6}$alkyl; R$^{7''}$ is —OR$^{11}$ or —N(R$^7$)$_2$);

$R^8$ is hydrogen, $C_{1-6}$alkyl, or $R^{9a}$ or $R^{9b}$ and $R^8$ together are (CH$_2$)$_n$ so as to form a cyclic ring that includes the adjoining N and C atoms; where n is 2 to 4;

$R^{9a}$ and $R^{9b}$ are (i) independently selected from hydrogen, $C_{1-6}$alkyl, cycloalkyl, —(CH$_2$)c(NR$^{9'}$)$_2$, $C_{1-6}$hydroxyalkyl, —CH$_2$SH, —(CH$_2$)$_2$S(O)(Me), —(CH$_2$)$_3$NHC(=NH)NH$_2$, (IH-indol-3-yl)methyl, (IH-imidazol-4-yl)methyl, —(CH$_2$)$_c$COR$^{9''}$, aryl and aryl(C$_{1-3}$alkyl)-, the aryl groups are optionally substituted with a group selected from hydroxyl, $C_{1-6}$alkyl, $C_{1-6}$alkoxy, halogen, nitro and cyano; (ii) $R^{9a}$ and $R^{9b}$ both are $C_{1-6}$alkyl; (iii) $R^{9a}$ and $R^{9b}$ together are (CH$_2$)$_r$ so as to form a spiro ring; (iv) $R^{9a}$ is hydrogen and $R^{9b}$ and $R^8$ together are (CH$_2$)$_n$ so as to form a cyclic ring that includes the adjoining N and C atoms (v) $R^{9b}$ is hydrogen and $R^{9a}$ and $R^8$ together are (CH$_2$)$_n$ so as to form a cyclic ring that includes the adjoining N and C atoms, where c is 1 to 6, n is 2 to 4, r is 2 to 5 and where $R^{9'''}$ is independently hydrogen or $C_{1-6}$ alkyl and $R^{9'''}$ is —OR$^{11}$ or —N(R$^{11}$)$_2$; (vi) $R^{9a}$ is hydrogen and $R^{9b}$ is hydrogen, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (vii) $R^{9a}$ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$((4'-OH)-Ph), CH$_2$SH, or lower cycloalkyl and $R^{9b}$ is hydrogen;

$R^{10}$ is hydrogen, $C_{1-6}$alkyl optionally substituted with an alkoxy, di(lower alkyl)-amino, or halogen; $C_{1-6}$haloalkyl, (C$_0$-C$_2$)(C$_{3-7}$cycloalkyl), (C$_0$-C$_2$)(heterocycloalkyl), aminoacyl, (C$_0$-C$_2$)(aryl), such as (C$_0$-C$_2$)(phenyl), (C$_0$-C$_2$)(heteroaryl), such as (C$_0$-C$_2$)(pyridinyl), substituted (C$_0$-C$_2$)(aryl), or substituted (C$_0$-C$_2$)(heteroaryl);

$R^{11}$ is an optionally substituted $C_{1-6}$alkyl, an optionally substituted cycloalkyl; an optionally substituted $C_{2-6}$alkynyl, an optionally substituted $C_{2-6}$alkenyl, or optionally substituted acyl;

or a racemate, an enantiomer, a diastereomer, an isotopically-labelled analog, or a pharmaceutically acceptable salt thereof.

16. The compound of claim 15, wherein the compound is a compound of Formula IV:

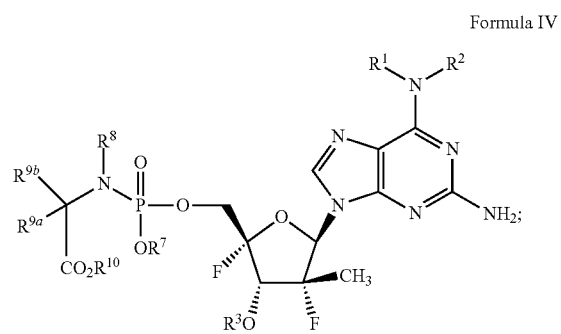

Formula IV or a racemate, an enantiomer, a diastereomer, an isotopically-labelled analog, or a pharmaceutically acceptable salt thereof.

17. The compound of claim 15, wherein the compound is a compound of Formula V:

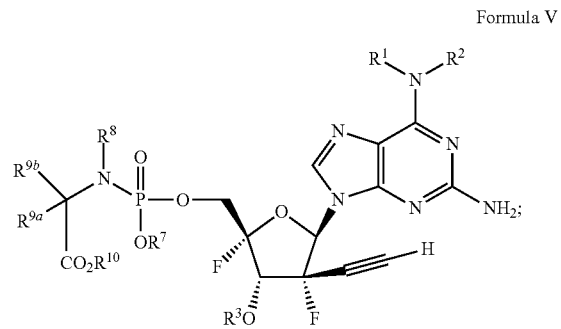

Formula V or a racemate, an enantiomer, a diastereomer, an isotopically-labelled analog, or a pharmaceutically acceptable salt thereof.

18. The compound of claim 1, wherein the compound is a compound of Formula VI:

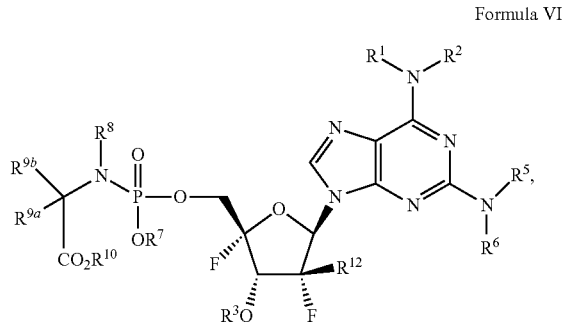

Formula VI wherein R⁷ is hydrogen, $C_{1-6}$alkyl; $C_{3-7}$cycloalkyl; heteroaryl, heterocyclic, or aryl, optionally substituted with $C_{1-6}$alkyl, $C_{2-6}$alkenyl, $C_{2-6}$ alkynyl, $C_{1-6}$alkoxy, F, Cl, Br, I, nitro, cyano, $C_{1-6}$haloalkyl, —N(R⁷')$_2$, $C_{1-6}$acylamino, NHSO$_2$C$_{1-6}$alkyl, —SO$_2$N(R⁷')$_2$, COR⁷'', and —SO$_2$C$_{1-6}$alkyl; (R⁷' is independently hydrogen or $C_{1-6}$alkyl; R⁷'' is —OR¹¹ or —N(R⁷)$_2$);

R⁸ is hydrogen, $C_{1-6}$alkyl, or R⁹ᵃ or R⁹ᵇ and R⁸ together are (CH$_2$)$_n$ so as to form a cyclic ring that includes the adjoining N and C atoms; where n is 2 to 4;

R⁹ᵃ and R⁹ᵇ are (i) independently selected from hydrogen, $C_{1-6}$alkyl, cycloalkyl, —(CH$_2$)$_c$(NR⁹')$_2$, $C_{1-6}$hydroxyalkyl, —CH$_2$SH, —(CH$_2$)$_2$S(O)(Me), —(CH$_2$)$_3$NHC (═NH)NH$_2$, (IH-indol-3-yl)methyl, (IH-imidazol-4-yl)methyl, —(CH$_2$)$_c$COR⁹'', aryl and aryl($C_{1-3}$alkyl)-, the aryl groups are optionally substituted with a group selected from hydroxyl, $C_{1-6}$alkyl, $C_{1-6}$alkoxy, halogen, nitro and cyano; (ii) R⁹ᵃ and R⁹ᵇ both are $C_{1-6}$alkyl; (iii) R⁹ᵃ and R⁹ᵇ together are (CH$_2$)$_r$ so as to form a spiro ring; (iv) R⁹ᵃ is hydrogen and R⁹ᵇ and R⁸ together are (CH$_2$)$_n$ so as to form a cyclic ring that includes the adjoining N and C atoms (v) R⁹ᵇ is hydrogen and R⁹ᵃ and R⁸ together are (CH$_2$)$_n$ so as to form a cyclic ring that includes the adjoining N and C atoms, where c is 1 to 6, n is 2 to 4, r is 2 to 5 and where R⁹' is independently hydrogen or $C_{1-6}$ alkyl and R⁹'' is —OR¹¹ or —N(R¹¹')$_2$; (vi) R⁹ᵃ is hydrogen and R⁹ᵇ is hydrogen, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$ ((4'-OH)-Ph), CH$_2$SH, or lower cycloalkyl; or (vii) R⁹ᵃ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$ ((4'-OH)-Ph), CH$_2$SH, or lower cycloalkyl and R⁹ᵇ is hydrogen;

R¹⁰ is hydrogen, $C_{1-6}$alkyl optionally substituted with an alkoxy, di(lower alkyl)-amino, or halogen; $C_{1-6}$haloalkyl, $(C_0$-$C_2)(C_{3-7}$cycloalkyl), $(C_0$-$C_2)$(heterocycloalkyl), aminoacyl, $(C_0$-$C_2)$(aryl), such as $(C_0$-$C_2)$ (phenyl), $(C_0$-$C_2)$(heteroaryl), such as $(C_0$-$C_2)$ (pyridinyl), substituted $(C_0$-$C_2)$(aryl), or substituted $(C_0$-$C_2)$(heteroaryl);

R¹¹ is an optionally substituted $C_{1-6}$alkyl, an optionally substituted cycloalkyl; an optionally substituted $C_{2-6}$alkynyl, an optionally substituted $C_{2-6}$alkenyl, or optionally substituted acyl;

or a racemate, an enantiomer, a diastereomer, an isotopically-labelled analog, or a pharmaceutically acceptable salt thereof.

19. The compound of claim 18, wherein the compound is a compound of Formula VII:

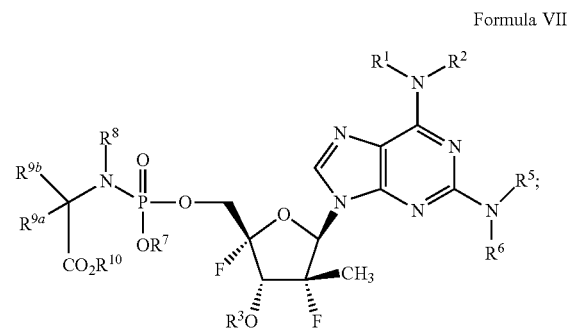

Formula VII or a racemate, an enantiomer, a diastereomer, an isotopically-labelled analog, or a pharmaceutically acceptable salt thereof.

20. The compound of claim 18, wherein the compound is a compound of Formula VIII:

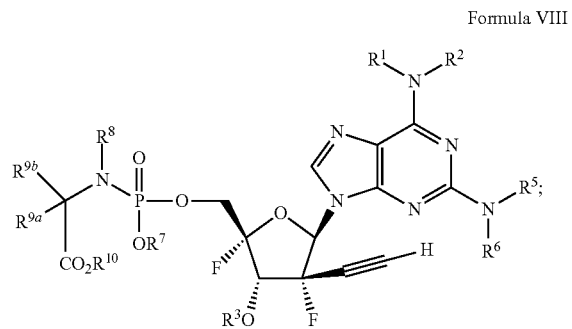

Formula VIII or a racemate, an enantiomer, a diastereomer, an isotopically-labelled analog, or a pharmaceutically acceptable salt thereof.

21. A method of treating a patient suffering from a hepatitis C virus (HCV) infection or HCV exposure comprising administering a therapeutically effective amount of the compound of claim 1 to the patient.

22. The method of claim 21, wherein said patient suffers from an anti-HCV antibody positive condition, an antigen positive condition, viral-based chronic liver inflammation, liver cancer resulting from advanced hepatitis C, cirrhosis, chronic or acute hepatitis C, fulminant hepatitis C, chronic persistent hepatitis C or anti-HCV-based fatigue.

23. A pharmaceutically acceptable composition comprising the compound of claim 1 and a pharmaceutically acceptable carrier.

24. The compound of claim 1, wherein said compound comprises an alkylated or acylated nucleotide group.

25. A compound having formula IX:

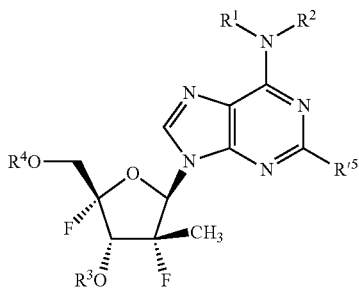

Formula IX wherein:
R$^1$ is C$_1$-C$_6$alkyl or —(C$_0$-C$_2$alkyl)(C$_3$-C$_6$cycloalkyl);
R$^2$ is hydrogen, C$_1$-C$_6$alkyl, CHF$_2$, CH$_2$F, CF$_3$, —(C$_0$-C$_2$alkyl) (C$_3$-C$_6$cycloalkyl), —C(O)R$^{3C}$, —C(S)R$^{3C}$, —(C$_0$-C$_2$alkyl)(aryl), —(C$_0$-C$_2$alkyl)(heterocycle), —(C$_0$-C$_2$alkyl)(heteroaryl); or
R$^1$ and R$^2$ together with the nitrogen to which they are bonded can form a heterocycle;
R$^3$ is hydrogen, $$\begin{array}{c} O \\ \| \\ R^{3B}-P- \\ | \\ R^{3A} \end{array},$$

diphosphate, triphosphate, an optionally substituted carbonyl linked amino acid, —C(S)R$^{3C}$, —C(S)R$^{3C}$, or —C(O)R$^{3C}$;
  R$^{3A}$ is selected from O$^-$, OH, an —O-optionally substituted aryl, an —O-optionally substituted heteroaryl, or an optionally substituted heterocyclyl;
  R$^{3B}$ is selected from O$^-$, OH, an optionally substituted N-linked amino acid or an optionally substituted N-linked amino acid ester;
  R$^{3C}$ is optionally substituted alkyl, optionally substituted alkenyl, optionally substituted alkynyl, optionally substituted —(C$_0$-C$_2$)(cycloalkyl), optionally substituted —(C$_0$-C$_2$)(heterocyclo), optionally substituted —(C$_0$-C$_2$)(aryl), optionally substituted —(C$_0$-C$_2$)(heteroaryl), optionally substituted —O-alkyl, optionally substituted —O-alkenyl, optionally substituted —O-alkynyl, optionally substituted —O—(C$_0$-C$_2$)(cycloalkyl), optionally substituted —O—(C$_0$-C$_2$)(heterocyclo), optionally substituted —O—(C$_0$-C$_2$)(aryl), optionally substituted —O—(C$_0$-C$_2$)(heteroaryl), optionally substituted —S-alkyl, optionally substituted —S-alkenyl, optionally substituted —S-alkynyl, optionally substituted —S—(C$_0$-C$_2$)(cycloalkyl), optionally substituted —S—(C$_0$-C$_2$)(heterocyclo), optionally substituted —S—(C$_0$-C$_2$)(aryl), or optionally substituted —S—(C$_0$-C$_2$)(heteroaryl);
R$^4$ is a monophosphate, diphosphate, triphosphate; or
R$^3$ and R$^4$ together with the oxygens that they are bonded to can form a 3',5'-cyclic ring;
R'$^5$ is Cl, Br, F, N$_3$, NHOCH$_3$, —ONHC(=O)OCH$_3$, CN, CONH$_2$, SO$_2$NH$_2$ and CF$_3$; or
a racemate, an enantiomer, a diastereomer, an isotopically-labelled analog, or a pharmaceutically acceptable salt thereof.

26. The compound of claim 25, wherein R$^4$ is a stabilized phosphate, a phosphoramidate, or a thiophosphoramidate.

27. The compound of claim 25, wherein the compound is a compound of Formula X:

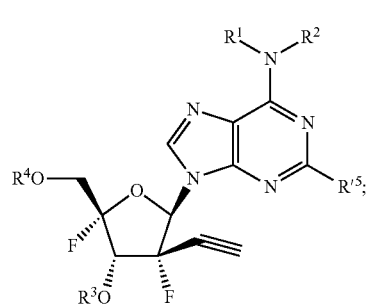

Formula X or a racemate, an enantiomer, a diastereomer, an isotopically-labelled analog, or
a pharmaceutically acceptable salt thereof.

28. The compound of claim 25, wherein R$^3$ is hydrogen and R$^4$ is

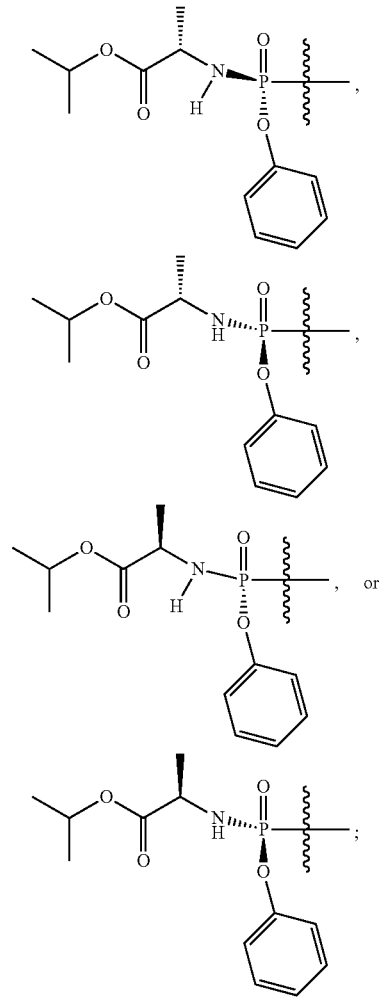

or a racemate, an enantiomer, a diastereomer, an isotopically-labelled analog, or a pharmaceutically acceptable salt thereof.

29. The compound of claim 25, wherein the compound is

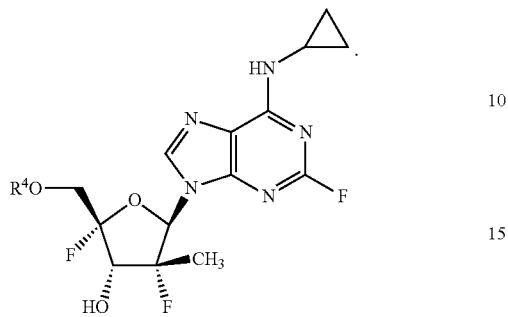

30. A method of treating a patient suffering from a hepatitis C virus (HCV) infection or HCV exposure comprising administering the compound of claim 25 to the patient.

31. A pharmaceutically acceptable composition comprising the compound of claim 25 and a pharmaceutically acceptable carrier.

32. The compound of claim 25, wherein said compound comprises an alkylated or acylated nucleotide group.

* * * * *